United States Patent
Fu et al.

(10) Patent No.: US 11,606,970 B2
(45) Date of Patent: Mar. 21, 2023

(54) VAPORIZER DEVICE WITH DIFFERENTIAL PRESSURE SENSOR

(71) Applicant: JUUL Labs, Inc., San Francisco, CA (US)

(72) Inventors: Joshua Fu, San Francisco, CA (US); Christopher Loental, San Francisco, CA (US); Marko Markovic, San Francisco, CA (US); Alexander Weiss, Oakland, CA (US); Alexander Ringrose, Oakland, CA (US); David Carlberg, Portland, OR (US); Robyn Nariyoshi, San Francisco, CA (US); Devin Spratt, Sunnyvale, CA (US); Nicholas J. Hatton, Oakland, CA (US); Yen Jen Chang, Taipei (TW); Chen Yu Li, Taipei (TW); Barry Tseng, Taipei (TW); Prince Wang, Taipei (TW); Thomas Germann, Aschau im Chiemgau (DE); Andreas Schaefer, Neubiberg (DE)

(73) Assignee: JUUL Labs, Inc., San Francisco, CA (US)

( * ) Notice: Subject to any disclaimer, the term of this patent is extended or adjusted under 35 U.S.C. 154(b) by 830 days.

(21) Appl. No.: 16/425,807

(22) Filed: May 29, 2019

(65) Prior Publication Data

US 2019/0364969 A1 Dec. 5, 2019

Related U.S. Application Data

(60) Provisional application No. 62/835,988, filed on Apr. 18, 2019, provisional application No. 62/834,307, (Continued)

(51) Int. Cl.
*A24F 40/10* (2020.01)
*A24D 1/14* (2006.01)
(Continued)

(52) U.S. Cl.
CPC .............. *A24D 1/14* (2013.01); *A24F 7/00* (2013.01); *A24F 40/40* (2020.01); *A61M 11/042* (2014.02);
(Continued)

(58) Field of Classification Search
CPC ... A24D 1/14; A24F 7/00; A24F 40/40; A24F 15/015; A61M 11/042; A61M 11/04;
(Continued)

(56) References Cited

U.S. PATENT DOCUMENTS 2,978,364 A 4/1961 Aaron
6,234,167 B1 5/2001 Cox et al.
(Continued)

FOREIGN PATENT DOCUMENTS

CA 2925018 A1 5/2015
CA 3027164 A1 3/2018
(Continued)

*Primary Examiner* — Huyen X Vo
(74) *Attorney, Agent, or Firm* — Mintz, Levin, Cohn, Ferris, Glovsky and Popeo, P.C.

(57) ABSTRACT

A vaporizer device may include a pressure sensor and an ambient pressure sensor. The pressure sensor may be configured to measure a first pressure in an air flow path in the vaporizer device. The ambient pressure sensor may be configured to measure a second pressure corresponding to an atmospheric pressure. The vaporizer device may further include a controller. The controller may be configured to transition the vaporizer device to a first standby mode when the first pressure is equal to or greater than the second pressure for a first threshold quantity of time. While the vaporizer device is in the first standby mode, the controller
(Continued)

may be further configured to transition the vaporizer device to a second standby mode when the second pressure is a threshold quantity greater than the first pressure and no motion event is detected for a second threshold quantity of time.

32 Claims, 83 Drawing Sheets

Related U.S. Application Data filed on Apr. 15, 2019, provisional application No. 62/802,598, filed on Feb. 7, 2019, provisional application No. 62/738,874, filed on Sep. 28, 2018, provisional application No. 62/725,875, filed on Aug. 31, 2018, provisional application No. 62/726,008, filed on Aug. 31, 2018, provisional application No. 62/725,964, filed on Aug. 31, 2018, provisional application No. 62/725,872, filed on Aug. 31, 2018, provisional application No. 62/726,024, filed on Aug. 31, 2018, provisional application No. 62/677,598, filed on Aug. 31, 2018.

(51) Int. Cl.

| | |
|---|---|
| *A61M 11/04* | (2006.01) |
| *A61M 15/00* | (2006.01) |
| *G01N 35/00* | (2006.01) |
| *A24F 7/00* | (2006.01) |
| *H05B 1/02* | (2006.01) |
| *H05B 3/00* | (2006.01) |
| *G08B 6/00* | (2006.01) |
| *H01R 13/52* | (2006.01) |
| *H05K 1/14* | (2006.01) |
| *H05K 1/18* | (2006.01) |
| *H02J 7/00* | (2006.01) |
| *A24F 40/40* | (2020.01) |
| *F17C 9/02* | (2006.01) |
| *F16J 15/02* | (2006.01) |
| *H01Q 1/22* | (2006.01) |
| *G01L 13/00* | (2006.01) |
| *G01P 15/00* | (2006.01) |
| *A24F 15/015* | (2020.01) |

(52) U.S. Cl.
CPC ... *A61M 15/0028* (2013.01); *G01N 35/00732* (2013.01); *G08B 6/00* (2013.01); *H01R 13/521* (2013.01); *H02J 7/00* (2013.01); *H05B 1/0244* (2013.01); *H05B 3/0014* (2013.01); *H05B 3/0019* (2013.01); *H05K 1/147* (2013.01); *H05K 1/189* (2013.01); *A24F 15/015* (2020.01); *A24F 40/10* (2020.01); *A61M 2205/8206* (2013.01); *F16J 15/02* (2013.01); *F17C 9/02* (2013.01); *G01L 13/00* (2013.01); *G01P 15/00* (2013.01); *H01Q 1/2283* (2013.01); *H05K 2201/10106* (2013.01); *H05K 2201/10121* (2013.01); *H05K 2201/10151* (2013.01); *H05K 2201/10189* (2013.01); *H05K 2201/10318* (2013.01)

(58) Field of Classification Search
CPC .............. A61M 15/0028; A61M 15/00; G01N 35/00732; G01N 35/00; G08B 6/00; H01R 13/521; H01R 13/52; H02J 7/00; H05B 1/0244; H05B 1/0247; H05B 1/02; H05B 3/0014; H05B 3/00; H05B 3/0019; H05K 1/147; H05K 1/148; H05K 1/14; H05K 1/189; H05K 3/326; H05K 1/18

See application file for complete search history.

(56) References Cited

U.S. PATENT DOCUMENTS

| | | | |
|---|---|---|---|
| 9,272,103 | B2 | 3/2016 | Storz |
| 9,462,832 | B2 | 10/2016 | Lord |
| 9,714,878 | B2 | 7/2017 | Powers et al. |
| 9,772,245 | B2 | 9/2017 | Besling et al. |
| 9,839,238 | B2 | 12/2017 | Worm et al. |
| 9,930,780 | B1 | 3/2018 | Ghabra et al. |
| 9,949,511 | B2 | 4/2018 | Liu |
| 9,980,513 | B2 | 5/2018 | Chen |
| 9,999,248 | B2 | 6/2018 | Liu |
| 9,999,250 | B2 | 6/2018 | Minskoff et al. |
| 10,051,889 | B2 | 8/2018 | Chen |
| 10,058,126 | B2 | 8/2018 | Chen |
| 10,117,461 | B2 | 11/2018 | Chen |
| 10,130,123 | B2 | 11/2018 | Hatton et al. |
| 10,131,532 | B2 | 11/2018 | Murison et al. |
| 10,195,370 | B2 | 2/2019 | Chen |
| 10,231,486 | B2 | 3/2019 | Bowen et al. |
| 10,375,990 | B2 | 8/2019 | Lord |
| 10,716,332 | B2 | 7/2020 | Biel et al. |
| 10,736,356 | B2 | 8/2020 | Jordan et al. |
| 10,792,685 | B2 | 10/2020 | Tong |
| 10,869,505 | B2 | 12/2020 | Borkovec et al. |
| 10,945,463 | B2 | 3/2021 | Dickens et al. |
| 11,116,254 | B2 | 9/2021 | Lord et al. |
| 2008/0315829 | A1 | 12/2008 | Jones et al. |
| 2010/0000943 | A1 | 1/2010 | Carson et al. |
| 2010/0097767 | A1 | 4/2010 | Jude et al. |
| 2014/0041655 | A1 | 2/2014 | Barron et al. |
| 2014/0150810 | A1 | 6/2014 | Hon |
| 2014/0276536 | A1 | 9/2014 | Estes |
| 2015/0136158 | A1 | 5/2015 | Stevens et al. |
| 2015/0208729 | A1 | 7/2015 | Monsees et al. |
| 2015/0237917 | A1 | 8/2015 | Lord |
| 2015/0320116 | A1 | 11/2015 | Bleloch et al. |
| 2016/0066619 | A1 | 3/2016 | Di Carlo |
| 2016/0150824 | A1 | 6/2016 | Memari et al. |
| 2016/0174611 | A1 | 6/2016 | Monsees et al. |
| 2016/0211693 | A1 | 7/2016 | Stevens et al. |
| 2016/0262457 | A1* | 9/2016 | Borkovec ........... A61M 15/002 |
| 2016/0366947 | A1 | 12/2016 | Monsees et al. |
| 2016/0374399 | A1 | 12/2016 | Monsees et al. |
| 2017/0014582 | A1 | 1/2017 | Skoda |
| 2017/0035115 | A1 | 2/2017 | Monsees et al. |
| 2017/0045150 | A1 | 2/2017 | Marsh |
| 2017/0045994 | A1 | 2/2017 | Murison et al. |
| 2017/0095005 | A1 | 4/2017 | Monsees et al. |
| 2017/0099878 | A1 | 4/2017 | Murison et al. |
| 2017/0136196 | A1 | 5/2017 | Davidson et al. |
| 2017/0156399 | A1 | 6/2017 | Freeman et al. |
| 2017/0196266 | A1 | 7/2017 | Chen |
| 2017/0231281 | A1 | 8/2017 | Hatton et al. |
| 2017/0231282 | A1 | 8/2017 | Bowen et al. |
| 2017/0259170 | A1 | 9/2017 | Bowen et al. |
| 2017/0304563 | A1 | 10/2017 | Adelson |
| 2017/0304567 | A1 | 10/2017 | Adelson |
| 2017/0347710 | A1 | 12/2017 | Hon |
| 2018/0020728 | A1 | 1/2018 | Alarcon et al. |
| 2018/0042306 | A1 | 2/2018 | Atkins et al. |
| 2018/0043114 | A1 | 2/2018 | Bowen et al. |
| 2018/0050164 | A1 | 2/2018 | Adelson |
| 2018/0077967 | A1 | 3/2018 | Hatton et al. |
| 2018/0177231 | A1 | 6/2018 | Woodbine et al. |
| 2018/0184715 | A1 | 7/2018 | Liu |
| 2018/0184722 | A1* | 7/2018 | Murison ............... F04B 43/046 |
| 2018/0255835 | A1 | 9/2018 | Crowe et al. |
| 2018/0263283 | A1 | 9/2018 | Popplewell et al. |
| 2018/0295886 | A1 | 10/2018 | Freeman et al. |
| 2018/0296777 | A1 | 10/2018 | Terry et al. |
| 2018/0303162 | A1 | 10/2018 | Zhang et al. |
| 2018/0317557 | A1 | 11/2018 | Monsees et al. |

(56) References Cited

U.S. PATENT DOCUMENTS

| | | |
|---|---|---|
| 2018/0333547 A1 | 11/2018 | Freeman et al. |
| 2018/0361086 A1 | 12/2018 | Crowe |
| 2018/0369514 A1 | 12/2018 | Adelson |
| 2018/0369516 A1 | 12/2018 | Adelson |
| 2019/0000148 A1 | 1/2019 | Atkins et al. |
| 2019/0069599 A1 | 3/2019 | Monsees et al. |
| 2019/0104767 A1 | 4/2019 | Hatton et al. |
| 2019/0159519 A1 | 5/2019 | Bowen et al. |
| 2019/0208821 A1 | 7/2019 | Fraser et al. |
| 2019/0335813 A1 | 11/2019 | Qiu |
| 2019/0373679 A1 | 12/2019 | Fu et al. |
| 2020/0000143 A1 | 1/2020 | Anderson et al. |
| 2020/0091608 A1 | 3/2020 | Alpman et al. |
| 2020/0130911 A1 | 4/2020 | Bhalla et al. |
| 2020/0136238 A1 | 4/2020 | Iwata et al. |
| 2020/0178389 A1 | 6/2020 | Min et al. |
| 2020/0352249 A1 | 11/2020 | Achtien et al. |
| 2021/0052829 A1 | 2/2021 | Dignum et al. |
| 2021/0153562 A1 | 5/2021 | Fishwick et al. |
| 2021/0307402 A1 | 10/2021 | Batley et al. |

FOREIGN PATENT DOCUMENTS

| | | |
|---|---|---|
| CN | 203643774 U | 6/2014 |
| EP | 3629783 B1 | 7/2021 |
| WO | WO-0021598 A1 | 4/2000 |
| WO | WO-2015174708 A1 | 11/2015 |
| WO | WO-2016210242 A1 | 12/2016 |
| WO | WO-2017011419 A1 | 1/2017 |
| WO | WO-2017021536 A2 | 2/2017 |
| WO | WO-2017033007 A1 | 3/2017 |
| WO | WO-2017036818 A1 | 3/2017 |
| WO | WO-2017036819 A1 | 3/2017 |
| WO | WO-2017036879 A1 | 3/2017 |
| WO | WO-2017139662 A1 | 8/2017 |
| WO | WO-2018048813 A1 | 3/2018 |
| WO | WO-2018/165758 A1 | 9/2018 |

\* cited by examiner

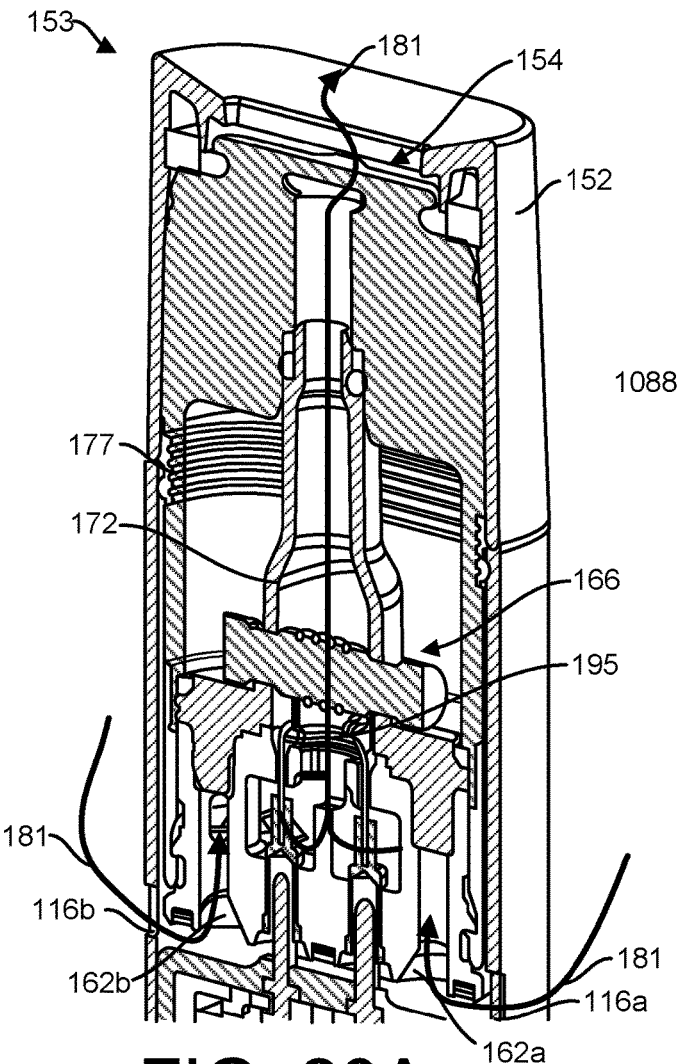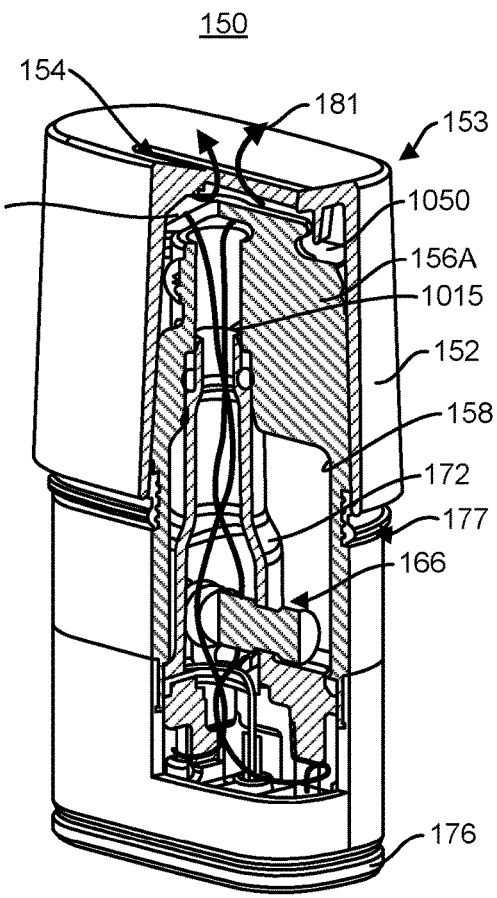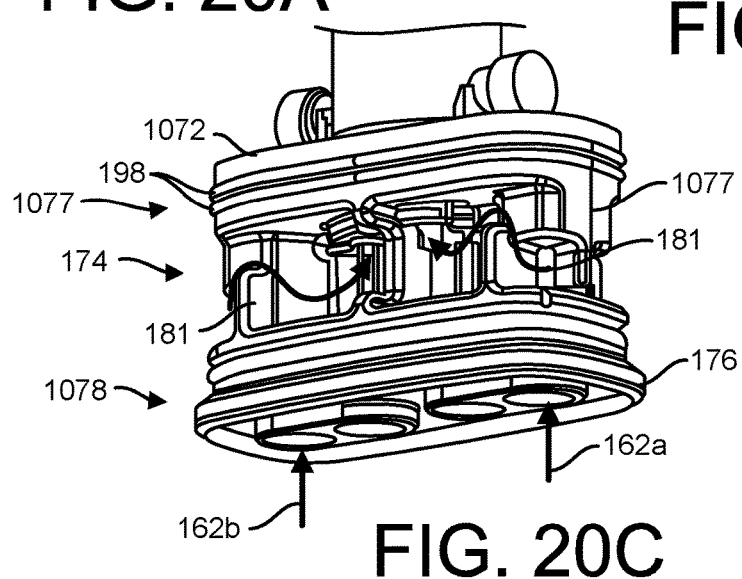
FIG. 20A
FIG. 20B
FIG. 20C

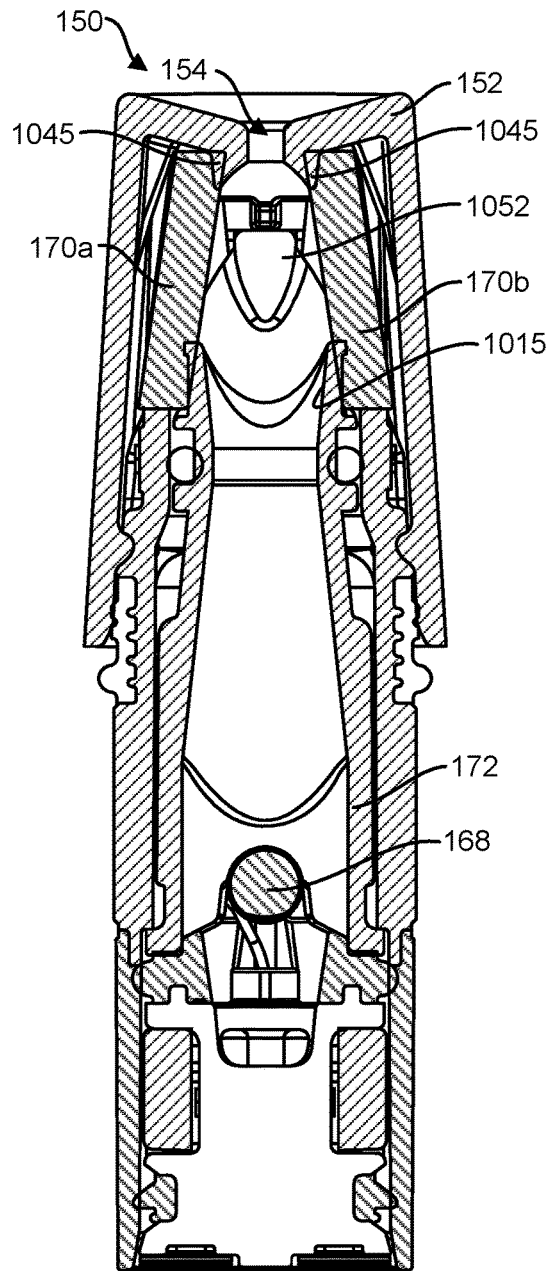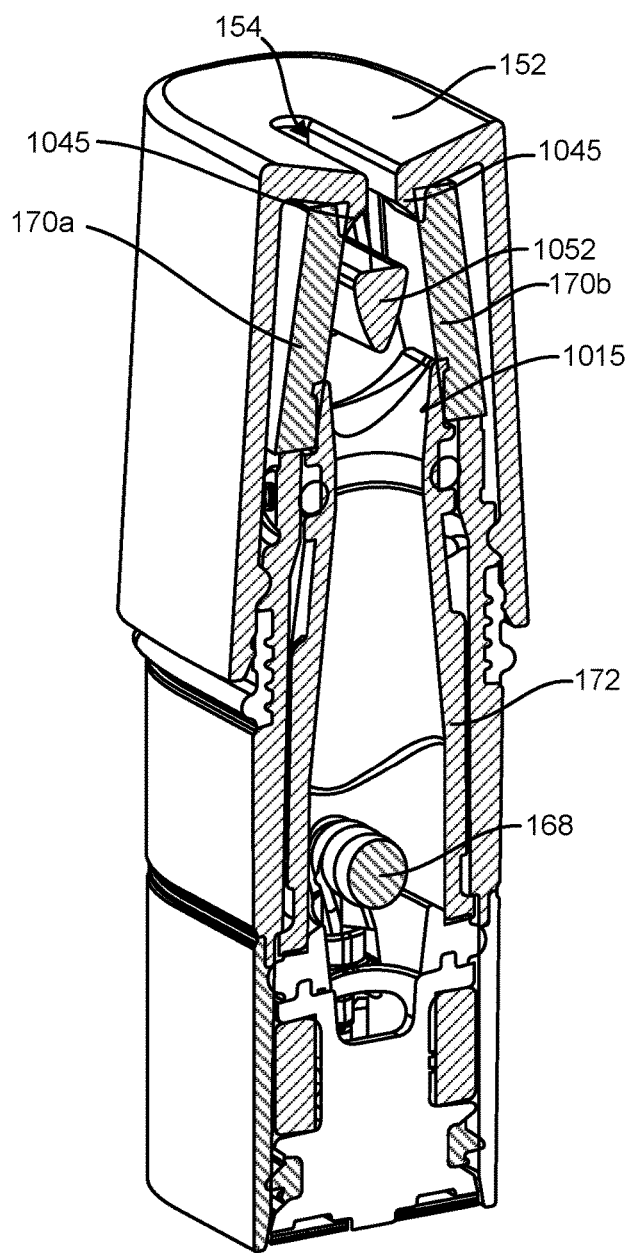
FIG. 34E
FIG. 34F

VAPORIZER DEVICE WITH DIFFERENTIAL PRESSURE SENSOR

CROSS-REFERENCE TO RELATED APPLICATIONS

This application claims priority to U.S. Provisional Patent Application Nos. 62/677,598, filed May 29, 2018; 62/726,008, filed Aug. 31, 2018; 62/725,872, filed Aug. 31, 2018; 62/725,964, filed Aug. 31, 2018; 62/725,875, filed Aug. 31, 2018; 62/726,024, filed Aug. 31, 2018; 62/738,874, filed Sep. 28, 2018; 62/802,598, filed Feb. 7, 2019; 62/834,307, filed Apr. 15, 2019; and 62/835,988, filed Apr. 18, 2019. These applications are incorporated herein by reference in their entirety.

TECHNICAL FIELD

The current subject matter described herein relates generally to vaporizer devices, such as portable, personal vaporizer devices for generating and delivering an inhalable aerosol from one or more vaporizable materials.

BACKGROUND

Vaporizing devices, including electronic vaporizers or e-vaporizer devices, allow the delivery of vapor containing one or more active ingredients by inhalation of the vapor. Electronic vaporizer devices are gaining increasing popularity both for prescriptive medical use, in delivering medicaments, and for consumption of nicotine, tobacco, other liquid-based substances, and other plant-based smokeable materials, such as, *cannabis*, including solid (e.g., loose-leaf) materials, solid/liquid (e.g., suspensions, liquid-coated) materials, wax extracts, and prefilled pods (cartridges, wrapped containers, etc.) of such materials. Electronic vaporizer devices in particular may be portable, self-contained, and convenient for use.

SUMMARY

Methods, apparatuses, and computer program products are provided for transitioning a vaporizer device between different operation modes based on a difference between atmospheric pressure and a pressure in an air flow path of the vaporizer device.

In one aspect, there is provided a vaporizer device. The vaporizer device may include a pressure sensor configured to measure a first pressure in an air flow path in the vaporizer device. The vaporizer device may further include an ambient pressure sensor configured to measure a second pressure corresponding to an atmospheric pressure. The vaporizer device may further include a controller. When the first pressure is equal to or greater than the second pressure for a first threshold quantity of time, the controller may transition the vaporizer device to a first standby mode. While the vaporizer device is in the first standby mode, the controller may transition the vaporizer device to a second standby mode when the first pressure is equal to or greater than the second pressure and no motion event is detected for a second threshold quantity of time.

In some variations, one or more of the features disclosed herein including the following features can optionally be included in any feasible combination. While the vaporizer device is in the first standby mode, the pressure sensor and/or the ambient pressure sensor may operate at a first sampling frequency. While the vaporizer device is in the second standby mode, the pressure sensor and/or the ambient pressure sensor may operate at a second sampling frequency. The second sampling frequency may be less than the first sampling frequency.

In some variations, the vaporizer device may remain in the first standby mode in response to a detection of the motion event within the second threshold quantity of time. In response to the motion event while the vaporizer device is in the second standby mode, the controller may transition the vaporizer device from the second standby mode to the first standby mode.

In some variations, the vaporizer device may include a motion sensor configured to detect the motion event. The motion sensor may be an accelerometer. The motion event may include a tapping and/or a rolling of the vaporizer device.

In some variations, the controller may be further configured to transition the vaporizer device to an active mode when a cartridge is coupled with the vaporizer device. The pressure sensor and/or the ambient pressure sensor may operate at a third sampling frequency when the vaporizer device is in the active mode. The third sampling frequency may be higher than each of the first sampling frequency and the second sampling frequency. When the first pressure remains equal to and/or greater than the second pressure for the first threshold quantity of time, the controller may transition the vaporizer device from the active mode to the first standby mode. The vaporizer device may remain in the active mode based at least on the first pressure being less than the second pressure within the first threshold quantity of time.

In some variations, the vaporizer device may include an interrupt request (IRQ) line. A presence or an absence of a signal on the interrupt request line may be indicative of whether the cartridge is coupled with the vaporizer device. The vaporizer device may further include a cartridge receptacle configured to couple the cartridge with the vaporizer device. The cartridge receptacle may be a part of a vaporizer body of the vaporizer device.

In some variations, the controller may determine that the first pressure is the threshold quantity less than the second pressure for a threshold quantity of samples taken by the pressure sensor and/or the ambient pressure sensor, while the vaporizer device is in the active mode. In response to determining that the first pressure is the threshold quantity less than the second pressure for the threshold quantity of samples, the controller may activate a heater in the cartridge to cause a vaporization of a vaporizable material contained in the cartridge. The controller may activate the heater by at least triggering a discharge of a battery to a heating coil in the heater. The first pressure being the threshold quantity less than the second pressure for the threshold quantity of samples may indicate air being drawn into the vaporizer device along the air flow path.

In another aspect, there is provided a method. The method may include measuring, by a pressure sensor, a first pressure in an air flow path of a vaporizer device. An ambient pressure sensor may measure a second pressure corresponding to an atmospheric pressure. The vaporizer device may be transitioned to a first standby mode when the first pressure is equal to or greater than the second pressure for a first threshold quantity of time. While the vaporizer device is in the first standby mode, the vaporizer device may be transitioned to a second standby mode when the first pressure is equal to or greater than the second pressure and no motion event is detected for a second threshold quantity of time.

In some variations, one or more of the features disclosed herein including the following features can optionally be included in any feasible combination. While the vaporizer device is in the first standby mode, the pressure sensor and/or the ambient pressure sensor may operate at a first sampling frequency. While the vaporizer device is in the second standby mode, the pressure sensor and/or the ambient pressure sensor operate at a second sampling frequency. The second sampling frequency may be less than the first sampling frequency.

In some variations, the vaporizer device may remain in the first standby mode in response to a detection of the motion event within the second threshold quantity of time. While the vaporizer device is in the second standby mode, the vaporizer device may be transitioned from the second standby mode to the first standby mode in response to the motion event.

In some variations, the motion event may be detected by a motion sensor. The motion sensor may be an accelerometer. The motion event may be a tapping and/or a rolling of the vaporizer device.

In some variations, the vaporizer device may be transitioned to an active mode when a cartridge is coupled with the vaporizer device. When the vaporizer device is in the active mode, the pressure sensor and/or the ambient pressure sensor may operate at a third sampling frequency. The third sampling frequency may be higher than each of the first sampling frequency and the second sampling frequency.

In some variations, the method may further include transitioning the vaporizer device from the active mode to the first standby mode when the first pressure remains equal to and/or greater than the second pressure for the first threshold quantity of time. The vaporizer device may remain in the active mode based at least on the first pressure being less than the second pressure within the first threshold quantity of time.

In some variations, whether the cartridge is coupled with the vaporizer device may be detected based at least on a presence or an absence of a signal on an interrupt request (IRQ) line.

In some variations, while the vaporizer device is in the active mode, the first pressure may be determined to be the threshold quantity less than the second pressure for a threshold quantity of samples taken by the pressure sensor and/or the ambient pressure sensor. In response to determining that the first pressure is the threshold quantity less than the second pressure for the threshold quantity of samples, a heater in the cartridge may be activated to cause a vaporization of a vaporizable material contained in the cartridge. The heater may be activated by at least triggering a discharge of a battery to a heating coil in the heater. The first pressure being the threshold quantity less than the second pressure for the threshold quantity of samples may indicate air being drawn into the vaporizer device along the air flow path.

In another aspect, there is provided a computer program product. The computer program product may include a non-transitory computer readable medium storing instructions. Executing the instructions by at least one data processor may result in operations. The operations may include transitioning a vaporizer device to a first standby mode when a first pressure is equal to or greater than a second pressure for a first threshold quantity of time. The first pressure may be a pressure in an air flow path of the vaporizer device. The second pressure may be an atmospheric pressure. While the vaporizer device is in the first standby mode, the vaporizer device may be transitioned to a second standby mode when the first pressure is equal to or greater than the second pressure and no motion event is detected for a second threshold quantity of time The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings:

FIG. 20A-FIG. 20C illustrate air flow paths through a cartridge of a vaporizer device consistent with implementations of the current subject matter;

FIG. 34A-FIG. 34F illustrate various features relating to a cartridge body and a mouthpiece of a cartridge of a vaporizer device consistent with implementations of the current subject matter;

When practical, similar reference numbers denote similar structures, features, or elements.

DETAILED DESCRIPTION

Figure 1A:
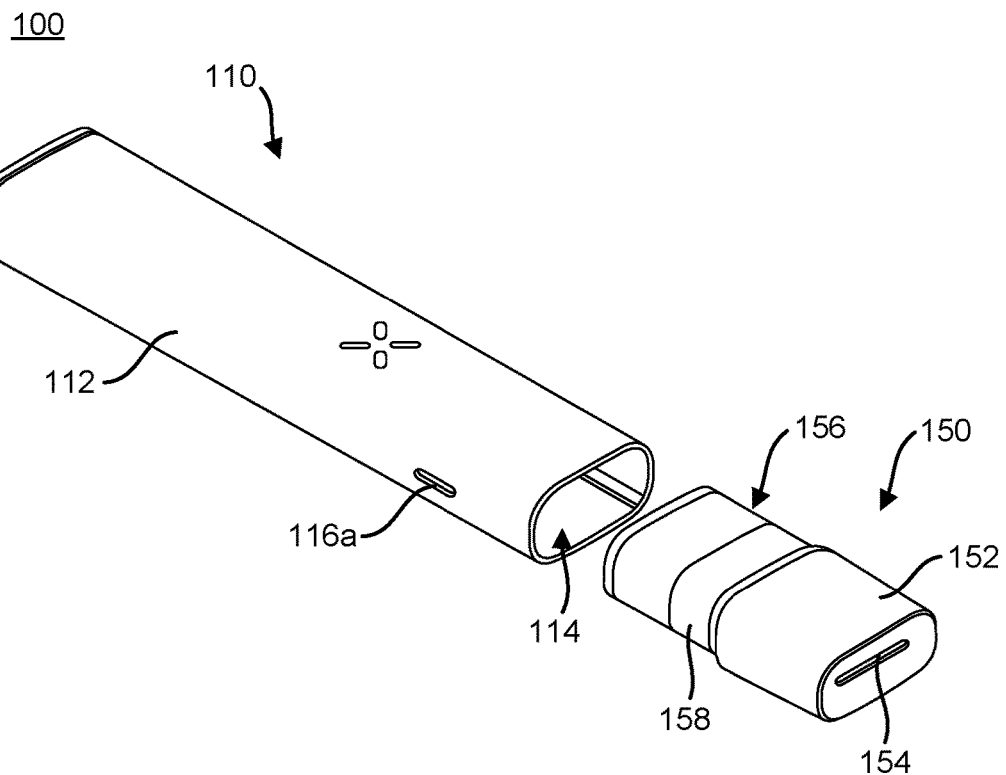
FIG. 1A-FIG. 1F illustrate features of a vaporizer device including a vaporizer body and a cartridge consistent with implementations of the current subject matter.

To maximize the battery life of a vaporizer device, the operation mode of the vaporizer device may be controlled based on whether the vaporizer device is in use. For example, the pressure in an air flow path of the vaporizer device may decrease when air is being drawn by a user into the vaporizer device. Accordingly, the vaporizer device may be activated, for example, to vaporize a vaporizable material from a cartridge coupled with the vaporizer device, based on the pressure in the air flow path of the vaporizer device. However, in addition to air being drawn into the air flow path by a user, the pressure in the air flow path may also decrease when the vaporizer device is subject to a decrease in overall atmospheric pressure, for example, when the vaporizer device is at a high altitude location. As such, controlling the operation mode of the vaporizer device based on the pressure in the air flow path alone may trigger false positives. In some example embodiments, to avoid such false positives, the vaporizer device may include one pressure sensor for measuring the pressure in the air flow path and another pressure sensor for measuring the atmospheric pressure. The operation mode of the vaporizer device may be controlled based on a difference between the atmospheric pressure and the pressure in the air flow path of the vaporizer device.

Implementations of the current subject matter include devices relating to vaporizing of one or more materials for inhalation by a user. The term "vaporizer" may be used generically in the following description and refers to a vaporizer device, such as, for example, an electronic vaporizer. Examples of vaporizers consistent with implementations of the current subject matter include electronic vaporizers, electronic cigarettes, e-cigarettes, or the like. In general, such vaporizers are often portable, hand-held devices that heat a vaporizable material to provide an inhalable dose of the material.

Vaporizer devices consistent with the current subject matter may be referred to by various terms such as, for example, inhalable aerosol devices, aerosolizers, vaporization devices, electronic vaping devices, electronic vaporizers, vape pens, etc.

An apparatus and/or method consistent with implementations of the current subject matter involves heating of a vaporizable material to result in production of one or more gas-phase components of the vaporizable material. A vaporizable material may include liquid and/or oil-type plant materials. The gas-phase components of the vaporizable material may condense after being vaporized such that an aerosol is formed in a flowing air stream that is deliverable for inhalation by a user. Such vaporizer devices may in some implementations of the current subject matter be particularly adapted for use with an oil-based vaporizable material, such as, for example, *cannabis* oils.

One or more features of the current subject matter, including one or more of a cartridge (also referred to as vaporizer cartridges and pods) and a reusable vaporizer device body (also referred to as a vaporizer device base, a body, a base, etc.), may be employed with a suitable vaporizable material (where suitable refers in this context to being usable with a device whose properties, settings, etc. are configured or configurable to be compatible for use with the vaporizable material). The vaporizable material can include one or more liquids, such as, for example, oils, extracts, aqueous or other solutions, etc., of one or more substances that may be desirably provided in the form of an inhalable aerosol.

In some implementations, the vaporizable material is *cannabis* oil. *Cannabis* oils may present particular challenges when vaporized using a cartridge and a vaporizer device. For example, *cannabis* oil is relatively sticky and viscous, particularly once it dries out. Thus, leakage may be a more serious consideration and challenge compared to other aqueous vaporizable materials. In particular, leakage of *cannabis* oil may result in clogging of the device and disturbing the electrical components, particularly the electrical contacts. The dried oil may also disrupt the electrical control of the vaporizer device due to its electrically insulating properties. The cartridges described herein may provide robust leak-resistant designs and may be configured to be used with viscous oil-based vaporizable materials, such as *cannabis* oil that may have a viscosity at room temperature of between about 40 cP and 113 KcP.

Before providing additional details regarding the cartridge (also referred to as a "pod"), the following provides a description of some example of vaporizer devices.

Figure 1B:
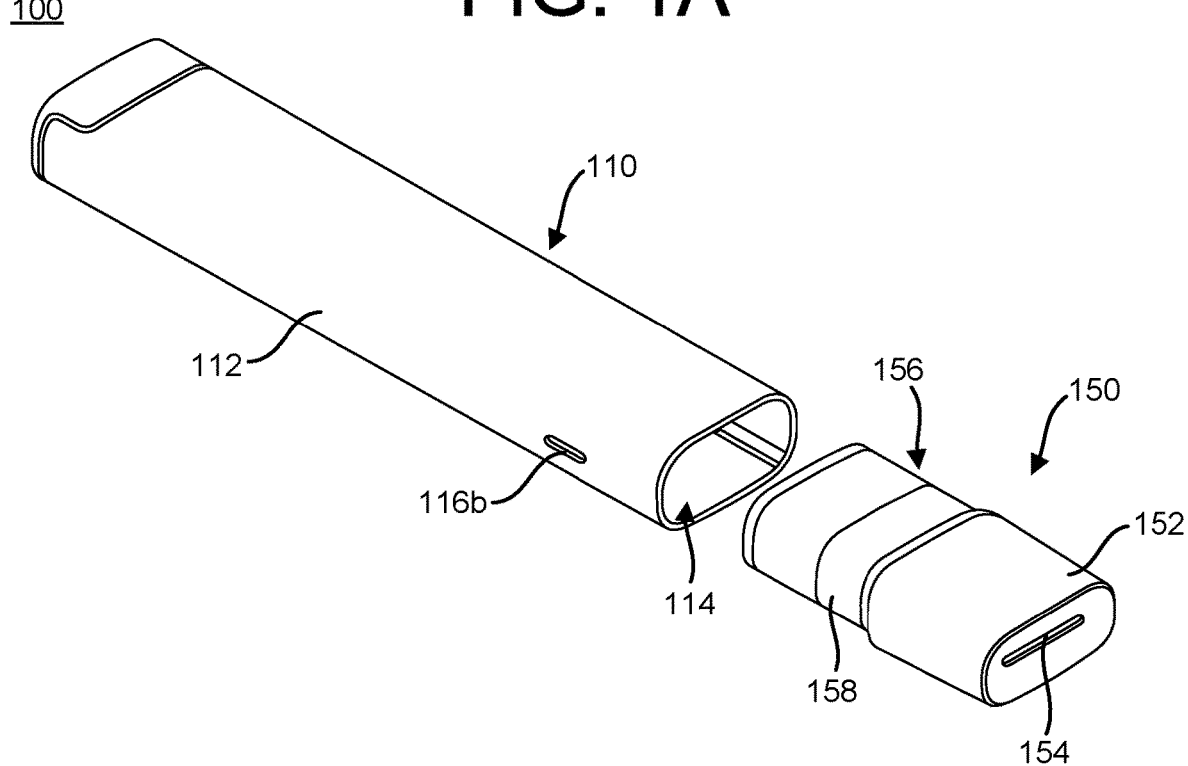
Figure 1C:
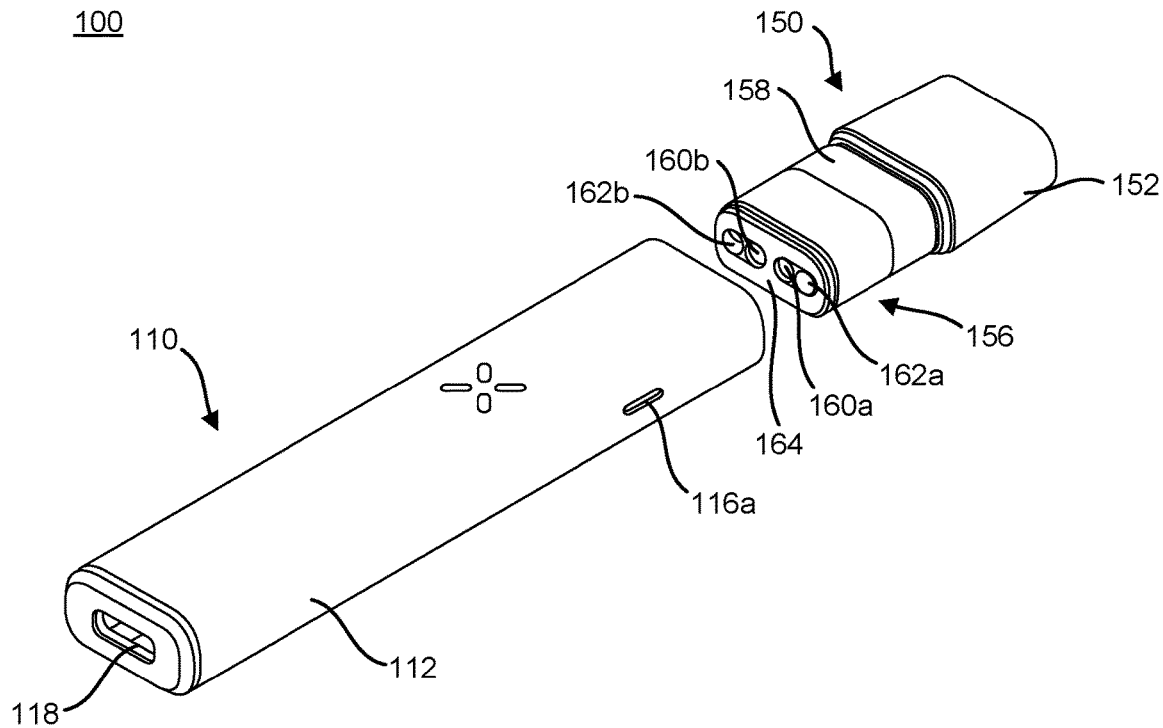
Figure 1D:
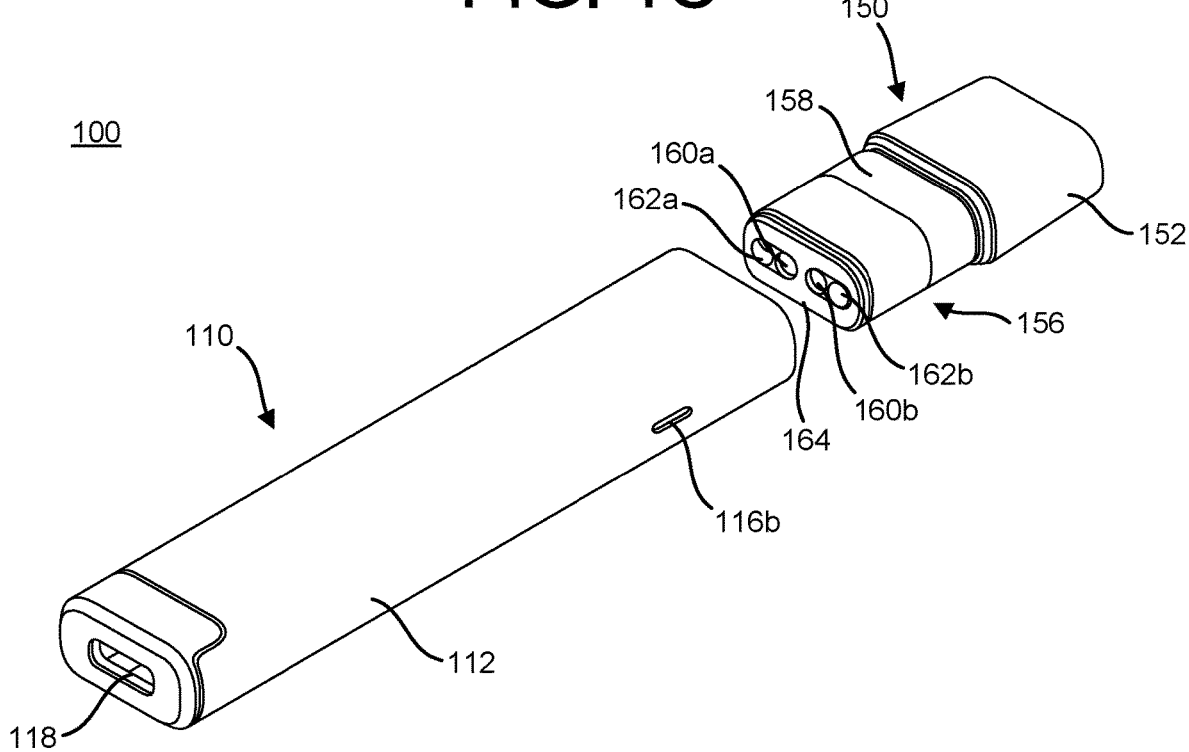
Figure 1E:
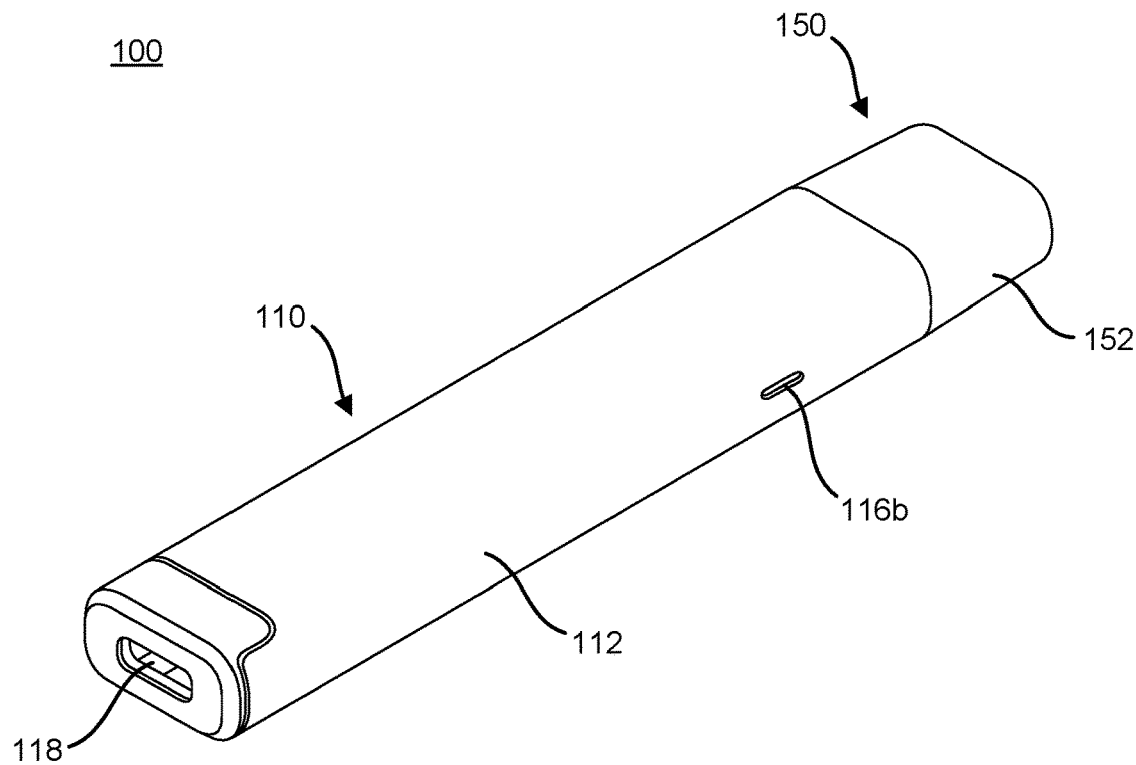
Figure 1F:
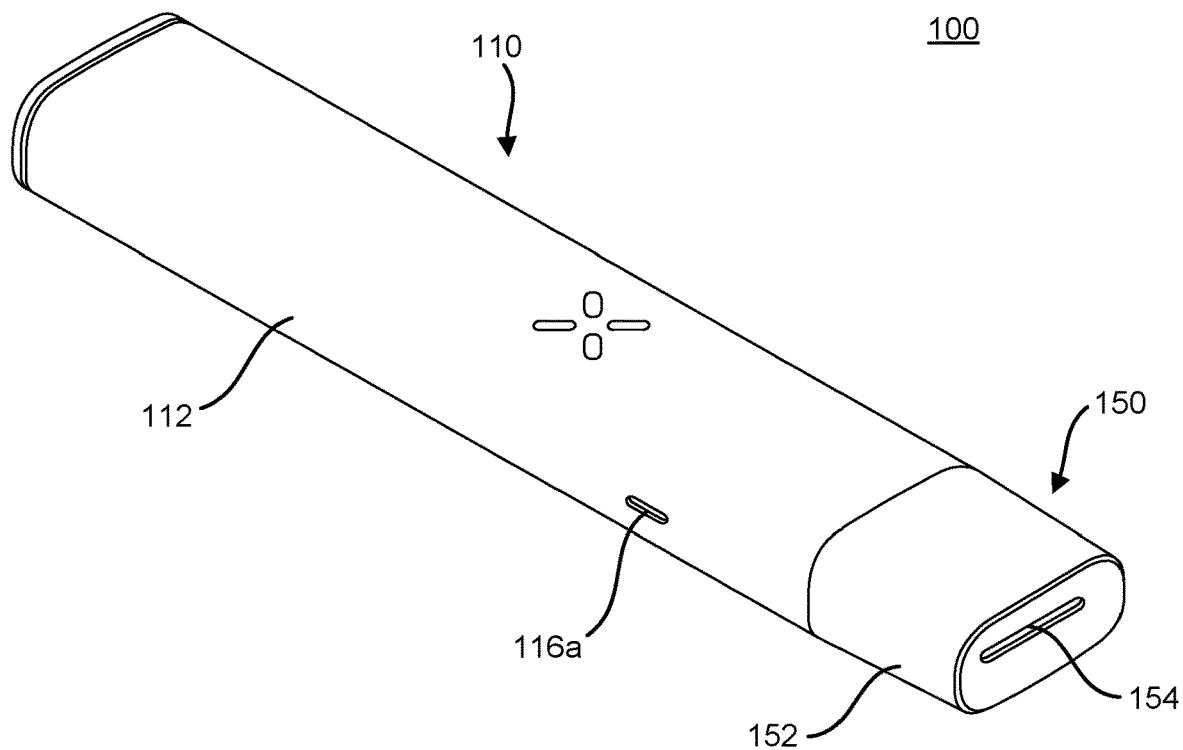

FIGS. 1A-1F illustrates features of a vaporizer device 100 including a vaporizer body 110 and a cartridge 150 consistent with implementations of the current subject matter. FIG. 1A is a bottom perspective view, and FIG. 1B is a top perspective view of the vaporizer device 100 with the cartridge 150 separated from a cartridge receptacle 114 on the vaporizer body 110. Both of the views in FIGS. 1A and 1B are shown looking towards a mouthpiece 152 of the cartridge 150. FIG. 1C is a bottom perspective view, and FIG. 1D is a top perspective view of the vaporizer device with the cartridge 150 separated from the cartridge receptacle 114 of the vaporizer body 110. FIGS. 1C and 1D are shown looking toward the distal end of the vaporizer body 110. FIG. 1E is a top perspective view, and FIG. 1F is a bottom perspective view of the vaporizer device 100 with the cartridge 150 engaged for use with the vaporizer body 110.

As shown in FIGS. 1A-1D, the cartridge 150 includes, at the proximal end, a mouthpiece 152 that is attached over a cartridge body 156 that forms a reservoir (or tank) 158 that holds a vaporizable material. The cartridge body 156 may be transparent, translucent, opaque, or a combination thereof. The mouthpiece 152 may include one or more openings 154 (see FIGS. 1A, 1B, 1F) at the proximal end out of which vapor may be inhaled, by drawing breath through the vaporizer device 100. The distal end of the cartridge body 156 may couple to and be secured to the vaporizer body 110 within the cartridge receptacle 114 of the vaporizer body 110. Power pin receptacles 160a,b (see FIGS. 1C, 1D) of the cartridge 150 mate with respective power pins (or contacts) 122a,b (see, for example, FIG. 4B) of the vaporizer body 110 that extend into the cartridge receptacle 114. The cartridge 150 also includes air flow inlets (or air flow openings) 162a,b on the distal end of the cartridge body 156.

A tag 164, such as a data tag, a near-field communication (NFC) tag, or other type of wireless transceiver or communication tag, may be positioned on at least a portion of the distal end of the cartridge body 156. As shown in FIGS. 1C and 1D, the tag 164 may substantially surround the power pin receptacles 160a,b and the air flow inlets 162a,b, although other configurations of the tag 164 may be implemented as well. For example, the tag 164 may be positioned between the power pin receptacle 160a and the power pin receptacle 160b, or the tag 164 may be shaped as a circle, partial circle, oval, partial oval, or any polygonal shape encircling or partially encircling the power pin receptacles 160a,b and the air flow inlets 162a,b or a portion thereof.

In the example of FIG. 1A, the vaporizer body 110 has an outer shell (or cover) 112 that may be made of various types of materials, including for example aluminum (e.g., AL6063), stainless steel, glass, ceramic, titanium, plastic (e.g., Acrylonitrile Butadiene Styrene (ABS), Nylon, Polycarbonate (PC), Polyethersulfone (PESU), and the like), and any hard, durable material. The proximal end of the vaporizer body 110 includes an opening forming the cartridge receptacle 114, and the distal end of the vaporizer body 110 includes a connection 118, such as, for example, a universal serial bus Type C (USB-C) connection and/or the like. The cartridge receptacle 114 portion of the vaporizer body 110 includes one or more air inlets (or openings) 116a,b that extend through the outer shell 112 to allow airflow therein, as described in more detail below. The vaporizer body 110 as shown has an elongated, flattened tubular shape that is curvature-continuous, although the vaporizer body 110 is not limited to such a shape. The vaporizer body 110 may take the form of other shapes, such as, for example, a rectangular box, a cylinder, and the like.

The cartridge 150 may fit within the cartridge receptacle 114 by a friction fit, snap fit, and/or other types of secure connection. The cartridge 150 may have a rim, ridge, protrusion, and/or the like for engaging a complimentary portion of the vaporizer body 110. While fitted within the cartridge receptacle 114, the cartridge 150 may be held securely within but still allow for being easily withdrawn to remove the cartridge 150.

Figure 2:
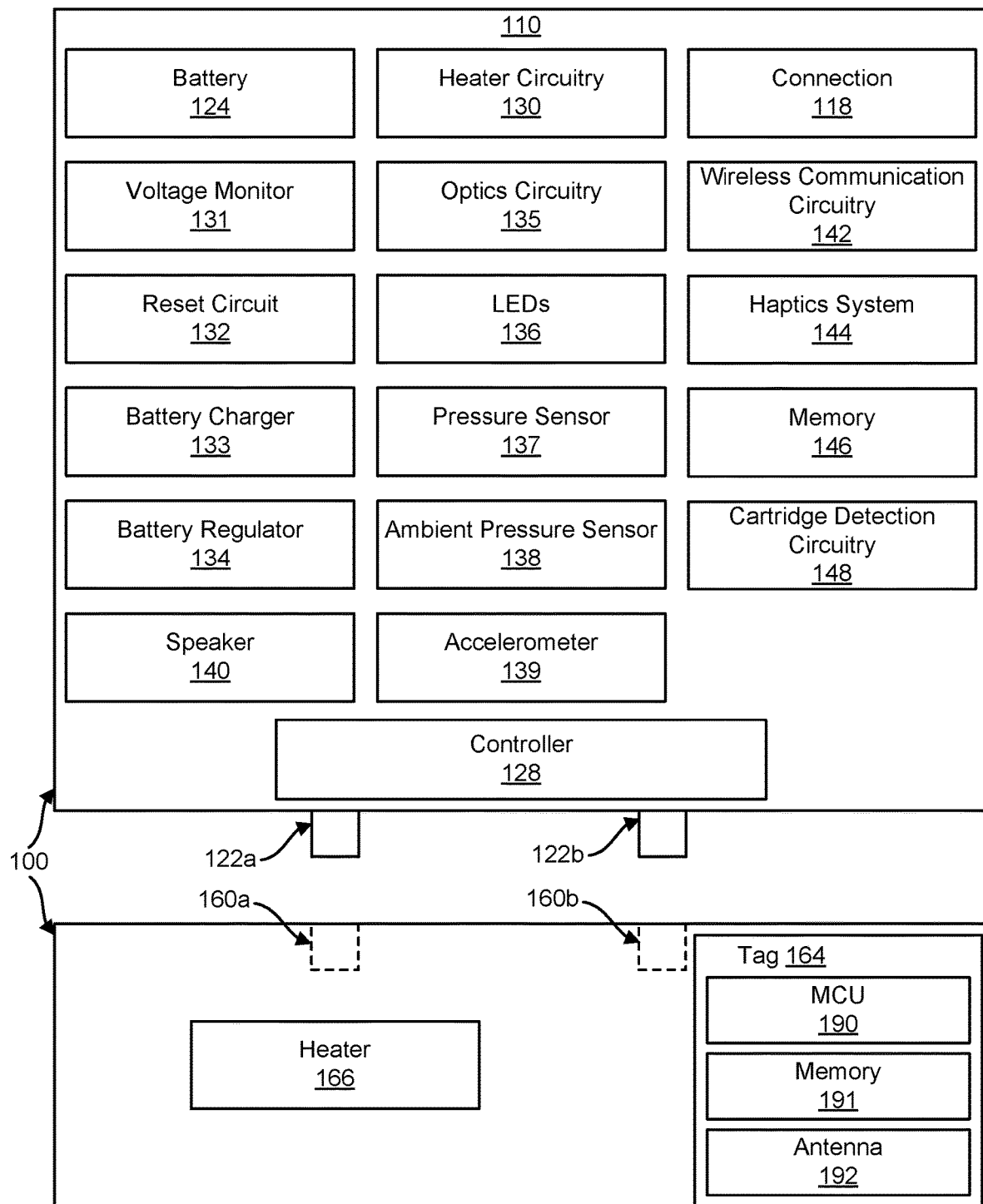
FIG. 2 is a schematic block diagram illustrating features of a vaporizer device having a cartridge and a vaporizer body consistent with implementations of the current subject matter.

FIG. 2 is a schematic block diagram illustrating components of a vaporizer device 100 having a cartridge 150 and a vaporizer body 110 consistent with implementations of the current subject matter. Included in the vaporizer body 110 is a controller 128 that includes at least one processor and/or at least one memory configured to control and manage various operations among the components of the vaporizer device 100 described herein.

Heater control circuitry 130 of the vaporizer body 110 controls a heater 166 of the cartridge 150. The heater 166 may generate heat to provide vaporization of the vaporizable material. For example, the heater 166 may include a heating coil (e.g., a resistive heater) in thermal contact with a wick, as described in further detail below.

A battery 124 is included in the vaporizer body 110, and the controller 128 may control and/or communicate with a voltage monitor 131 circuitry configured to monitor the battery voltage, a reset circuit 132 configured to reset (e.g., shut down the vaporizer device 100 and/or restart the vaporizer device 100 in a certain state), a battery charger 133, and a battery regulator 134 (which may regulate the battery output, regulate charging/discharging of the battery, and provide alerts to indicate when the battery charge is low, etc.).

The power pins 122a,b (see also FIG. 4B) of the vaporizer body 110 engage complementary power pin receptacles 160a,b of the cartridge 150 when the cartridge 150 is engaged with the vaporizer body 110. Alternatively, the power pins may be part of the cartridge 150 for engaging complementary power pin receptacles of the vaporizer body 110. The engagement allows for the transfer of energy from an internal power source (e.g., the battery 124) to the heater 166 in the cartridge 150. The controller 128 may regulate the power flow (e.g., an amount or current and/or a voltage amount) to control a temperature at which the heater 166 heats a vaporizable material contained in the reservoir 158. According to implementations of the current subject matter, a variety of electrical connectors other than a pogo-pin and complementary pin receptacle configuration may be used to electrically connect the vaporizer body 110 and the cartridge 150, such as for example, a plug and socket connector.

Figure 5A:
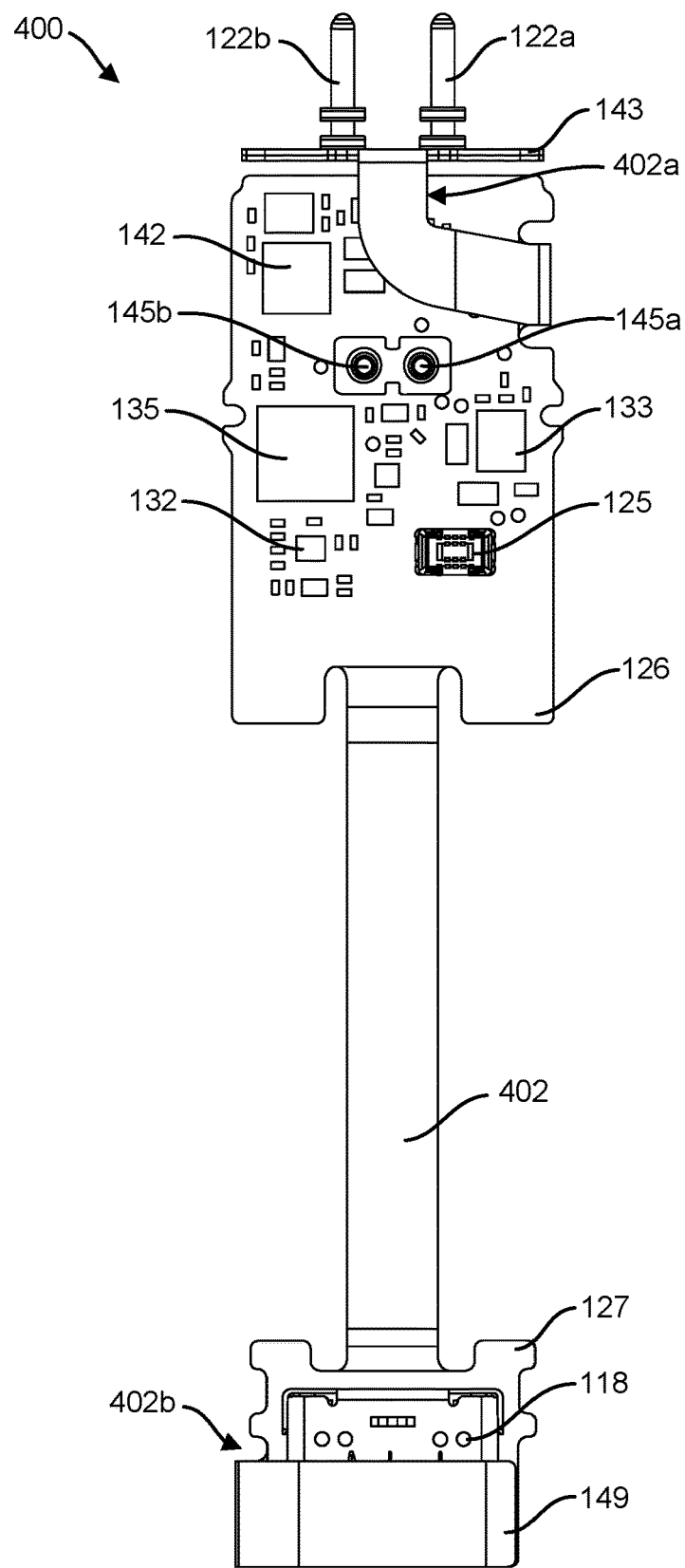
FIG. 5A-FIG. 5F illustrate features of an integrated board assembly and a printed circuit board assembly of a vaporizer device consistent with implementations of the current subject matter.
Figure 5B:
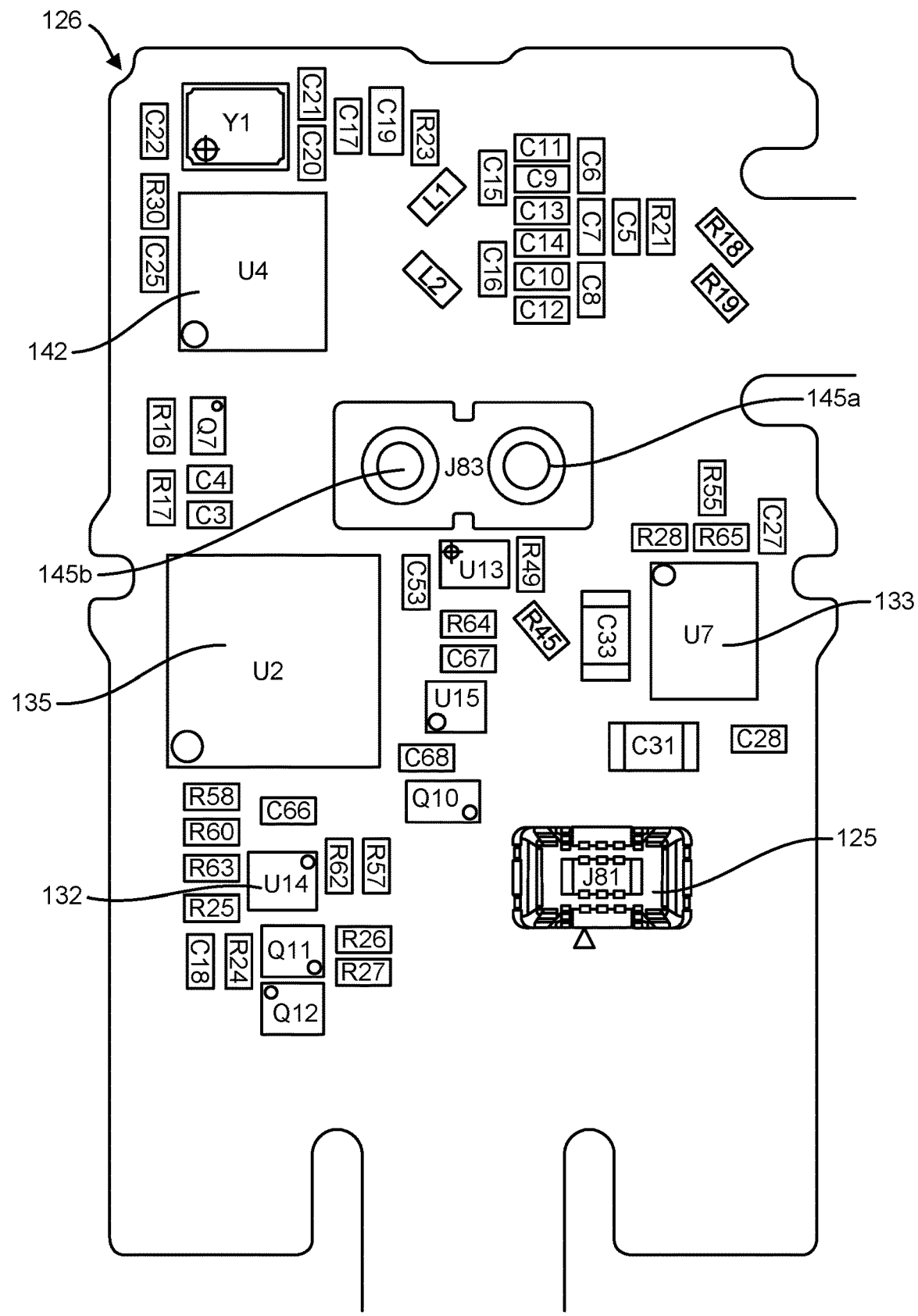

The controller 128 may control and/or communicate with optics circuitry 135 (which controls and/or communicates with one or more displays such as LEDs 136, an example of which are depicted at FIG. 5B), a pressure sensor 137, an ambient pressure sensor 138, an accelerometer 139, and/or a speaker 140 configured to generate sound or other feedback to a user.

The pressure sensor 137 may be configured to sense a user drawing (i.e., inhaling) on the mouthpiece 152 and activate the heater control circuitry 130 of the vaporizer body 110 to accordingly control the heater 166 of the cartridge 150. In this way, the amount of current supplied to the heater 166 may be varied according the user's draw (e.g., additional current may be supplied during a draw, but reduced when there is not a draw taking place). The ambient pressure sensor 138 may be included for atmospheric reference to reduce sensitivity to ambient pressure changes and may be utilized to reduce false positives potentially detected by the pressure sensor 137 when measuring draws from the mouthpiece 152.

The accelerometer 139 (and/or other motion sensors, capacitive sensors, flow sensors, strain gauge(s), or the like) may be used to detect user handling and interaction, for example, to detect movement of the vaporizer body 110 (such as, for example, tapping, rolling, and/or any other deliberate movement associated with the vaporizer body 110). The detected movements may be interpreted by the controller 128 as one or more predefined user commands. For example, one particular movement may be a user command to gradually increase the temperature of the heater 166 as the user intends to begin using the vaporizer device 100.

The vaporizer body 110, as shown in FIG. 2, includes wireless communication circuitry 142 that is connected to and/or controlled by the controller 128. The wireless communication circuitry 142 may include a near-field communication (NFC) antenna that is configured to read from and/or write to the tag 164 of the cartridge 150 and also automatically detect a cartridge 150. The wireless communication circuitry 142 may include additional components/circuitry for other communication modes, such as, for example, Bluetooth, Bluetooth Low Energy, and/or Wi-Fi chips and associated circuitry (e.g., control circuitry), for communication with other devices. For example, the vaporizer body 110 may be configured to wirelessly communicate with a remote processor (e.g., smartphone, tablet, wearable electronics, cloud server, and/or the like) through the wireless communication circuitry 142, and through this communication may receive control information and/or configuration parameters (e.g., information or parameters for setting temperature (i.e., a predetermined temperature), setting a dose (i.e., a predetermined dose), resetting a dose counter, etc.) from and/or transmit output information (e.g., dose information, operational information, error information, temperature setting information, charge/battery information, etc.) to one or more of the remote processors.

The tag 164, as previously described, may be a type of wireless transceiver and may include a microcontroller unit (MCU) 190, a memory 191, and an antenna 192 (e.g., an NFC antenna) to perform the various functionalities described below with further reference to FIG. 3. The tag 164 may be, for example, a 1 Kbit or a 2 Kbit NFC tag that is of type ISO/IEC 15693. NFC tags with other specifications may also be used.

Figure 3:
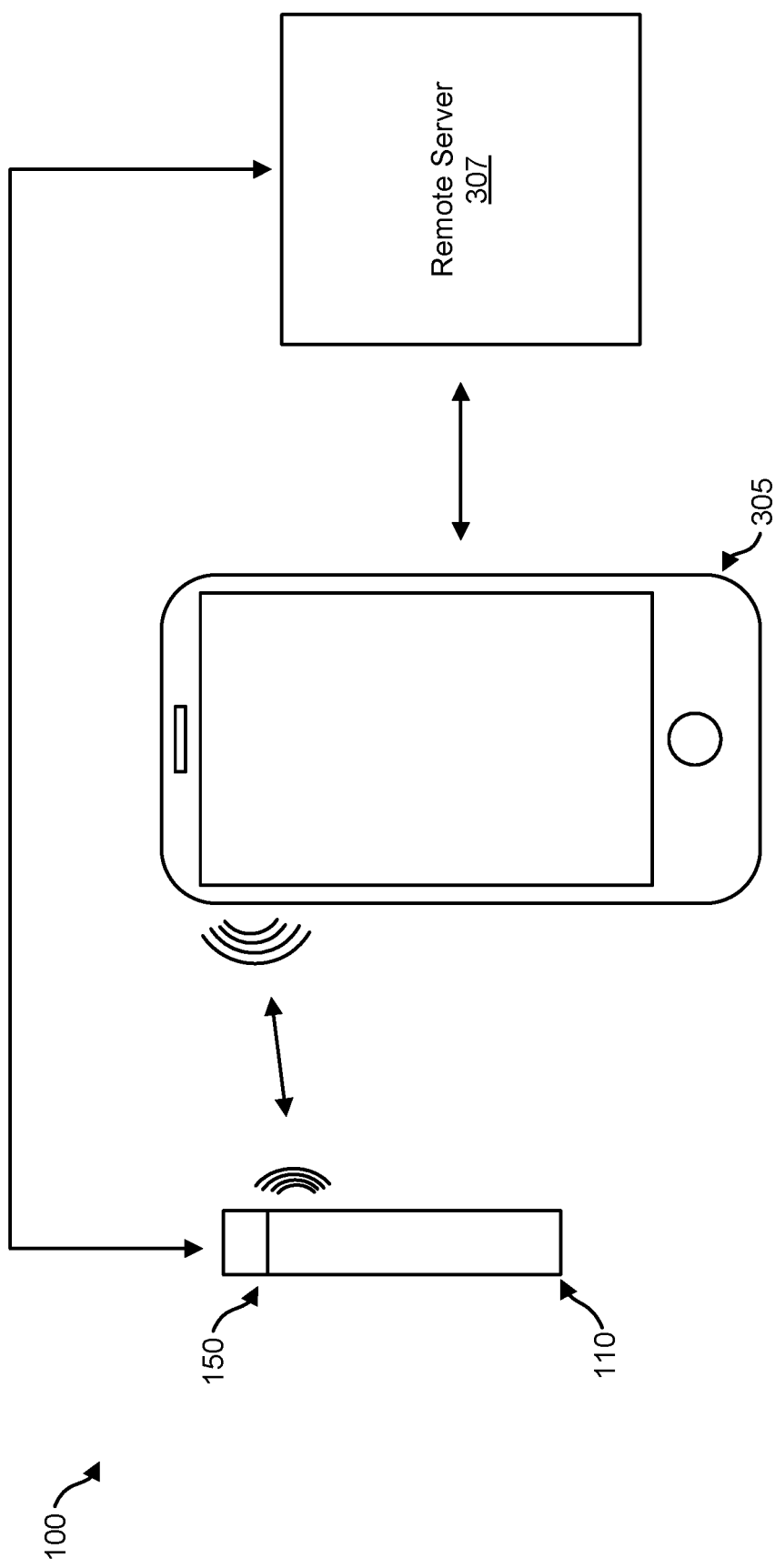
FIG. 3 illustrates communication between a vaporizer device, a user device, and a server consistent with implementations of the current subject matter.

FIG. 3 illustrates communication between a vaporizer device 100 (including the vaporizer body 110 and the cartridge 150), a user device 305 (e.g., a smartphone, tablet, laptop, and/or the like), and a remote server 307 (e.g., a server coupled to a network, a cloud server, and/or the like) consistent with implementations of the current subject matter. The user device 305 wirelessly communicates with the vaporizer device 100. A remote server 307 may communicate directly with the vaporizer device 100 or through the user device 305. The vaporizer body 110 may communicate with the user device 305 and/or the remote server 307 through the wireless communication circuitry 142. In some implementations, the cartridge 150 may establish communication with the user device 305 and/or the remote server 307 through the tag 164.

An application software ("app") running on at least one of the remote processors (the user device 305 and/or the remote server 307) may be configured to control operational aspects of the vaporizer device 100 and receive information relating to operation of the vaporizer device 100. For example, the app may provide a user with capabilities to input or set desired properties or effects, such as, for example, a particular temperature or desired dose, which is then communicated to the controller 128 of the vaporizer body 110 through the wireless communication circuitry 142. The app may also provide a user with functionality to select one or more sets of suggested properties or effects that may be based on the particular type of vaporizable material in the cartridge 150. For example, the app may allow adjusting heating based on the type of vaporizable material, the user's (of the vaporizer device 100) preferences or desired experience, and/or the like.

The app may allow a user to perform a hard-reset of the vaporizer device 100. For example, a user may indicate through the app that the vaporizer device should be reset, which may cause the vaporizer device 100 to shut down, which may be performed by the reset circuit 132. Following shut-down, the vaporizer device 100 may enter a standby mode or may resume operation, depending upon a variety of factors, such as for example the reason (if known) for the reset.

The input and/or user selections may act as control signals for the controller 128 to perform a corresponding function (e.g., reach and hold a defined temperature, provide a certain dose, reduce heat after a certain time period, reset, etc.). Likewise, the controller 128 may transmit information, through the wireless communication circuitry 142, to one of the remote processors for display via the app. For example, a summary of use of the vaporizer device 100 throughout a day may be tracked and sent to the user device 305.

Data read from the tag 164 from the wireless communication circuitry 142 of the vaporizer body 110 may be transferred to one or more of the remote processors (e.g., the user device 305 and/or the remote server 307) to which it is connected, which allows for the app running on the one or more processors to access and utilize the read data for a variety of purposes. For example, the read data relating to the cartridge 150 may be used for providing recommended temperatures, dose control, usage tracking, and/or assembly information.

Additionally, the cartridge 150 may communicate directly, through the tag 164, with one or more remote processors (e.g., the user device 305), such as, for example, a smartphone, tablet, assembly equipment, and/or filling equipment. This enables data relating to the cartridge to be written to/read from the tag 164, without interfacing with the vaporizer body 110. The tag 164 thus allows for identifying information related to the cartridge 150 to be associated with the cartridge 150 by one or more remote processors. For example, when the cartridge 150 is filled with a certain type of vaporizable material, this information may be transmitted to the tag 164 by filling equipment. Then, the vaporizer body 110 is able to obtain this information from the tag 164 to identify the vaporizable material currently being used and accordingly adjust the controller 128 based on, for example, user-defined criteria or pre-set configuration parameters associated with the particular type of vaporizable material (set by a manufacturer or as determined based upon user experiences/feedback aggregated from other users). For example, a user may establish (via the app) a set of criteria relating to desired effects for or usage of one or more types of vaporizable materials. When a certain vaporizable material is identified, based on communication via the tag 164, the controller 128 accordingly adopts the established set of criteria, which may include, for example, temperature and dose, for that particular vaporizable material.

Other information related to the cartridge 150 may be transmitted to and stored on the tag 164, such as information relating to components of the cartridge 150, for example heating components. The controller 128 of the vaporizer body 110 may use this information to control a usage session for a user. A manufacturer may thus transmit manufacturing information to the tag 164 for storage for subsequent use by the controller 128 or other remote processors (e.g., the user device 305 and/or the remote server 307).

Types of data that may be stored on the tag 164 include manufacturing data (e.g., tag serial number, tag manufacturer identifier, tag IC product code, cartridge serial number, cartridge hardware revision code, date of assembly, manufacture (MFG) lot code, MFG test equipment serial number (S/N), MFG test data (e.g., coil resistance, leak/flow rate test, cosmetic check, etc.), MFG test parameters, material logging (e.g., coil type, wick type, etc.), and/or mass of empty cartridge); filler data (which may be added after the cartridge is filled with a vaporizable material, for example, batch identifier (ID), vendor ID, product ID, strain code, mass of filled cartridge, viscosity, default/min/max temperature setting, tetrahydrocannabinol (THC) content percentage (%), cannabidiol (CBD) %, terpene %, extraction method, and/or fill date); and/or usage data (e.g., total puffs taken, total puff time, drop count, total energy delivered to cartridge (joules), date of first/most recent puff, cartridge lock (for locking cartridge to specific device/child lock), cartridge kill (initiating lock out of cartridge), min/max temperature set by user/device, min/max "baseline" resistance measured, count of bad connections (where cartridge did not properly dock and measure baseline resistance), and/or various device error codes). As previously described, the data stored on the tag 164 may also include pre-set or user-established configuration parameters relating to operation of the vaporizer body 110 with respect to the particular cartridge 150 and/or the particular type of vaporizable material (e.g., a predetermined temperature and/or parameters associated with a dose). The tag data may be encrypted and/or hashed, and the tag 164 may be password protected.

Returning to FIG. 2, the vaporizer body may include a haptics system 144, such as, for example, an actuator, a linear resonant actuator (LRA), an eccentric rotating mass (ERM) motor, or the like that provide haptic feedback such as, for example, a vibration as a "find my device" feature or as a control or other type of user feedback signal. For example, using an app running on a user device (such as, for example, the user device 305), a user may indicate that he/she cannot locate his/her vaporizer device 100. Through communication via the wireless communication circuitry 142, the controller 128 sends a signal to the haptics system 144, instructing the haptics system 144 to provide haptic feedback (e.g., a vibration). The controller 128 could additionally or alternatively provide a signal to the speaker 140 to emit a sound or series of sounds. The haptics system 144 and/or speaker 140 may also provide control and usage feedback to the user of the vaporizer device 100; for example, providing haptic and/or audio feedback when a particular amount of a vaporizable material has been used or when a period of time since last use has elapsed. Alternatively or additionally, haptic and/or audio feedback may be provided as a user cycles through various settings of the vaporizer device 100. Alternatively or additionally, the haptics system 144 and/or speaker 140 may signal when a certain amount of battery power is left (e.g., a low battery warning and recharge needed warning) and/or when a certain amount of vaporizable material remains (e.g., a low vaporizable material warning and/or time to replace the cartridge).

The vaporizer body 110 also includes the connection (e.g., USB-C connection, micro-USB connection, and/or other types of connectors) 118 for coupling the vaporizer body to a charger to enable charging the battery 124. Alternatively or additionally, electrical inductive charging (also referred to as wireless charging) may be used, in which case the vaporizer body 110 would include inductive charging circuitry to enable charging. The connection 118 at FIG. 2 may also be used for a data connection between a computing device and the controller 128, which may facilitate development activities such as, for example, programming and debugging, for example.

The vaporizer body 110 may also include a memory 146 that is part of the controller 128 or is in communication with the controller 128. The memory 146 may include volatile and/or non-volatile memory or provide data storage. In some implementations, the memory 146 may include 8 Mbit of flash memory, although the memory is not limited to this and other types of memory may be implemented as well.

Figure 4A:
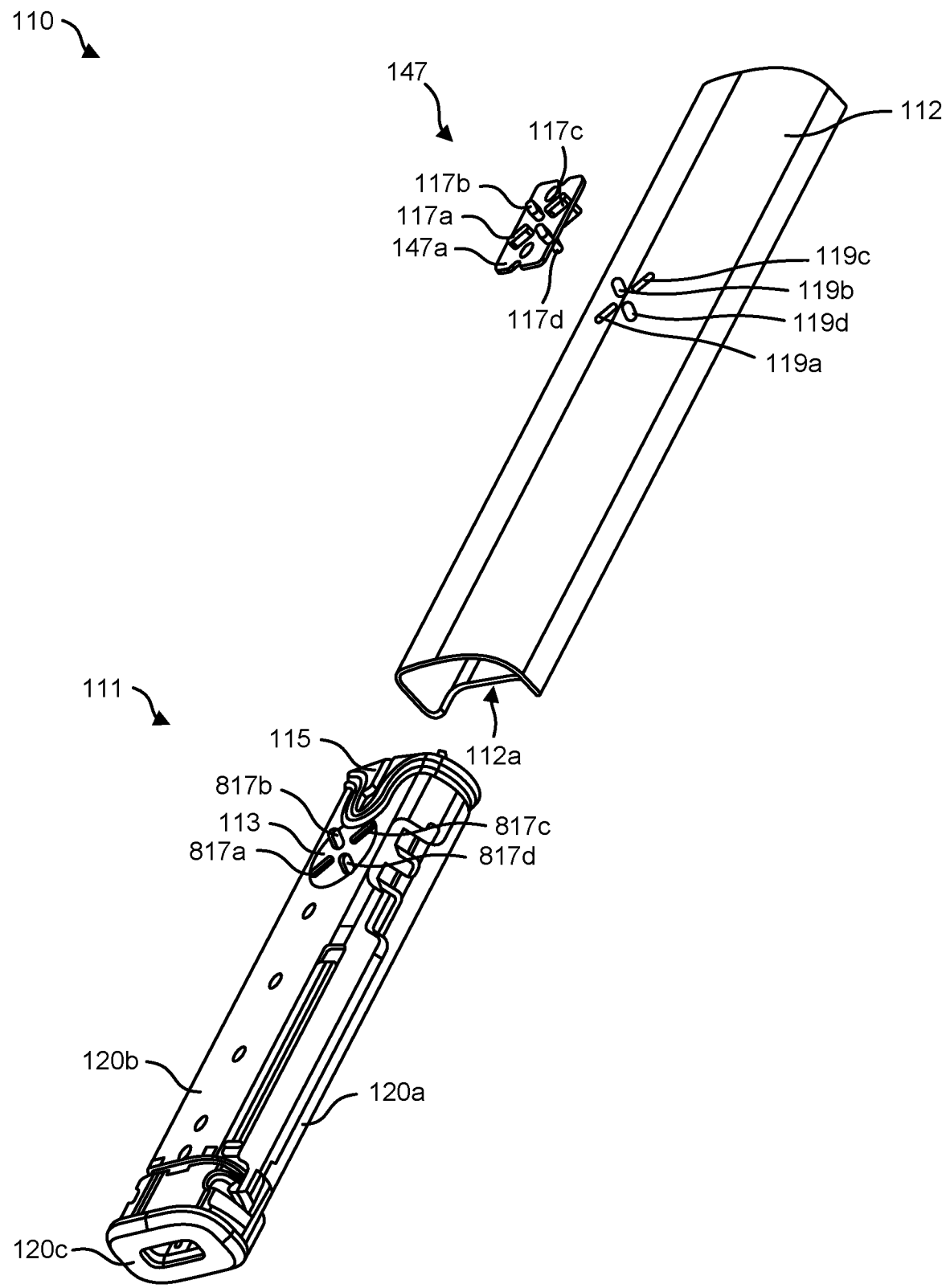
FIG. 4A is an exploded view illustrating features of a vaporizer body prior to assembly consistent with implementations of the current subject matter.
Figure 4B:
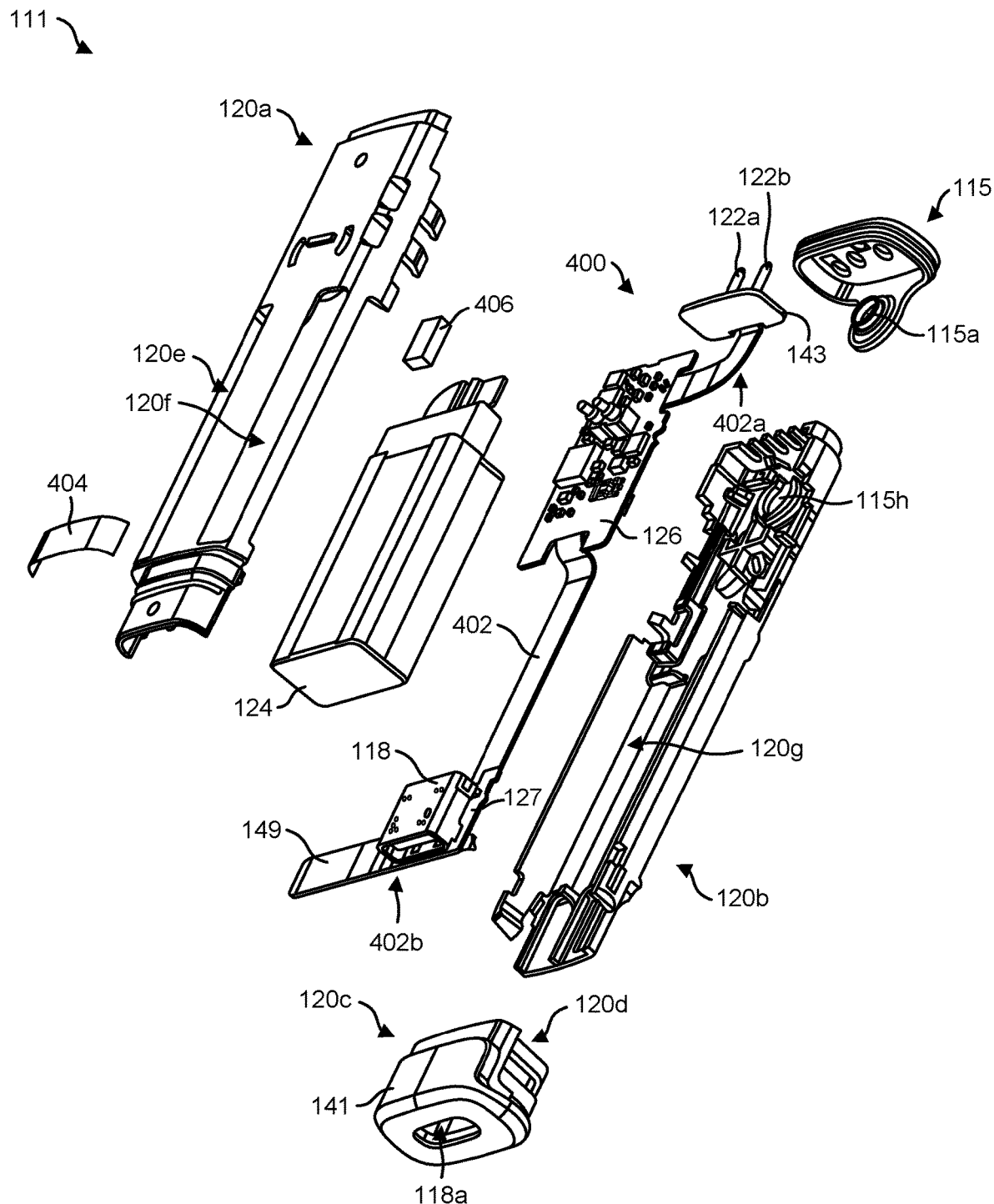
FIG. 4B is an exploded view illustrating features of an inner assembly of a vaporizer body prior to assembly consistent with implementations of the current subject matter.
Figure 4C:
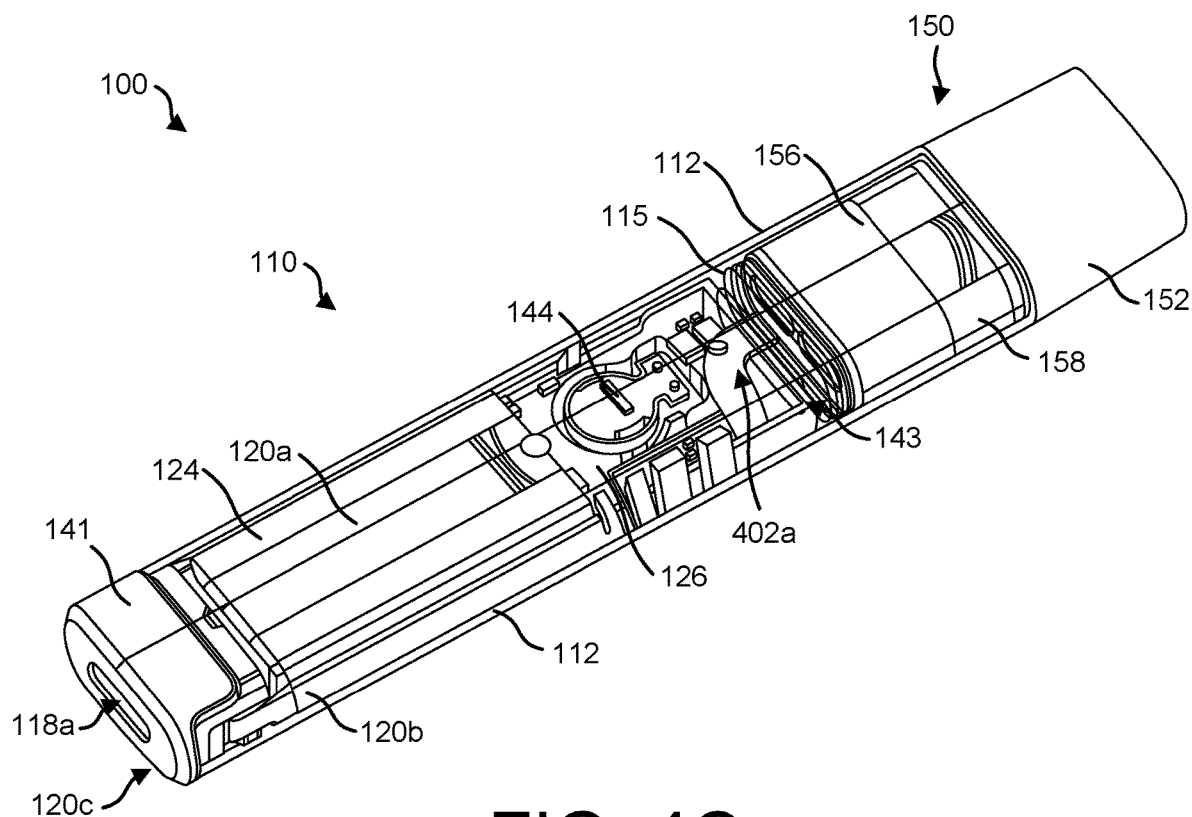
FIG. 4C-FIG. 4E illustrate internal features of an assembled vaporizer body consistent with implementations of the current subject matter.
Figure 4D:
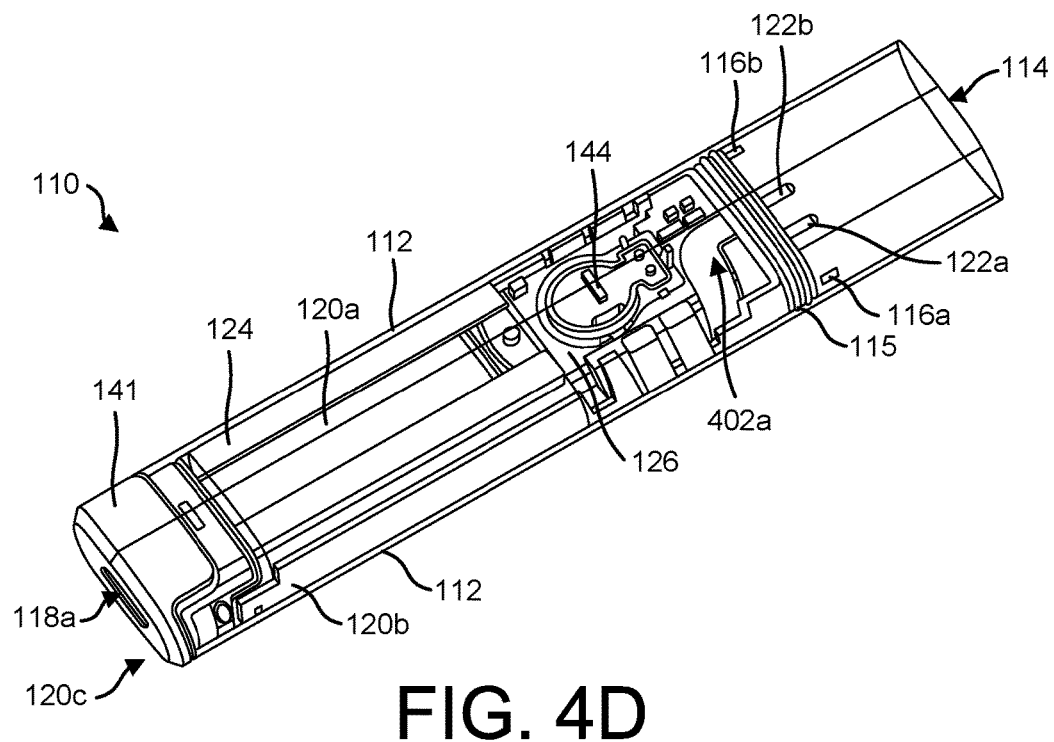
Figure 4E:
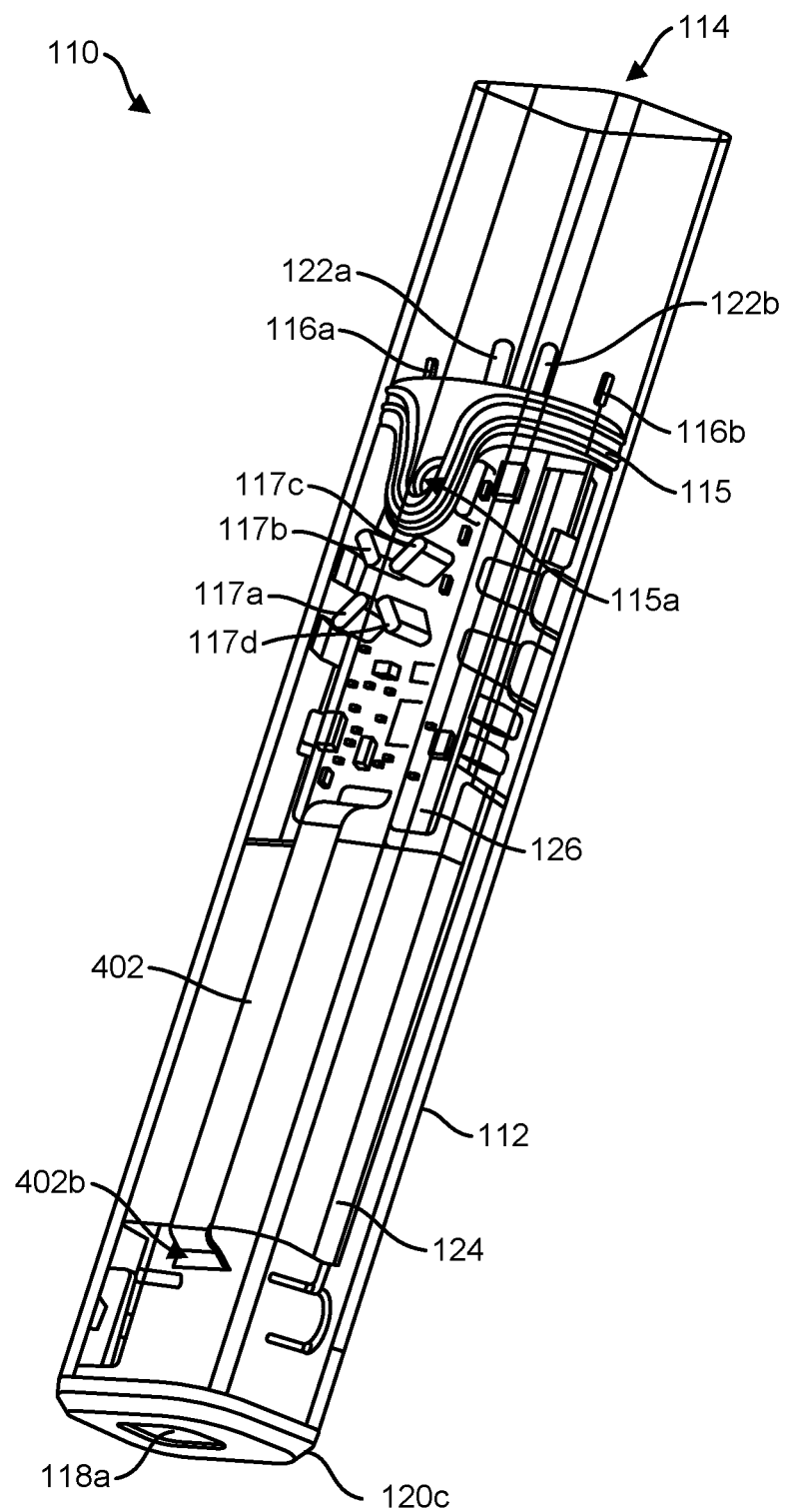

FIG. 4A is an exploded, bottom perspective view looking toward the distal end of the vaporizer body 110 prior to assembly consistent with implementations of the current subject matter. FIG. 4B is an exploded, top perspective view illustrating features of an inner assembly 111 of the vaporizer body 110 (looking toward the distal end of the vaporizer body 110) prior to assembly consistent with implementations of the current subject matter. FIGS. 4C-4E illustrate internal features of the vaporizer body 110 in an assembled form consistent with implementations of the current subject matter;

With reference to FIG. 4A, an exploded view of the vaporizer body 110, prior to assembly, is provided. As described above with reference to FIGS. 1A-1F, the vaporizer body 110 has an outer shell (or cover) 112 that may have (as shown) an elongated, flattened tubular shape that is curvature-continuous, although the vaporizer body 110 is not limited to such a shape as described above. The outer shell 112 includes an inner region 112a defined by the sidewall of the outer shell 112. The inner assembly 111 of the vaporizer body 110 is provided and is sized and shaped to fit within the inner region 112a of the outer shell 112. For example, the inner assembly 111 may slide or otherwise securely (e.g., snugly) fit into or within the inner region 112a of the outer shell 112.

A light pipe 147 may be provided to mount in a surface of the outer shell 112 and aid in securing the inner assembly 111 to the outer shell 112. The light pipe 147 may include one or more individual light pipe components 117 (attached to a carriage unit 147a described in greater detail elsewhere in the specification) sized and shaped to fit within corresponding openings 119 formed through the surface of the outer shell 112 and to be secured within a mating structure 113 with corresponding recesses 817 formed on a surface of the inner assembly 111. Thus when the inner assembly 111 is inserted (e.g., slid) within the outer shell 112 such that the openings 119 align with the recesses 817, the light pipe 147 may be mounted to secure the inner assembly 111 and the outer shell 112 to one another, as further described below with reference to FIGS. 8A-8F. Although four individual light pipe components 117a,b,c,d, corresponding to openings 119a,b,c,d, and corresponding recesses 817a,b,c,d are shown, the vaporizer body 110 is not limited to this number or this configuration and any other configuration of light pipe components 117, openings 119, and recesses 817 may be provided. For example, the light pipe components 117 may vary in number, size, and shape to form various types of patterns and arrangements.

As shown in FIG. 4A, the inner assembly 111 includes outer structural supports 120a, 120b, and 120c and gasket 115. With reference to FIG. 4B, an exploded view of the inner assembly 111, prior to assembly, is provided. A top support structure 120a, a bottom support structure 120, a bottom cap 120c, and the gasket 115 are provided to form a support structure of the inner assembly 111 and form a storage region in which various components for operation of the vaporizer body 110 with the cartridge 150 are positioned. The connection of the various components within the support structure and the connection of the top support structure 120a, the bottom support structure 120, the bottom cap 120c, and the gasket 115 are described with reference to FIGS. 11A-11V in accordance with one implementation of the current subject matter.

The top support structure 120a and the bottom support structure 120b are two opposing halves of the support structure of the inner assembly 111. Both the top and bottom support structures 120a, 120b have an elongate shape that when joined together mirrors or substantially mirrors the elongated, flattened tubular shape of the outer shell 112 to provide a secure fit within the inner region 112a. The top and bottom support structures 120a, 120b may have other shapes, such as a rectangular or other profile, that fits within the inner region 112a. Various openings, such as lengthwise-extending openings 120e, 120f, 120g, may be formed along various portions of the top and bottom support structures 120a, 120b. These openings may help prevent internal components from over-heating (e.g., the openings provide air flow in and around internal components), and may be of various shapes and dimensions, such as for example narrow slits and/or wider and shorter openings (e.g., rectangular or circular openings). In some embodiments, one or both of the top and bottom support structures 120a, 120b do not have openings and are solid, lengthwise-extending support pieces. In other implementations, additional openings in the top and bottom support structures 120a, 120b may be provided.

The bottom cap 120c includes an inner cap region 120d defined by a cap sidewall extending from a cap plate. An opening 118a is formed through the cap plate of the bottom cap 120c. A distal end of the top and bottom support structures 120a, 120b when connected are configured to fit within the inner cap region 120d. One or more portions of the cap sidewall may be an antenna window 141 configured to align with a second antenna 149 when the inner assembly 111 is in an assembled configuration.

The gasket 115 has a sealing ring 115a and is configured to be installed at a proximal end of the top and bottom support structures 120a, 120b when connected, where the sealing ring 115a interfaces with the opening 115h extending through the bottom support structure 120b. The gasket 115 is further described below with reference to FIGS. 11S and 11T.

As shown in FIG. 4B, an integrated board assembly 400, configured to fit within the storage region defined by the outer structural supports 120a, 120b, 120c, and 115, is a rigid-flexible assembly with a first antenna 143 (such as an integrated near-field communication (NFC) antenna) and the second antenna 149 (such as an integrated Bluetooth antenna). This design combines a printed circuit board assembly (PCBA) 126, the power pins 122a,b, the connection 118 (such as a USB-C connection) on a connector PCBA 127, and the first and the second antennae 143 and 149 into a single part that provides for more usable board space as well as a simple assembly. This design may advantageously eliminate the need for a coaxial cable or other connector, commonly used to join a flexible circuit containing a USB connector, such as for example a micro-USB, to a main circuit board to transmit charging power from the USB port to charging circuitry on the main circuit board. This design also advantageously eliminates additional connectors for the first and the second antennae 143 and 149 to the PCBA 126.

As further shown in FIG. 4B, a flexible layer 402, which is an inner layer of the PCBAs 126, 127, extends between and from the PCBAs 126, 127. The first antenna 143 is integrated at a proximal end 402a of the flexible layer 402, and the second antenna 149 is integrated at a distal end 402b of the flexible layer 402. As shown in FIG. 4B, and according to one implementation, the proximal end 402a of the flexible layer 402 may extend from a side region of the PCBA 126, and may include a sideward extending portion and a forward extending portion at about 90 degrees with respect to the sideward extending portion. The distal end 402*b* of the flexible layer 402 may extend from a side portion of the connector PCBA 127. Other configurations are possible for either or both the proximal end 402*a* and the distal end 402*b* of the flexible layer 402. For example, the proximal end 402*a* may extend from a proximal (e.g., front) end of the PCBA 126, as described below with respect to FIGS. 32A-32H.

The PCBA 126 is adjacent the proximal end 402*a*, and the connector PCBA 127 is adjacent the distal end 402*b*. The PCBAs 126, 127 are comprised of multiple layers that together form a rigid assembly with top and bottom layers on which various components (described in detail herein) may be mounted.

The power pins 122*a,b* are coupled (e.g., soldered) to the proximal end 402*a* of the flexible layer 402 at the first antenna 143 (e.g., a near-field communication antenna) to engage complementary power pin receptacles 160*a,b* of a cartridge 150 when the cartridge 150 is engaged with the vaporizer body 110 (as described above with reference to FIGS. 1A-1F and 2). The engagement allows for the transfer of energy from an internal power source (e.g., the battery 124) to the heater 166 in the cartridge 150.

A connector component (e.g., the connection 118, such as, for example, a universal serial bus Type C (USB-C) connection and/or the like) is coupled to the connector PCBA 127 and configured to connect the vaporizer device body with one or more external devices (e.g., a charger, a computing device, a light source, a fan, etc. that may provide power). The connection 118 aligns with the opening 118*a* formed through the cap plate of the bottom cap 120*c* when the inner assembly 111 is assembled.

Also shown in FIG. 4B is the battery 124, which is configured to fit along a portion of the flexible layer 402 of the integrated board assembly 400, proximate to the connection 118, and coupled to the PCBA 126 via a board-to-board connection, as described in greater detail with reference to FIGS. 10A and 10B.

Additional components of the inner assembly 111 shown in FIG. 4B include an antenna adhesive 404 configured to assist in securing the second antenna 149 within the inner assembly 111; and a foam piece 406 configured to assist in securing in place the battery 124 via battery connector point 124*a* to a battery connector 125 on the PCBA 126 (as described in greater detail with reference to FIGS. 10A-10B and 11E-11G), each of which are described with reference to the assembly diagrams in FIGS. 11A-11V.

The configuration of the inner assembly 111 and the integrated board assembly 400 shown in FIG. 4B is one example configuration. Other configurations, including alternate layouts of some of the components, are possible, such as that shown and described with respect to FIGS. 32A-32H.

FIGS. 4C, 4D, and 4E provide partial internal views of the vaporizer body 110 (internal to the outer shell 112) in an assembled configuration consistent with implementations of the current subject matter. Some portions of the outer structural supports 120*a*, 120*b*, and 120*c* are removed or shaded to better illustrate placement of the various internal components. FIGS. 4C and 4D are top perspective views of the vaporizer body 110, and FIG. 4E is a bottom perspective view of the vaporizer body 110. A cartridge 150 is shown inserted into the cartridge receptacle 114 in FIG. 4C, while FIGS. 4D and 4E illustrate the vaporizer body 110 without a cartridge inserted. FIGS. 4C, 4D, and 4E illustrate placement of the battery 124 with respect to the PCBA 126, the connection 118, and the connector PCBA 127. Also shown are portions of the PCBA 126 (described in detail with reference to FIGS. 5A-5D), connection of the haptics system 144 (e.g., a LRA), and placement of the individual light pipe components 117*a,b,c,d* of the light pipe 147.

Figure 5C:
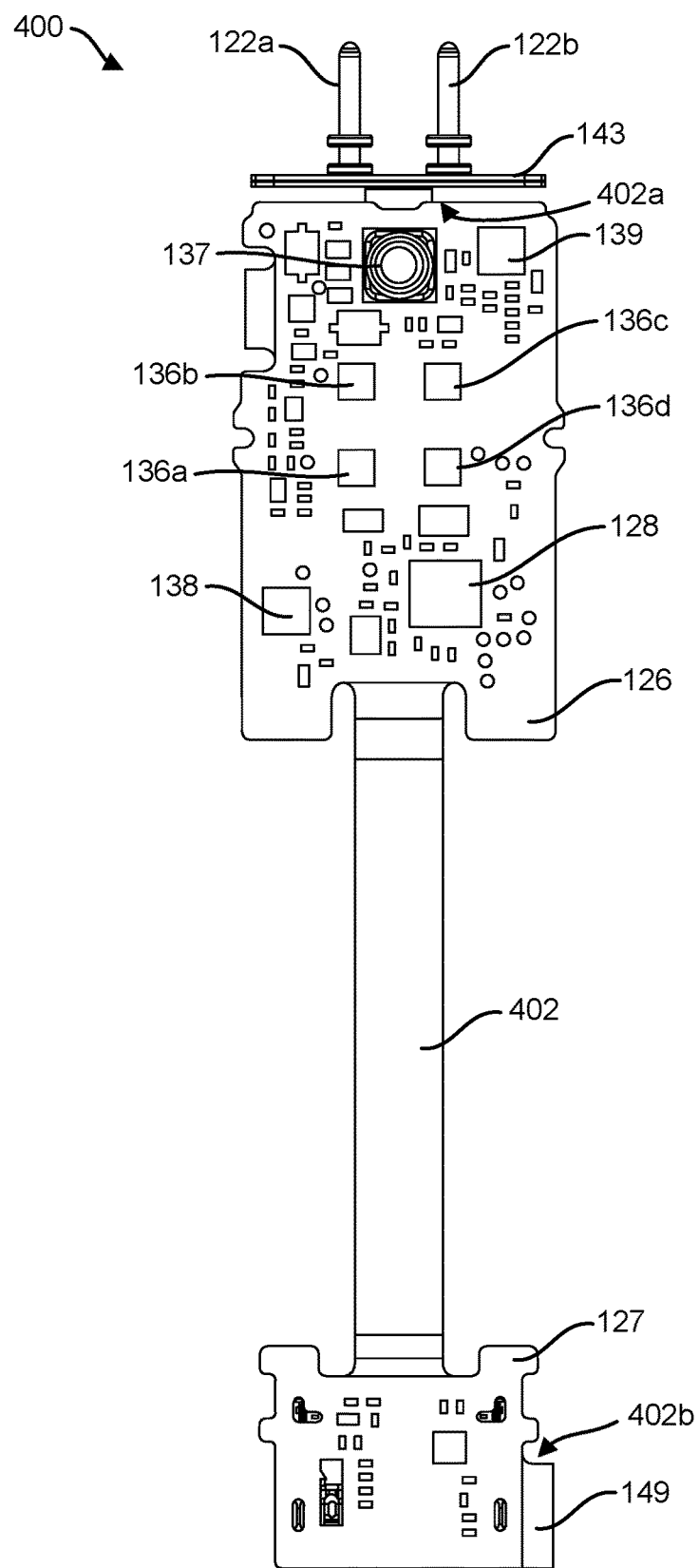
Figure 5D:
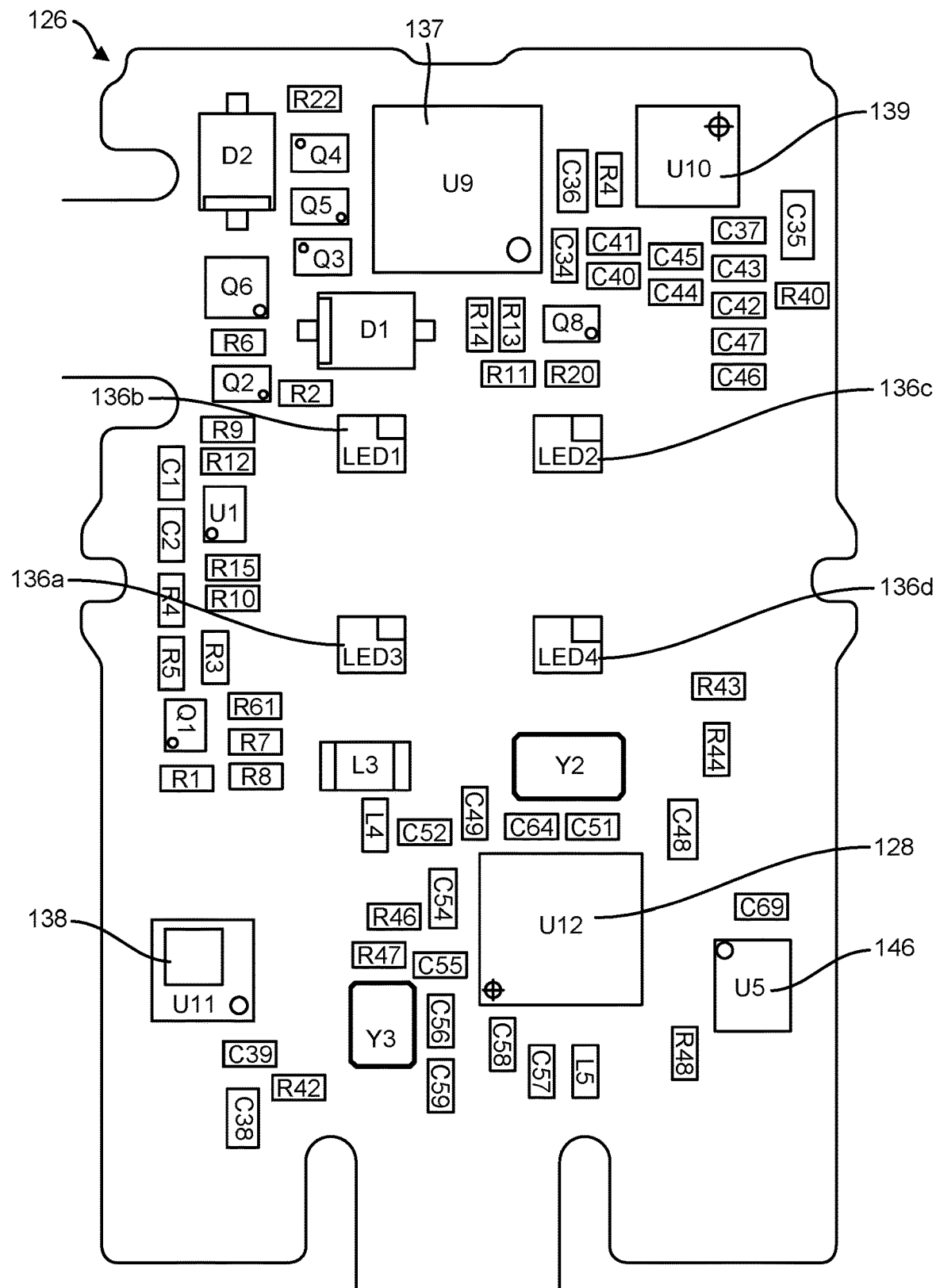
Figure 5E:
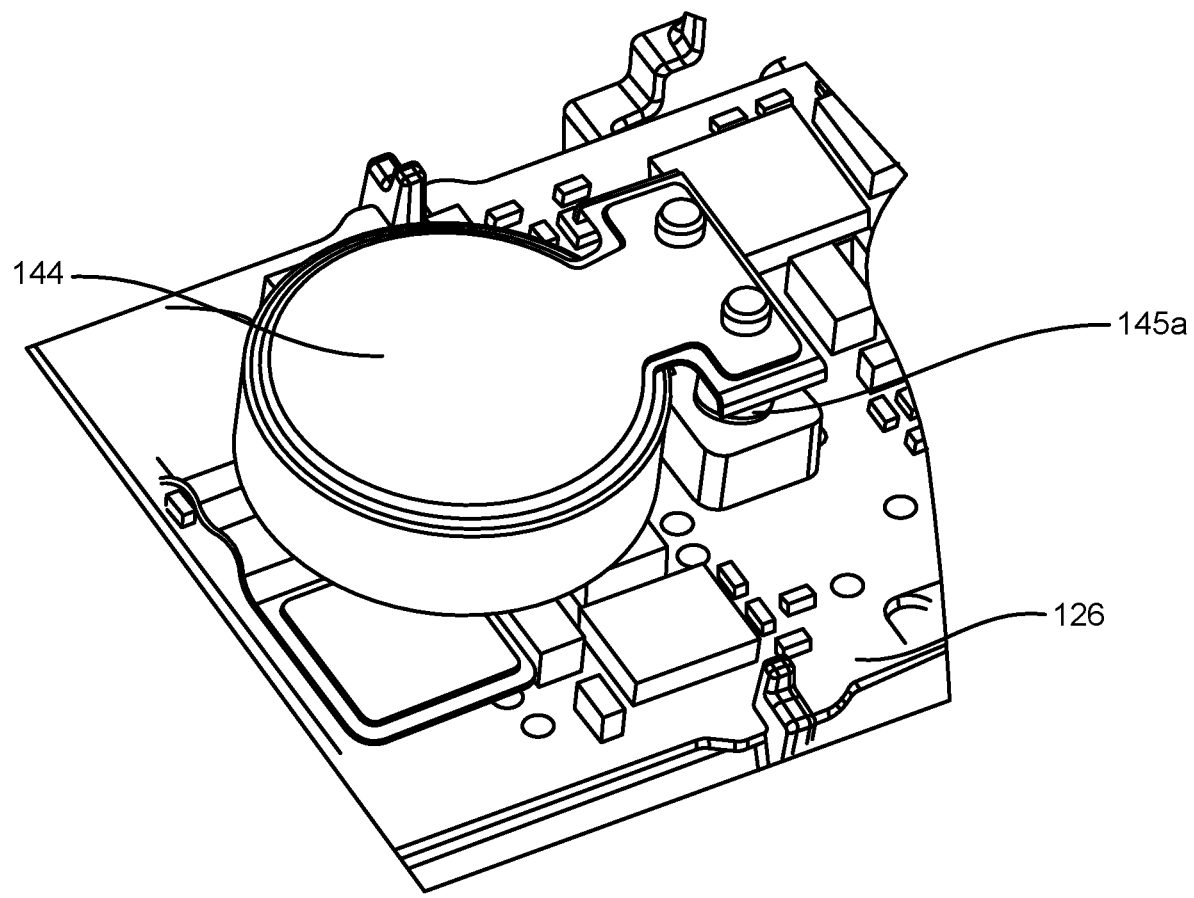

FIGS. 5A and 5C illustrate details, via a top view and a bottom view respectively, of the integrated board assembly 400, according to some aspects of the current subject matter. FIGS. 5B and 5D illustrate details, via a top view and a bottom view respectively, of the PCBA 126 consistent with some implementations of the current subject matter. FIG. 5E illustrates a close-up view of a top portion of the PCBA 126.

Figure 5F:
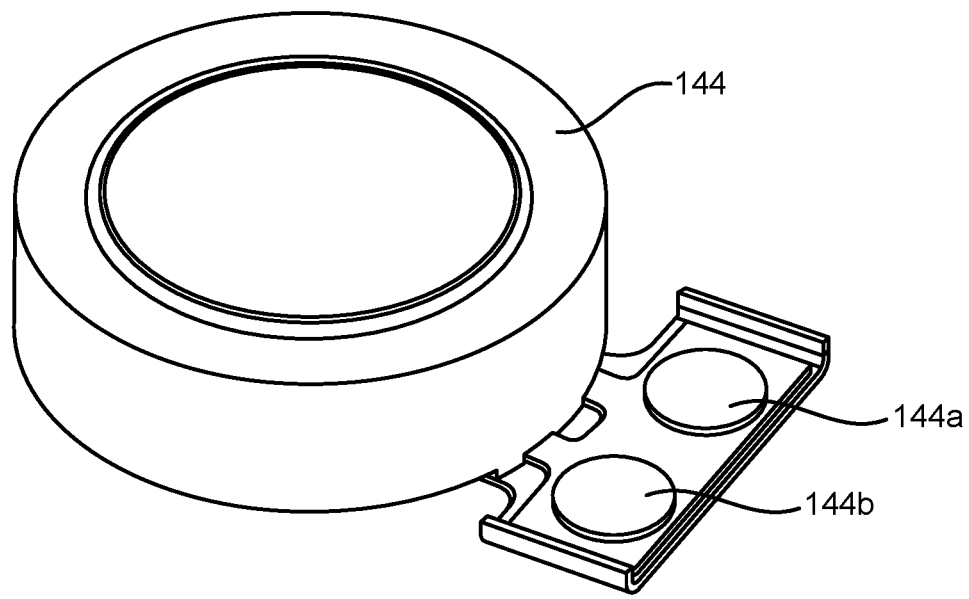

As shown in FIGS. 5A and 5B, spring contacts 145*a,b* (such as, for example, pogo pins, although other types of pins, contacts, etc. may be used as well) on the PCBA 126 are provided for connection with the haptics system 144. FIG. 5F provides a close-up view of the haptics system 144 with connection pads 144*a,b* that are configured to contact the spring contacts 145*a,b*, as shown in the top perspective view of a portion of the PCBA 126 in FIG. 5E.

As shown in FIGS. 5A and 5B, optics circuitry 135 may be provided and is configured for controlling and/or communicating with one or more LEDs 136*a,b,c,d* (shown in the bottom views of FIGS. 5C and 5D). The battery connector 125 is provided for connection with a battery 124. Reset circuit 132, battery charger 133, and wireless communication circuitry 142 are provided on the top portion of the PCBA 126.

The second antenna 149 (e.g., a Bluetooth antenna) is positioned near the distal end of the integrated board assembly 400. The connection 118 and the connector PCBA 127 are also at the distal end of the flexible layer 402 (at 402*b*).

The first antenna 143 is at the proximal end of the flexible layer 402 (at 402*a*), which is proximate the position of the tag 164, when the cartridge 150 is engaged with the vaporizer body 110 in which the PCBA 126 is positioned. The power pins 122*a,b* are shown in FIGS. 5A and 5C and are coupled to the proximal end 402*a* of the flexible layer 402 at the first antenna 143.

Shown in FIGS. 5C and 5D, on the bottom portion or layer of the PCBA 126 are the controller 128, the LEDs 136*a,b,c,d*, the pressure sensor 137, the ambient pressure sensor 138, and the accelerometer 139. The memory 146 may also be provided on the bottom portion or layer of the PCBA 126, as shown in FIG. 5D.

The PCBA 126 may be of various shapes and sizes and is not limited to the particular configurations shown in FIGS. 5A-5E. For example, the individual components may be situated in a variety of configurations on the PCBA 126, and the PCBA 126 itself may be of a variety of shapes and sizes to fit within the inner region of the inner assembly 111.

Figure 6A:
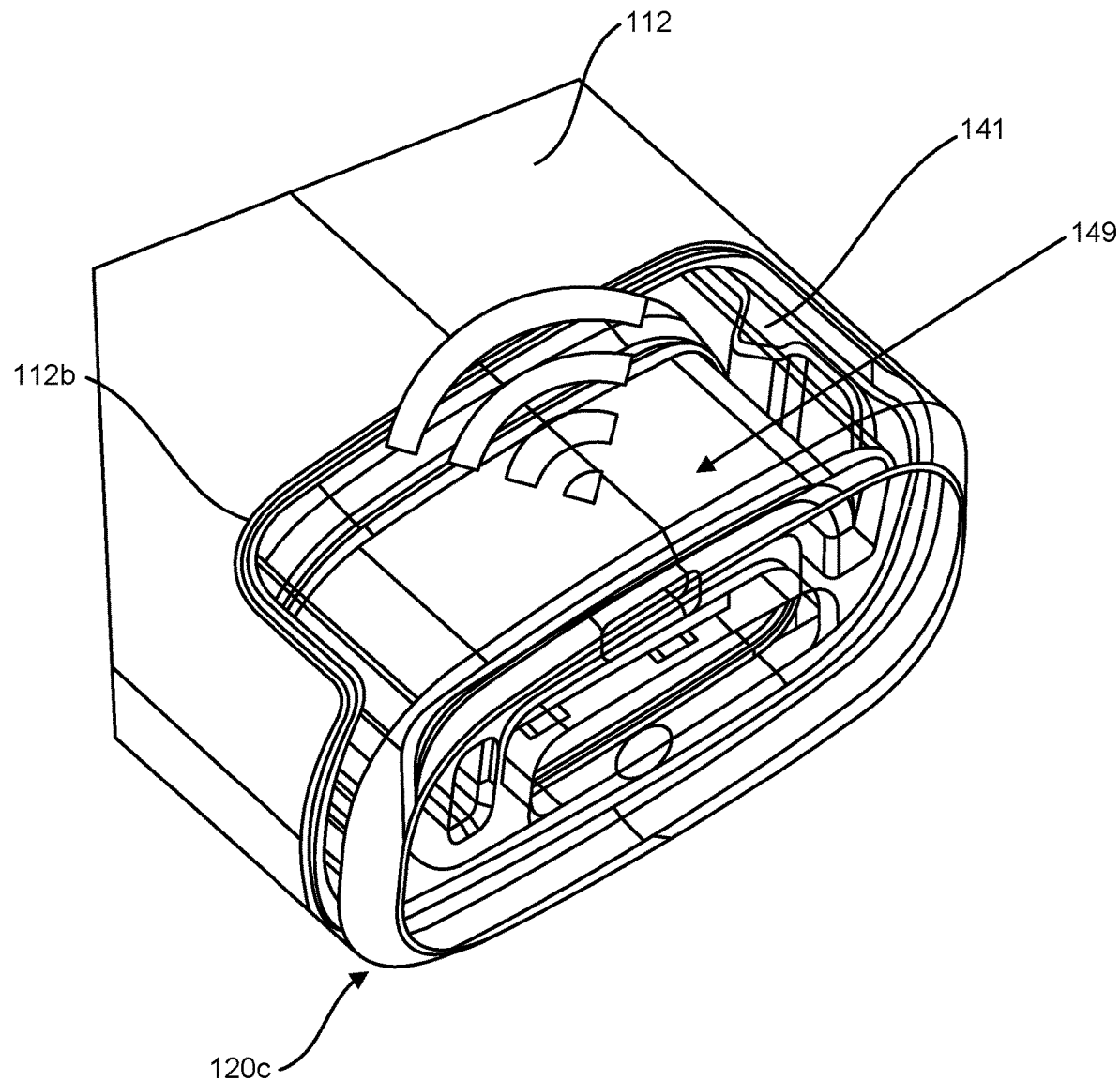
FIG. 6A-FIG. 6C illustrate features of antenna designs incorporated in a vaporizer device consistent with implementations of the current subject matter.

FIG. 6A is a top perspective view of a portion of the vaporizer body 110 looking towards the distal end of the vaporizer body 110, illustrating features of the second antenna such as the second antenna 149 consistent with implementations described herein. As described above, the second antenna 149 is integrated within the integrated board assembly 400 and assembled within the inner assembly 111. An antenna window 141 may be formed along one or more sidewalls of the bottom cap 120*c*. When the inner assembly 111 is in an assembled configuration, in which the bottom cap 120*c* is connected with the top and the bottom support structures 120*a*, 120*b* to provide a support structure for the inner assembly 111, the antenna window 141 may align or partially align with the second antenna 149. When the inner assembly 111 is inserted within the outer shell 112, the antenna window 141 may fit within a cut-out region 112*b* of the outer shell 112. The antenna window 141 may be a material, such as for example plastic, that provides for improved radiation of signals to and from the second antenna 149 compared with other materials, such as metal, that can block signals. The antenna window 141 may be made of other materials that are electromagnetically transparent to the radio frequencies being transmitted/received, which in this example are Bluetooth.

Figure 6B:
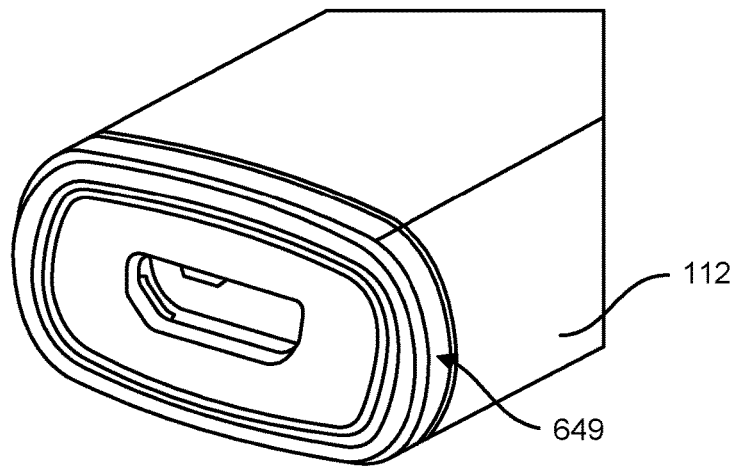
Figure 6C:
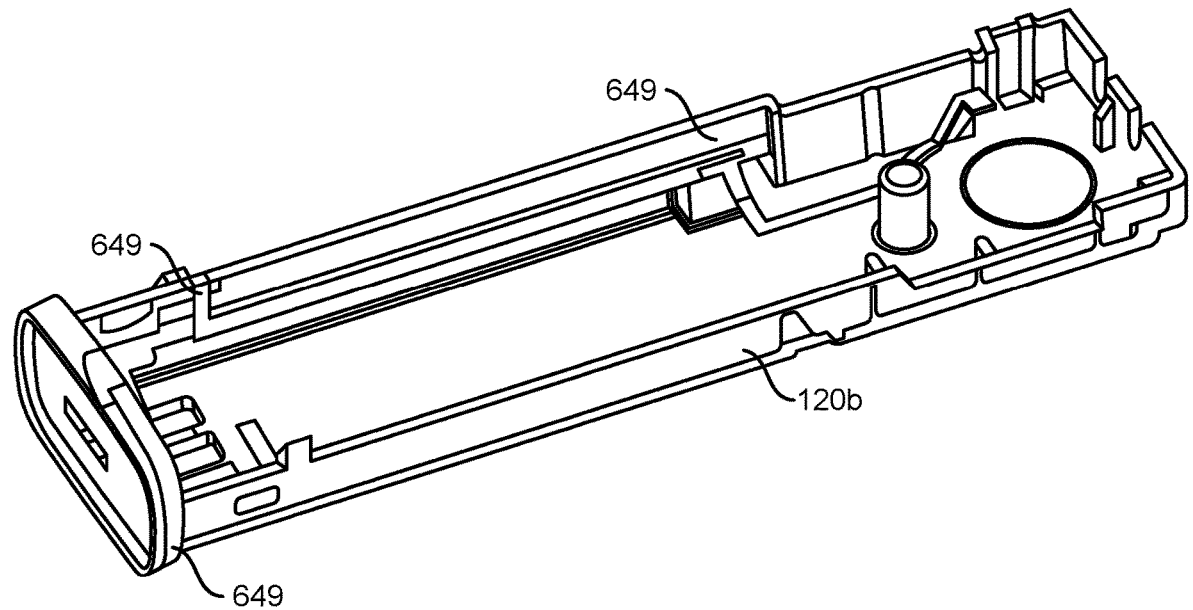

FIGS. 6B and 6C illustrate features of an alternative second antenna 649 such as a Bluetooth antenna. In this alternative, the alternative second antenna 649 is traced with laser direct structuring (LDS) on one or more portions of the support structure, such as the top support structure 120a, the bottom support structure 120b, and/or the bottom cap 120c, at the distal end of the vaporizer body 110 and may be covered with a hard outer coating, such as, for example, an ultraviolet (UV) hard coat. The trace of the alternative second antenna 649 continues along the length of the vaporizer body 110 to a controller (not shown in this view). At least a portion of the trace is on the exterior of the vaporizer body to enable transmission and/or reception of the radio frequencies being transmitted/received, which in this example are Bluetooth.

Although FIGS. 5A-6C depict certain configurations of the first antenna, the second antenna, and the power pins, other configurations may be used as well.

Figure 7A:
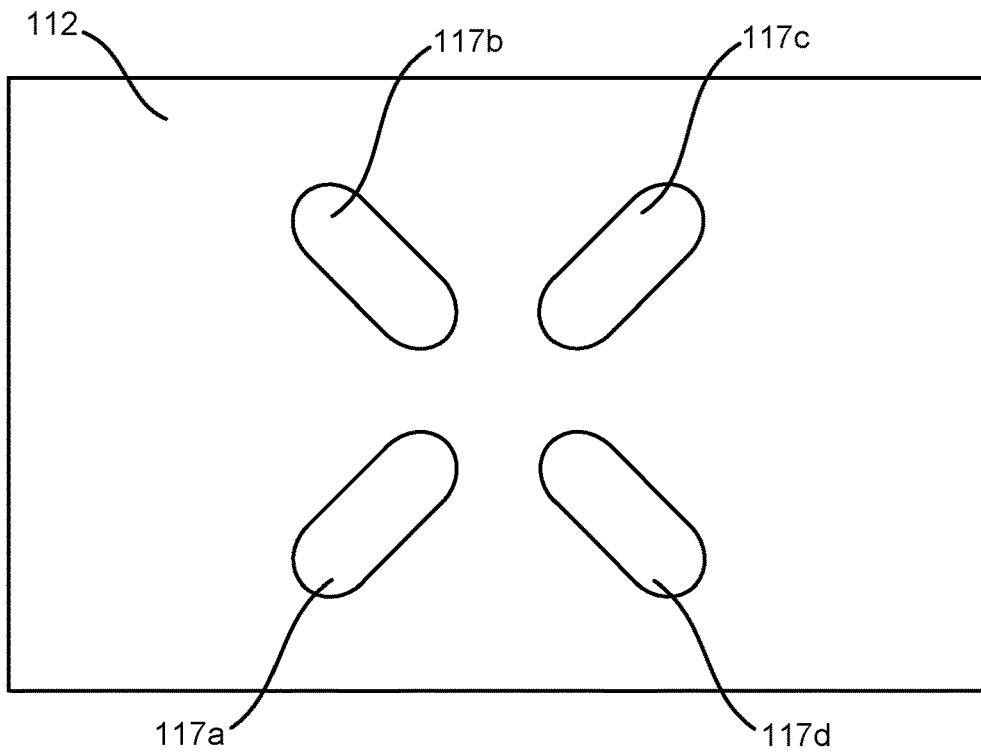
FIG. 7A-FIG. 7B and FIG. 8A-FIG. 8F illustrate illumination features of a vaporizer device consistent with implementations of the current subject matter.
Figure 7B:
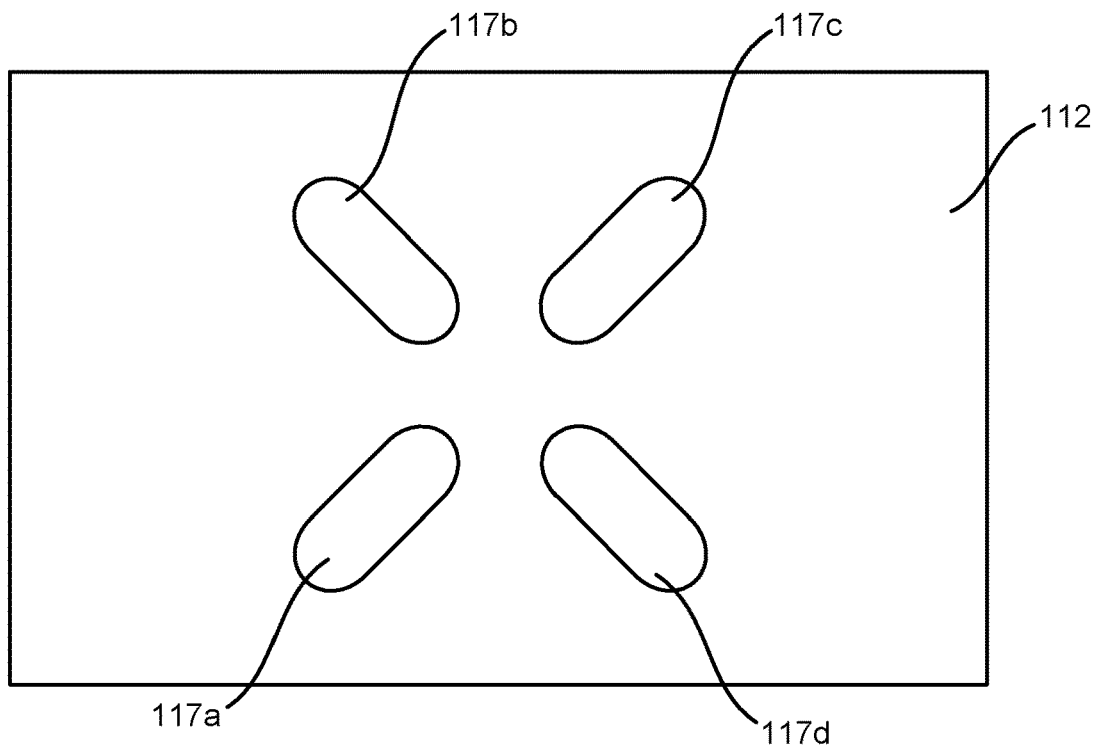

In some implementations, the light pipe 147 including individual light pipe components 117 is mounted in the surface of an outer shell 112 and in alignment over one or more LEDs 136 of the PCBA 126 to distribute the light provided by the LEDs 136, which may provide visual indicators for signaling, for example, operation status of the vaporizer device 100 (e.g., temperature, battery levels, etc.) or for other purposes, such as for example a variety of games that may be played on the vaporizer device 100. In some implementations, the light pipe 147 may be flush with the surface of the outer shell 112, but may in other implementations be mounted to project above or alternatively to be recessed below the surface of the outer shell 112. FIGS. 7A and 7B illustrate features, via a bottom view, of an exemplary light pipe 147 with individual light pipe components 117a,b,c,d. The outer surface of the light pipe 147 may be a reflective and/or metallic finish. When the LEDs 136 are off (FIG. 7A), the surface of the light pipe 147 may appear to be reflective. When the LEDs 136 are on (FIG. 7B), the light of the LEDs 136 shines through the light pipe 147.

While the light pipe components 117a,b,c,d and the LEDs 136 are shown in a specific pattern, implementations of the current subject matter are not so limited. Fewer or additional LEDs, and a corresponding light pipe structure, may be incorporated in various patterns, arrangements, sizes, and shapes.

Figure 8A:
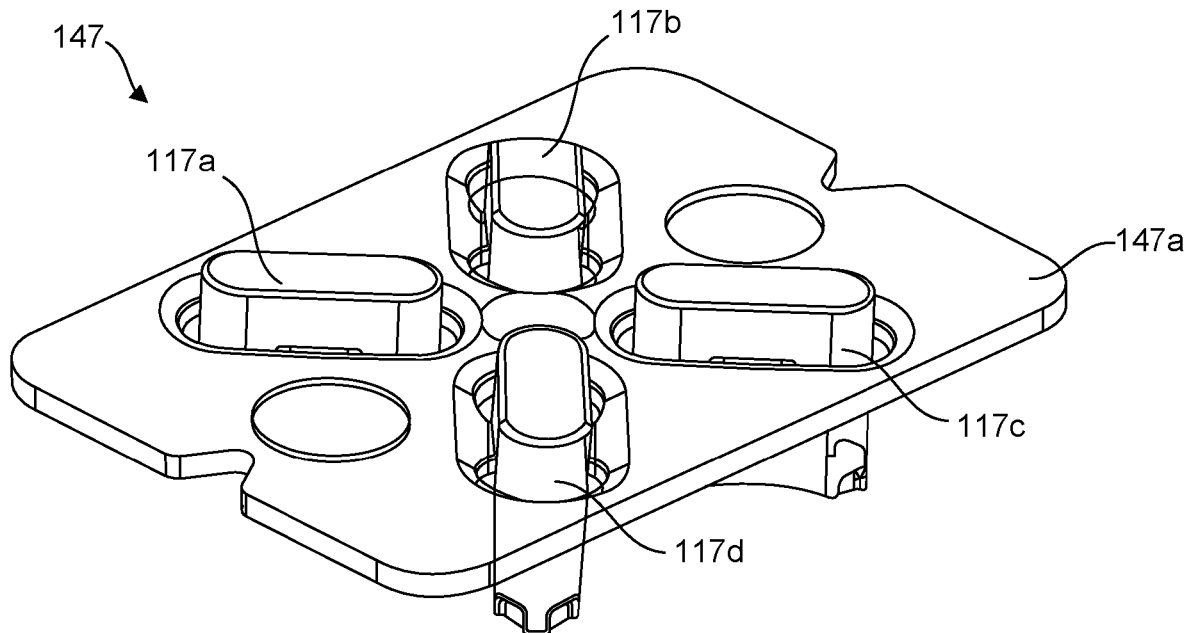
Figure 8B:
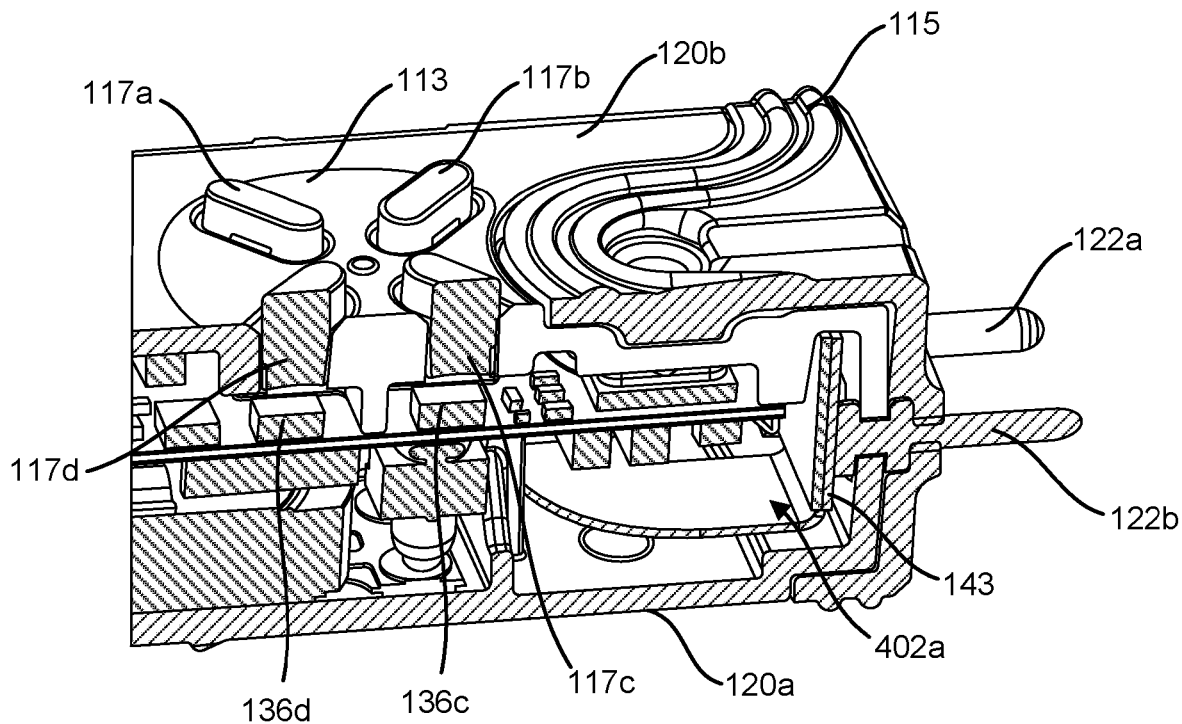
Figure 8C:
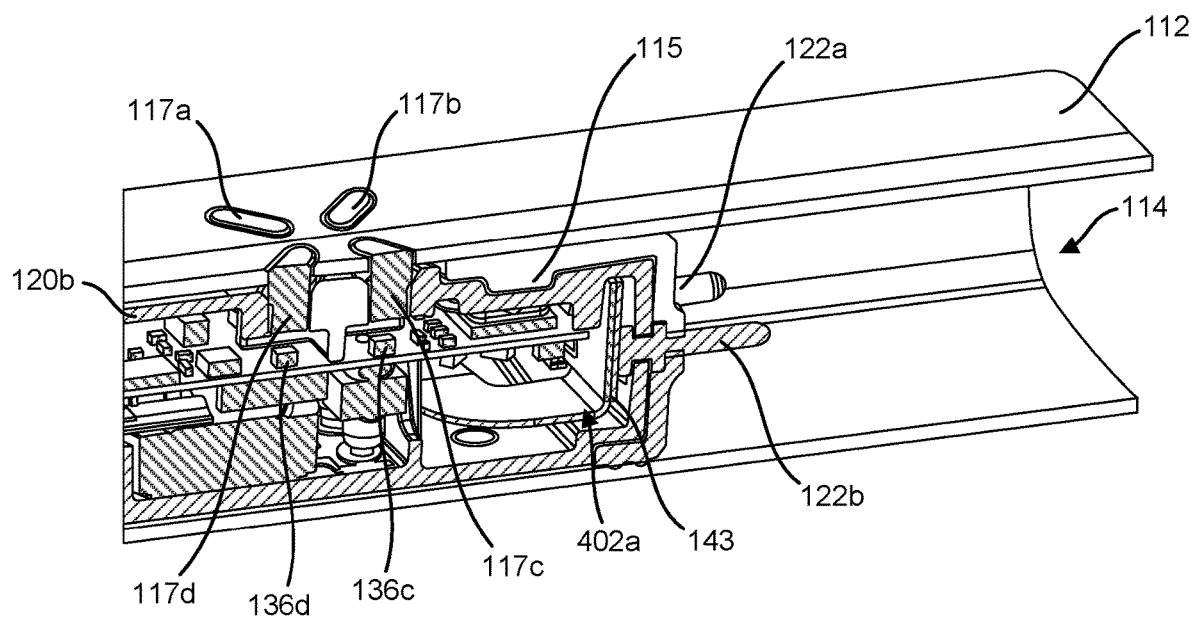
Figure 8D:
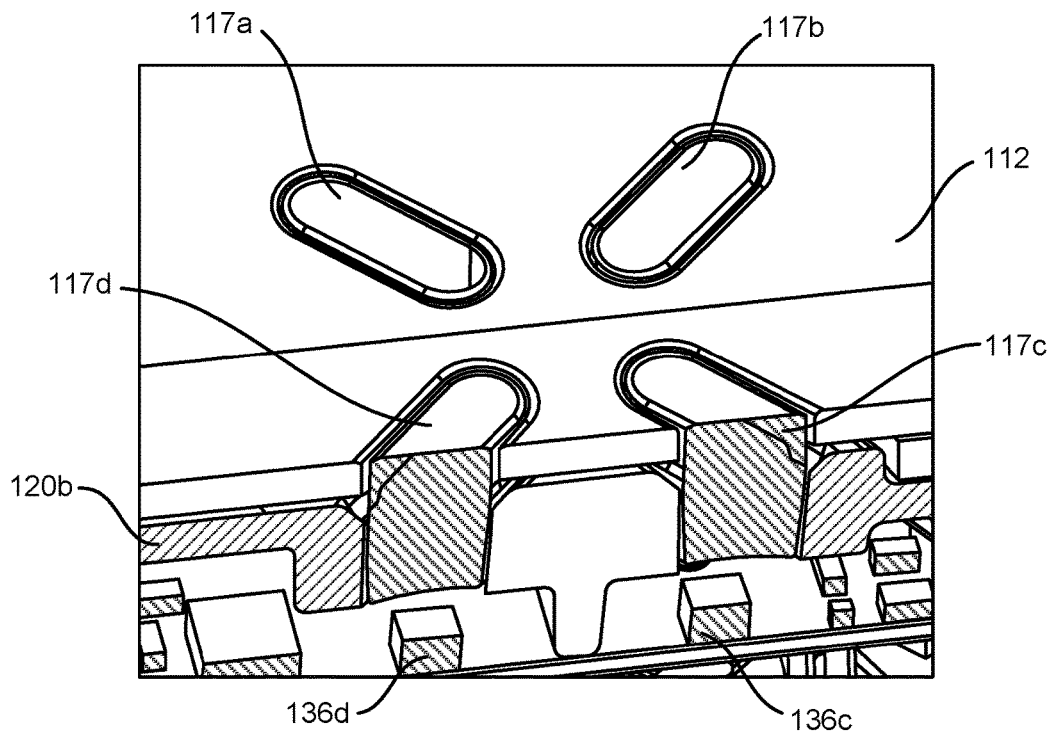
Figure 8E:
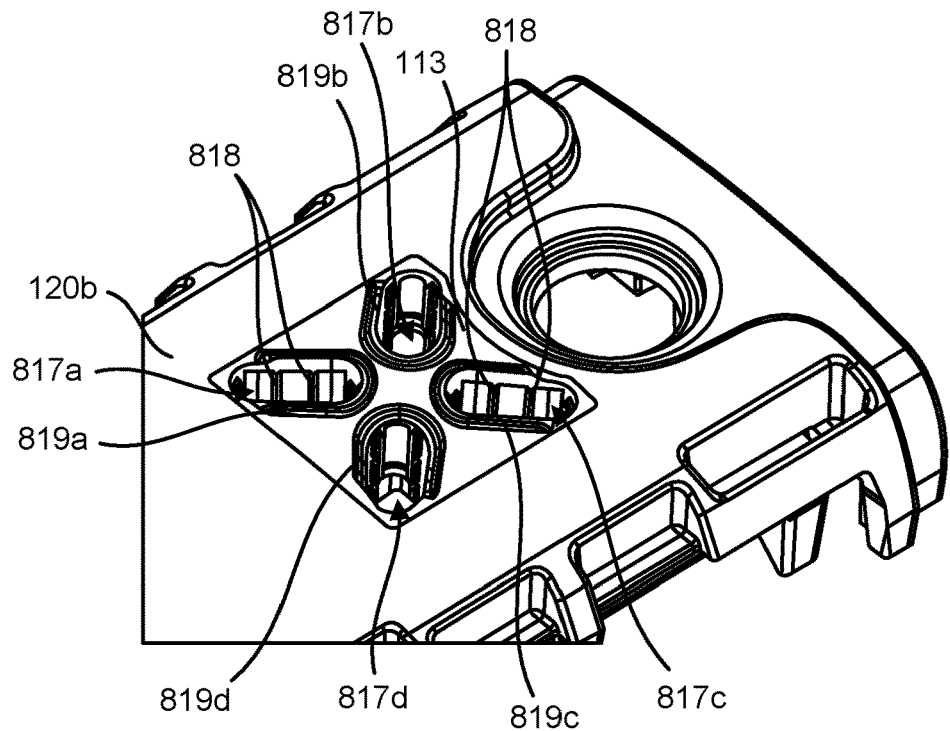
Figure 8F:
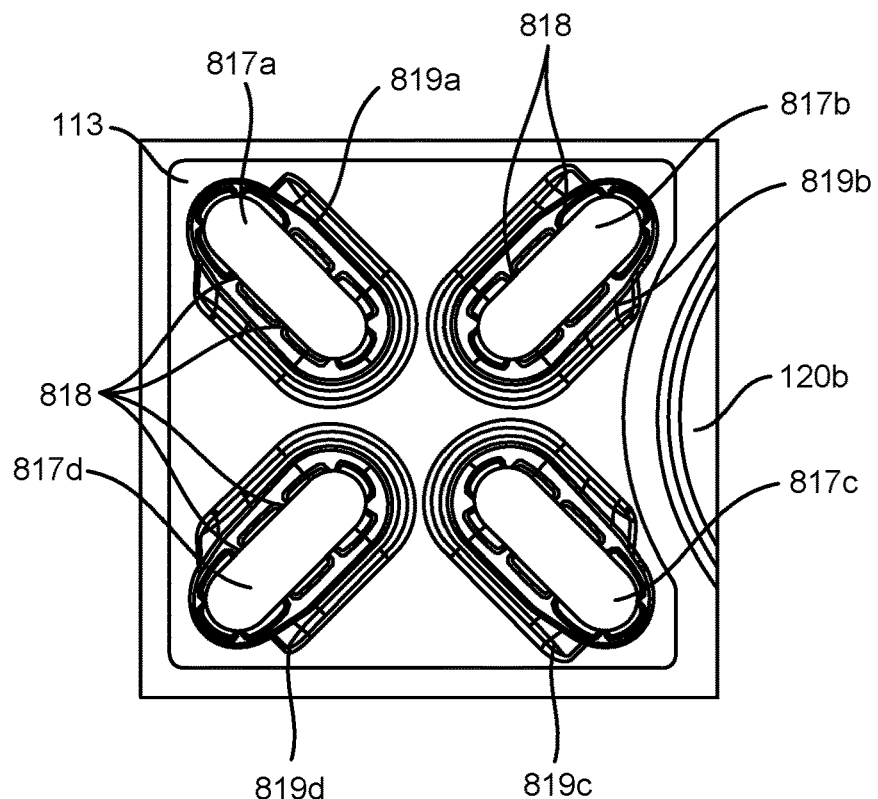

FIGS. 8A-8F illustrate manufacturing and assembly features of the light pipe 147. Shown in a top perspective view of FIG. 8A is a carriage unit 147a to which individual light pipe components 117a,b,c,d of the light pipe 147 are releasably attached. FIGS. 8B-8D are bottom, perspective, cross-sectional views of a vaporizer body 110 illustrating placement of the individual light pipe components 117a,b,c,d within the outer shell 112 and the inner assembly 111 (see also FIG. 4A). FIG. 8E is a top perspective view of a portion of the bottom support structure 120b, and FIG. 8F is a top view of the bottom support structure.

In particular, the light pipe components 117a,b,c,d correspond in size and shape to openings 119a,b,c,d of the outer shell 112 and recesses 817a,b,c,d of the mating structure 113 which is, consistent with implementations of the current subject matter, part of an upper surface of the bottom support structure 120b of the inner assembly 111. When the inner assembly 111 is inserted (e.g., slid) within the outer shell 112 such that the openings 119a,b,c,d align with the recesses 817a,b,c,d, the light pipe 147 may be mounted, which aids in securing the inner assembly 111 and the outer shell 112 to one another. The light pipe 147 may be placed into or inserted such that the light pipe components 117a,b,c,d are placed within the openings 119a,b,c,d on the outer shell 112 and the recesses 817a,b,c,d of the mating structure 113. Slight pressure placed on the light pipe 147, to press the light pipe components 117a,b,c,d into their respective openings, causes the light pipe 147 to break away from the carriage unit 147a. The carriage unit 147a may be discarded, and the individual light pipe components 117a,b,c,d are flush-mounted within the outer shell 112 via installation as one unit.

Each recess 817a,b,c,d of the mating structure 113 may include one or more crush ribs 818, as shown in FIGS. 8E and 8F, on internal side portions that push against the respective light pipe component 117 to hold it in place after assembly. For example, each recess 817a,b,c,d may include eight crush ribs 818 spaced around the inner circumference of each recess 817a,b,c,d, as shown in FIGS. 8E and 8F. Fewer or additional crush ribs 818 may be incorporated to aid in securing the light pipe components 117a,b,c,d within respective recesses 817a,b,c,d. Additionally, consistent with some implementations of the current subject matter, an upward extending edge 819a,b,c,d (for example, a lip) may extend around a portion of the upper circumference of each recess 817a,b,c,d. As shown in FIG. 8E, the upward extending edge 819a,b,c,d may have a sloped surface extending upward and outward from the upper circumference of each recess 817a,b,c,d. The upward extending edge 819a,b,c,d may aid in installation of the light pipe components 117a,b,c,d to achieve a smooth or flat position with respect to the outer shell 112.

The light pipe design according to implementations of the current subject matter advantageously reduces crosstalk between the various individual light pipe components 117a,b,c,d as each one is discrete from the others after installation.

Figure 9A:
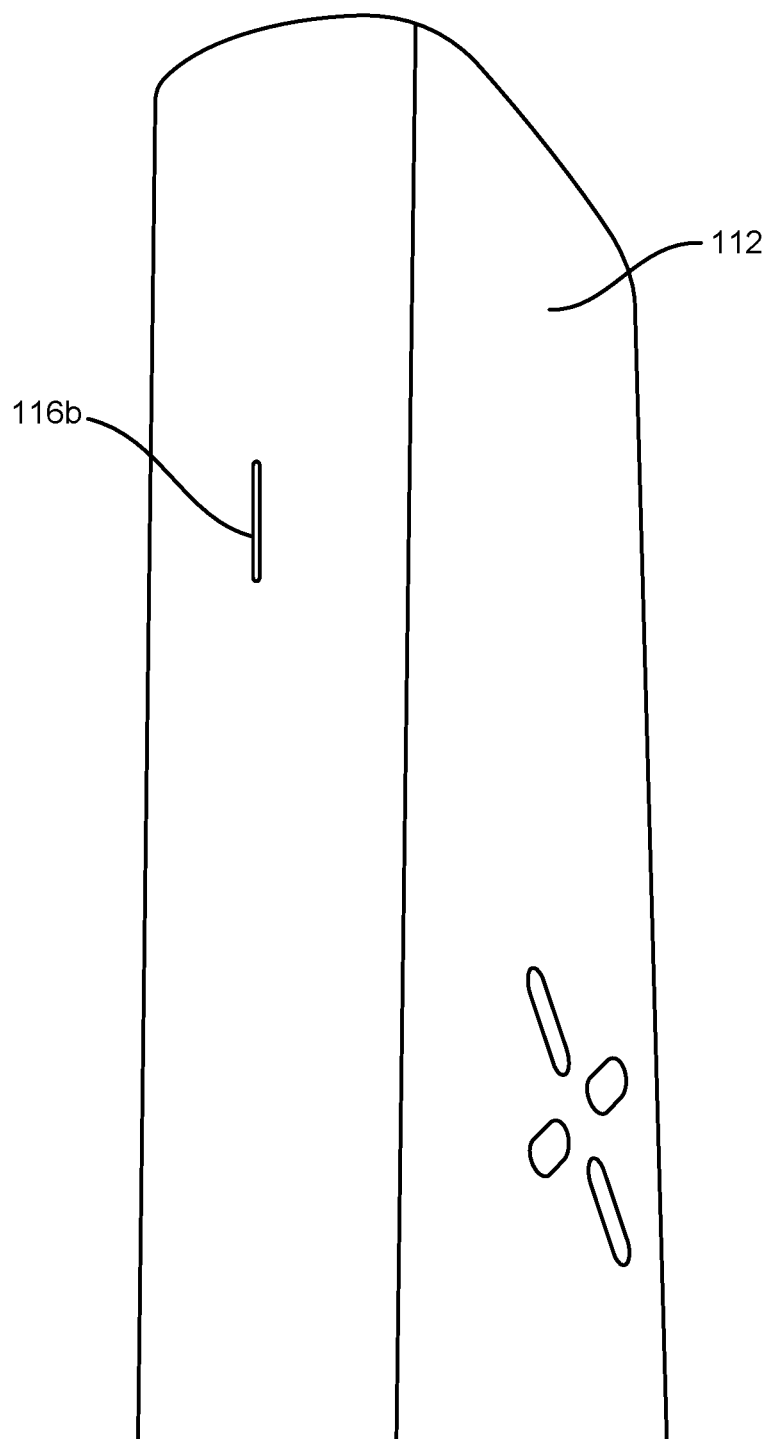
FIG. 9A-FIG. 9E illustrate additional features of a vaporizer body consistent with implementations of the current subject matter.

FIG. 9A is a perspective, right-side view illustrating features of a vaporizer body 110 consistent with implementations of the current subject matter. As shown, the air inlet 116b may be a slot that extends lengthwise along the side of the outer shell 112. The slot may be configured as a long, relatively narrow aperture as shown at FIG. 9A. In the example of FIG. 9A, the slot forms an opening having two parallel sides which meet at both ends to form the slot. The air inlet 116a, opposite the air inlet 116b, can have a similar or equivalent configuration, or the air inlet 116a can have a different configuration from that of the air inlet 116b. The orientation and size of the air inlets 116a,b may allow for a user to adjust air flow through the vaporizer device 100 by placing a finger over at least a portion of the air inlets 116a,b. The user can stop or restrict air flow through the vaporizer device 100 by completely or partially covering the air inlets 116a,b. Air flow enters the vaporizer device 100 through the air inlets 116a,b and flows through the cartridge 150, as described elsewhere herein with respect to the cartridge 150.

Although FIG. 9A depicts a slot for the air inlet 116b, other sizes and/or shapes of the air inlets 116a,b may be used as well. For example, the air inlets 116a,b may be a thicker rectangular shape (with the long edges oriented parallel, perpendicular, or at an angle with respect to the length of the vaporizer body 110). Alternatively, the air inlets 116a,b may be a circle, an oval, a square, or any type of polygon. FIGS. 9D and 9E illustrate, via a perspective, right-side view of the vaporizer body 110 and a right-side view of the vaporizer body 110 respectively, a slot for the air inlet 116*b* having two parallel opposing lengthwise oriented sides with curved ends to connect the sides.

In an implementation, the air inlets 116*a,b* may be circular with a diameter of from about 0.2 mm to about 4.0 mm, from about 0.5 mm to about 2.0 mm, from about 0.6 mm to about 1.5 mm, from about 0.7 mm to about 1.35 mm, from about 0.8 mm to about 1.0 mm, or about 0.85 mm. In another implementation, the air inlets 116*a,b* may be rectangular slots with a width of about 0.3 mm to about 0.8 mm, about 0.4 mm to about 0.7 mm, or about 0.5 mm to about 0.6 mm; and a length of about 0.8 mm to about 4.0 mm, about 1.0 mm to about 3.8 mm, about 1.5 mm to about 3.3 mm, or about 2.0 mm to about 2.8 mm. In yet another implementation, the air inlets 116*a,b* may be rectangular slots with a width of about 0.80 mm and a length of about 1.0 mm to about 2.0 mm. Various other sizes, orientations, and shapes may be utilized, consistent with implementations of the current subject matter. In some implementations, the air inlets 116*a,b* may include a plurality of individual air slots. For example, the air inlet 116*a* may be a grouping of circular, square, rectangular, triangular, oval, and/or other-shaped air slots arranged in a variety of configurations.

Figure 9B:
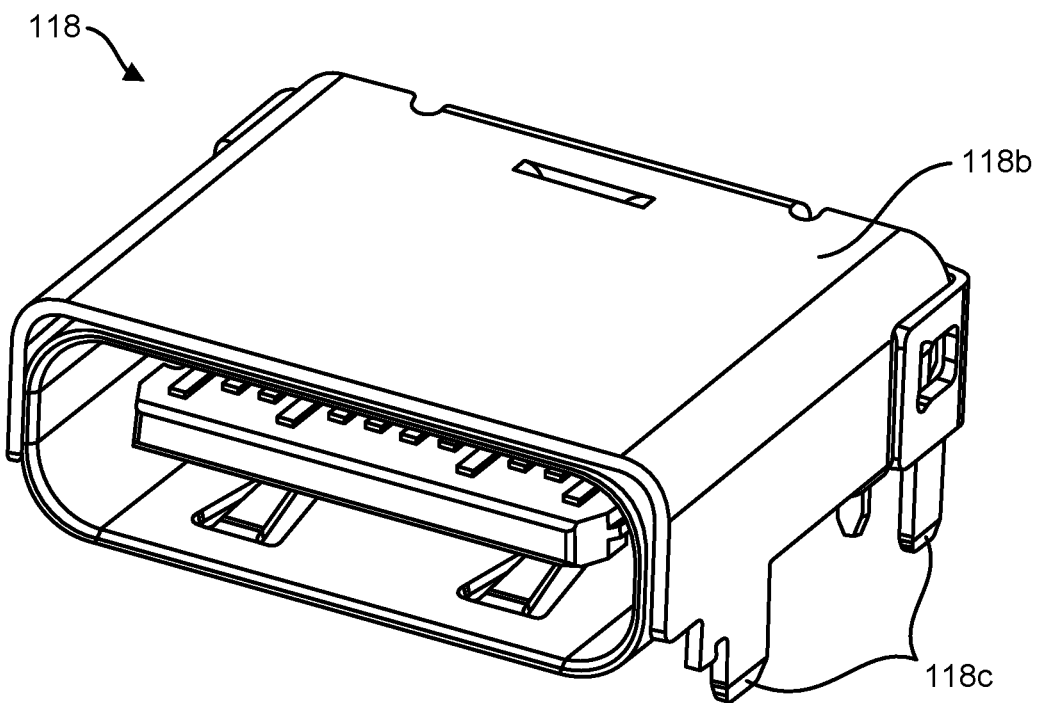
Figure 9C:
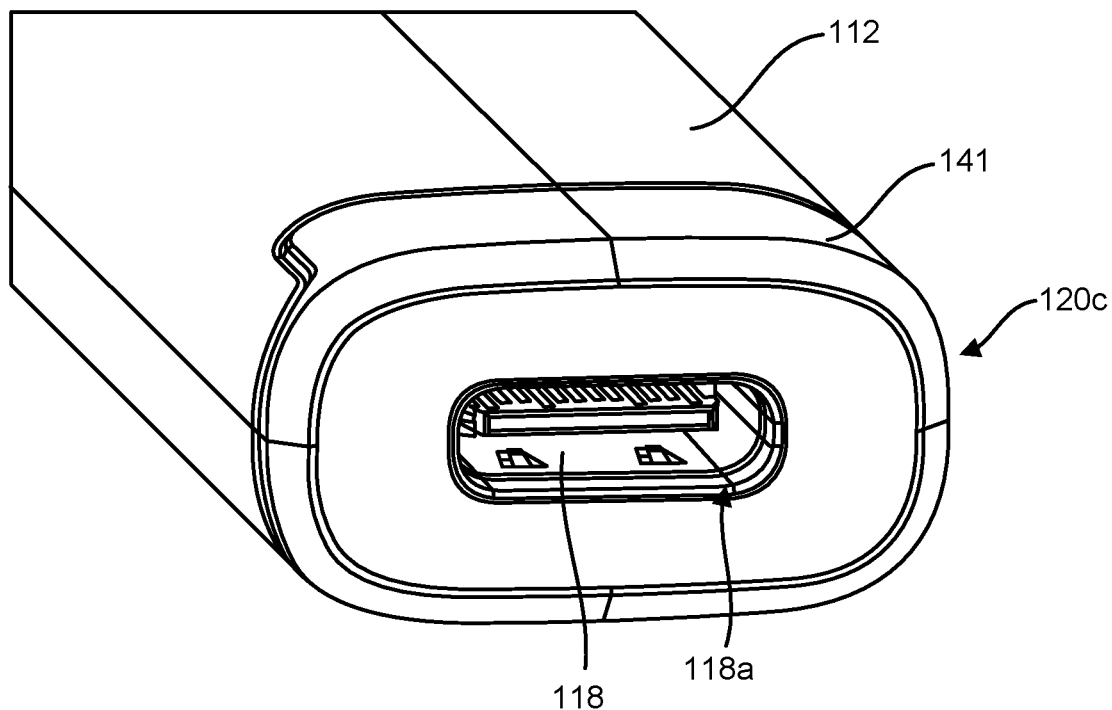
Figure 9D:
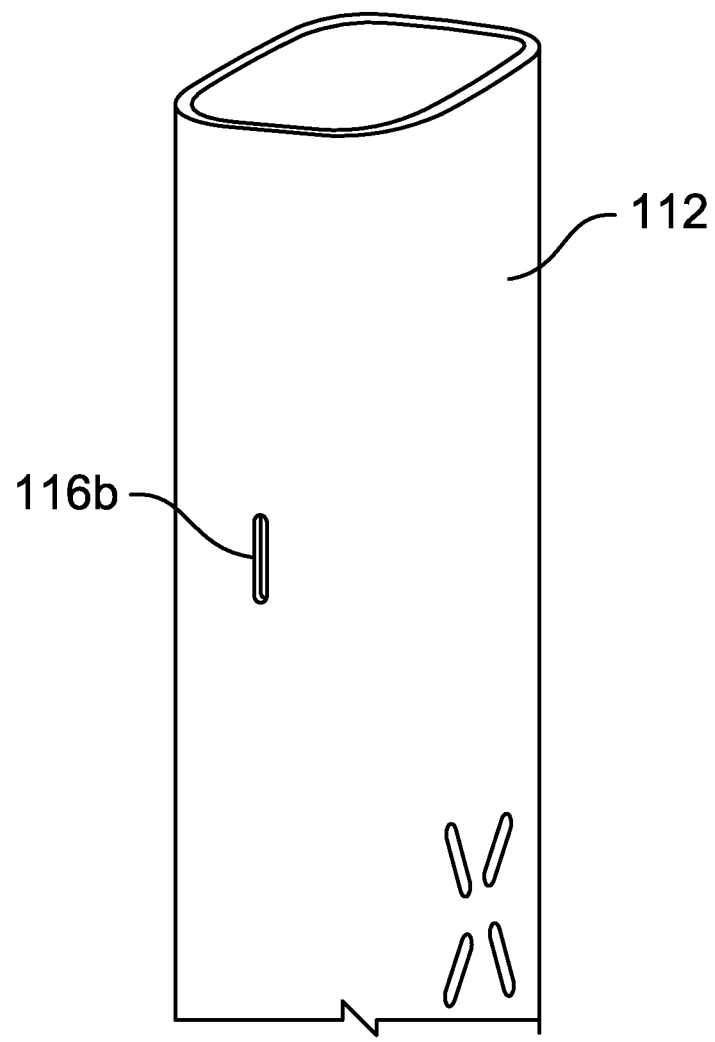
Figure 9E:
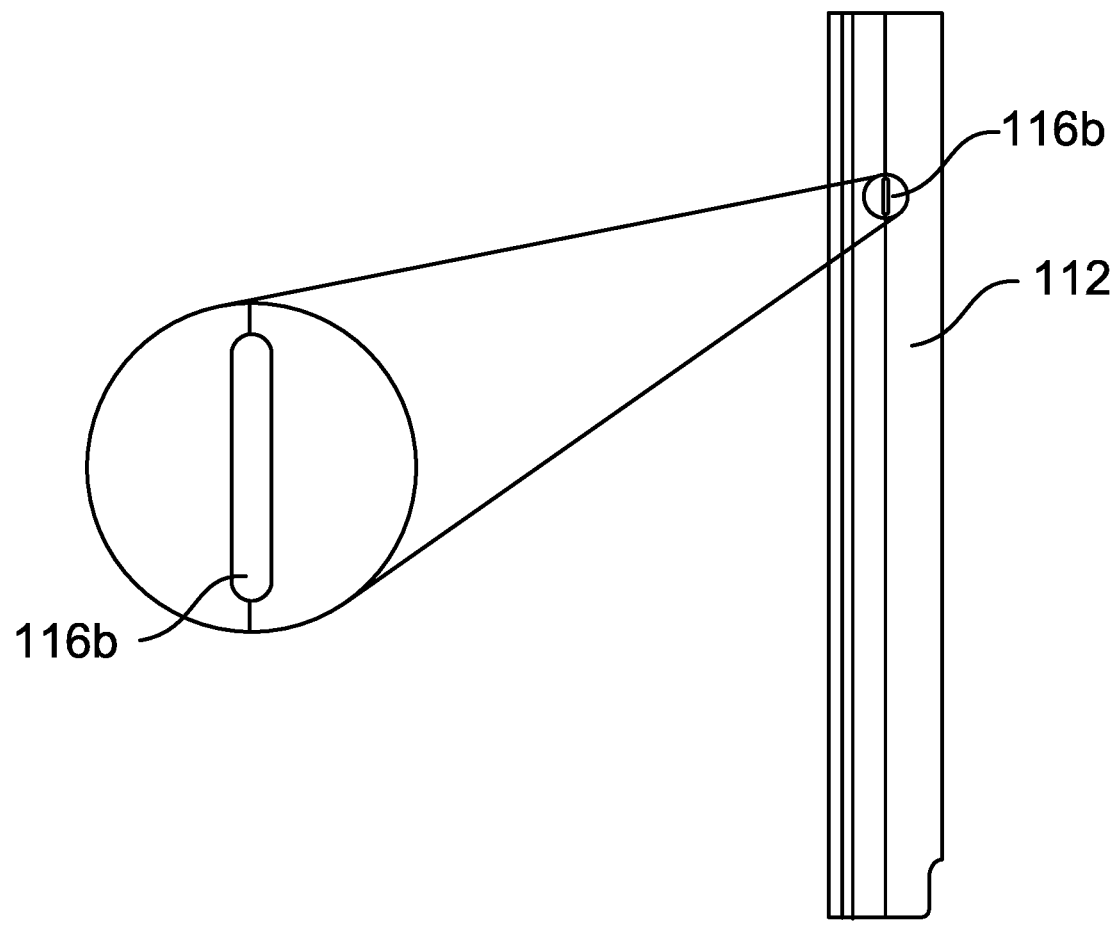

FIGS. 9B and 9C illustrate features (via top perspective views looking toward the distal end) of a connector component (e.g., connection 118, such as, for example, a universal serial bus Type C (USB-C) connection and/or the like). The connection 118 may be formed of, for example, black nickel plating to create a uniform appearance with the bottom cap 120*c* with which the connection 118 is aligned. The connection 118 may include an outer shell 118*b* with connection points 118*c* that allow for soldering to the connector PCBA 127. For example, the outer shell 118*b* and the connection points 118*c* may be formed of standard nickel plating that allows for better soldering to the connector PCBA 127. Other materials for the connection 118 and the outer shell 118*b* with the connection points 118*c* may be used.

Figure 10A:
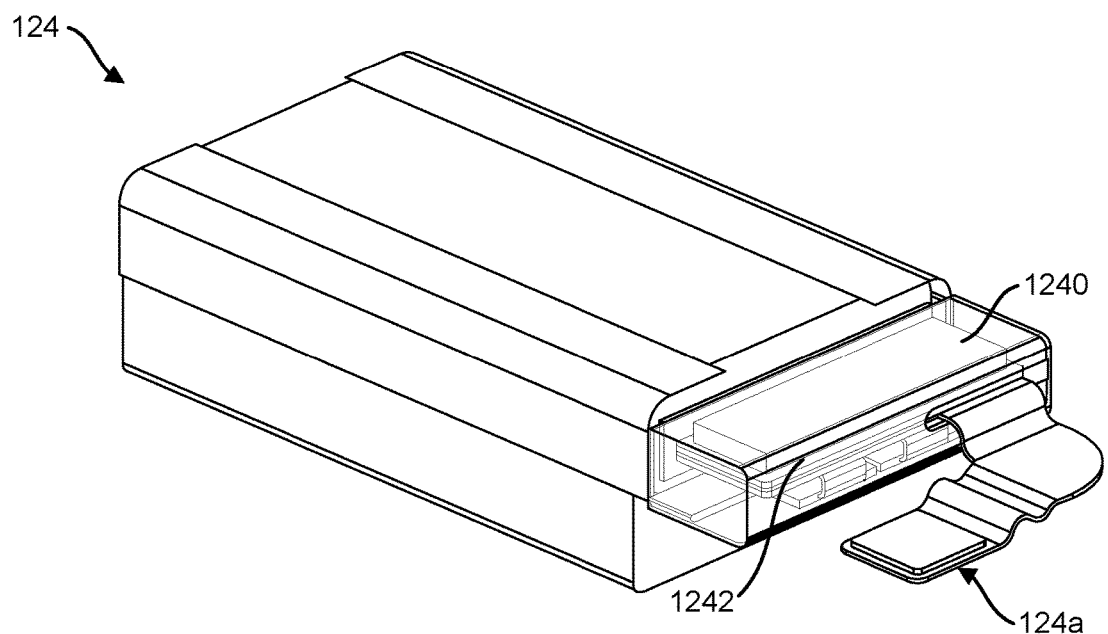
FIG. 10A-FIG. 10B illustrate features of a battery incorporated in a vaporizer device consistent with implementations of the current subject matter.
Figure 10B:
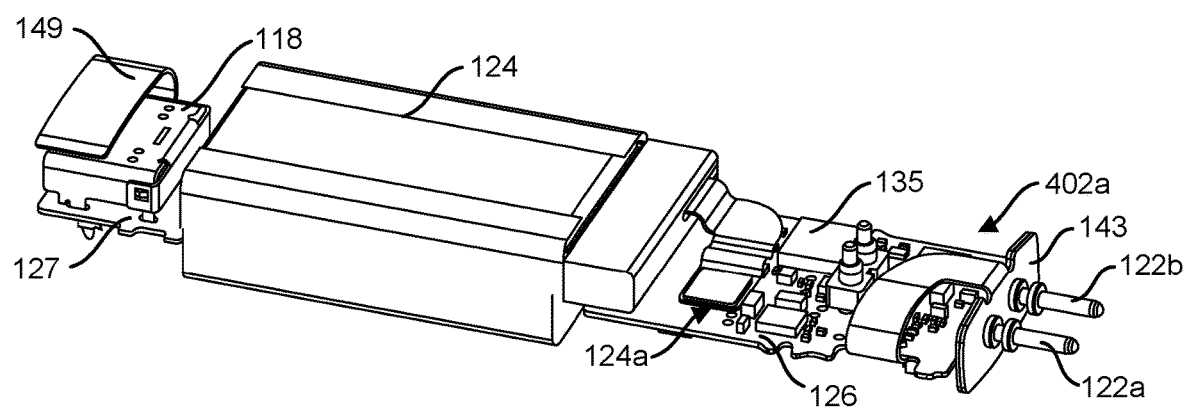

FIGS. 10A-10B illustrate (via top perspective views) features of the battery 124 configured to be incorporated in the vaporizer body 110 consistent with implementations of the current subject matter. FIG. 10A shows the battery 124, and FIG. 10B illustrates the battery 124 connected to the PCBA 126. As shown in FIG. 5A, The battery connector 125 is provided on a top surface of the PCBA 126 for connection with the battery 124 via the battery connector point 124*a*. The battery connecter 125 may conveniently replace a solder connection for connecting the battery to the PCBA 126. Although the battery 124 can be located in other locations, the battery placement at the opposite end from the heater 166 may avoid issues related to overheating the battery. The battery connector 125 can also allow for the controller 128 to communicate with a battery fuel gauge to determine battery level, battery health/faults, battery temperature, discharge/charge current, battery voltage, and the like.

Consistent with some implementations of the current subject matter, the battery 124 may be a high energy density battery with over current and thermal protection, under voltage lockout, fuel gauge, and a protection circuit module (PCM) 1240 (attached to a PCM board 1242) that may disconnect the battery 124 in over voltage or over current events. The battery 124 may be a rechargeable lithium-ion polymer (LiPo) battery with a fast charge mode, such as a 2C charge mode, and/or may have a battery capacity of, for example, from about 274 mAh to about 280 mAh. A variety of other types of batteries with other specifications may be utilized for the vaporizer device 100, consistent with implementations of the current subject matter.

Figure 11A:
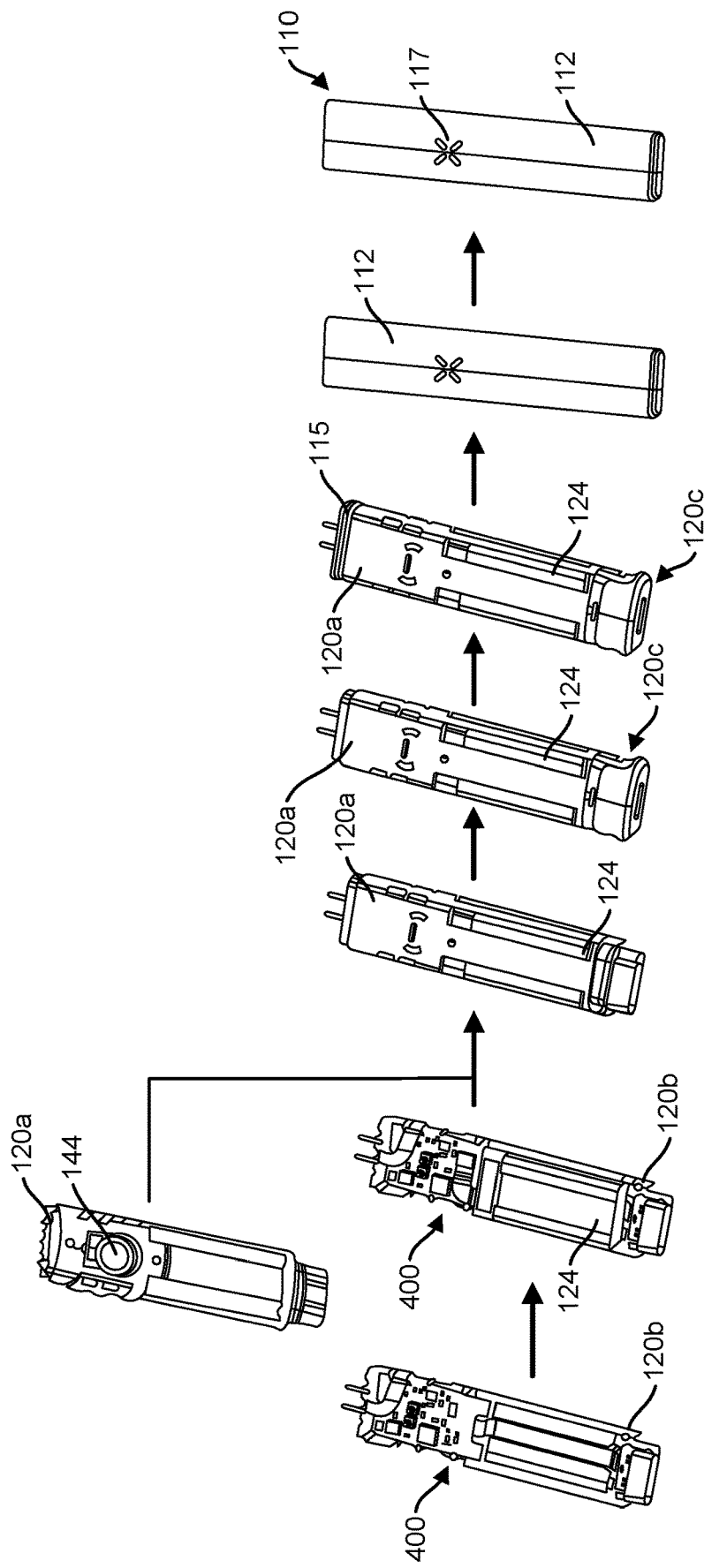
FIG. 11A-FIG. 11V illustrate various assembly steps of a vaporizer body consistent with implementations of the current subject matter.
Figure 11B:
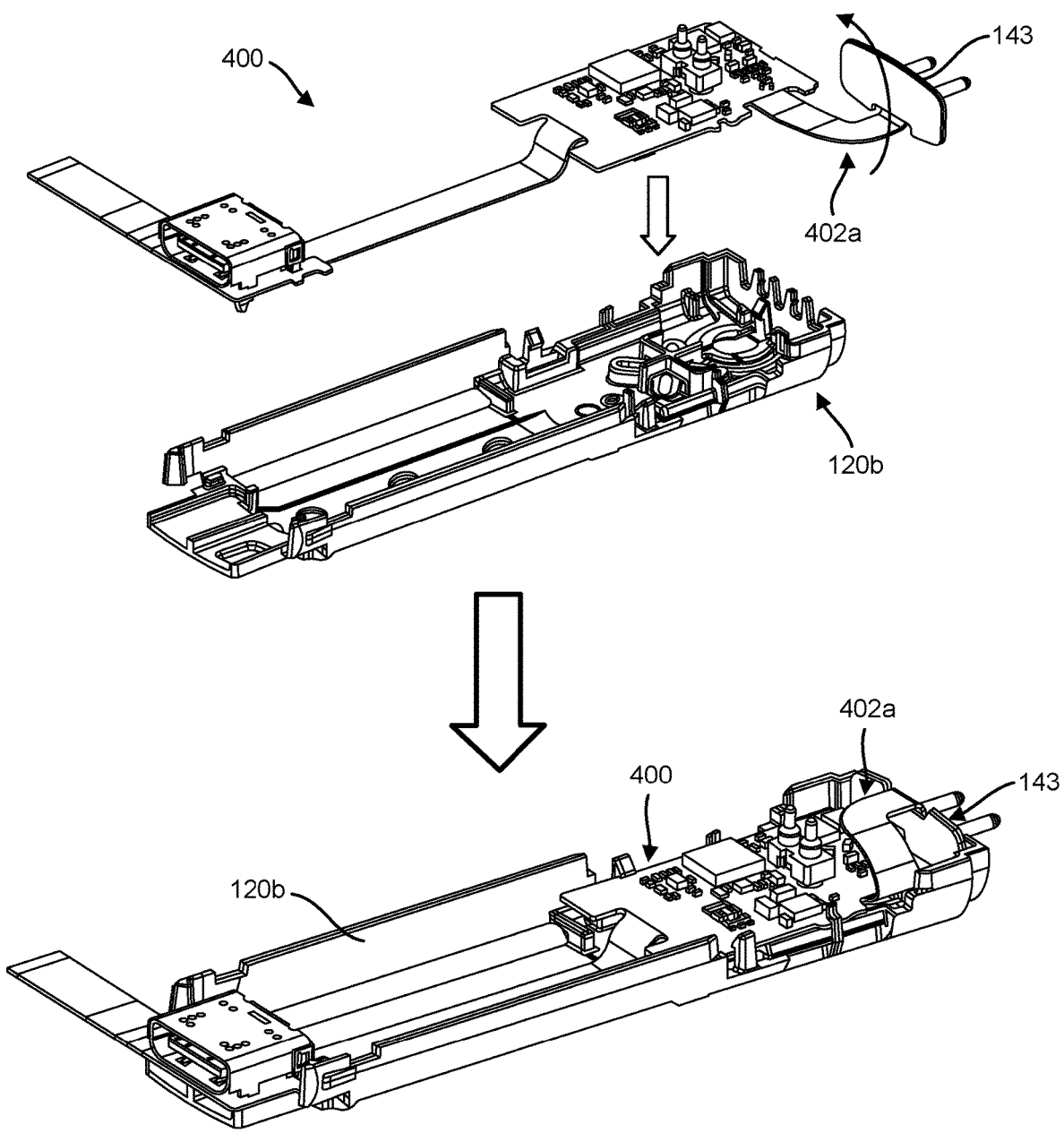
Figure 11C:
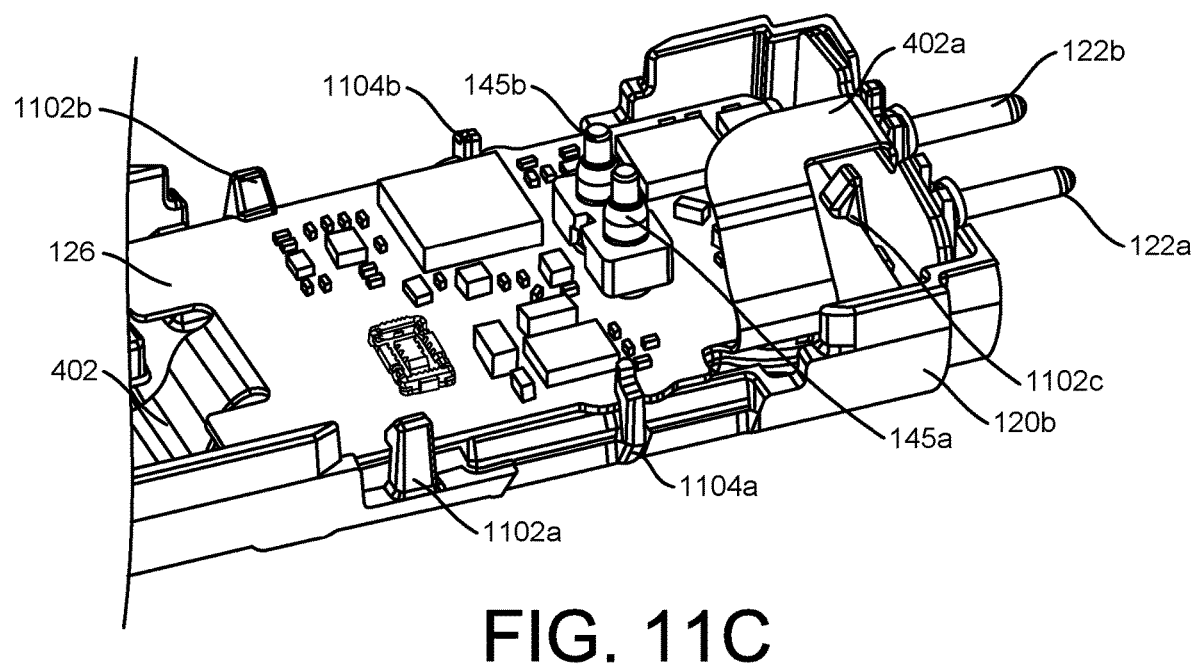
Figure 11D:
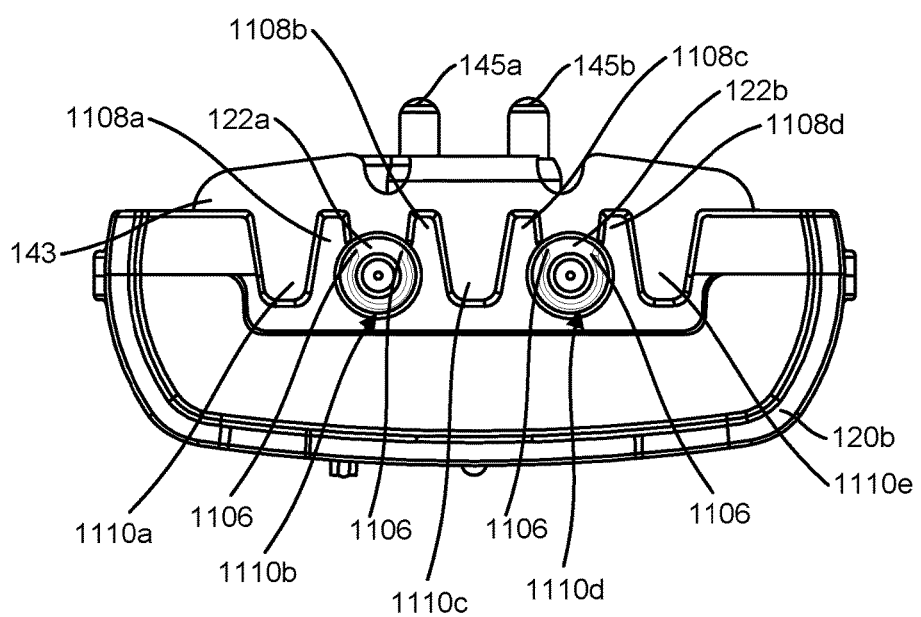
Figure 11E:
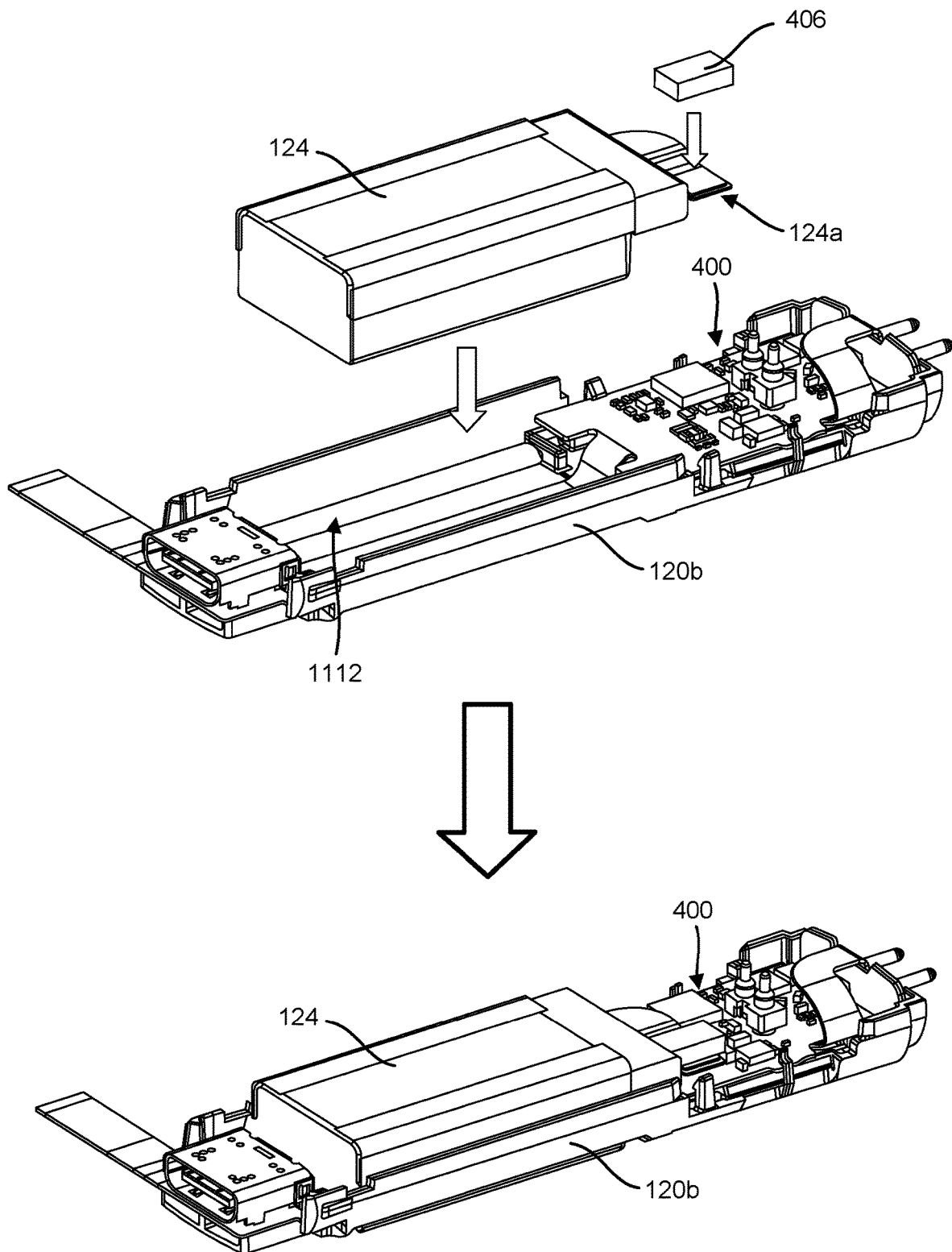
Figure 11F:
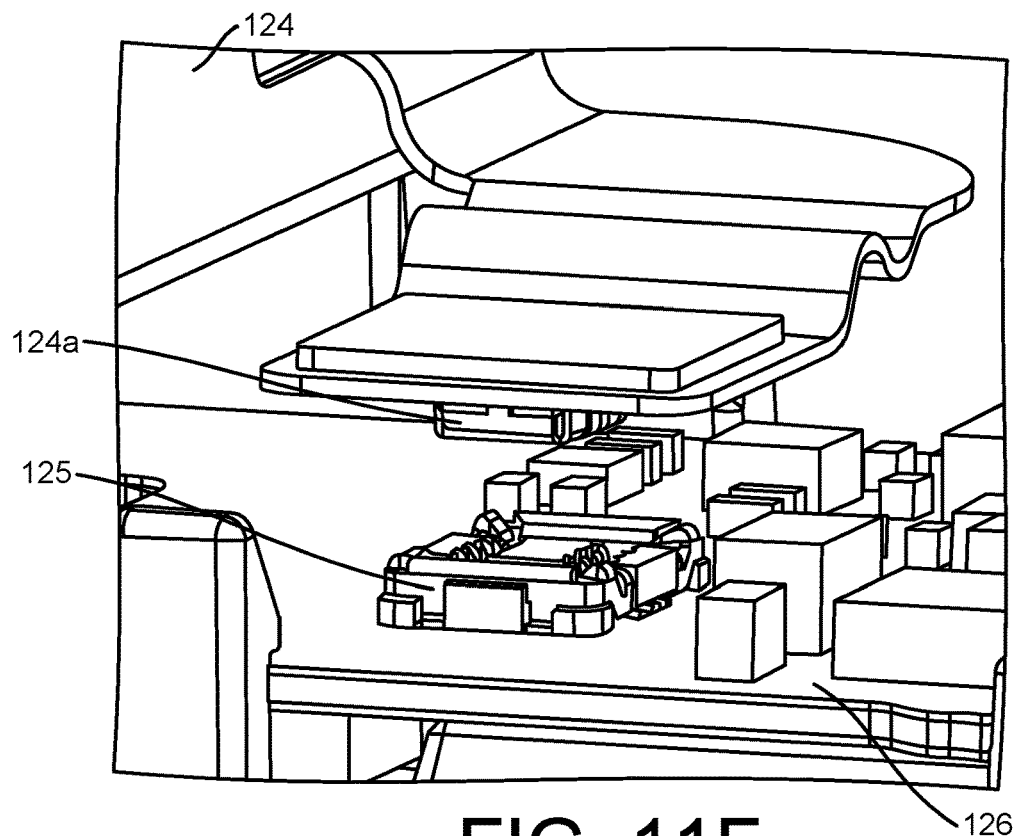
Figure 11G:
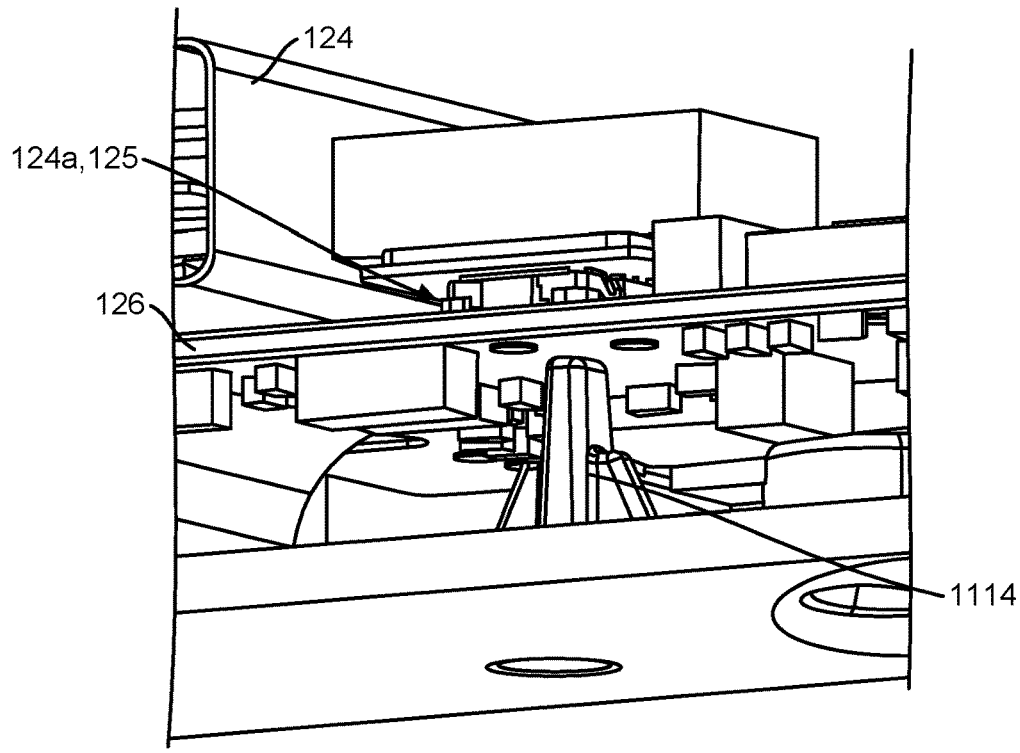
Figure 11H:
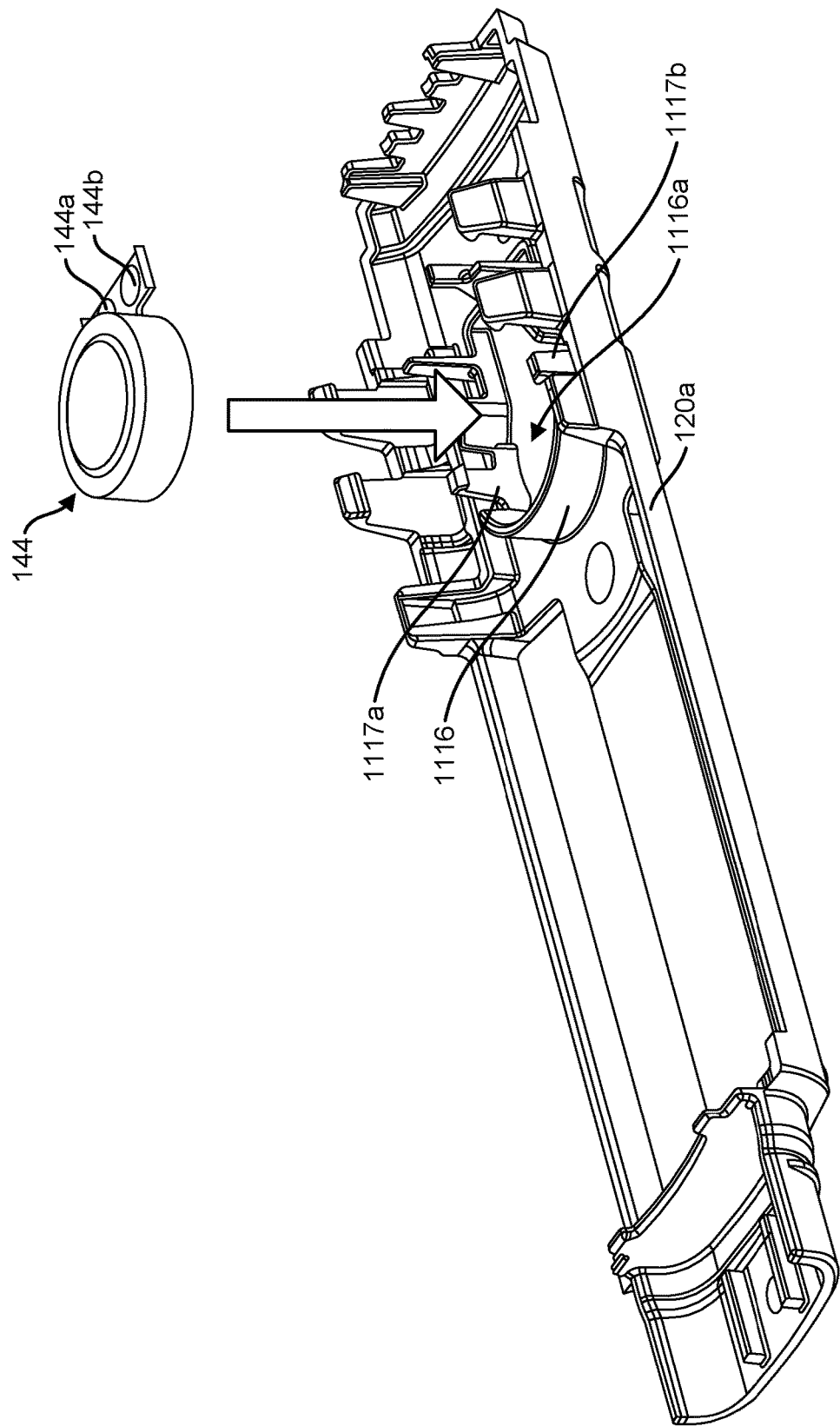
Figure 11I:
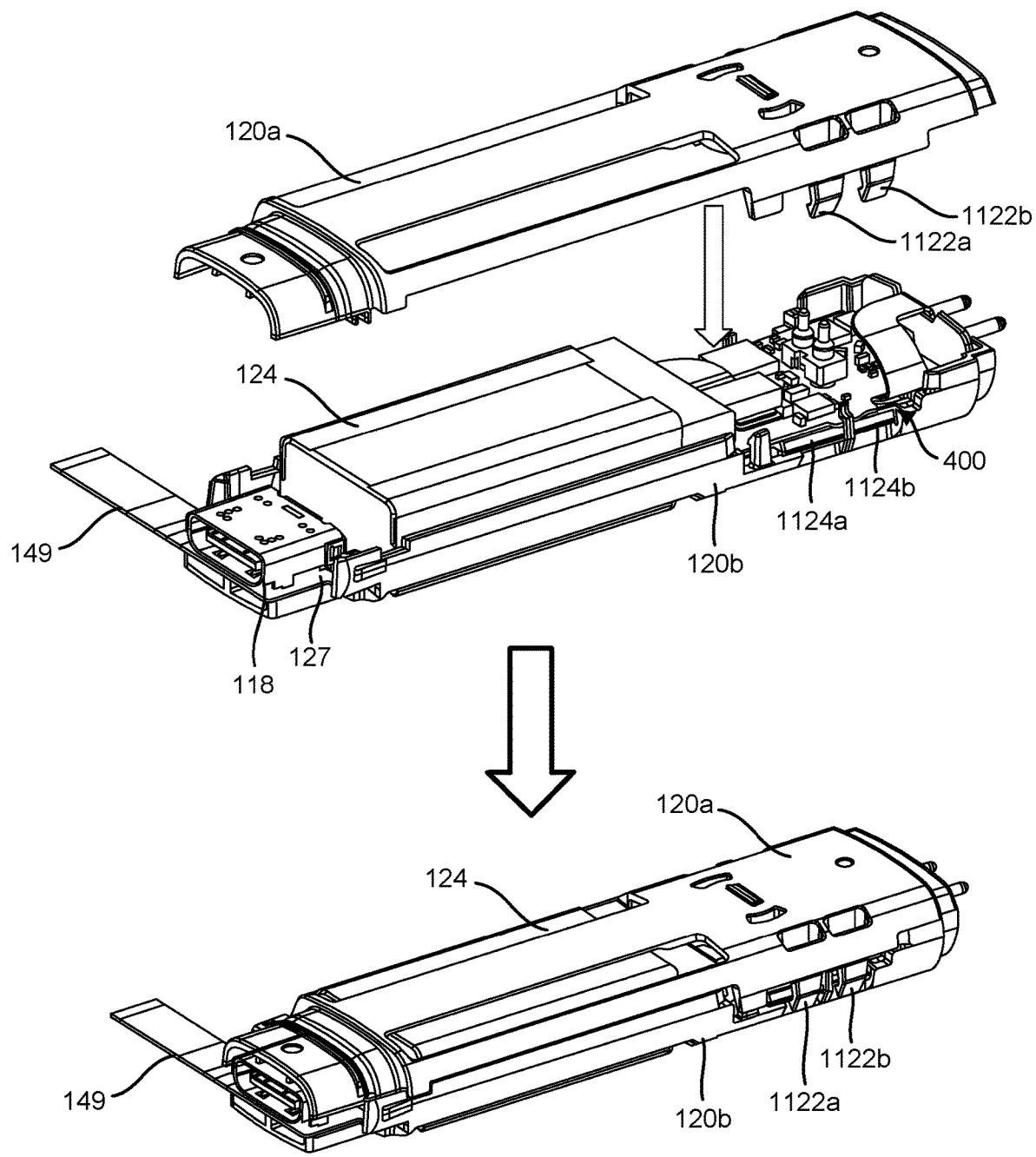
Figure 11J:
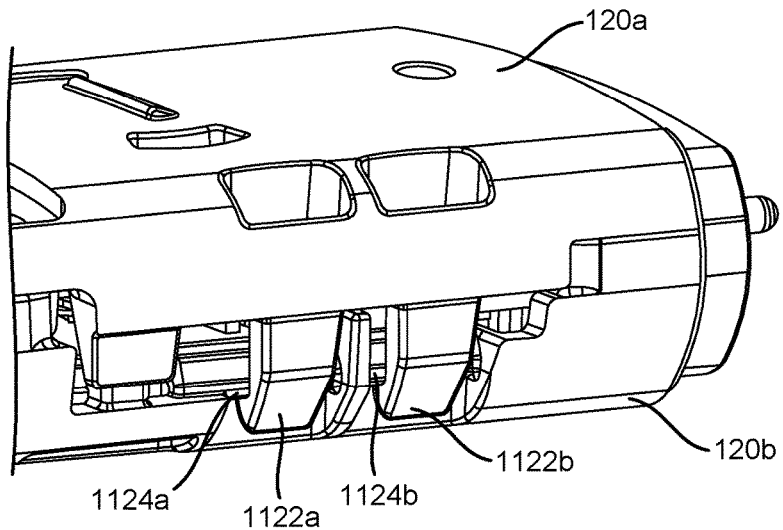
Figure 11K:
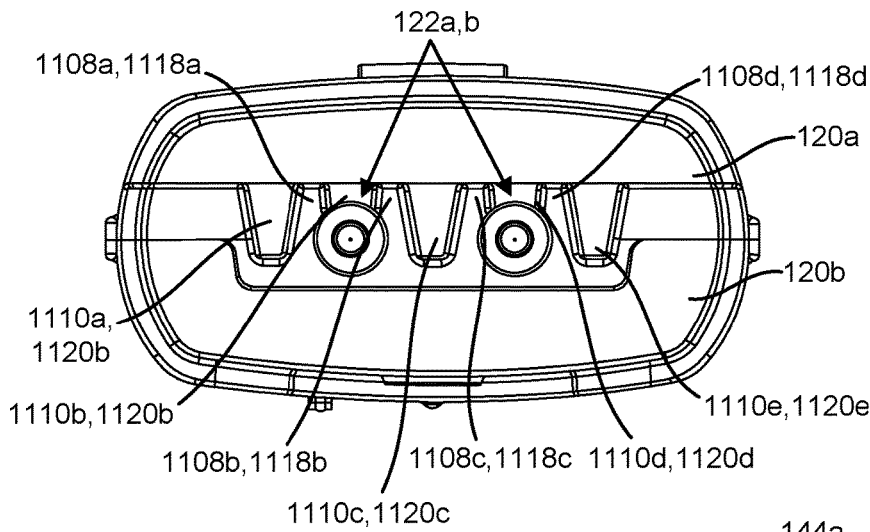
Figure 11L:
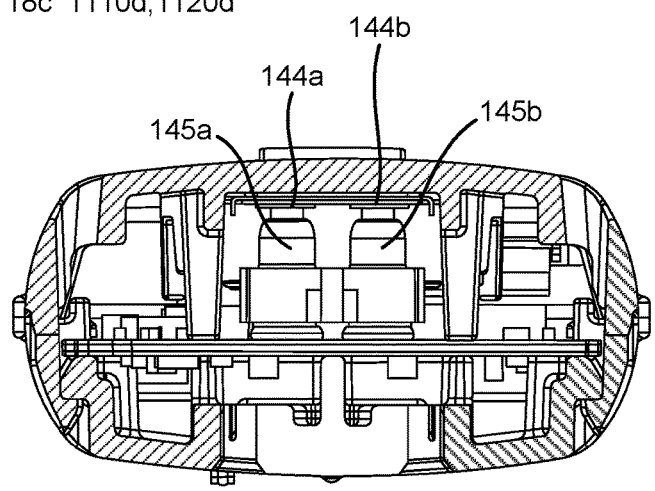
Figure 11M:
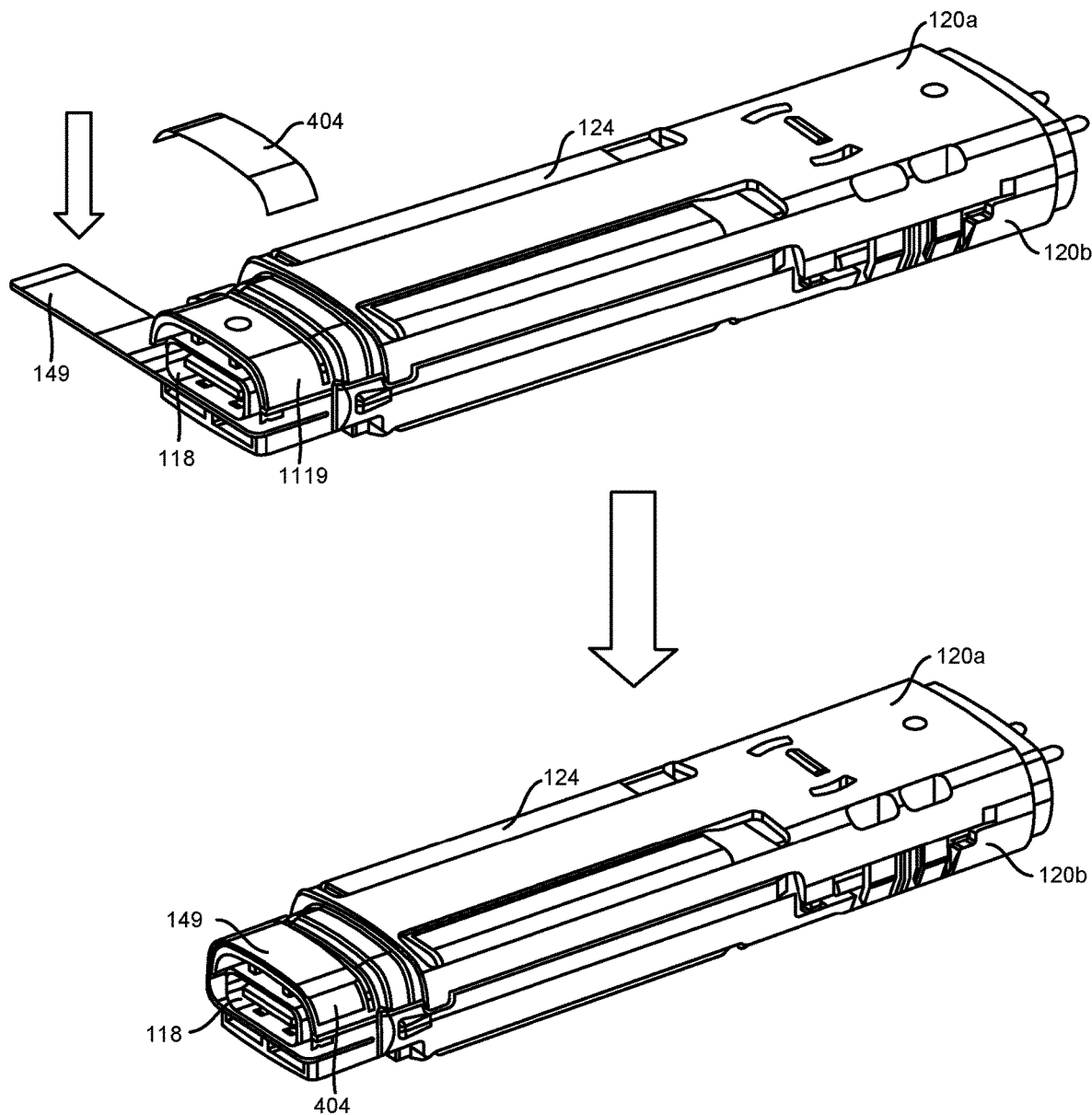
Figure 11N:
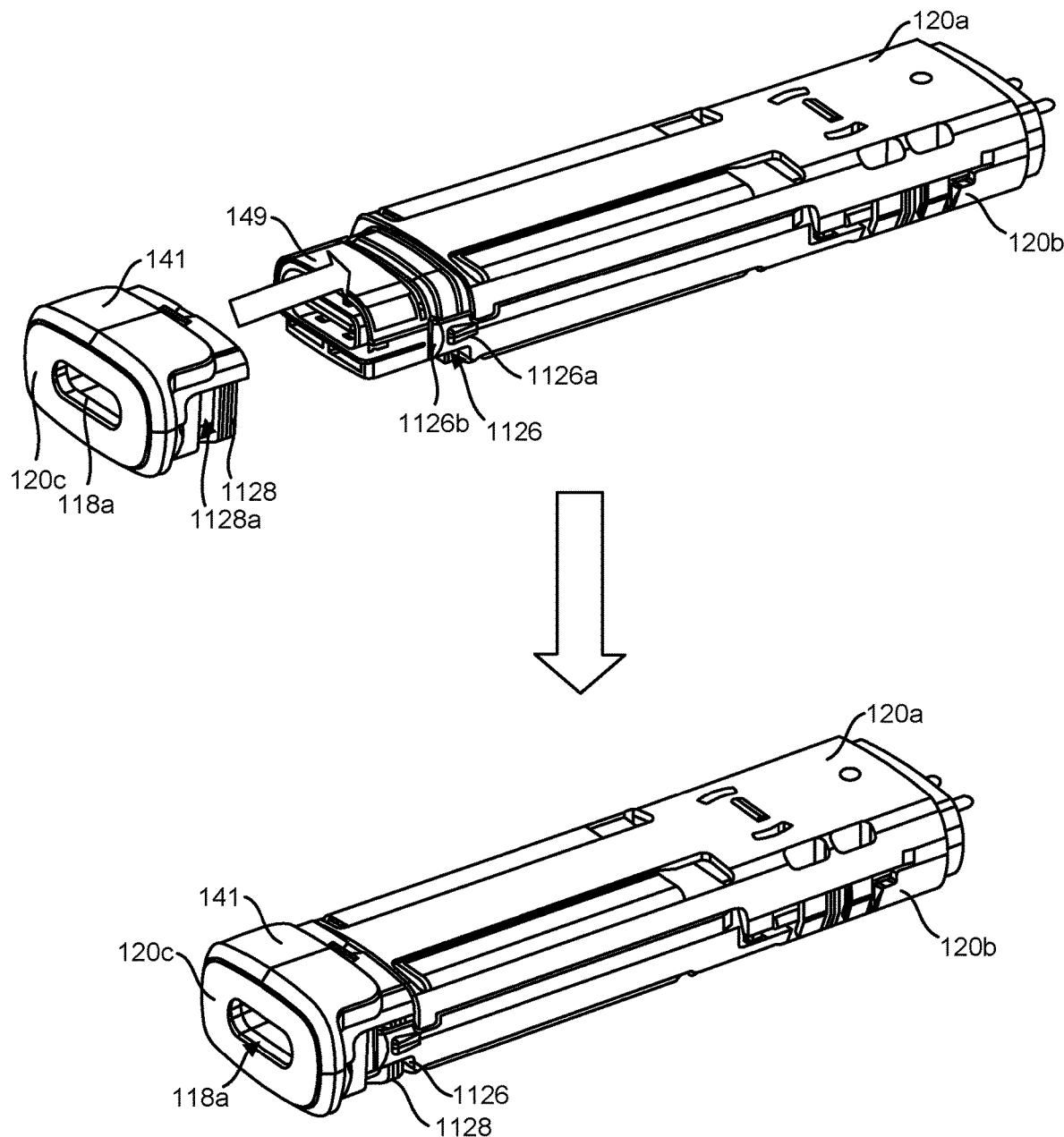
Figure 11O:
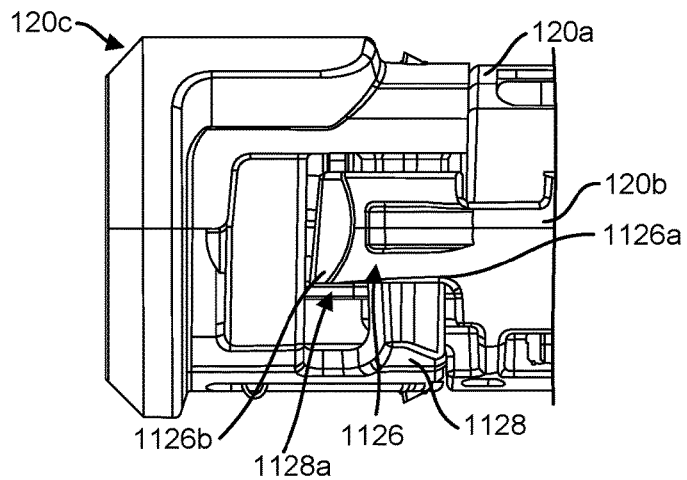
Figure 11P:
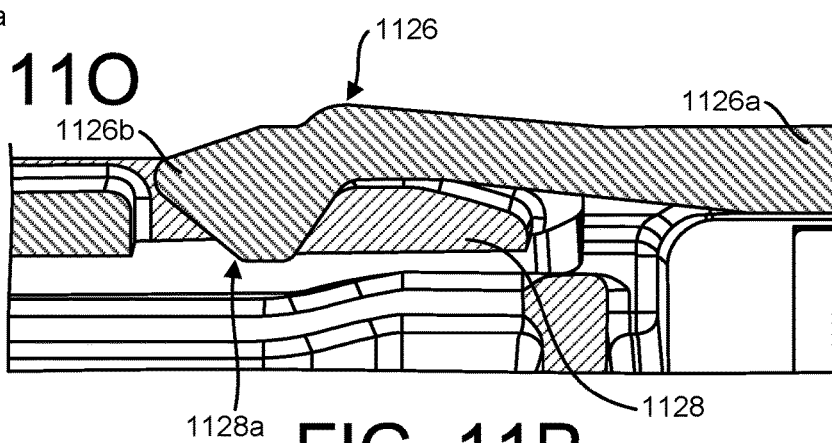
Figure 11Q:
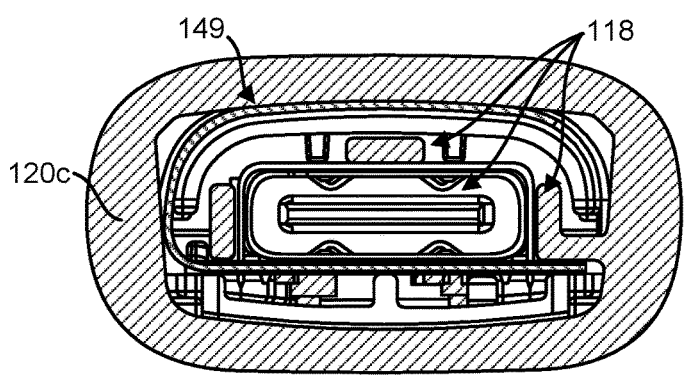
Figure 11R:
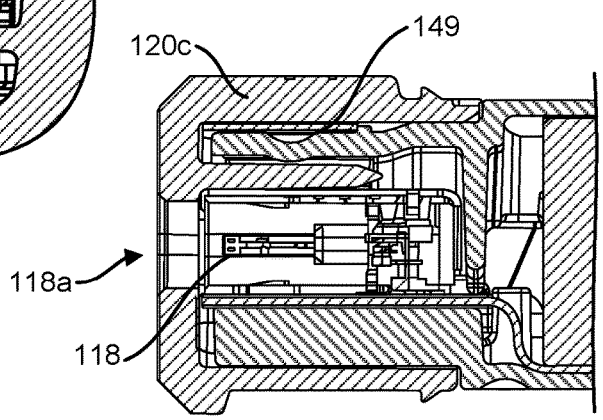
Figure 11S:
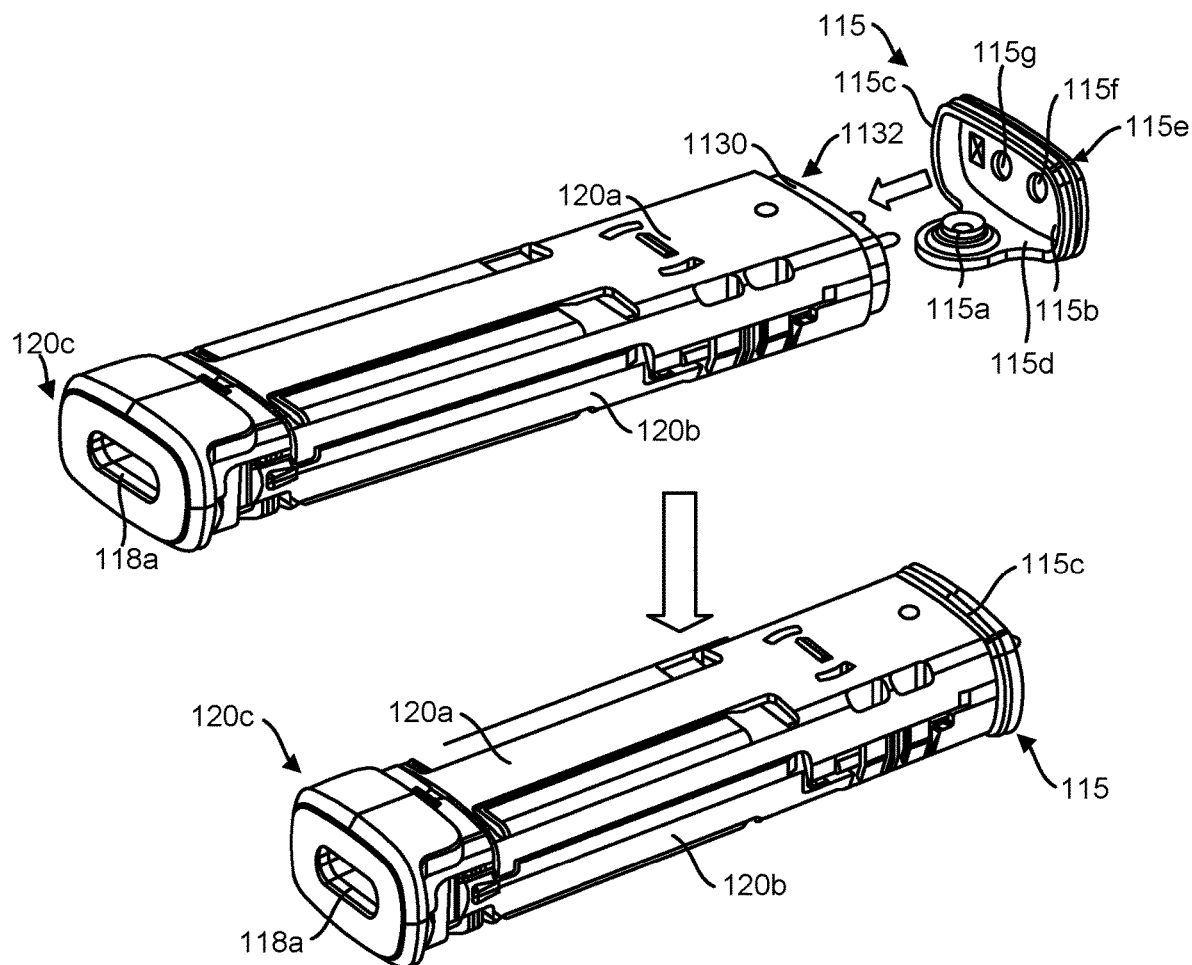
Figure 11T:
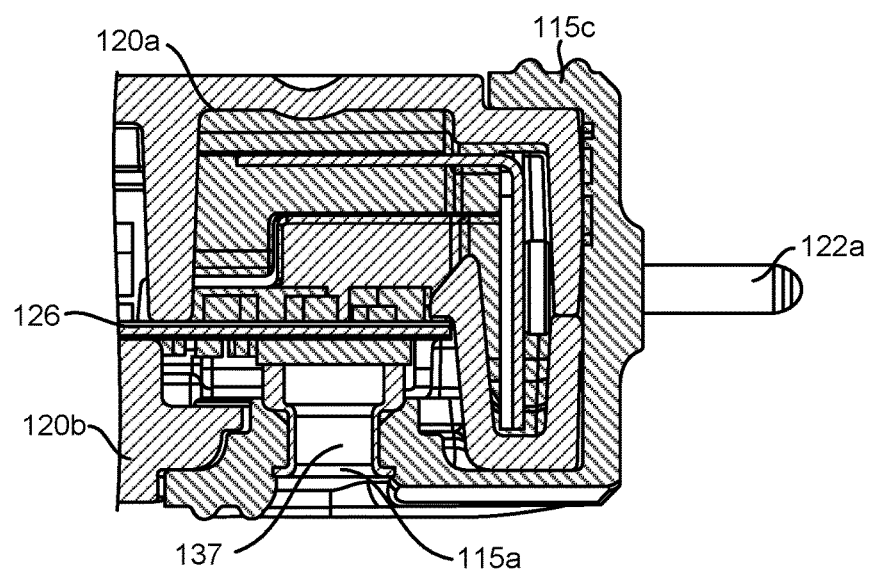
Figure 11U:
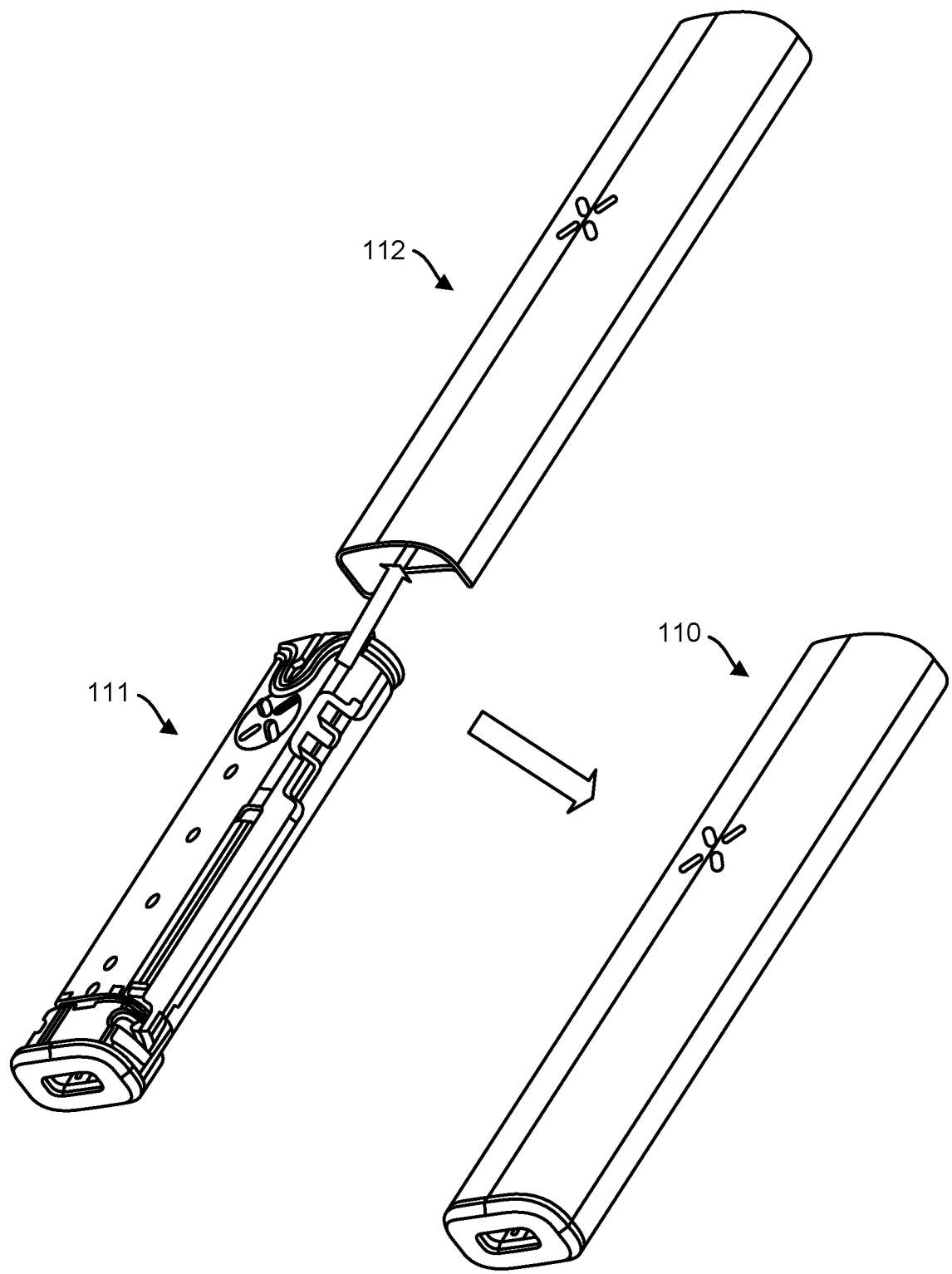
Figure 11V:
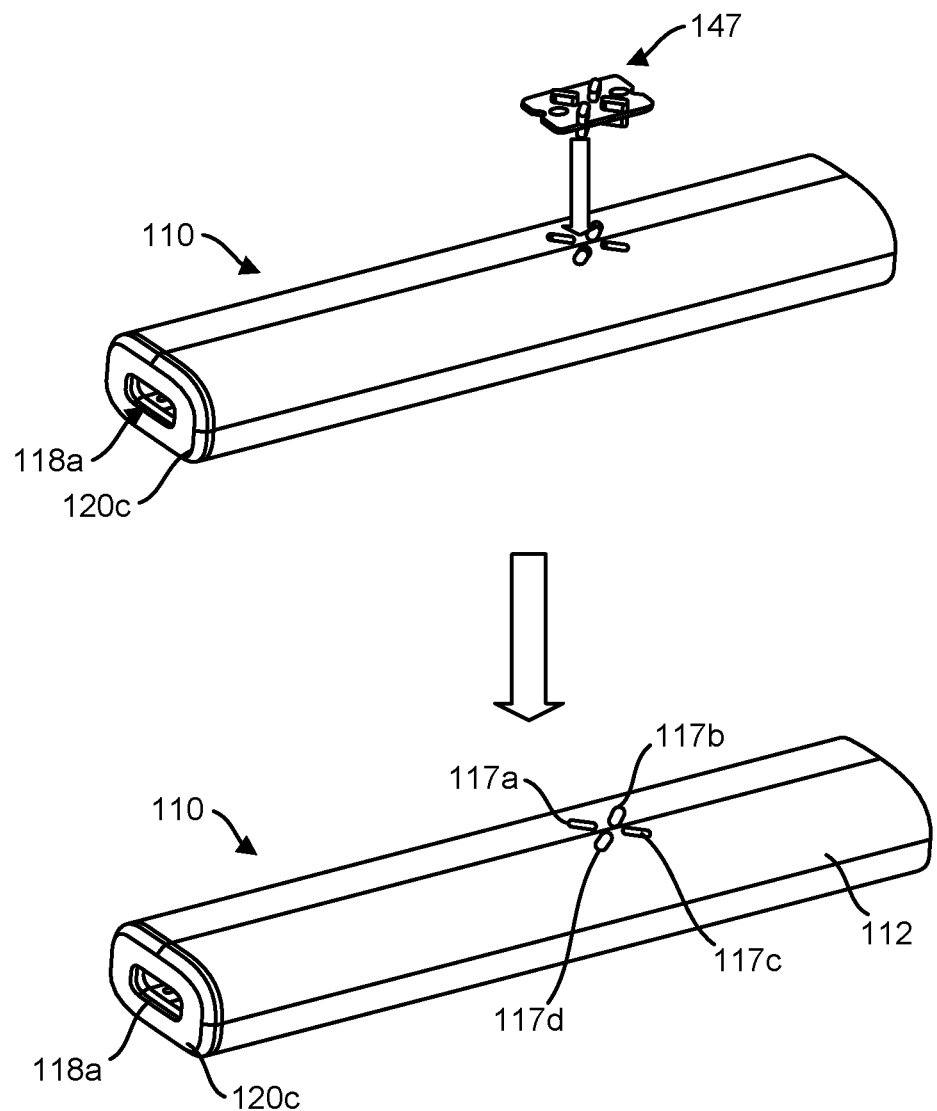

FIGS. 11A-11V illustrate various assembly steps of the vaporizer body 110 consistent with implementations of the current subject matter. As previously noted, the inner assembly 111 has a support structure for securely holding various components within the outer shell 112. The support structure may include the bottom support structure 120*b*, the top support structure 120*a*, the bottom cap 120*c*, and the gasket 115. FIG. 11A provides an example overview of the assembly of the vaporizer body 110 from a top perspective viewpoint. As initial steps, the integrated board assembly 400 is snapped or otherwise fitted into the bottom support structure 120*b*, the battery 124 is connected to the integrated board assembly 400, and the haptics system (e.g., LRA) 144 is snapped or otherwise inserted into and secured within the top support structure 120*a* (the interior or bottom side of the top support structure 120*a* is shown). The top support structure 120*a* and the bottom support structure 120*b* are then snapped or otherwise connected together. The bottom cap 120*c*, which can include an antenna window 141 for the second antenna 149, is snapped on to the assembled structure (i.e., the top and the bottom support structures 120*a*, 120*b* connected together). The gasket 115 is installed at a proximal end of the assembled structure (i.e., the top and the bottom support structures 120*a*, 120*b* connected together), the entirety of which can then be slid into an outer shell 112. Finally, the light pipe 147 may be added, as described above with respect to FIGS. 8A-8D.

FIGS. 11B-D provide views of the integrated board assembly 400 being inserted into the bottom support structure 120*b* consistent with some implementations of the current subject matter. FIG. 11B is a top perspective view indicating placement of the integrated board assembly 400 with respect to the bottom support structure 120*b*, and FIG. 11C is a top perspective view of the integrated board assembly 400 in the bottom support structure 120*b*. First, the proximal end 402*a* of the flexible layer 402, at which the first antenna 143 and the power pins 122*a,b* are integrated, is folded 180 degrees, as indicated in FIG. 11B. In an alternative implementation, the proximal end 402*a* may be oriented in such a way that it does not need to be folded (e.g., the proximal end 402*a* extends from the proximal end of the flexible layer 402).

The PCBA 126 portion of the integrated board assembly 400 is snapped into the bottom support structure 120*b* by engaging side snaps 1102*a,b* that extend upward from respective side portions of the bottom support structure 120*b*, as shown in FIGS. 11B and 11C. The side snaps 1102*a,b* are depressed by a force applied to the PCBA 126 when in contact with the side snaps 1102*a,b*, and the side snaps 1102*a,b* release to extend over side portions of the PCBA 126 when the PCBA 126 is forced below the side snaps 1102*a,b*. An internal front snap 1102*c* may also be provided to secure a proximal end of the PCBA 126, as shown in FIG. 11C. Locating bosses 1104*a,b*, extending upward from respective side portions of the bottom support structure 120*b*, may also be provided. The locating bosses 1104*a,b* are vertically-extending posts that fit within a corresponding cut-out region of the PCBA 126.

The quantity and location of side snaps 1102 and locating bosses 1104 may vary, and fewer or additional of each may be provided. In some implementations, side snaps are not required and the PCBA 126 is placed within the bottom support structure 120*b*. In some implementations, the locating bosses 1104 are not provided. In some implementations, additional side snaps 1102 are provided near, for example, the proximal end of the bottom support structure 120b.

As shown in the front view looking towards the proximal end of the bottom support structure 120b of FIG. 11D, the proximal end of the bottom support structure 120b may have a teeth configuration including alternating valleys 1110a,b,c,d,e and peaks 1108a,b,c,d, which may be sized and shaped to hold the power pins 122a,b in valleys 1110b,d, respectively. Side snaps 1106 may be formed on each side of the valleys 1110b,d. When the integrated board assembly 400 is inserted into the bottom support structure 120b, the side snaps 1106 may be engaged by the respective power pins, causing the power pins 122a,b to be pushed below the side snaps 1106, which serve to secure the power pins 122a,b within the respective valleys 1110b,d.

FIGS. 11E-11G provide views of the battery 124 being connected to the integrated board assembly 400 within the bottom support structure 120b. FIG. 11E is a top perspective view indicating placement of the battery 124 with respect to the bottom support structure 120b. FIG. 11F is a top perspective view of the battery 124 being connected to the PCBA 126 in the bottom support structure 120b, while FIG. 11G is a cross-sectional, bottom perspective view illustrating connection of the battery 124 on the PCBA 126.

A bottom liner on a bottom portion of the battery 124 may be provided to protect an adhesive portion on the bottom portion of the battery 124. The bottom liner is removed and the battery connector point 124a is pressed into the battery connector 125 on the PCBA 126 to ensure a proper engagement (see FIG. 11F). As shown in FIG. 11G, a board support 1114 may extend upward from the bottom support structure 120b to engage the portion of the PCBA 126 where the battery connector 125 is located.

The battery 124 is seated into an opening 1112 in the bottom support structure 120b sized and shaped to hold the battery 124, and a force may be applied to adhere the adhesive portion of the battery 124 to the bottom support structure 120b.

A bottom liner from the foam piece 406 is removed, and the foam piece 406 is adhered to a top side of the battery connector point 124a. The foam piece 406 may serve to fill a gap above the battery connector point 124a and also serve to keep in place the connection between the battery connector point 124a and the battery connector 125. An additional foam piece may be provided to sit on and adhere to a top surface of the battery 124. Such an additional foam piece may be approximately the same size of the upper surface of the battery 124 or may be of a slightly smaller or larger size with similar lengthwise and widthwise proportions. The additional foam piece may help ensure that the battery 124 stays in place during use of the vaporizer device 100.

FIG. 11H illustrates the connection of the haptics system (e.g., LRA) 144 into the top support structure 120a. FIG. 11H is a bottom perspective view indicating placement of the haptics system 144 with respect to the top support structure 120a. A cavity 1116a defined by a sidewall 1116 extending upward from an inner portion of the top support structure 120a is provided, and is sized and shaped to hold within the haptics system 144. A bottom liner from the haptics system 144 may be provided and removed to expose an adhesive portion, and the haptics system 144 may be snapped into the cavity 1116a by engaging side snaps 1117a,b that extend upward from the sidewall 1116. The side snaps 1117a,b are depressed by a force applied to the haptics system 144 when in contact with the side snaps 1117a,b, and the side snaps 1117a,b release to extend over side portions of the haptics system 144 when the haptics system 144 is forced below the side snaps 1117a,b. A force may be applied to adhere the adhesive portion of the haptics system 144 to the inner portion of the top support structure 120a. In some implementations, the adhesive portion is not provided. In some implementations, the side snaps 1117a,b are not provided, while in other implementations, fewer or additional side snaps may be included.

FIGS. 11I-11L provide views of the top support structure 120a and the bottom support structure 120b being snapped together. FIG. 11I is a top perspective view indicating placement of the top support structure 120a and the bottom support structure 120b with respect to one another. One or more outer side snaps 1122a,b may extend vertically downward from an outer perimeter of the top support structure 120a and may be configured to engage respective side tabs 1124a,b that extend outward from an outer perimeter of the bottom support structure 120b. When a force is applied to the top support structure 120a, the side tabs 1124a,b cause the outer side snaps 1122a,b to deflect outward and engage the side tabs 1124a,b (as shown in FIG. 11I and the top perspective view in FIG. 11J). Although one side of the top and the bottom support structures 120a, 120b is shown, the other side may have equivalent snaps and tabs. Moreover, in some embodiments, fewer or additional snaps/tabs may be incorporated.

With reference to FIG. 11K (a front view looking towards the proximal ends of the top support structure 120 and the bottom support structure 120b), the proximal end of the top support structure 120a may have a teeth configuration configured to align and mate with that of the proximal end of the bottom support structure 120b (described with reference to FIG. 11D). In particular, an alternating peak 1120a,b,c,d,e of the top support structure 120a may securely fit within a corresponding valley 1110a,b,c,d,e of the bottom support structure 120b, and an alternating peak 1108a,b,c,d of the bottom support structure 120b may securely fit within a corresponding valley 1118a,b,c,d of the top support structure 120a. When the top support structure 120a and the bottom support structure 120b are aligned, the corresponding teeth configurations are thus matched. The peaks 1120b,d correspond to the positioning of the power pins 122a,b in valleys 1110b,d. The peaks 1120b,d are sized and shaped to fit above the power pins 122a,b and securely engage with the side snaps 1106.

In some implementations, the teeth configuration may include fewer or additional peaks and valleys, and/or the peaks and valleys may be in the form of alternate shapes. For example, rounded or pointed edges may be provided. Moreover, in some implementations, a configuration other than the teeth configuration shown in FIG. 11K may be incorporated on the proximal ends of the top support structure 120a and the bottom support structure 120b. For example, an opening surrounding the power pins 122a,b may be provided in the bottom support structure 120b, while a corresponding mating structure may be provided in the top support structure 120a to match and align with the opening in the bottom support structure 120b. One opening and corresponding mating structure may be provided to surround both of the power pins 122a,b, while in some implementations, a dedicated opening and corresponding mating structure may be provided for each power pin 122a,b.

When the top support structure 120a and the bottom support structure 120b are snapped together, the connection pads 144a,b of the haptics system 144 connect to the spring contacts 145a,b on the PCBA 126, as shown in the cross-sectional front view at the proximal end of FIG. 11L.

FIG. 11M illustrates (via a top perspective view) the second antenna 149 being positioned on the inner assembly 111. A bottom liner and a top liner from the antenna adhesive 404 may be removed, and the antenna adhesive 404 is applied to a region 1119 at the distal end of the top support structure 120a. The distal end 402b of the flexible layer 402, at which the second antenna 149 is integrated, is folded 180 degrees and aligned with the antenna adhesive 404 on the region 1119. Other configurations in which folding of the distal end 402b of the flexible layer 402 is not required may be provided.

FIGS. 11N-11R provide views of the bottom cap 120c being installed on the distal end of the connected top support structure 120a and bottom support structure 120b (i.e., the top and the bottom support structures 120a, 120b connected together). FIG. 11N is a top perspective view; FIGS. 11O and 11P are side views; FIG. 11Q is a cross-sectional view looking towards the distal end of the connected structure (where the connected structure is defined as the top and the bottom support structures 120a, 120b connected together); and FIG. 11R is a cross-sectional side view of the distal end of the connected structure (i.e., the top and the bottom support structures 120a, 120b connected together). FIG. 11Q is a back cross-sectional view and FIG. 11R is a side cross-sectional view, illustrating the bottom cap 120c installed and connected on the connected structure (i.e., the top and the bottom support structures 120a, 120b connected together).

A distal side snap 1126 may be provided on a side portion of the distal end of the bottom support structure 120b. The distal side snap 1126 is connected at first end 1126a to the side portion of the distal end of the bottom support structure 120b, while the second end 1126b is free and configured to flex inward and outward. The bottom cap 120c has a side snap engagement component 1128 that is sized and shaped to engage with the distal side snap 1126. When pressure is exerted on the bottom cap 120c to push the bottom cap onto the connected structure (i.e., the top and the bottom support structures 120a, 120b connected together), the second end 1126b of the distal side snap is forced outward while the side snap engagement component 1128 slides underneath the distal side snap 1126. The second end 1126b rests in opening 1128a (see FIGS. 11O and 11P). Although one side of the bottom cap 120c is shown, the other side may have equivalent engagement features. Moreover, in some implementations, an alternative connection component for the assembly of the bottom cap 120c on the distal end of the connected structure (i.e., the top and the bottom support structures 120a, 120b connected together) may be provided. In some implementations, side snaps are not provided. Rather, the bottom cap snap-fits via a friction fit or the like onto the connected structure.

FIGS. 11S and 11T illustrate the gasket 115 being installed on the proximal end of the connected structure (i.e., the top and the bottom support structures 120a, 120b connected together). FIG. 11S is a top perspective view and FIG. 11T is a side cross-sectional view indicating placement of the gasket 115 with respect to the connected structure.

When connected, the proximal end of the connected structure forms a front plate 1132 with a recessed region 1130 surrounding a circumference of the front plate 1132. The gasket 115 is sized and shaped with a flat top portion 115e and an opposing flat bottom portion 115b that is substantially equivalent in size and shape to the front plate 1132. A lip 115c extends downward around a circumference of the gasket 115, surrounding the bottom portion 115b. The lip 115c may have one or more ridges formed along its outer circumference. The gasket 115 also includes a tab 115d that extends from a back end of the lip 115c. A front end tab may also be provided to assist in the sealing functions of the gasket 115. The sealing ring 115a is formed through the tab 115d. Gasket openings 115f,g are formed through the top and bottom portions 115e, 115b and are configured to surround the power pins 122a,b when the gasket 115 is installed on the connected structure.

When the gasket 115 is installed on the connected structure, the lip 115c engages and surrounds the recessed region 1130 of the connected structure. The tab 115d extends along a bottom portion of the bottom support structure 120b, and the sealing ring 115a securely interfaces with the pressure sensor 137 through opening 115h extending through the bottom support structure 120b (see FIG. 4B). The outer circumference of the sealing ring 115a provides a tight seal with the pressure sensor 137, as shown in the side cross-sectional view of FIG. 11T (also see FIG. 4E).

The gasket 115 thus serves to seal the pressure sensor 137 and seal the power pins 122a,b, thereby creating a sealed chamber when a cartridge 150 is inserted into the cartridge receptacle 114, adjacent to the gasket 115. This allows the pressure sensor 137 to detect pressure changes when a user draws on the cartridge 150. The gasket 115 also serves to protect the internal components of the inner assembly 111 from the vaporizable material contained in the cartridge 150 or from other materials (e.g., water, debris, etc.) that may come into contact with the gasket 115 via the receptacle.

FIG. 11U illustrates (via a bottom perspective view) the inner assembly 111 being inserted (e.g., slid) into the outer shell 112, and FIG. 11V illustrates (via a bottom perspective view) the light pipe 147 being mounted on the outer shell 112, as described in detail with reference to FIGS. 8A-8D, to attach the inner assembly 111 to the outer shell 112, thereby forming the vaporizer body 110.

The vaporizer body 110 assembly process, consistent with implementations described herein, advantageously does not require a soldered connection for the battery 124 or for the haptics system 144. Moreover, the PCBA 126 may be easily snapped into place without mounting pins, additional flex components, and/or tape to hold the flex in place.

Although various connections and engagements are described with reference to assembling the components of the inner assembly 111 and the vaporizer body 110, these connections and engagements are exemplary and non-limiting examples of how the various components may be assembled. For example, different types of snaps and engagements may be utilized and incorporated. In some instances as noted herein, snaps and connection mechanisms may not be incorporated and instead various components may fit within or connect to each other without snapping or connecting.

Figure 32A:
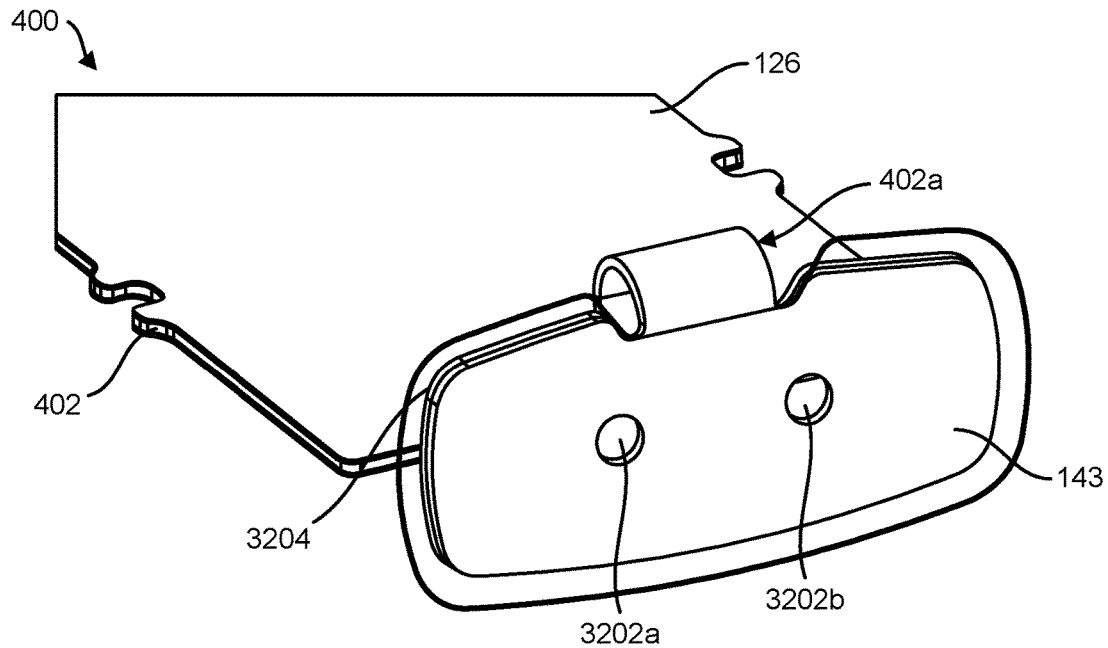
FIG. 32A-FIG. 32H illustrate features of an integrated board assembly and a support structure of a vaporizer device consistent with implementations of the current subject matter.
Figure 32B:
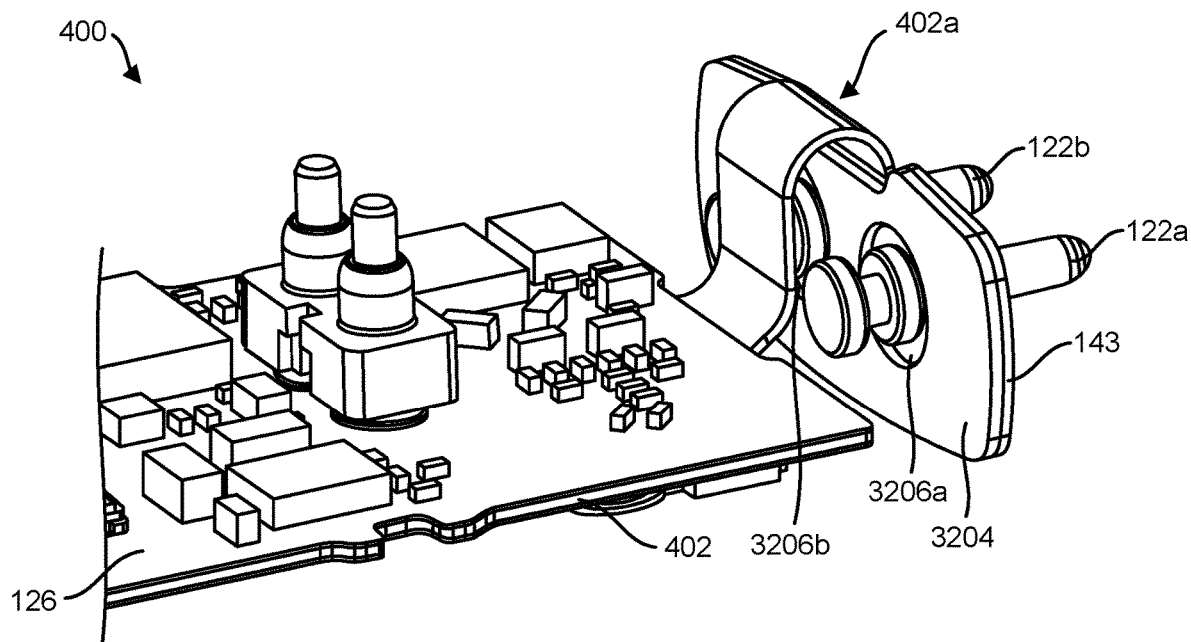

FIGS. 32A-32H illustrate features of the integrated board assembly 400 and the support structure in accordance with an alternative implementation of the current subject matter. FIG. 32A is a top perspective view of a portion of the integrated board assembly 400 looking from the proximal end, and FIG. 32B is a top perspective view of a portion of the integrated board assembly 400 looking from the distal end. As previously noted, the proximal end 402a (at which the first antenna 143 is integrated) of the flexible layer 402 may extend from a proximal (e.g., front) end of the PCBA 126, as shown in FIGS. 32A and 32B. The proximal end 402a of the flexible layer 402, in this configuration, may extend outward from the proximal end of the PCBA 126 and curve or bend so that the planar surface (having a front surface and a back surface) of the first antenna 143 is positioned in a perpendicular configuration with respect to the top and bottom surfaces of the PCBA 126. For example, the proximal end 402a of the flexible layer 402 may be curved approximately 180 degrees so that the planar surface of the first antenna 143 is properly oriented. In some implementations, the proximal end 402a of the flexible layer 402 may be bent at one or more angles so that the planar surface of the first antenna 143 is properly oriented.

Antenna through-holes 3202a,b may extend through the planar surface of the first antenna 143. The power pins 122a,b may be positioned to extend through respective ones of the antenna through-holes 3202a,b, and may be connected (e.g., soldered) to the back surface of the first antenna 143. A support plate 3204 may be provided and may have a planar surface adjacent to and that aligns with that of the first antenna 143. The support plate 3204 may include support openings 3206a,b that align with the antenna through-holes 3202a,b respectively, and the power pins 122a,b extend through the support openings 3206a,b. The support openings 3206a,b may be of a larger diameter than those of the antenna through-holes 3202a,b to provide sufficient space for distal ends of the power pins 122a,b, as shown in FIG. 32B. A front surface of the support plate 3204 may be attached to (e.g., adhered to or otherwise connected to) the back surface of the first antenna 143. The support plate 3204 may be of various resilient materials that maintain their form and that do not interact with the first antenna 143 and the PCBA 126, such as an FR-4 PCB material. The support plate 3204 may have a thickness of approximately 0.25 mm although other thicknesses may be utilized. The planar surface of the support plate 3204 may be slightly larger than or slightly smaller than that of the first antenna 143, and may be of a similar shape or may have a dissimilar shape.

Figure 32C:
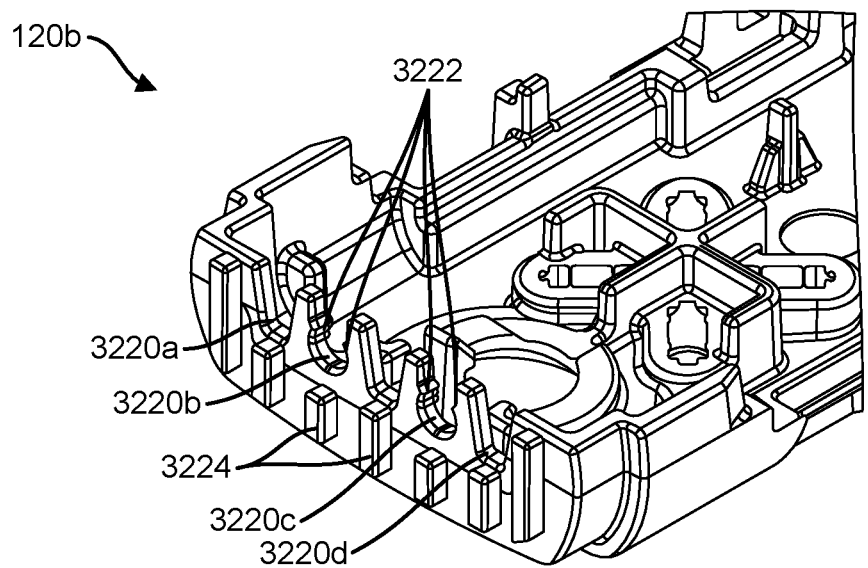
Figure 32D:
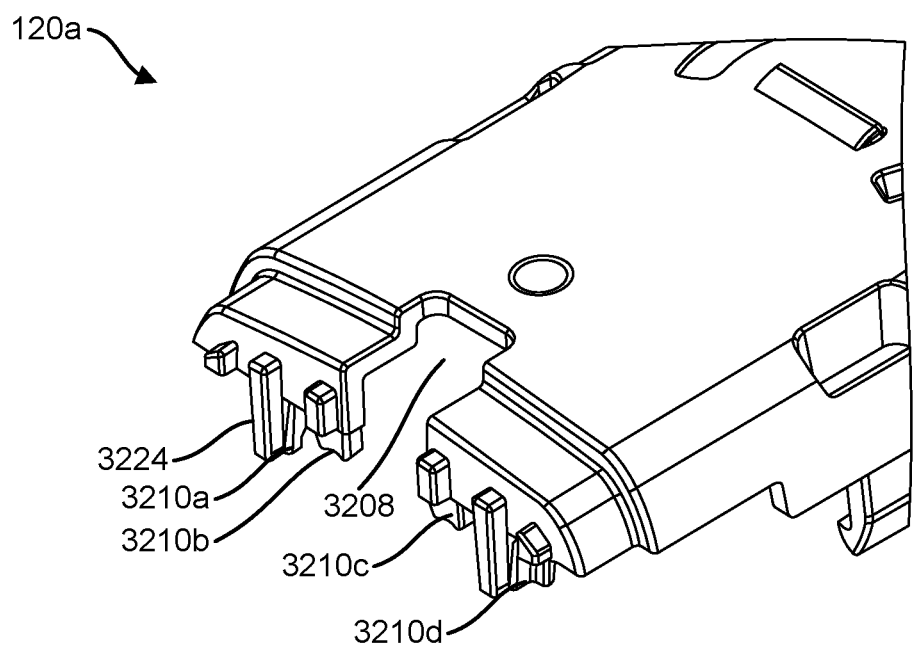
Figure 32E:
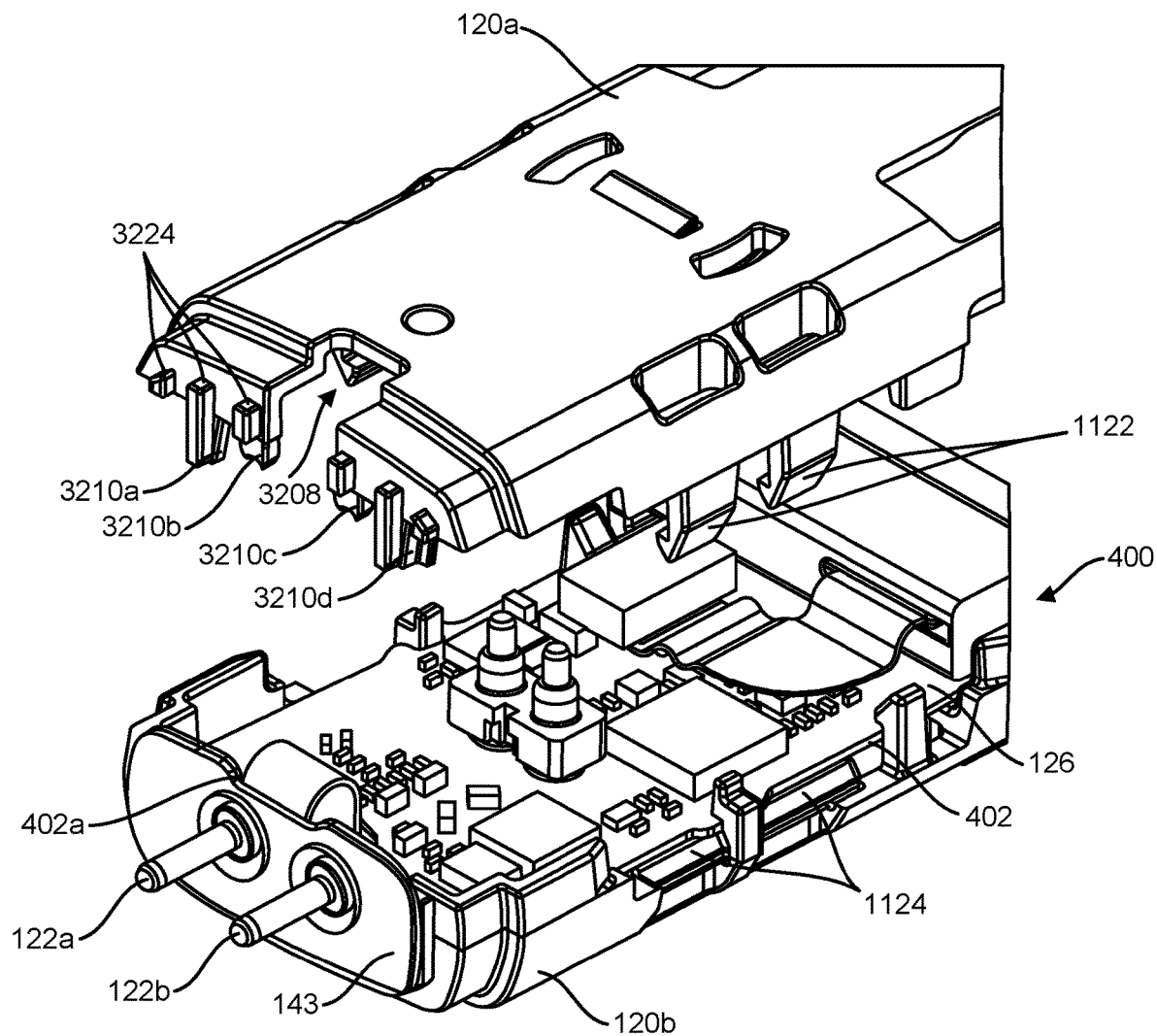

FIG. 32C is a top perspective view of a portion of the bottom support structure 120b looking from the proximal end, and FIG. 32D is a top perspective view of a portion of the top support structure 120a looking from the proximal end. FIG. 32E is a top perspective view showing alignment of the top support structure 120a, the integrated board assembly 400, and the bottom support structure 120b, looking from the proximal ends of each.

An opening 3208 on the top surface at the proximal end of the top support structure 120a is sized and shaped to accommodate the proximal end 402a of the flexible layer 402 in the configuration in which the proximal end 402a extends from the proximal end of the PCBA 126.

A teething configuration on proximal ends of the top support structure 120a and the bottom support structure 120b is provided to allow for alignment and connection of the respective proximal ends. In particular, a teething configuration of the top support structure 120a may include downward-extending protrusions 3210a,b,c,d that mate (e.g., with a friction fit) with corresponding upward-extending openings (or gaps) 3220a,b,c,d that are formed in the proximal end of the bottom support structure 120b. The openings 3220b,c may be sized and shaped to hold the power pins 122a,b respectively, with the power pins 122a,b extending longitudinally outward through the openings 3220b,c. The corresponding protrusions 3210b,c may be of a downward length sufficient to allow the power pins 122a,b respectively to securely fit within the openings 3220b,c and engage flexible side protrusions 3222 with for example a friction fit. The side protrusions 3222 may be formed on each side of the openings 3220b,c and protrude inward in the respective openings 3220b,c. The power pins 122a,b contact the side protrusions 3222 upon a force being applied to the power pins 122a,b, and the side protrusions releasably secure the power pins 122a,b within the openings 3220b,c below a bottom surface of the side protrusions 3222. When the integrated board assembly 400 is inserted into the bottom support structure 120b, the side protrusions 3222 may be engaged by the respective power pins, causing the power pins 122a,b to be pushed below the side protrusions 3222, which serve to secure the power pins 122a,b within the respective openings 3220b,c.

As shown in FIG. 32E, when the integrated board assembly 400 is inserted into the bottom support structure 120b, the first antenna 143 and the support plate 3204 are positioned on an outer side of the proximal end of the bottom structure 120b. The configuration of the proximal end 402a of the flexible layer 402 and the first antenna 143, as shown in FIGS. 32A and 32B, provides for the planar surface of the first antenna 143 to align with the proximal end of the bottom support structure 120b.

The top support structure 120a and the bottom support structure 120b may then be connected by proper alignment and engagement of the respective teething configurations to align the proximal ends of the top and the bottom support structures 120a, 120b. Additionally, as described with respect to FIGS. 11I and 11J, outer side snaps 1122a,b may engage side tabs 1124a,b to secure the top and the bottom support structures 120a, 120b to one another.

Outward-extending tabs 3224 may be provided on the proximal ends of the top support structure 120a and the bottom support structure 120b to provide one or more flat surfaces against which the back end of the support plate 3204 may contact.

Figure 32F:
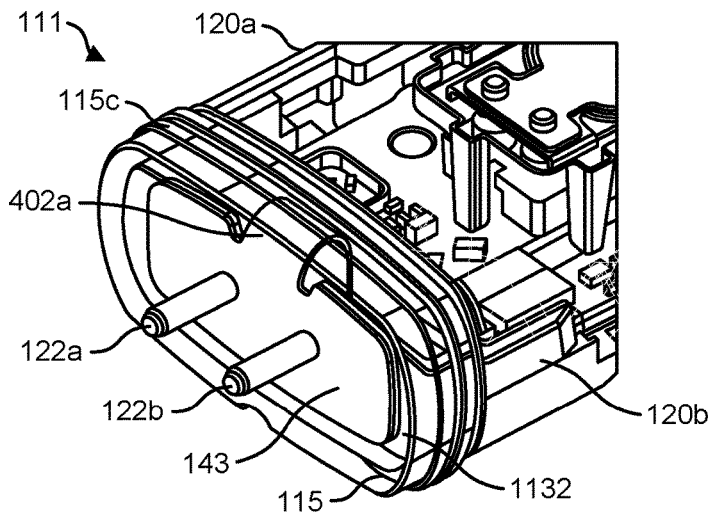
Figure 32G:
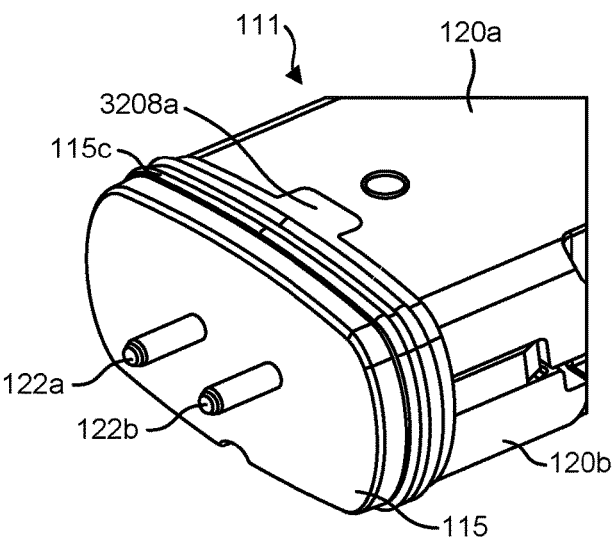

FIGS. 32F and 32G are top perspective views, looking from the proximal ends, showing the inner assembly 111 in which the integrated board assembly 400 is secured, the top and the bottom support structures 120a, 120b connected to one another, and the gasket 115 installed on the proximal end of the connected structure (i.e., the top and the bottom support structures 120a, 120b connected together). The connected structure and the gasket 115 are semi-transparent in FIG. 32F to illustrate the placement of the various components with respect to these outer structures.

When the top support structure 120a and the bottom support structure 120b are connected together, the planar surface of the first antenna 143 aligns with the outer side of the proximal ends of the connected structure as shown in FIG. 32F.

As described above with respect to FIGS. 11S and 11T, the lip 115c of the gasket 115 is configured to engage and surround the recessed region 1130 at the proximal end of the connected structure when installed on the connected structure so that the planar surface of the gasket 115 aligns with the front plate 1132 of the connected structure. As the first antenna 143 is positioned adjacent to the front plate 1132, the first antenna 143 is positioned or sandwiched (e.g., substantially parallel) between the front plate 1132 and the gasket 115, with the power pins 122a,b extending through the gasket 115 (e.g., through the gasket openings 115f,g formed through the planar surface of the gasket 115 and configured to surround the power pins 122a,b when the gasket 115 is installed on the connected structure as described with respect to FIG. 11S). The gasket 115 may additionally have a tab 3208a extending from the lip 115c of the gasket 115 to mate with the opening 3208 on the top surface at the proximal end of the top support structure 120a.

Figure 32H:
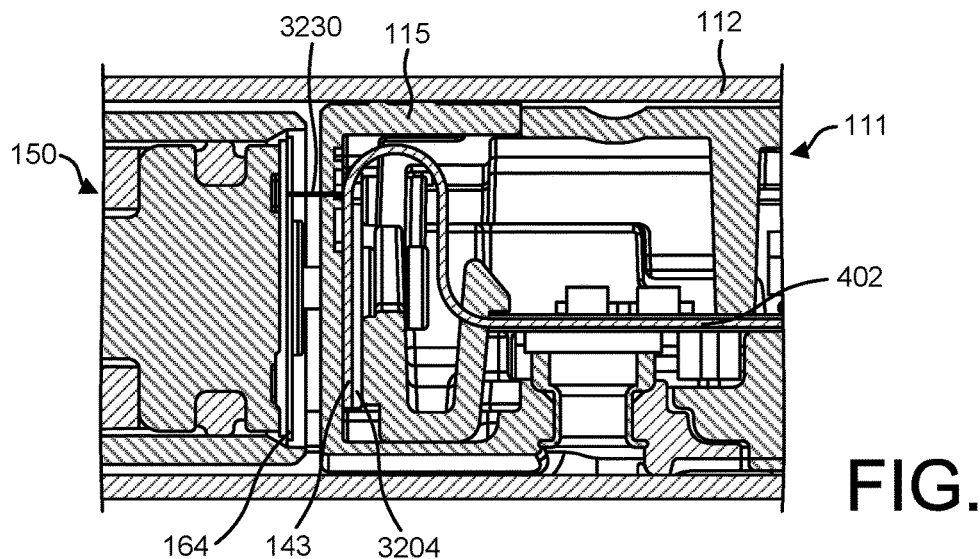

FIG. 32H is a cross-sectional side view showing a portion of the vaporizer device 100 with the cartridge 150 inserted into the cartridge receptacle 114 formed by the outer shell 112 of the vaporizer body 110 in which the inner assembly 111 is inserted. In particular, the portion shown includes the distal end of the cartridge 150, on or near which the data tag 164 is positioned, and the proximal end of the inner assembly 111 at which the first antenna 143 is positioned between the gasket 115 and the proximal end of the connected structure. As shown in FIG. 32H, this configuration results in a reduced spacing 3230 between the data tag 164 and the first antenna 143 which advantageously results in improved communication between the cartridge 150 and the vaporizer body 110.

Additionally, the antenna configuration shown in FIGS. 32A-32H provides an improved mounting for the power pins 122a,b as the power pins 122a,b extend lengthwise through both the support openings 3206a,b of the support plate 3204 and the antenna through-holes 3202a,b. This results in increased support for the power pins 122a,a. Moreover, the orientation of the proximal end 402a of the flexible layer 402 provides for more efficient use of space of the PCBA 126 during manufacturing.

Figure 33A:
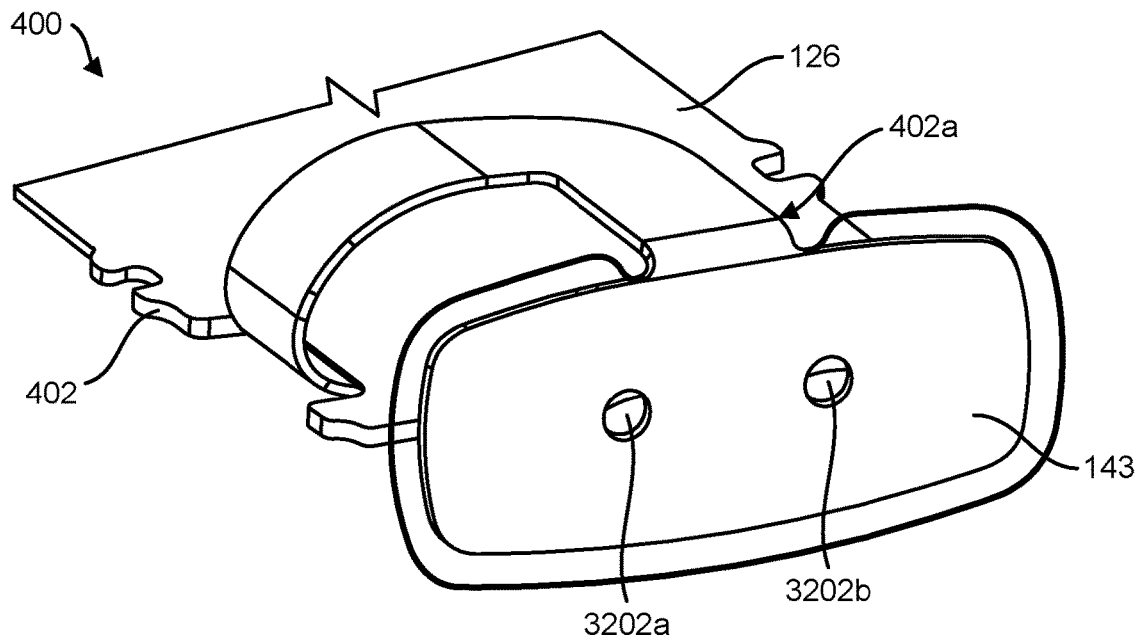
FIG. 33A-FIG. 33G illustrate features of an integrated board assembly and a support structure of a vaporizer device consistent with implementations of the current subject matter.
Figure 33B:
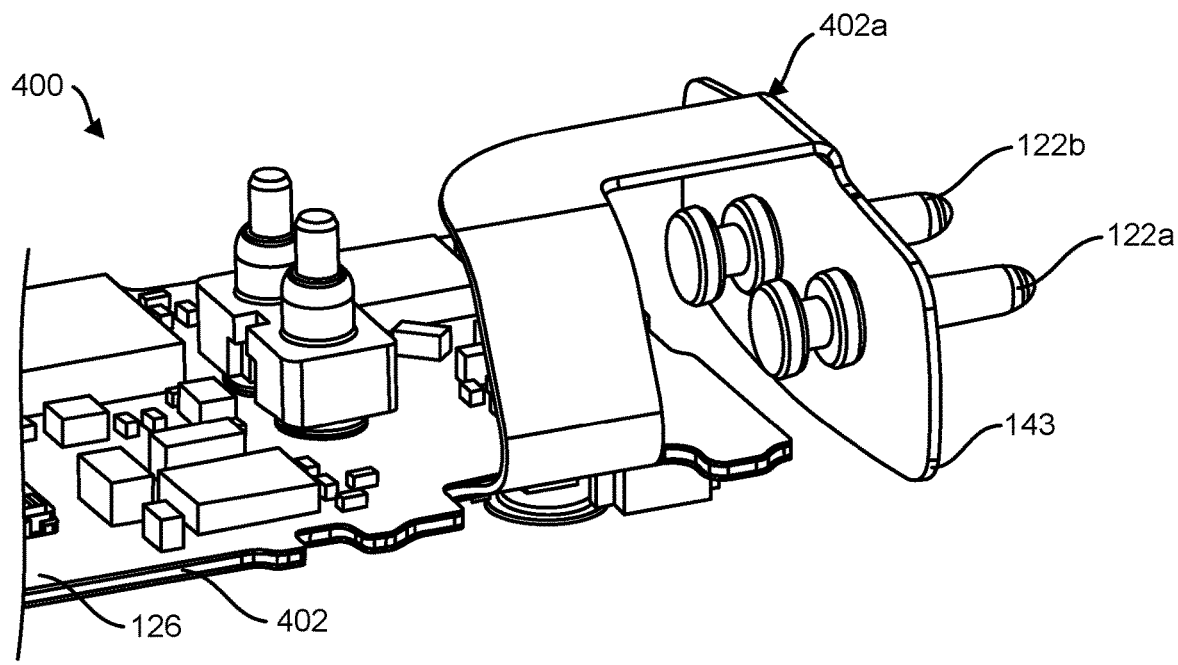

FIGS. 33A-33E illustrate features of the integrated board assembly 400 and the support structure of a vaporizer device consistent with additional implementations of the current subject matter in which the proximal end 402a of the flexible layer 402 extends from a side region of the PCBA 126 and in which the first antenna 143 is oriented such that it is positioned external to the connected structure, as described with reference to FIGS. 33A-33E. FIG. 33A is a top perspective view of a portion of the integrated board assembly 400 looking from the proximal end, and FIG. 33B is a top perspective view of a portion of the integrated board assembly 400 looking from the distal end.

As previously described with respect to FIG. 4B, the proximal end 402a (at which the first antenna 143 is integrated) of the flexible layer 402 may extend from a side region of the PCBA 126, and may include a sideward extending portion and a forward extending portion at about 90 degrees with respect to the sideward extending portion. The first antenna 143 may extend from the forward extending portion such that the planar surface of the first antenna 143 is positioned in a perpendicular configuration with respect to the top and bottom surfaces of the PCBA 126. The proximal end 402a of the flexible layer 402 is folded or bent 180 degrees (as described with reference to FIG. 11B) to achieve the configuration shown in FIGS. 33A and 33B. In this configuration, the planar surface of the first antenna 143 is aligned with the proximal end of the PCBA 126 (e.g., side edges of the planar surface of the first antenna 143 align with side edges of the proximal end of the PCBA 126).

Antenna through-holes 3202a,b may extend through the planar surface of the first antenna 143. The power pins 122a,b may be positioned to extend through respective ones of the antenna through-holes 3202a,b, and may be connected (e.g., soldered) to the back surface of the first antenna 143. A support plate may be provided as described with reference to FIG. 32B.

Figure 33C:
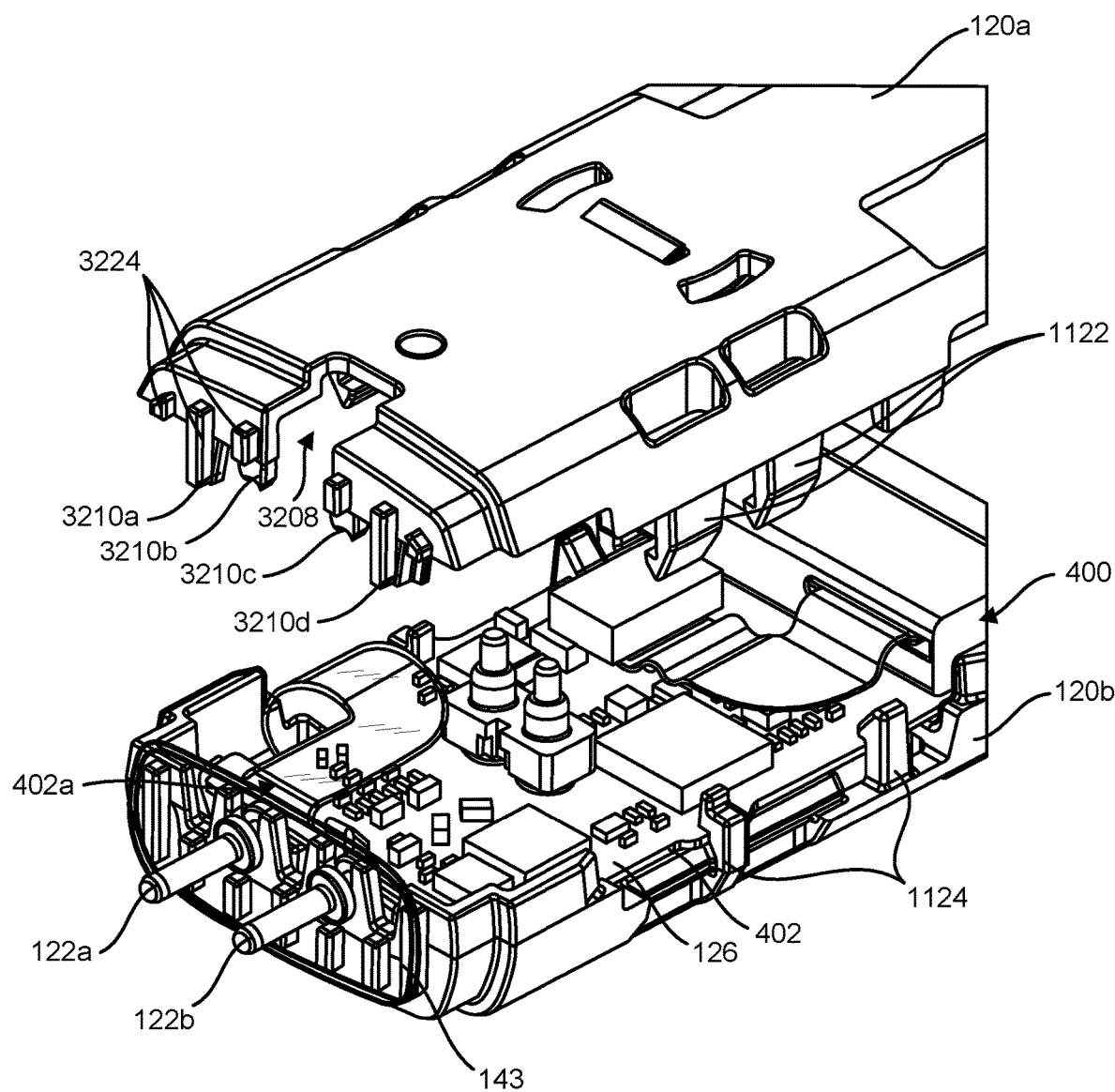

FIG. 33C is a top perspective view showing alignment of the top support structure 120a, the integrated board assembly 400, and the bottom support structure 120b, looking from the proximal ends of each. Features of the top support structure 120a and the bottom support structure 120b may be similar or equivalent to those described elsewhere in the description. For example, the teething configuration of the proximal ends of the top support structure 120a and the bottom support structure 120b, configured to allow for alignment and connection of the respective proximal ends, may be similar to that shown in FIGS. 32C and 32D.

As shown in FIG. 33C, when the integrated board assembly 400 is inserted into the bottom support structure 120b, the first antenna 143 is positioned on an outer side of the proximal end of the bottom structure 120b. The configuration of the proximal end 402a of the flexible layer 402 and the first antenna 143, as shown in FIGS. 33A and 33B, provides for the planar surface of the first antenna 143 to align with the proximal end of the bottom support structure 120b.

The top support structure 120a and the bottom support structure 120b may then be connected by alignment and engagement of the respective teething configurations to align the proximal ends of the top and the bottom support structures 120a, 120b. Additionally, as described with respect to FIGS. 11I and 11J, outer side snaps 1122a,b may engage side tabs 1124a,b to secure the top and the bottom support structures 120a, 120b to one another.

Figure 33D:
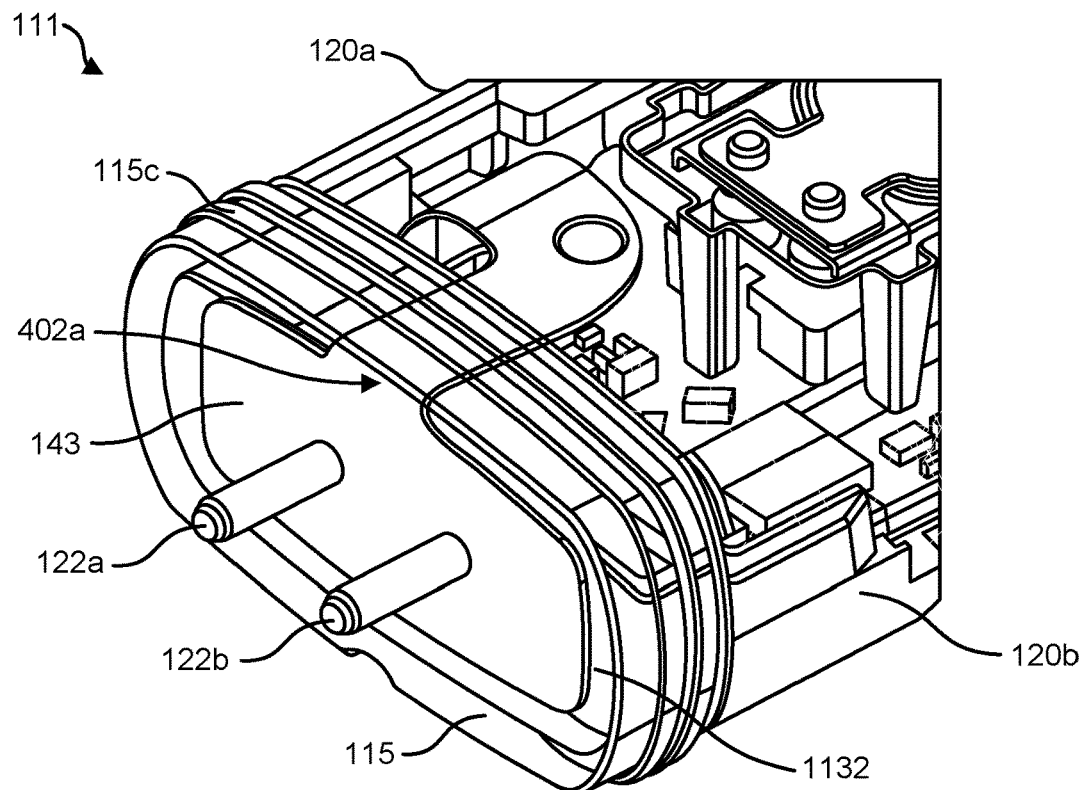

FIG. 33D is a top perspective view, looking from the proximal end, showing the inner assembly 111 in which the integrated board assembly 400 is secured, the top and the bottom support structures 120a, 120b connected to one another, and the gasket 115 installed on the proximal end of the connected structure. The connected structure and the gasket 115 are semi-transparent in FIG. 33D to illustrate the placement of the various components with respect to these outer structures.

When the top support structure 120a and the bottom support structure 120b are connected together, the planar surface of the first antenna 143 aligns with the outer side of the proximal ends of the connected structure as shown in FIG. 33D.

Features of the gasket 115 may be similar to those described with respect to FIGS. 11S, 11T, and 32F. In particular, as the first antenna 143 is positioned adjacent to the front plate 1132 of the connected structure, the first antenna 143 is sandwiched (e.g., substantially parallel to) or positioned between the front plate 1132 and the gasket 115, with the power pins 122a,b extending lengthwise through the gasket 115.

Figure 33E:
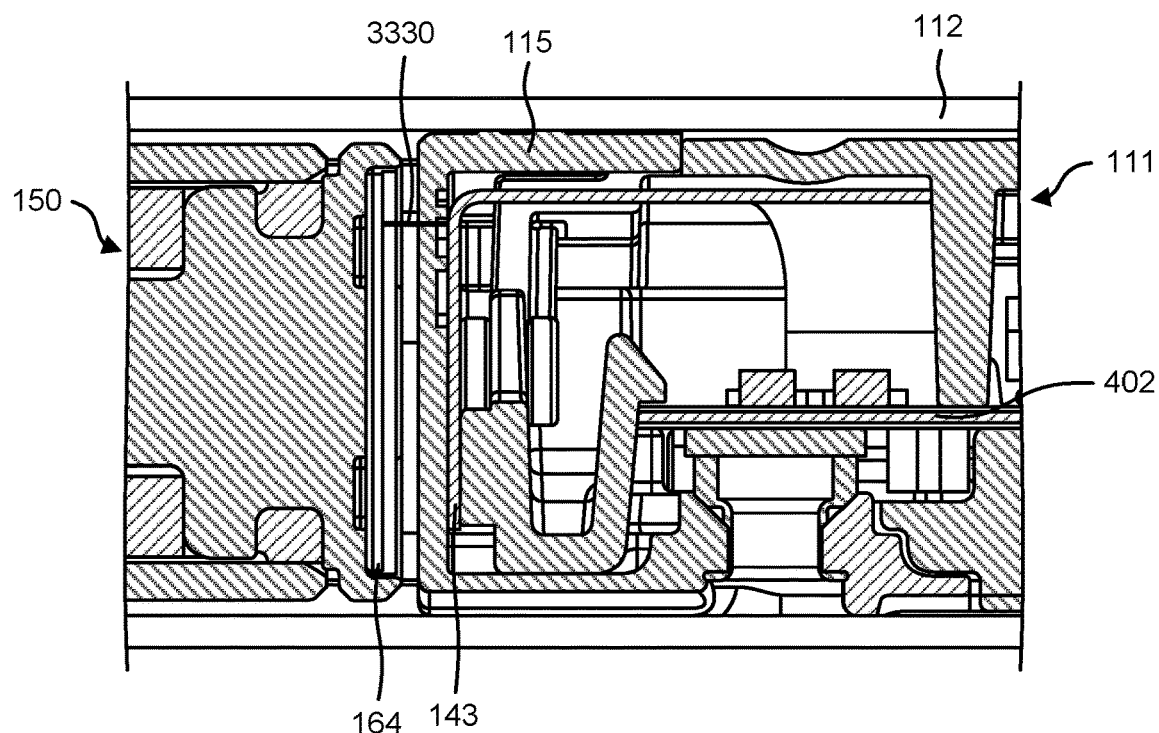

FIG. 33E is a cross-sectional side view showing a portion of the vaporizer device 100 with the cartridge 150 inserted into the cartridge receptacle 114 formed by the outer shell 112 of the vaporizer body 110 in which the inner assembly 111 is inserted. In particular, the portion shown includes the distal end of the cartridge 150, on or near which the data tag 164 is positioned, and the proximal end of the inner assembly 111 at which the first antenna 143 is positioned between the gasket 115 and the proximal end of the connected structure 120a,b. As shown in FIG. 33E, this configuration results in a reduced spacing 3330 between the data tag 164 and the first antenna 143 which advantageously results in improved communication between the cartridge 150 and the vaporizer body 110.

Figure 33F:
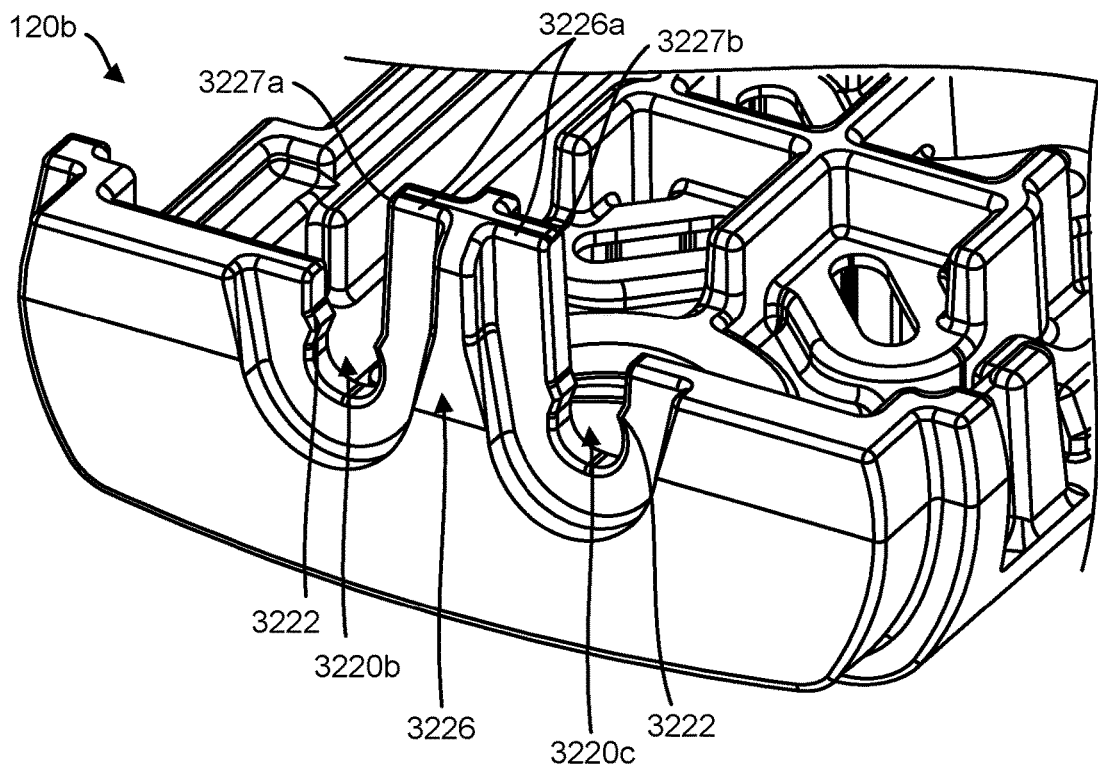
Figure 33G:
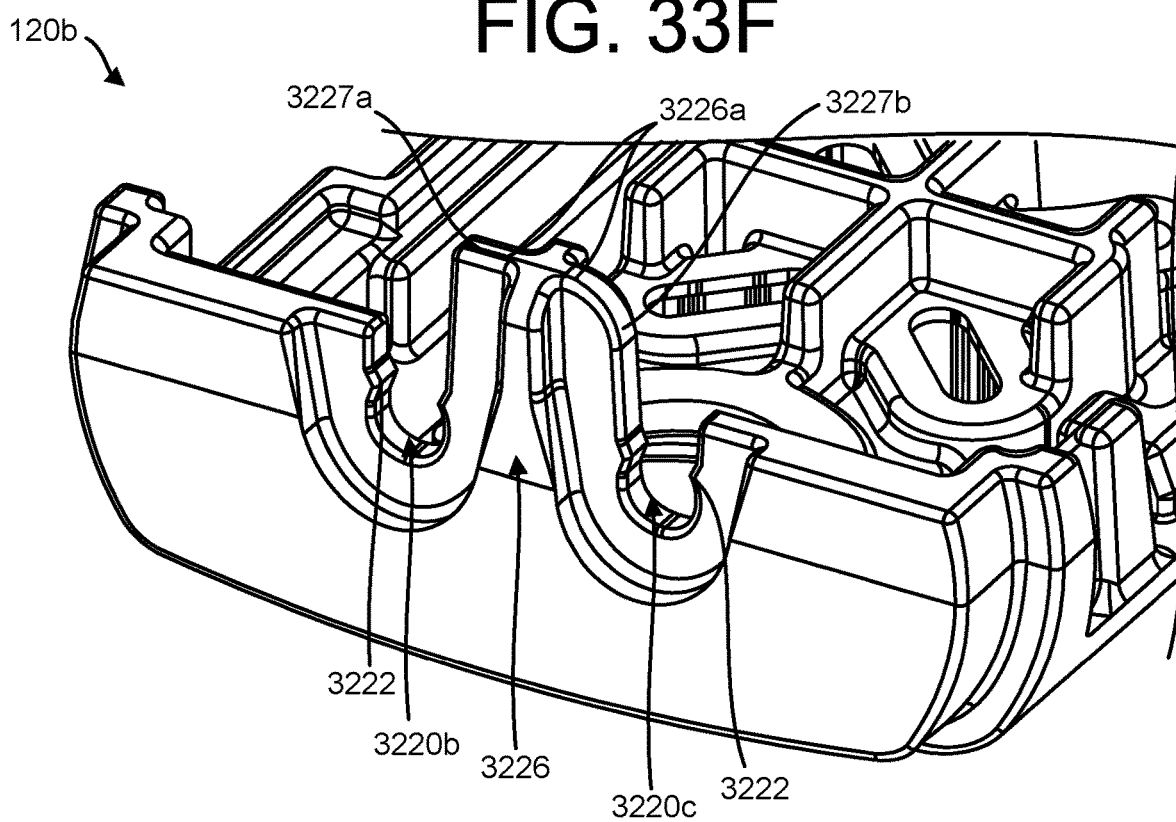

FIGS. 33F and 33G are top perspective views of the proximal end of the bottom support structure 120b according to additional implementations. As previously described elsewhere herein, the openings 3220b,c of the proximal end of the bottom support structure 120b are sized and shaped to hold the power pins 122a,b, respectively, with the power pins 122a,b extending longitudinally outward through the openings 3220b,c upon installation of the integrated board assembly 400 into the bottom support structure 120b. The power pins 122a,b engage the flexible side protrusions 3222 with for example a friction fit. The side protrusions 3222 may be formed on each side of the openings 3220b,c and protrude inward in the respective openings 3220b,c. The power pins 122a,b contact the side protrusions 3222 upon a force being applied to the power pins 122*a,b*, and the side protrusions releasably secure the power pins 122*a,b* within the openings 3220*b,c* below a bottom surface of the side protrusions 3222. When the integrated board assembly 400 is inserted into the bottom support structure 120*b*, the side protrusions 3222 may be engaged by the respective power pins 122*a,b*, causing the power pins 122*a,b* to be pushed below the side protrusions 3222, which serve to secure the power pins 122*a,b* within the respective openings 3220*b,c*.

As further shown in FIGS. 33F and 33G, a portion of the proximal end of the bottom support structure 120*b* forms a support wall 3226 positioned between the openings 3220*b,c*. The support wall 3226 is sized and shaped to provide support between the openings 3220*b,c* such that this portion of the proximal end of the bottom support structure 120*b* does not flex or otherwise bend, thus providing additional support for the power pins 122*a,b* and the first antenna 143. The support wall 3226 may have for example a cross-shaped cross-section or other cross-section of a suitable configuration and thickness (e.g., rectangular, x-shaped, etc.) to provide a supportive wall between the openings 3220*b,c*. In some configurations, such as those shown in FIGS. 33F and 33G, the support wall 3226 may have a lengthwise-extending wall 3226*a* that extends along a portion of the proximal end of the bottom support structure 120*b*. In the implementation shown in FIG. 33G, one or more corners 3227*a,b* may have a rounded profile. For example, as shown in FIG. 33G, a second corner 3227*b* has a rounded profile. The rounded profile may aid in installation of the proximal end 402*a* of the flexible layer 402 at which the first antenna 143 is oriented. As described elsewhere herein, in some implementations the proximal end 402*a* of the flexible layer 402 is folded or rotated 180 degrees (for example as described with reference to FIG. 11B) to achieve the configuration shown in FIGS. 33A and 33B. The rounded profile of the second corner 3227*b* provides a larger clearance to accommodate for folding or rotating the proximal end 402*a* of the flexible layer 402 into place.

Figure 39A:
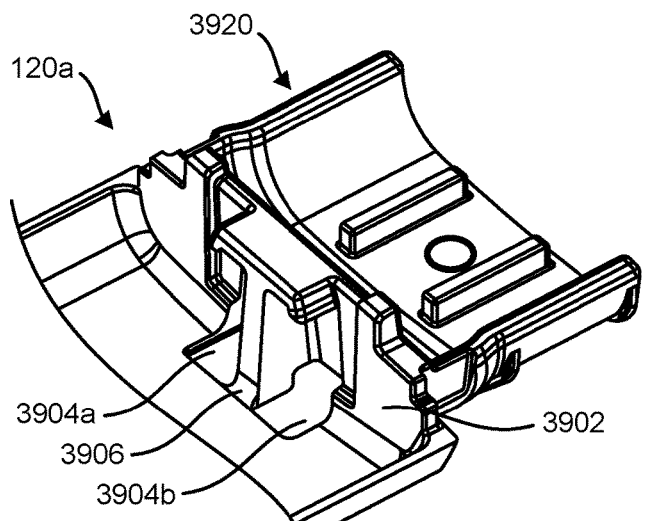
FIG. 39A-FIG. 39D illustrate features of a top support structure of an inner assembly of a vaporizer device consistent with implementations of the current subject matter.
Figure 39B:
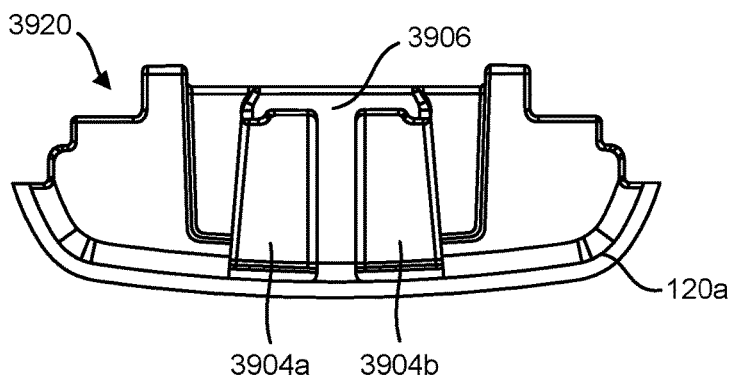

FIG. 39A is a bottom perspective view of the distal end of the top support structure 120*a* (the end at which the bottom cap 120*c* is connected) consistent with implementations of the current subject matter. A cap connection region 3920 is at the distal end of the top support structure 120*a*, and it is the cap connection region 3920 which fits within the inner cap region 120*d* of the bottom cap 120*c* (see also FIGS. 4B and 11N). Adjacent to the cap connection region is a cross support bar 3902 that extends longitudinally across the width of the top support structure 120*a*, as shown in FIG. 39A. FIG. 39B is a cross-sectional front view of the cross support bar 3902. Two openings 3904*a,b* are formed through the top support structure 120*a* and are adjacent the cross support bar 3902 on the side opposite the cap connection region 3920 moving away from the distal end. Consistent with implementations of the current subject matter, the two openings 3904*a,b* may be separated by a cross rib 3906 that extends down from an upper portion of the cross support bar 3902 to separate the two openings 3904*a,b* and to connect to the top support structure 120*a*. The configuration of the two openings 3904*a,b* and the cross rib 3906 may aid in material flow during injection molding of the top support structure 120*a*, thereby reducing warped regions that may otherwise occur.

Figure 39C:
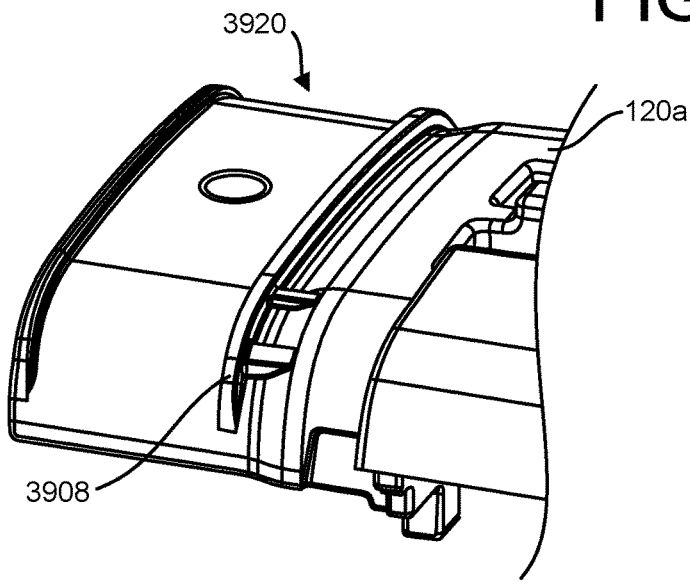

FIG. 39C is a top perspective view of the distal end of the top support structure 120*a* consistent with implementations of the current subject matter. FIG. 39C illustrates additional details of the cap connection region 3920. In particular, an antenna rib 3908 protrudes upward from and extends widthwise across an upper surface of the top support structure 120*a* parallel to the region at which the second antenna 149 extends (see also FIG. 11N). The antenna rib 3908 serves as a boundary for the second antenna 149 and provides backing support for the bottom cap 120*c* when placed over the top support structure 120*a*. An inner area of the bottom cap 120*c*, when the bottom cap 120*c* is installed on the connected support structure, engages the antenna rib 3908, which provides additional support between the bottom cap 120*c* and the top support structure 120*a*.

Figure 39D:
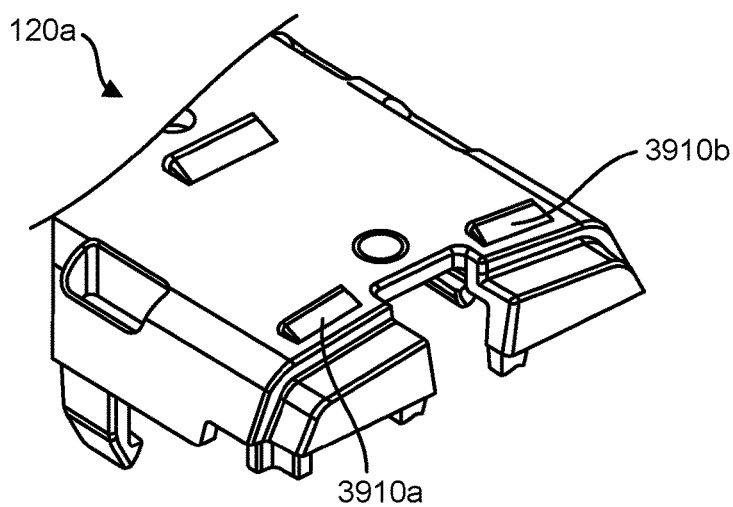

FIG. 39D is a top perspective view of the proximal end of the top support structure 120*a*. As described elsewhere herein, various crush ribs may be incorporated on surfaces of the inner assembly 111, including the top support structure 120*a*, the bottom support structure 120*b*, and the bottom cap 120*c*, to aid in providing a secure and tight fit within the outer shell 112. The crush ribs engage an inner surface of the outer shell 112 when in contact with the outer shell 112, which provides for a secure and tight fit. As shown in FIG. 39D, top support structure crush ribs 3910*a,b* are provided on a top surface of the top support structure 120*a* near the proximal end to assist in securing the top support structure 120*a* within the outer shell 112 during installation of the light pipe components 117.

Figure 40A:
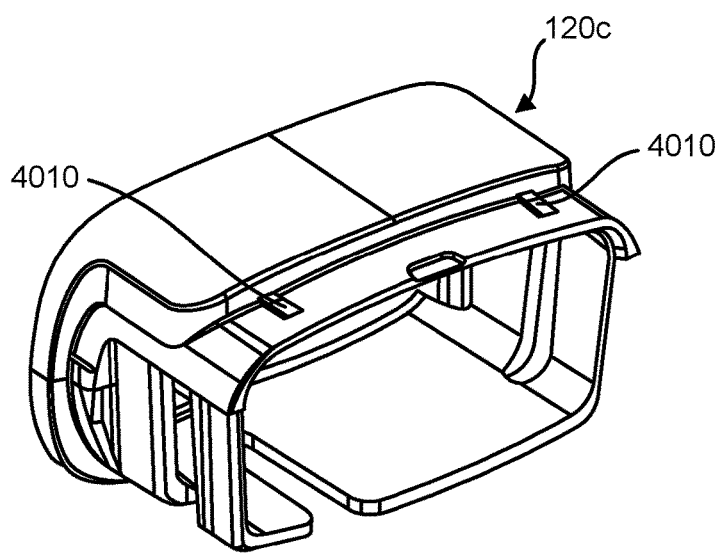
FIG. 40A and FIG. 40B illustrate features of a bottom cap of an inner assembly of a vaporizer device consistent with implementations of the current subject matter.
Figure 40B:
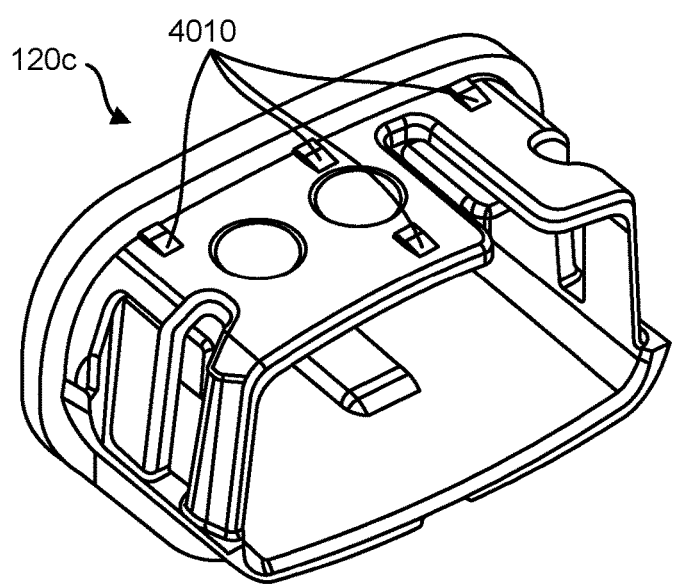

FIG. 40A is a top perspective view of the bottom cap 120*c*, and FIG. 40B is a bottom perspective view of the bottom cap 120*c*. To aid in supporting the bottom cap 120*c* against the outer shell 112 after assembly, various bottom cap crush ribs 4010 may be provided along the outer circumference of the bottom cap 120*c* at positions in which the bottom cap 120*c* interfaces with or contacts the outer shell 112.

The quantity and positions of the crush rubs, for example the top support structure crush ribs 3910*a,b* and the bottom cap crush ribs 4010, may vary and are not limited to the configurations shown. For example, in some implementation, fewer crush ribs may be incorporated and may be spaced apart at positions on surfaces of the top support structure 120*a*, the bottom support structure 120*b*, and the bottom cap 120*c* to achieve a secure and tight fit within the outer shell 112. In some implementations, no crush ribs are included. In other implementations, additional crush ribs are placed to aid in the desired secure and tight fit of the inner assembly 111 within the outer shell 112.

Figure 29:
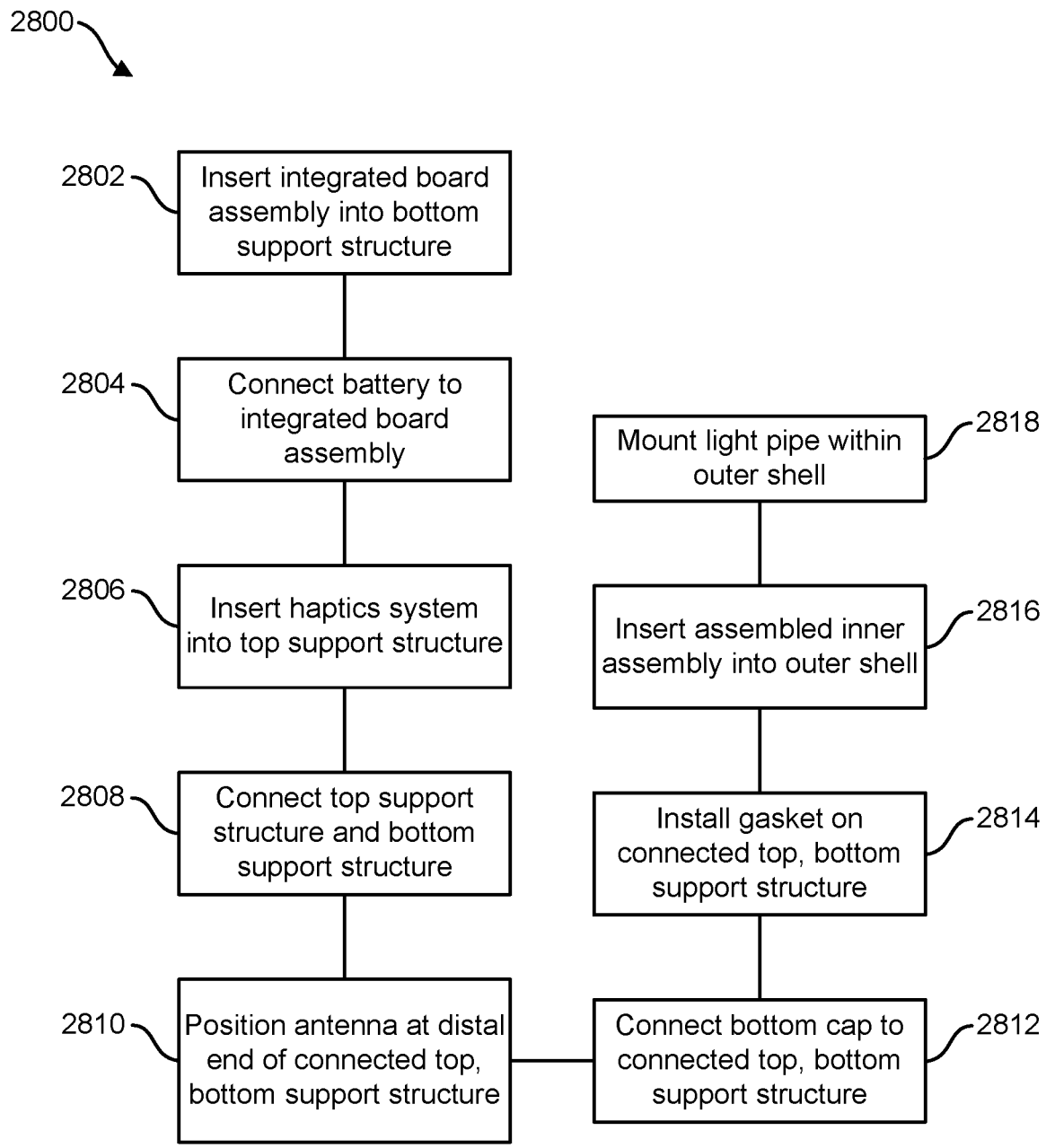
FIG. 29 shows a process flowchart illustrating features of a process consistent with implementations of the current subject matter.

With reference to FIG. 29, a process flow chart 2800 illustrates features of a method, which may optionally include some or all of the following. At 2802, the integrated board assembly 400 is inserted into the bottom support structure 120*b*. For example, the PCBA 126 portion of the integrated board assembly 400 may be snapped into the bottom support structure by engaging one or more snaps 1102*a,b,c*. 2802 may also include alignment and insertion of the power pins 122*a,b* with and into respective openings, for example the teeth configuration described with reference to FIG. 11D, at a proximal end of the bottom support structure 120*b*.

At 2804, the battery 124 is connected to the integrated board assembly 400. For example, the bottom liner on the bottom portion of the battery 124 may be removed to expose an adhesive portion, the battery connector point 124*a* may be pressed into the battery connecter 125 on the PCBA 126, and the battery 124 may be pressed into the opening 1112 in the bottom support structure 120*b*.

At 2806, the haptics system (e.g., LRA) 144 is inserted into the top support structure 120*a*. For example, the haptics system 144 may be placed and/or connected into the cavity 1116*a* on an inner portion of the top support structure 120*a*.

Adhesive and/or the side snaps 1117*a,b* may be utilized to secure the haptics system 144 within the cavity 1116*a*.

At 2808, the top support structure 120*a* and the bottom support structure 120*b* are connected together. For example, the top support structure 120*a* and the bottom support structure 120*b* may be aligned, and the outer side snaps 1122*a,b* of the top support structure 120*a* may engage the respective side tabs 1124*a,b* of the bottom support structure 120*b* when a force is applied to one or more of the top support structure 120*a* and the bottom support structure 120*b*. The teeth configuration of the proximal end of the top support structure 120*a* may also be aligned and mated with that of the proximal end of the bottom support structure 120*b*.

At 2810, the second antenna 149 is positioned on an outer edge of the distal end of the connected structure (i.e., the top and the bottom support structures 120*a*, 120*b* connected together). The antenna adhesive 404 may be applied to the region 1119 at the distal end of the top support structure 120*a*, and the second antenna 149 may be folded and aligned with the antenna adhesive 404.

At 2812, the bottom cap 120*c*, is connected to the connected structure at the distal end thereof. For example, the side snap engagement component 1128 of the bottom cap may engage the distal side snap 1126 of the bottom support structure 120*b* upon the bottom cap 120*c* being aligned with and inserted on the distal end of the connected structure.

At 2814, the gasket 115 is installed at the proximal end of the connected structure, to form the inner assembly 111 in an assembled form. For example, the gasket 115 may be installed such that the sealing ring 115*a* of the gasket 115 interfaces with the opening 115*h* extending through the bottom support structure 102*b* and with a pressure sensor 137 mounted to the PCBA 126.

At 2816, the inner assembly 111 is inserted into the outer shell 112. For example, the inner assembly 111 may be slid into the outer shell 112.

At 2818, the light pipe 147 is mounted within the outer shell 112. For example the individual light pipe components 117 of the light pipe 147 are aligned with and inserted within the corresponding openings 119 formed through the surface of the outer shell 112. Pressure may be applied to the light pipe 147 to secure the individual light pipe components 117 within the mating structure 113 with corresponding recesses 817. The applied pressure may cause the carriage unit 147*a* to become detached from the individual light pipe components 117.

As mentioned above, the vaporizer device 100 includes the cartridge 150 configured to operatively couple with the vaporizer body 110. In some implementations, the cartridge 150 is disposable whereas the vaporizer body 110 is durable and/or re-usable. The cartridge 150 may also be configured to be reused as described elsewhere herein.

Figure 12:
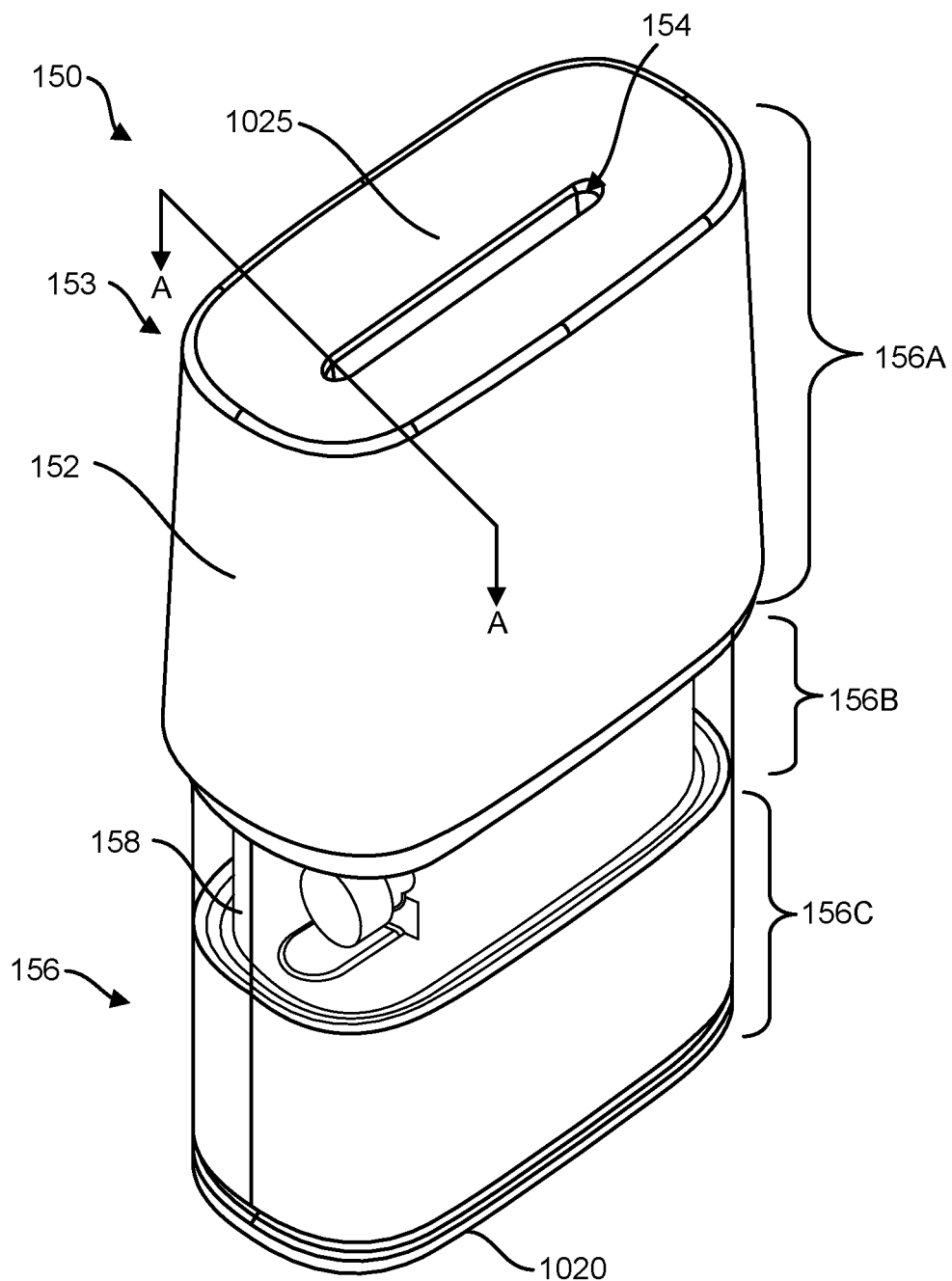
FIG. 12 illustrates features of a cartridge of a vaporizer device consistent with implementations of the current subject matter.
Figure 13:
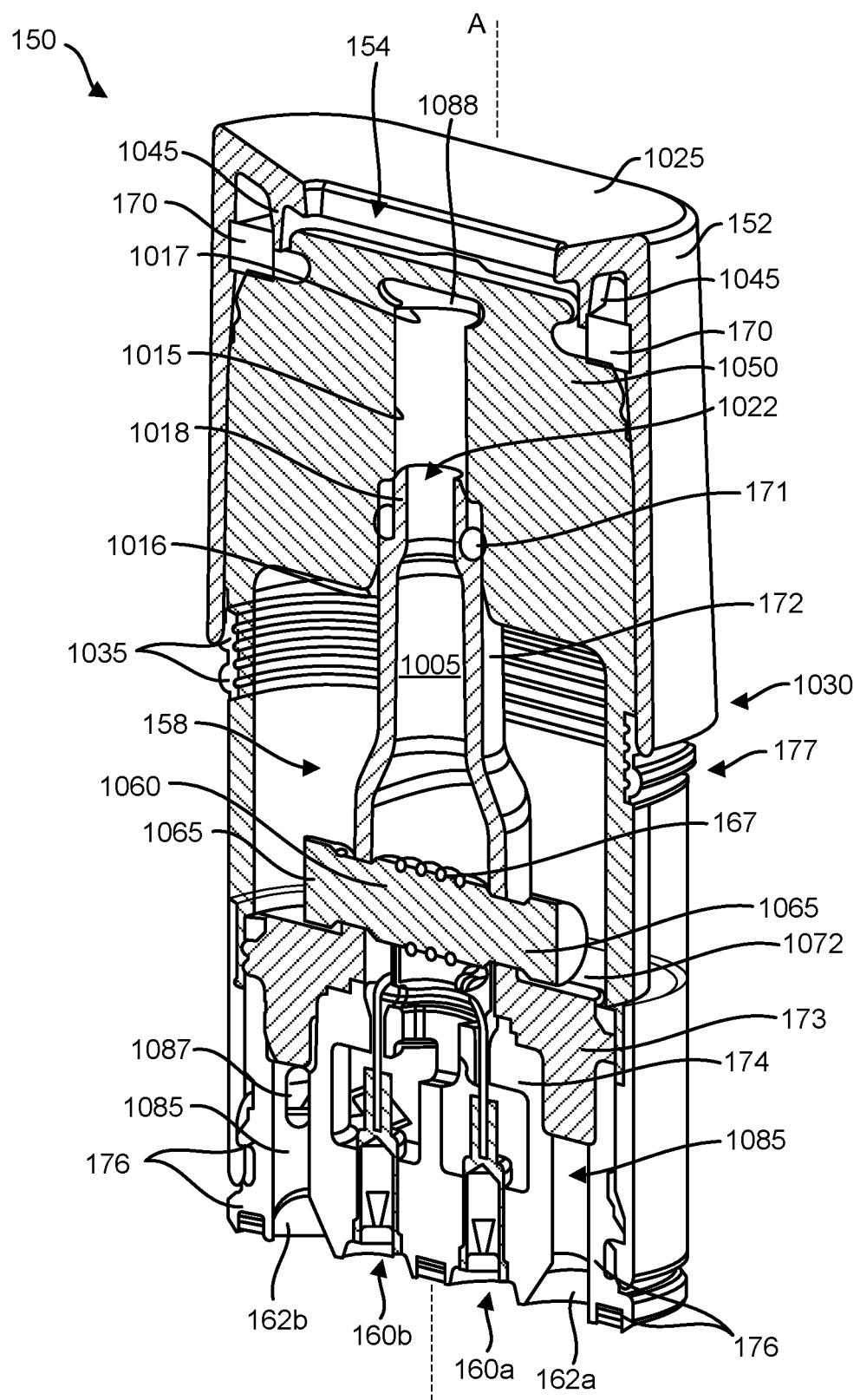
FIG. 13 illustrates, via a cross-sectional view, features of a cartridge of a vaporizer device consistent with implementations of the current subject matter.
Figure 14:
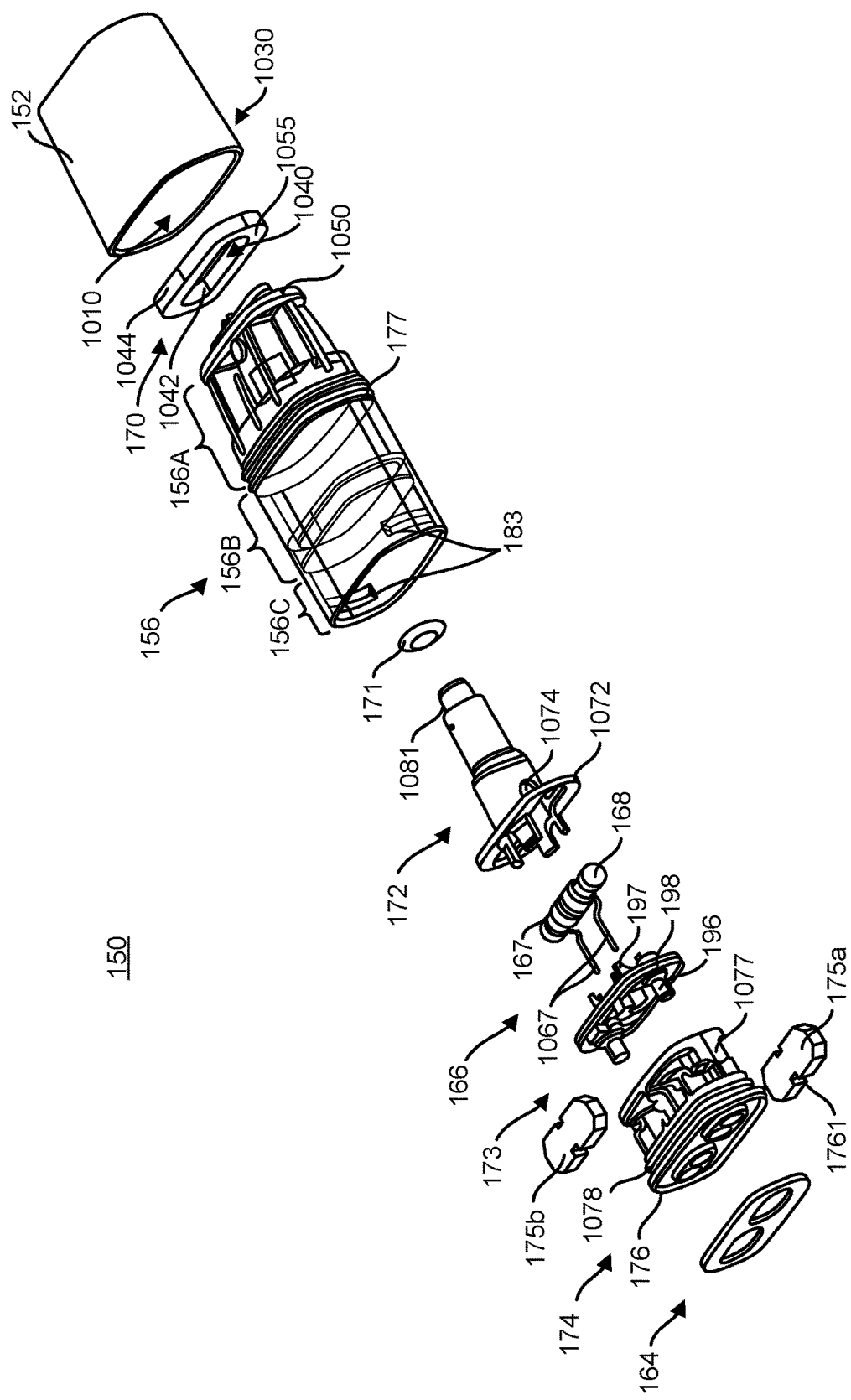
FIG. 14 illustrates, via an exploded view, features of a cartridge of a vaporizer device consistent with implementations of the current subject matter.

FIGS. 12-14 illustrate features of a cartridge 150 of a vaporizer device 100 consistent with implementations of the current subject matter. The cartridge 150 may include the cartridge body 156 defining, at least in part, a reservoir 158 configured to contain vaporizable material, a mouthpiece 152, and a vaporizing assembly of vapor-generating components positioned within the cartridge body 156 and configured to vaporize the vaporizable material. Each will be described in more detail below.

The cartridge body 156 can be divided, generally, into a proximal end region 156A, a central region 156B, and a distal end region 156C. The proximal end region 156A of the cartridge body 156 can be coupled to the mouthpiece 152 configured to deliver the vapor to the user. The central region 156B includes a tank or reservoir 158 defined, at least in part, by the cartridge body 156 and configured to contain an amount of the vaporizable material. The distal end region 156C of the cartridge body 156 may house one or more components configured to vaporize the material from the reservoir 158 into a vaporization chamber 1005. The mouthpiece 152 is configured to interface with the user to release the vapor from the vaporization chamber 1005 to the user through one or more openings 154 in the mouthpiece 152, for example, upon the user drawing a breath through the vaporizer device 100. Each of these components will be described in more detail below.

In some implementations, the vaporizable material is *cannabis* oil. *Cannabis* oils can present particular challenges when vaporized using a cartridge and a vaporizer device. For example, *cannabis* oil is relatively sticky and viscous, particularly once it dries out. Thus, leakage may be a more serious consideration and challenge compared to other aqueous vaporizable materials. In particular, leakage of *cannabis* oil may result in clogging of the device and disturbing the electrical components, particularly the electrical contacts. The dried oil can also disrupt the electrical control of the vaporizer device due to its electrically insulating properties. The cartridges described herein may in certain implementations provide robust leak-resistant designs and may be configured to be used with viscous oil-based vaporizable materials, such as *cannabis* oil that can have a viscosity at room temperature of between about 40 cP and 113 KcP.

As mentioned, the cartridge body 156 can be divided generally into the upper, proximal end region 156A, the lower, distal end region 156C, and the central region 156B located between the proximal and distal end regions 156A, 156C (see FIG. 14). The upper, proximal end region 156A of the cartridge body 156 is configured to couple with the mouthpiece 152, for example, by inserting within an internal volume 1010 of the mouthpiece 152 such that an exterior surface of the cartridge body 156 near the upper proximal end region 156A seals with an inner surface of the mouthpiece 152. The proximal end region 156A of the cartridge body 156 can define a central channel 1015 for directing vapor from the vaporization chamber 1005 towards the one or more openings 154 through the mouthpiece 152. The lower, distal end region 156C of the cartridge body 156 may house components configured to couple with the vaporizer body 110, for example, by inserting within the cartridge receptacle 114, which will also be described in more detail below. The central region 156B of the cartridge body 156 positioned between the proximal and distal end regions 156A, 156C and remains hollow such that it may define, in part, the reservoir 158.

As mentioned, the distal end region 156C of the cartridge body 156 may be configured to couple to and be secured with the vaporizer body 110, for example, by inserting within the cartridge receptacle 114 (see FIGS. 4A-4B). The cartridge receptacle 114 may have a proximal opening and an inner diameter sufficient to receive the outer diameter of the distal end region 156C of the cartridge body 156. Additionally, the cartridge receptacle 114 may have a depth sufficient to slide the cartridge body 156 into the cartridge receptacle 114 up to about the level of the mouthpiece 152. Thus, the walls of the cartridge receptacle 114 may surround the cartridge body 156 on the distal end 1020 and all four sides of the distal end region 156C and the central region 156B. Other configurations of coupling between the cartridge body 156 and the vaporizer body 110 are considered herein. For example, in some implementations, the cartridge body 156 may insert within the cartridge receptacle 114 from a side opening rather than from a proximal opening. Alternatively, in some implementations, the cartridge body 156 need not insert within a receptacle that fully surrounds the distal end region 156C of the cartridge body 156, for example, if the cartridge body 156 and vaporizer body 110 form a seal sufficient to sense a pressure drop. The cartridge body 156 may include a receptacle configured to receive a proximal end region of the vaporizer device 100. In another implementation, the cartridge body 156 may insert within a slot of the vaporizer body 110 such that at least one wall of the distal end region 156C of the cartridge body 156 forms an outer surface and completes the outer contour of the vaporizer device 100 upon coupling between the cartridge 150 and the vaporizer body 110. The cartridge body 156 and the vaporizer body 110 may also snap together on their respective distal and proximal ends without the exterior walls of the cartridge body 156 being contained by or covered by a receptacle wall of the vaporizer body 110. For example, the distal end 1020 of the cartridge body 156 may include a coupling mechanism configured to fixedly attach and seal with the proximal end of the vaporizer body 110.

The cartridge 150 can couple within the cartridge receptacle 114 by a friction-fit, snap-fit, and/or other types of secure connection. In some implementations, any of a variety of complementary coupling features may be incorporated, including but not limited to tab, indent, magnetic lock, channel, rim, lip, ridge, protrusion, groove, rib, etc., that are configured to engage with a complementary feature (not shown) of the vaporizer body 110. For example, in some implementations the cartridge 150 and vaporizer body 110 may incorporate one or more coupling features having corresponding male and female parts that allow the cartridge 150 to snap into place in operable contact with the vaporizer body 110. The distal end region 156C of the cartridge body 156 may include substantially straight or inwardly tapered sides and include one or more coupling features that secure the cartridge 150 within the cartridge receptacle 114 of the vaporizer body 110. The one or more coupling features may be configured to engage with a complementary feature on the vaporizer body 110, such as within the cartridge receptacle 114, when the cartridge 150 engages with the vaporizer body 110. For example, the one or more coupling features may be male parts such as a pair of tabs or a circumferential rib on an outer surface of the distal end region 156C of the cartridge body 156 that inserts within a complementary female part such as a pair of indents or a circumferential groove on an inner surface of the cartridge receptacle 114. The male parts may snap into the female parts upon downward insertion of the cartridge 150 within the cartridge receptacle 114 to provide a secure fit and reversed upon withdrawing the cartridge 150 upward out of the cartridge receptacle 114.

In some implementations, the one or more coupling features is a circumferential rib on an outer surface of the cartridge 150, for example, near where proximal end region 156A meets the central region 156B (see FIG. 13). The circumferential rib may be an elastomeric element configured to provide an interference fit with an inner surface of the cartridge receptacle 114 such that the cartridge 150 securely couples with the vaporizer body 110 without needing to engage with a corresponding feature on the inner surface of the cartridge receptacle 114 (see, for example, FIG. 4A). The circumferential rib may be part of a mouthpiece seal 177 positioned between and configured to seal between an inner surface of the mouthpiece 152 and an outer surface of the cartridge body 156, which will be described in more detail below. The compliant material of the mouthpiece seal 177 may wedge against and engage with the inner surface of the cartridge receptacle 114 providing a secure fit. The mouthpiece seal 177 may provide a snap-fit feel upon seating the cartridge 150 within the cartridge receptacle 114 of the vaporizer device.

The cartridge 150 may have an elongate and flattened tubular body extending in a distal to a proximal axis (longitudinal axis A). The cartridge 150 may be described as having a length (sometimes referred to herein as a height), a width, and a depth (sometimes referred to herein as a thickness). The height is a length from the proximal end to the distal end of the cartridge 150 along the longitudinal axis A (see, for example, FIG. 13). The width of the cartridge is measured transverse the longitudinal axis A along a major axis of the cartridge 150 and thus refers to the length of the longer sides of the cartridge. The depth of the cartridge 150 is also measured transverse the longitudinal axis A, but along the minor axis of the cartridge 150 and thus refers to the length of the shorter sides. The width may be 1.2 times, 1.3 times, 1.4 times, 1.5 times, 1.6 times, 1.7 times, 1.8 times, 1.9 times, etc. or greater than the depth. The cartridge 150 may be between about 1 cm and 10 cm long, between about 2 cm and 7 cm long, between 3 cm and 5 cm long. The length of the cartridge 150 may be less than 8 cm, less than 7 cm, less than 6 cm, less than 5.5 cm, less than 5 cm, etc. In some implementations, the cartridge 150 may have a total length of about 3.3 cm, a width (i.e., across the major axis of the cartridge) of about 1.7 cm, and a depth (i.e., across the minor axis of the cartridge) of about 0.85 cm.

The cross-sectional shape of the cartridge body 156 may be any of a variety of shapes, including circular, round, or non-round shapes, such as an approximately oval, elliptical, rectangular, square, trapezoidal, or other cross-sectional shape. The cross-sectional shape may be geometric or free-form shape. Non-round shapes, particularly flattened shapes may be preferred to prevent rolling when the vaporizer device 100 is placed on its side. The shape of the cartridge 150, including the cartridge body 156 and the mouthpiece 152, resembles or is a continuation of the general shape of the vaporizer body 110 such that upon coupling the cartridge 150 and the vaporizer body 110 together, the vaporizer device 100 has a substantially sleek profile. The coupling between the cartridge 150 and the vaporizer body 110 may allow for the vaporizer device 100 to have continuous edges that provide a seamless unibody profile from end to end.

Because the overall shape of the cartridge 150 may be somewhat flattened, the coupling between the cartridge 150 and the vaporizer body 110 may occur upon relative sliding along the longitudinal axis A of the vaporizer device 100 as shown at FIG. 13. However, depending on the shape and configuration of the cartridge body 156 and the cartridge receptacle 114, other relative movements are considered herein, such as rotation around the longitudinal axis A or side-to-side movements orthogonal to the longitudinal axis A of the vaporizer device 100. In some implementations, the cartridge receptacle 114 and the cartridge 150 have bilateral symmetry such that the cartridge 150 may be flipped horizontally relative to the cartridge receptacle 114 and still operatively couple with the vaporizer body 110. In other implementations, the cartridge receptacle 114 and cartridge 150 have lateral dissymmetry such that they engage with one another in only a single orientation.

The fit between the cartridge body 156 and the vaporizer body 110 may be sufficient to provide a secure fit to prevent inadvertent uncoupling, but may still allow for the cartridge 150 to be easily withdrawn or disengaged from the vaporizer body 110 to remove and replace the cartridge 150. In some implementations, the engagement between the cartridge body 156 and the vaporizer body 110 may include a release button or other feature that is configured to actively disengage the cartridge 150 from the device. The outer surface of the cartridge 150 may incorporate one or more three-dimensional features such as slots, knurling, or other type of finger grips that aid a user during installation and removal of the cartridge 150 from the vaporizer body 110. The coupling, such as a snap-fit coupling, may provide a visual, audible and/or tactile confirmation that the cartridge body 156 is positioned properly relative to the vaporizer body 110.

Again with respect to FIGS. 12-14, the proximal end region 156A of the cartridge body 156 is configured to couple with the mouthpiece 152. The mouthpiece 152 can include the internal volume 1010 sized such that the mouthpiece 152 may be attached over the proximal end region 156A of the cartridge body 156. As such, the mouthpiece 152 may form the proximal end of the cartridge 150. The mouthpiece 152 may have an external surface that is generally amenable to a user placing their lips over the proximal end 153 of the mouthpiece 152 to inhale the vapor. The external surface of the mouthpiece 152 may have a variety of configurations. In some implementations, the external surface may have smooth edges that are pleasing to the lips and tongue. The mouthpiece may also have a length along the longitudinal axis A sufficient to be inserted a distance between the lips for inhaling. As mentioned above, the cartridge 150 may have a total length along the longitudinal axis A from the proximal end to the distal end that is between about 3 cm and 5 cm, a width (i.e., across the major axis of the cartridge) of between about 1 cm and about 2 cm, and a depth (i.e., across the minor axis of the cartridge) of between about 0.5 cm and about 1 cm. In some implementations, the mouthpiece 152 may have a length along the longitudinal axis A that is about 0.5 cm, about 0.75 cm, about 1 cm, about 1.25 cm, about 1.5 cm, about 1.75 cm, about 2.0 cm, about 2.25 cm, about 2.5 cm, up to about 3.0 cm in length. The length of the mouthpiece 152 along the longitudinal axis A may be a fraction of the total length of the cartridge 150 as a whole, for example, at least 25%, at least 30%, at least 35%, at least 40%, up to about 50% the total length of the cartridge 150. As described elsewhere herein, the cartridge 150 may be somewhat flattened in shape creating a rectangular shape such that a width of the cartridge 150 is greater than the depth. The mouthpiece 152 of the cartridge may also have a somewhat flattened shape. For example, the mouthpiece 152 may have a length that is about 1.5 cm, a width (across the major axis) that is about 1.7 cm, and a depth (across the minor axis) that is about 0.85 cm. It should be appreciated that the proximal end region of the mouthpiece 152 may taper slightly such that the thickness of the mouthpiece 152 across the minor axis may be less at the proximal end than the thickness at the distal end of the mouthpiece 152.

One or more openings 154 may extend through the proximal end surface 1025 into the internal volume 1010 of the mouthpiece 152. The one or more openings 154 allow for the vapor produced within the cartridge 150 to be inhaled by the user. The one or more openings 154 may be aligned with the central, longitudinal axis A of the device or positioned off-set from the longitudinal axis A. The proximal end surface 1025 of the mouthpiece 152 may be sloped inwardly away from the outer edges towards the one or more openings 154. The relative size of the one or more openings 154 may be minimized to hide from view internal components positioned beneath the mouthpiece 152 from the proximal end 153 of the cartridge 150 and aid in reducing the amount of dirt/lint that may enter the mouthpiece 152, while at the same time being of sufficient size to permit the sufficient flow of vapor to the user. In some implementations, the one or more openings 154 through the proximal end surface 1025 of the mouthpiece 152 is a single, elongate slot that has a relatively narrow width providing a generally thin, rectangular shape to the opening 154. However, other shapes, sizes, and/or configurations of the mouthpiece opening 154 may be utilized. For example, the mouthpiece opening 154 may be an oval shape, or two more openings of the same or different shapes may be used.

In some implementations, the elongate opening 154 may have a length along the major axis of the mouthpiece 152 that is a fraction of the total width of the mouthpiece 152 along the major axis. For example, the opening 154 may have a length that is at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, up to at least about 90% of the total width of the mouthpiece along the major axis. The elongate opening 154 may have a narrow width along the minor axis of the mouthpiece 152. For example, the opening 154 may have a width that is no greater than 50%, no greater than 45%, no greater than 40%, no greater than 35%, no greater than 30%, no greater than 25%, no greater than 20%, no greater than 15%, or no greater than 10% of the total width of the mouthpiece along the minor axis. For example, the width of the mouthpiece 152 along the major axis may be about 2 cm and the width of the mouthpiece 152 along the minor axis may be about 1 cm. The opening 154 of the mouthpiece 152 may have a length along the major axis that is about 0.5 cm to about 1.8 cm and a width along the minor axis that is about 0.1 cm to about 0.5 cm. In some implementations, the opening 154 of the mouthpiece 152 has a length that is about 10 mm, about 11 m, about 12 mm, about 13 mm, about 14 mm, up to about 15 mm and has a width of about 1 mm, 1.25 mm, about 1.5 mm, about 1.75 mm, about 2 mm, about 2.25 mm, about 2.5 mm, up to about 3 mm. The dimensions of the opening 154 may vary. The dimensions of the opening 154 may be sufficient to allow vapor to be easily drawn through the opening 154 while the internal components within the cartridge 150 are substantially hidden from view.

Figure 26:
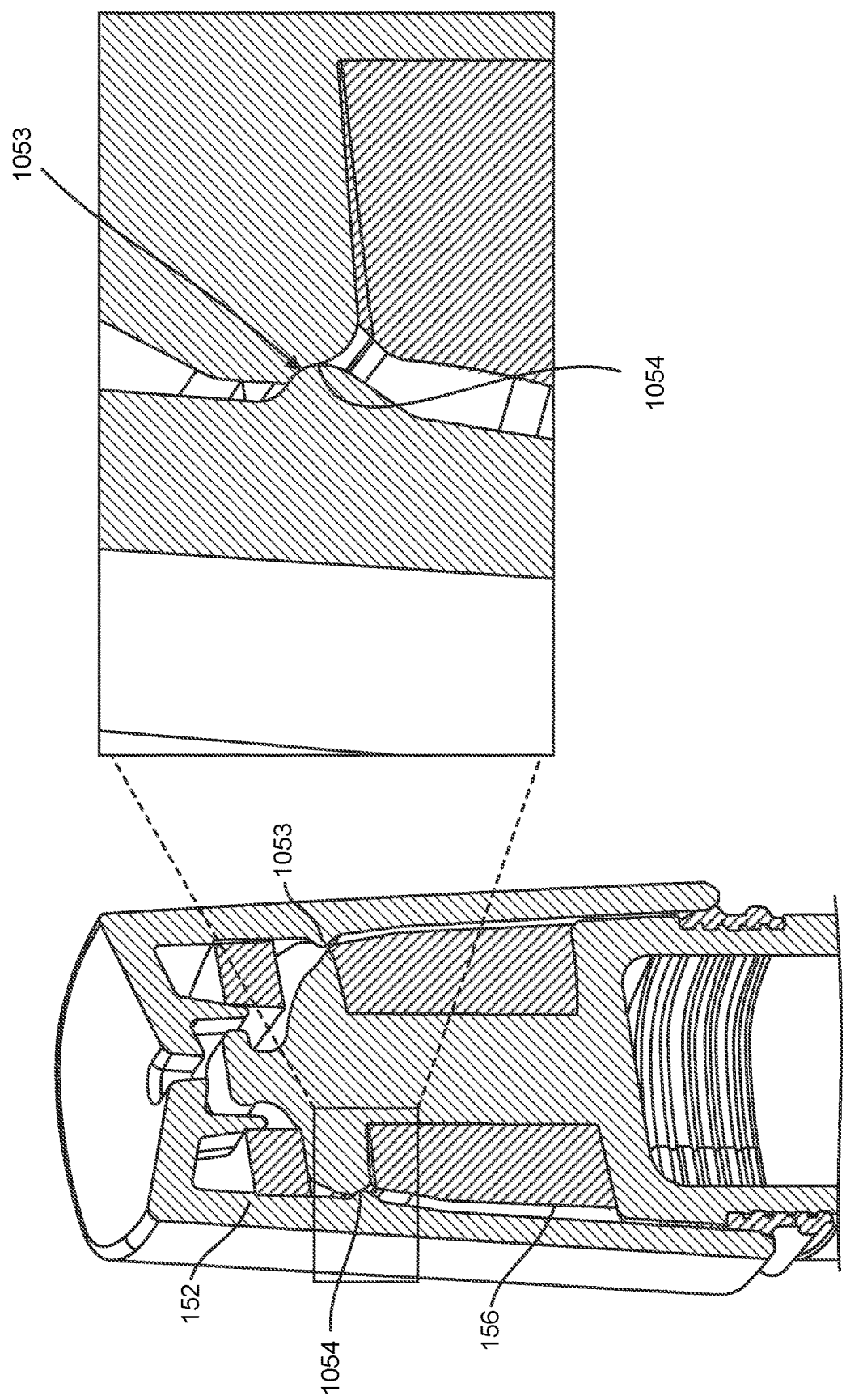
FIG. 26 shows a cross-sectional view of a cartridge taken along a plane shown by arrows A-A of FIG. 12.

The mouthpiece 152 may couple (e.g., snap-fit) onto the proximal end region 156A of the cartridge body 156 to snugly mate with the cartridge body 156. The configuration of the coupling between the cartridge body 156 and the mouthpiece 152 may vary. The coupling may incorporate corresponding male and female parts configured to mate together. For example, an inner surface of the mouthpiece 152 (or the external surface of the cartridge body 156) may incorporate a lip, flange, rib, or other outwardly projecting coupling feature configured to slide past and/or into a corresponding feature on an exterior surface of the cartridge body 156 (or the inner surface of the mouthpiece 152). FIG. 26 is a cross-sectional view of the cartridge 150 taken along a plane shown by arrows A-A of FIG. 12. FIG. 26 illustrates an outwardly-projecting coupling feature 1053 on an inner surface of the mouthpiece 152 that is sized and shaped to project into a corresponding coupling feature 1054 on an exterior surface of the cartridge body 156. The feature 1054 may be an undercut or indentation near the proximal end region 156A of the cartridge body 156. The feature 1054 may be a circumferential indentation completely encircling the proximal end region 156A of the cartridge body 156. The feature 1054 may also be formed by one or more discrete indentations. Similarly, the corresponding outwardly-projecting coupling feature 1053 on the mouthpiece 152 may be a circumferential projection or the outwardly-projecting coupling feature 1053 may be formed by one or more discrete projections.

The mouthpiece 152 may be permanently affixed to the cartridge body 156 by the coupling or may be configured to be removed by a user. For example, the mouthpiece 152 may be removed from the cartridge body 156 in order to refill the reservoir and attached again following refilling for reuse. The cartridge 150 may be disposable and not configured to be refilled. It should be appreciated that the mouthpiece 152 need not be a part of the cartridge 150 itself. For example, the cartridge 150 may include a reservoir and be configured to attach with the vaporizer body 110 independent of the mouthpiece 152.

Figure 15A:
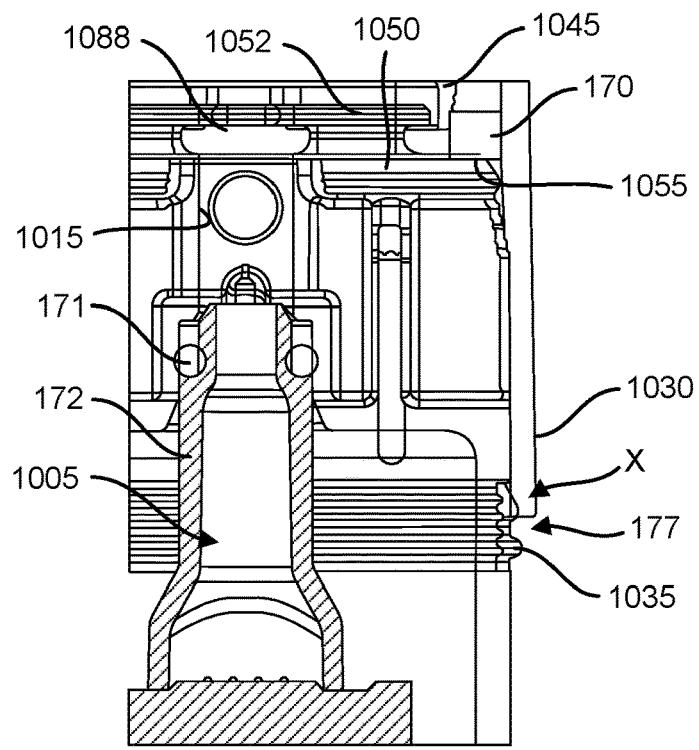
FIG. 15A-15B illustrate features of various seals incorporated in a cartridge of a vaporizer device consistent with implementations of the current subject matter.

Mating between the mouthpiece 152 and the proximal end region 156A of the cartridge body 156 may provide a seal with an exterior surface of the cartridge body 156. For example, the mouthpiece seal 177 may be incorporated between where the mouthpiece 152 and the proximal end region 156A of the cartridge body 156 couple together. The sealing of the mouthpiece seal 177 may eliminate, or at least aid in reduction of, air leaks at the junction between the mouthpiece 152 and the cartridge body 156, for example, near or at the point indicated by "X" in FIG. 15A (see also FIGS. 13-14). Preventing air flow leaks into the mouthpiece 152 at this junction, in turn, may improve drawing vapor through the at least one opening in the mouthpiece by blocking gas flow between the inner surface of the mouthpiece and the outer surface of the cartridge body and thereby may increase air flow through the cartridge 150, which will be described in more detail below. The sealing may also eliminate, or aid in the reduction of, vapor leaks from the mouthpiece 152.

Figure 15B:
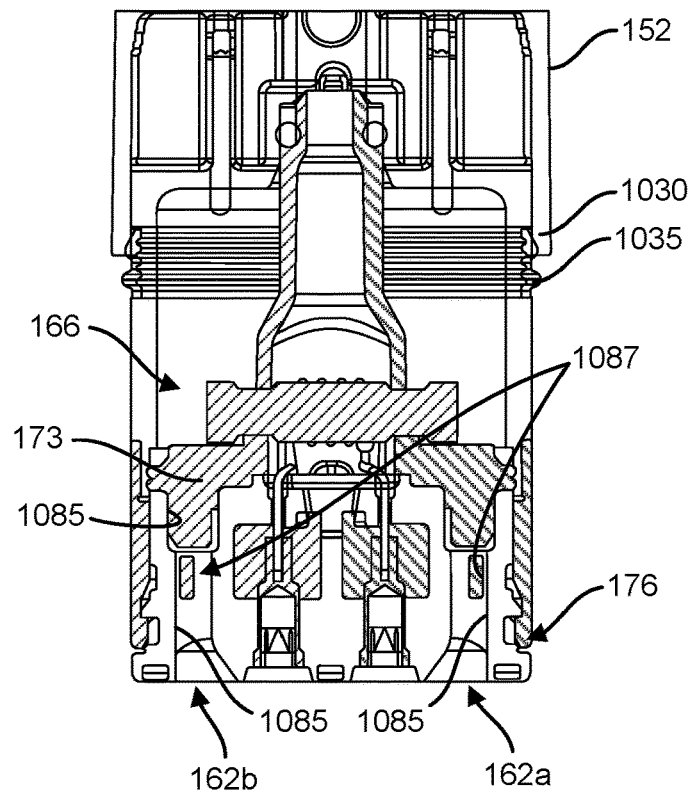

As mentioned above, the mouthpiece seal 177 may be incorporated between where the mouthpiece 152 and the cartridge body 156 couple together. The mouthpiece seal 177 may be dual-purpose in that it may provide a seal or barrier between the mouthpiece 152 and the cartridge body 156 to prevent leaks as discussed above. The mouthpiece seal 177 also may aid in coupling the cartridge 150 to the cartridge receptacle 114 of the vaporizer body 110 by providing a seal between the cartridge 150 and the cartridge receptacle 114. Thus, the mouthpiece seal 177 simplifies manufacturing in that a single element may perform more than a single function. In some implementations, the mouthpiece seal 177 may be an elastomeric element such as an O-ring or flattened band positioned over the exterior surface of the cartridge body 156. In other implementations, the mouthpiece seal 177 may be formed around (e.g., by over-molding) the exterior surface of the cartridge body 156. The mouthpiece seal 177 may be an elastomeric element that encircles the exterior surface of the cartridge body 156 near the proximal end region 156A, for example where the proximal end region 156A meets the central region 156B of the cartridge body 156. The mouthpiece seal 177 may engage the internal surface of the mouthpiece 152 near its distal end region 1030. The mouthpiece seal 177 may be a generally annular feature having a flat inner diameter configured to be affixed or engaged flush with the external surface of the cartridge body 156. The outer surface of the mouthpiece seal 177 may have at least one, two, three, or more circumferential sealing beads or ribs 1035 (see FIG. 15A-15B). The ribs 1035 may provide a redundancy to the sealing between the mouthpiece 152 and the cartridge body 156 as well as a redundancy to the coupling between the cartridge 150 and the vaporizer body 110. The ribs 1035 may provide a maximum outer diameter for the mouthpiece seal 177 that is slightly oversized compared to an inner diameter of the distal end region 1030 of the mouthpiece 152. Thus, when the mouthpiece 152 is inserted over the proximal end region 156A of the cartridge body 156, the inner diameter of the mouthpiece 152 compresses one or more of the ribs 1035 of the mouthpiece seal 177 slightly thereby providing an airtight, circumferential seal between the two components. In some implementations, the mouthpiece seal 177 is an over-molded element on the proximal end region of the cartridge body 156 thereby eliminating a hand assembly step in production. The over-molded design may also improve performance of the seal in that the mouthpiece seal 177 is less likely to twist or roll relative to the cartridge body 156 that might occur with an O-ring. In some implementations, the mouthpiece seal 177 may be positioned or over-molded within a groove formed in the exterior surface to provide better fixation of the mouthpiece seal 177 to the exterior surface of the cartridge body 156. The groove in the exterior surface of the cartridge body 156 may have a surface that is conducive to coupling with the inner diameter of the mouthpiece seal 177. For example, the surface of the groove may be etched or otherwise textured. In some implementations, the inner surface of the distal end region 1030 of the mouthpiece 152 may have an inwardly-projecting feature configured to snap over and position within a groove between the ribs 1035 of the mouthpiece seal 177. The mouthpiece seal 177 may be positioned on the cartridge body 156 near where the distal end region 1030 of the mouthpiece 152 encircles the body 156. This allows for the mouthpiece seal 177 to provide sealing between the mouthpiece 152 and the cartridge body 156 as well as between the cartridge 150 and the cartridge receptacle 114 of the vaporizer body 110 upon coupling of the two. For example, the mouthpiece seal 177 may have width such that one or more of the ribs 1035 near a proximal end of the mouthpiece seal 177 may engage with the distal end region 1030 of the mouthpiece 152 and block gas flow between the inner surface of the mouthpiece 152 and the outer surface of the cartridge body 156 and one or more of the ribs 1035 near a distal end of the mouthpiece seal 177 remain available and seal within the opening of the cartridge receptacle 114 upon coupling with the vaporizer body 110 (see FIG. 20A, for example). The second sealing rib 1035 may be configured to provide an interference fit between the outer surface of the cartridge body 156 and the inner surface of the cartridge receptacle 114 of the vaporizer device. The second sealing rib 1035 may provide a snap-fit with the cartridge receptacle 114 when inserted within the cartridge receptacle 114. It should be appreciated that the position of the mouthpiece seal 177 relative to the mouthpiece 152 may vary. Additionally, the mouthpiece 152 may incorporate more than the mouthpiece seal 177, for example, the mouthpiece seal 177 near the distal end region 1030 as well as a seal (such as an O-ring) closer to the proximal end 153 of the mouthpiece 152.

Again with respect to FIGS. 13-14, the mouthpiece 152 may be coupled to the proximal end region 156A of the cartridge body 156. The mouthpiece 152 may include an internal volume 1010 and an external surface defining at least one opening 154 into the internal volume 1010. The at least one opening 154 may be configured to release vapor from the vaporizing assembly in the cartridge. The internal volume 1010 of the mouthpiece 152 may be mostly filled by the proximal end region 156A of the cartridge body 156. The internal volume 1010 of the mouthpiece 152 may include a region, for example, near the proximal end 153 of the cartridge 150 adjacent the one or more openings 154 of the mouthpiece 152, that is configured to contain one or more absorbent pads 170 within the internal volume 1010. The one or more pads 170 may be positioned within the internal volume 1010 of the mouthpiece 152 near or proximate to the one or more openings 154 through which vapor may be inhaled, e.g., by drawing breath through the vaporizer device 100, such that it may capture moisture just prior to inhalation by the user. The one or more absorbent pads 170 may prevent or reduce the flow of fluid, such as the vaporizable material, into and out of the one or more openings 154. The one or more pads 170 may be pushed against the interior surface of the mouthpiece 152 or may be pulled away from interior walls so as to maximize the surface area available for moisture absorption. The pads s may have any of a variety of shapes including rectangular, circular, ovoid, triangular, square, ring, or other shape. The size and shape of the pads 170 may be selected to minimize interference with the vapor path through the openings 154 while maximizing moisture and particle collection. Thus, the pads 170 may capture deposited and/or condensed liquid from the vapor flowing through the cartridge 150 without requiring the vapor to pass through the pads 170.

In an implementation, the absorbent pad 170 is configured to be positioned within the internal volume 1010 of the mouthpiece 152 near the opening 154 without obstructing vapor flow through the opening 154. The pad 170 may be positioned within the mouthpiece 152 such that the pad 170 is generally off-axis relative to the opening 154 allowing unobstructed vapor flow through the opening 154. In other implementations, the pad 170 may be coaxial with the opening 154 and the shape of the pad 170 allows the pad to avoid obstructing vapor flow through the opening 154.

FIGS. 13-14 shows the pad 170 may be a flattened disk defining a central opening 1040 and thus, has a ring-like shape. In an implementation, an external surface of the mouthpiece may define the opening 154 into the internal volume as a narrow, elongate slit. The central opening 1040 of the pad 170 may have a shape that corresponds to a shape of the opening 154 such that it may surround the opening 154. The pad 170 may be wedged within the internal volume of the mouthpiece to avoid blocking gas flow through the opening 154. The ring-shaped pad 170 may have an inner perimeter or wall 1042 defining the central opening 1040 that is sized and shaped to surround the opening 154 through the upper end of the mouthpiece 152. The pad 170 may also have an outer perimeter or wall 1044 sized and shape to engage with the inner sides of the mouthpiece 152. It should be appreciated the pad 170 may have a ring shape, but need not be a circular ring-shaped object. Rather, the absorbent pad 170 may be a flat, non-circular ring having a perimeter in the shape of an oval, ellipse, or rectangle. The outer wall 1044 may have a shape configured to mate with an inner surface of the mouthpiece 152. In some implementations, the outer wall 1044 of the pad 170 may engage with the internal surfaces or inner sides of the mouthpiece 152 (e.g., the major sides of the generally flattened shape of the mouthpiece 152) such that the outer wall 1044 generally matches the flattened cross-sectional geometry of the mouthpiece 152. For example, if the cross-sectional geometry of the mouthpiece 152 is a flattened oval or rectangular, the geometry defined by the outer wall 1044 of the pad 170 is likewise a flattened oval or rectangular. Likewise, the inner wall 1042 of the pad 170 defining the central opening 1040 may have a shape configured to mirror the shape of the opening 154 through the mouthpiece 152 such that the pad 170 does not obstruct vapor flow through the opening 154. The mouthpiece 152 may include a projecting flat collar forming an internal flange 1045 surrounding the opening 154 and extending into the internal volume 1010 of the mouthpiece 152. The internal flange 1045 may have an inner diameter and an outer diameter. The inner wall 1042 of the pad 170 may be sized to engage with the outer diameter of the internal flange 1045 such that the central opening 1040 of the pad 170 aligns generally with the opening 154 of the mouthpiece 152.

As mentioned above, the mouthpiece 152 may be attached over the proximal end region 156A of the cartridge body 156. The pad 170 may be positioned (e.g., sandwiched) against an upper, proximal surface 1050 of the cartridge body 156 (see FIGS. 13, 14, and 15A). The upper, proximal surface 1050 of the cartridge body 156 abuts against the lower surface 1055 of the pad 170 such that the pad 170 is wedged between the internal flange 1045, the inner sides of the mouthpiece 152, and the proximal surface 1050 of the cartridge body 156. The pad 170 may be wedged into place and affixed without an adhesive although it should be appreciated that adhesives may also be used to affix the pad 170. The upper, proximal surface 1050 of the cartridge body 156 may also include a central, upper element 1052 sized insert through the central opening 1040 of the absorbent pad 170 and the internal diameter of the internal flange 1045. The absorbent pad 170 thereby encircles the central, upper element 1052, which in turn, projects through central opening 1040 and into the internal flange 1045 of the mouthpiece (see FIG. 13 and also FIG. 24). The shape of the pad along with its wedged coupling with the internal flange 1045 of the mouthpiece, the proximal surface 1050 and upper element 1052 of the cartridge body 156 prevent shifting of the pad 170 during use and handling. Shifting of the pad 170 may cause the pad 170 to obstruct vapor flow through the device.

The pad 170 need not be formed by a single absorbent element. Rather, the pad 170 may be formed by multiple absorbent elements positioned relative to the opening 154 to provide absorption without impeding, restricting, or blocking vapor flow through the openings 154 in the mouthpiece 152. Use of the term "pad" is not intended to be limiting. The pad 170 may be any absorbent member (e.g., sponge, pad, felts, fiber, fabric, etc.) that may absorb an amount of a fluid. The one or more pads 170 may include any absorbent material configured to wick moisture relatively quickly and allow it to disperse quickly therethrough. The absorbent material may be hydrophilic, including cotton, non-woven cotton linter paper, felt, cellulose, or hydrophilic polymers. The pad 170 may be formed of thin sheets of layered material.

Figure 34A:
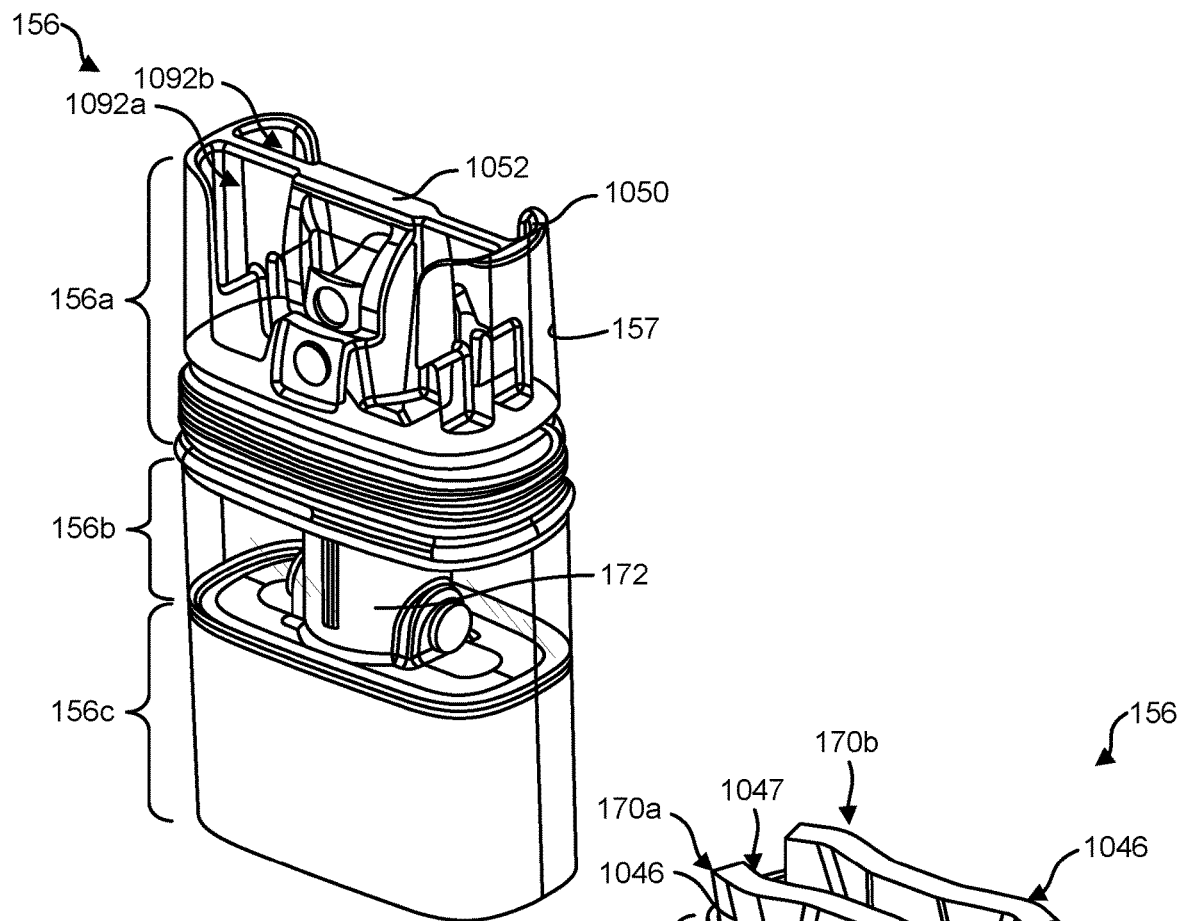
Figure 34B:
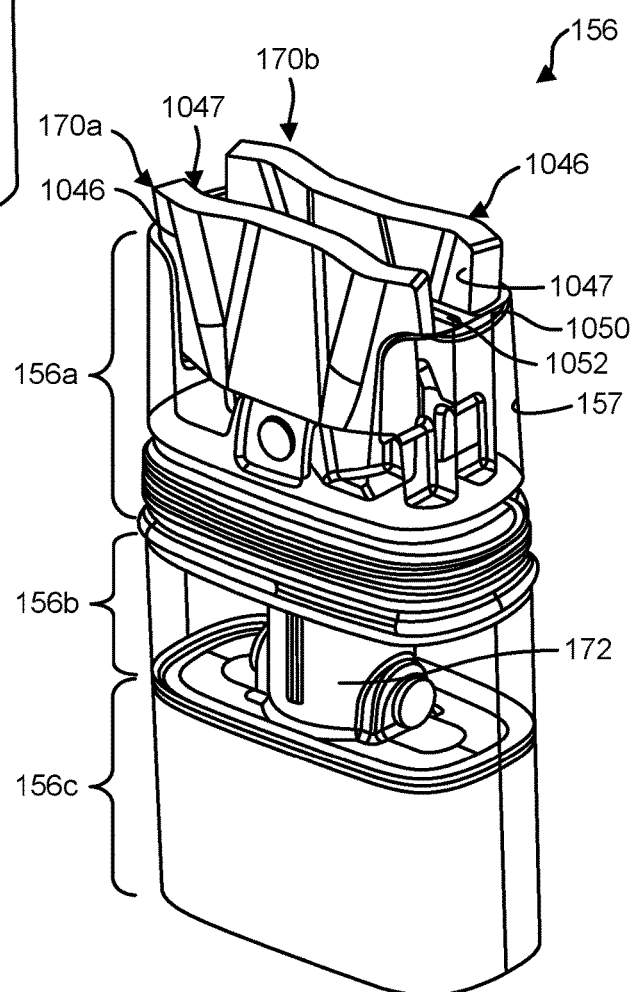
Figure 34C:
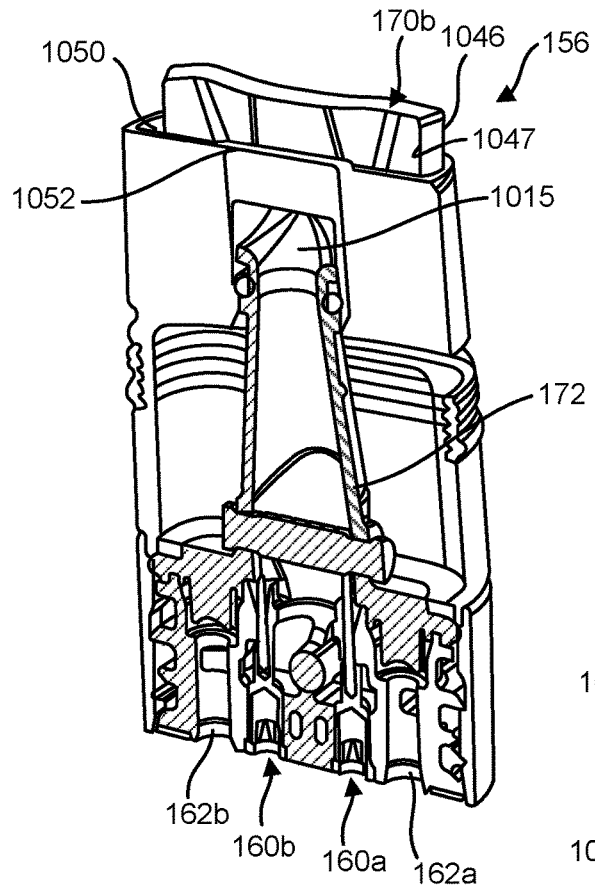
Figure 34D:
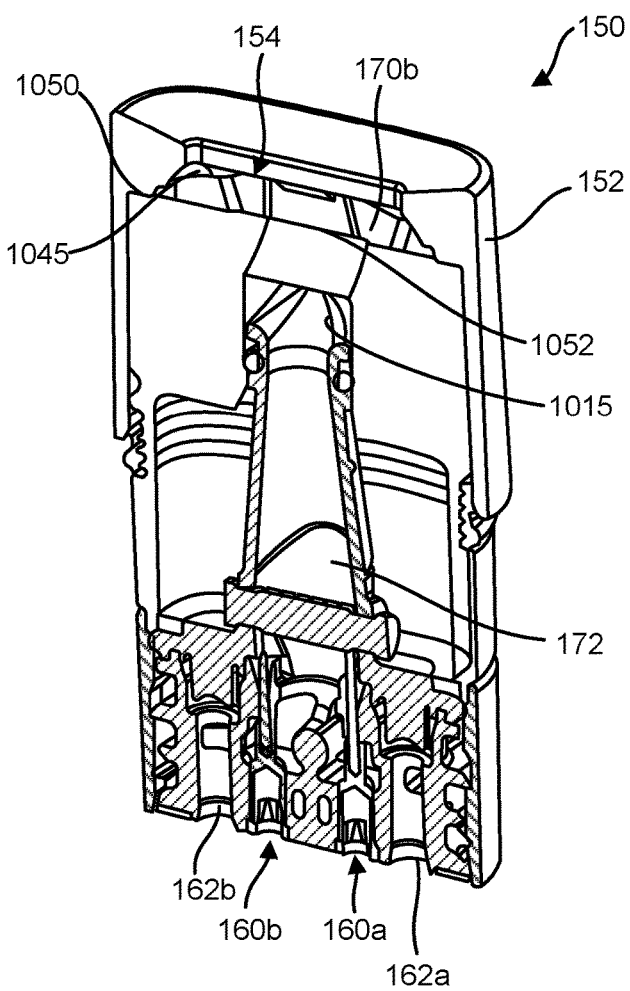

FIGS. 34A-34F illustrate an implementation consistent with the current subject matter in which two absorbent pads 170a,b are provided to fit within the proximal end region 156A of the cartridge body 156. FIG. 34A is a front perspective view of the cartridge body 156, and FIG. 34B is a front perspective view of the cartridge body 156 with the two pads 170a,b inserted in respective openings of the proximal end region 156A of the cartridge body 156 as further described below. FIG. 34C is a perspective, front cross-sectional view of the cartridge body 156 shown in FIG. 34B. FIG. 34D is a perspective, front cross-sectional view of the cartridge 150 with the two pads 170a,b inserted in the cartridge body 156 and with the mouthpiece 152 attached to the proximal end region 156A of the cartridge body 156. FIG. 34E is a cross-sectional view of the cartridge 150 taken along a plane shown by arrows A-A of FIG. 12, and FIG. 34F is a front perspective view thereof.

Two recesses 1092a,b may be formed in the proximal end region 156A of the cartridge body 156 and may be partially defined by sidewall 157 of the proximal end region 156A with openings to the recesses 1092a,b provided in the upper, proximal surface 1050 of the cartridge body 156, as shown in FIG. 34A. As shown in FIGS. 34B and 34C, the recesses 1092a,b may be sized and shaped to contain therein a respective one of the pads 170a,b such that the pads 170a,b are held opposite one another. The recesses 1092a,b may be separated across the major axis of the cartridge body 156 by the central, upper element 1052 of the upper, proximal surface 1050 of the cartridge body 156. As described elsewhere herein, the internal volume 1010 of the mouthpiece 152 may be mostly filled by the proximal end region 156A of the cartridge body 156. Thus, when the mouthpiece 152 is secured to the cartridge body 156, the pads 170a,b are contained within the internal volume 1010 as further described below.

The pads 170a,b may be of a generally rectangular shape with an outer or back wall 1046 and an opposing inner wall 1047, each having a planar surface that may deform (e.g., curve, buckle, bend, or flex) under pressure or contact. In some implementations, each of the pads 170a,b may have a uniform thickness along their length between the outer wall 1046 and the inner wall 1047 that is about 1.0 mm, about 1.1 mm, about 1.2 mm, about 1.3 mm, about 1.4 mm, about 1.5 mm, about 1.6 mm, up to about 1.7 mm. The thicknesses of each of the recesses 1092a,b may be equal to or slightly larger (e.g., about 1%, about 2%, about 3%, about 4%, up to about 5% larger) than the thickness of the pads 170a,b, to achieve a secure fit of the pads 170a,b in their respective recesses 1092a,b. In some implementations, the thickness of the recesses 1092a,b compared to that of the thickness of the pads 170a,b is such that the pads 170a,b fit loosely widthwise within the recesses 1092a,b. In some implementations, the thickness along the length of the pads 170a,b may vary. In some implementations, each pad 170a,b may have a length that is about 7 mm, about 8 mm, about 9 mm, about 10 mm, about 11 mm, about 12 mm, about 13 mm, up to about 14 mm, and may have a height that is about 3.5 mm, about 4 mm, about 4.5 mm, about 5 mm, about 5.5 mm, about 6 mm, about 6.5 mm, up to about 7 mm. In some implementations, the length of each of the recesses 1092a,b is equal to or slightly larger than the length of the pads 170a,b. When the pads 170a,b are inserted in the recesses 1092a,b, the pads 170a,b may curve or buckle such that the pads 170a,b are shaped around the central channel 1015 and not impeding flow to the mouthpiece 152. Further, when the pads 170a,b are inserted in the recesses 1092a,b, the pads 170a,b may extend above the sidewalls of the recesses 1092a,b, as shown in FIGS. 34B and 34C. The pads 170a,b may extend above the sidewalls of the recesses 1092a,b by about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, up to about 1.5 mm.

As described elsewhere herein, the mouthpiece 152 may include a projecting flat collar forming the internal flange 1045 surrounding the opening 154 and extending into the internal volume 1010 of the mouthpiece 152. The internal flange 1045 may have an inner diameter and an outer diameter. The thickness of the pads 170a,b may be sized to engage with the internal flange 1045, such that pads 170a,b are held within the internal flange 1045 when the mouthpiece 152 is installed on the cartridge body 156, as shown in FIGS. 34D, 34E, and 34F. The thickness between the inner diameter and the outer diameter of the internal flange 1045 may be slightly less than that of the thickness of the pads 170a,b, causing the pads 170a,b to be slightly compressed (e.g., from thickness of about 1.5 mm to thickness of about 1.4 mm) at an area where the pads 170a,b interface with the internal flange 1045 so that the pads 170a,b do not move within the mouthpiece 152. The resulting configuration, when the mouthpiece 152 is installed on the cartridge body 156, provides for the pads 170a,b to be spaced apart on opposing sides of the central channel 1015 across which the central, upper element 1052 extends and through which vapor flows before exiting the mouthpiece 152 (i.e., off-axis from the vapor flow path). The central opening between the pads 170a,b aligns generally with the opening 154 of the mouthpiece 152. The internal flange 1045 may be positioned within the mouthpiece 152 in such a way that upon installation of the mouthpiece 152 on the cartridge body 156, upper ends of the pads 170a,b are forced slightly inward so that the pads 170a,b are held at an angle with respect to a vertical axis of the cartridge 150, as shown in FIGS. 34E and 34F. This may be caused by the positioning of the internal flange 1045 being offset, in a vertical orientation, from the recesses 1092a,b. In some implementations, the pads 170a,b are at an angle, from the vertical axis, of about 0 degrees, about 1 degree, about 2 degrees, about 3 degrees, about 4 degrees, about 5 degrees, about 6 degrees, about 7 degrees, about 8 degrees, about 9 degrees, about 10 degrees, about 11 degrees, about 12 degrees, about 13 degrees, about 14 degrees, about 15 degrees, about 16 degrees, about 17 degrees, about 18 degrees, about 19 degrees, up to about 20 degrees. Additionally, the internal flange 1045 may cause the pads 170a,b to further flex and curve at one or more regions along the length of the pads 170a,b.

The configuration of the pads 170a,b, in which the pads 170a,b are positioned opposite one another, spaced apart on opposing sides of the central channel 1015, and off-axis from the opening 154 of the mouthpiece 152, may result in the capture of large particles yet allow smaller particles through to the opening 154. In some implementations, a large particle may have a diameter of at least about 10 microns. In some implementations, a large particle may have a diameter of at least about 8 microns, about 9 microns, about 10 microns, about 11 microns, up to about 12 microns. As larger particles have more inertia, the larger particles will hit the pads 170a,b whereas smaller particles will curl around the central, upper element 1052 to exit the mouthpiece 152, as further described below.

Figure 35A:
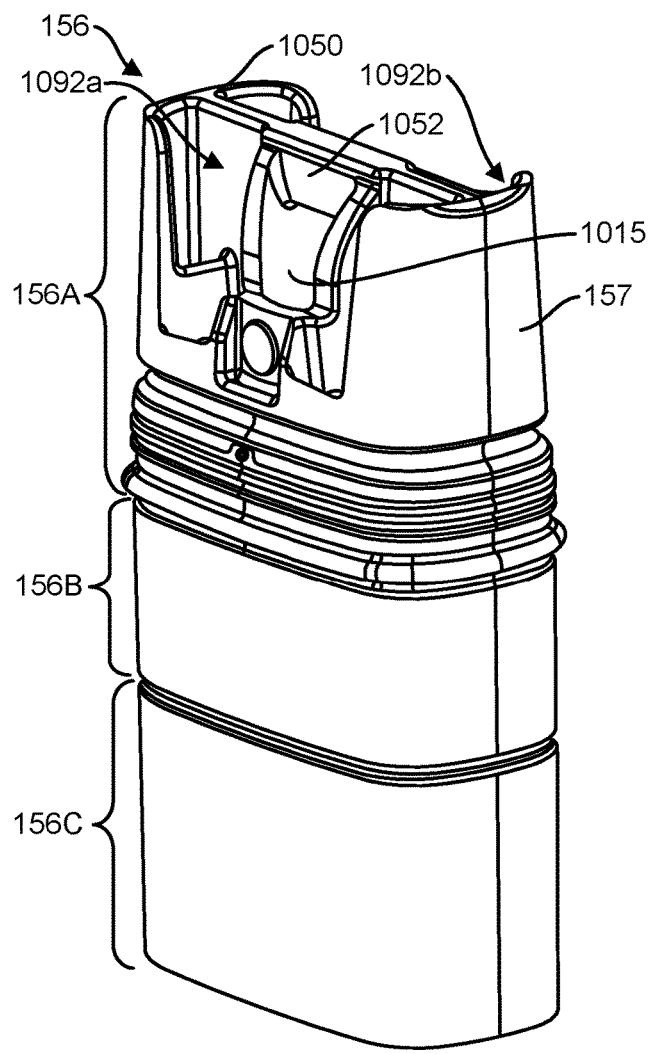
FIG. 35A and FIG. 35B illustrate features of a cartridge body of a cartridge of a vaporizer device consistent with implementations of the current subject matter.
Figure 35B:
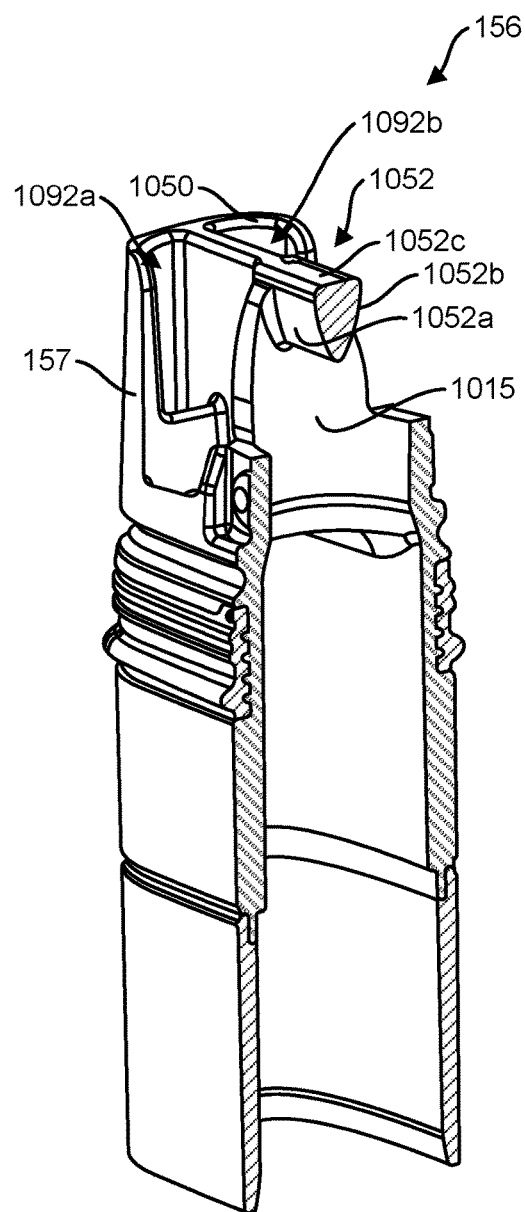

FIGS. 35A and 35B illustrate features of the central, upper element 1052 that extends across the major axis of the upper, proximal surface 1050 of the cartridge body 156, consistent with implementations of the current subject matter. FIG. 35A is front perspective view of the cartridge body 156, and FIG. 35B is a side cross-sectional view thereof. As shown, the central, upper element 1052 is positioned above the top end portion of a central cannula 172 in the central channel 1015 (see FIGS. 34C-34F). In some implementations, the central, upper element 1052 is about 0 mm, about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, up to about 2.0 mm above the top end portion of the central cannula 172.

The size and shape of the central, upper element 1052 may aesthetically block off the internal components from a user (through the opening 154 of the mouthpiece 152) as well as direct or split vapor flow around it. By directing the flow around the central, upper element 1052, larger particles are trapped in the pads 170a,b due to their inherent inertial properties described above. The central, upper element 1052 thus splits the vapor flow to allow for flow around the central, upper element 1052 and thereby reducing the amount of excess material that is collected on the central, upper element 1052 and elsewhere in the cartridge body 156.

In an implementation, as shown in FIGS. 35A and 35B, the central, upper element 1052 has a side cross-sectional profile with a sharpened end, curved and angled sides, and a blunt top that splits, due to the sharpened end and the curved and angled sides, the flow of vapor around the central, upper element 1052 for larger particles to be captured and entrained by the pads 170*a,b*, which are off-axis with respect to direction of the vapor flow. The central, upper element 1052 may be an airfoil with a leading edge and a closed trailing edge. The side cross-sectional profile of the central, upper element 1052 may be parabolic or triangular, as shown in FIG. 35A as well as FIGS. 34E and 34F, with a flat top surface 1052*c* and with angled side portions 1052*a* and 1052*b* that meet at the sharpened end. This configuration may prevent vapor impaction on surfaces within the cartridge body 156 (including the central, upper element 1052 itself), which can lead to a build-up of oil condensation. In some implementations, the angled side portions 1052*a,b* may be, with respect to the flat top surface 1052*c*, at an angle of about 45 degrees, about 50 degrees, about 55 degrees, about 60 degrees, about 65 degrees, about 70 degrees, about 75 degrees, up to about 80 degrees. A bounding box defining the side cross-sectional area of the central, upper element 1052 may have a length of about 1.5 mm, about 1.6 mm, about 1.7 mm, about 1.8 mm, about 1.9 mm, up to about 2.0 mm, and may have a height of about 2.0 mm, about 2.1 mm, about 2.2 mm, about 2.3 mm, about 2.4 mm, about 2.5 mm, about 2.6 mm, up to about 2.7 mm.

In some implementations, other side cross-sectional profiles as well as variations of those described herein may be used for the central, upper element 1052, where such profiles aid in the splitting and directing of the flow of vapor, such as other shapes with a sharpened or pointed end, including for example a diamond, a teardrop, an arrow, or a round or rounded edge profile.

Again with respect to FIGS. 12-14, the cartridge body 156 includes a central region 156B that defines, in part, a tank or reservoir 158 configured to hold an amount of vaporizable material within the cartridge 150. The reservoir 158 may be sealed on a distal or bottom end by an internal sealing gasket 173 positioned within the distal end region 156C of the cartridge body 156, which will be described in more detail below. The reservoir 158 may be sealed on a proximal or top end by a sealing ring 171. The central cannula 172 may extend through the reservoir 158 from near the distal end region 156C of the cartridge body 156 to the proximal end region 156A of the cartridge body 156. As best shown in FIG. 13, the proximal end region 156A of the cartridge body 156 defines a central channel 1015 that extends between a first opening 1016 at an upper end of the reservoir 158 to a second opening 1017 that may be coaxially aligned with the opening 154 through the proximal end surface of the mouthpiece 152. A proximal tap 1018 of the central cannula 172 encircled by the sealing ring 171 may extend through the first opening 1016 a distance into the central channel 1015. The sealing ring 171 may seal with the surface of the central channel 1015 and thereby seal the reservoir 158 on the upper end.

The sealing ring 171 may provide a seal between the central cannula 172 and the mouthpiece 152 to prevent or reduce the likelihood of fluid, such as the vaporizable material, from flowing into and out of the mouthpiece opening 154. The sealing ring 171 may be any of a variety of sealing element and can, but need not, have an annular shape. The shape of the sealing ring 171 may be configured to match the shape of the proximal tap 1018 of the central cannula 172 on its inner diameter and match the shape of the central channel 1015 on its outer diameter. In some implementations, the sealing ring 171 may be an elastomeric material configured to be compressed slightly upon insertion of the central cannula 172 into the central channel 1015 thereby providing fluid sealing and preventing the vaporizable fluid stored in the reservoir 158 from exiting the cartridge 150 through the central channel 1015.

The reservoir 158 may be arranged to surround the central cannula 172, which may be positioned coaxial with the longitudinal axis A of the cartridge 150. The reservoir 158 may thereby be generally ring-shaped such that the outer wall(s) of the reservoir 158 are formed by the cartridge body 156 and the inner wall(s) of the reservoir 158 are formed by the central cannula 172 extending through the reservoir 158. The reservoir 158 need not be arranged symmetrically around the longitudinal axis A of the cartridge 150 with the central cannula 172 extending through it. Other configurations are considered herein.

Figure 16A:
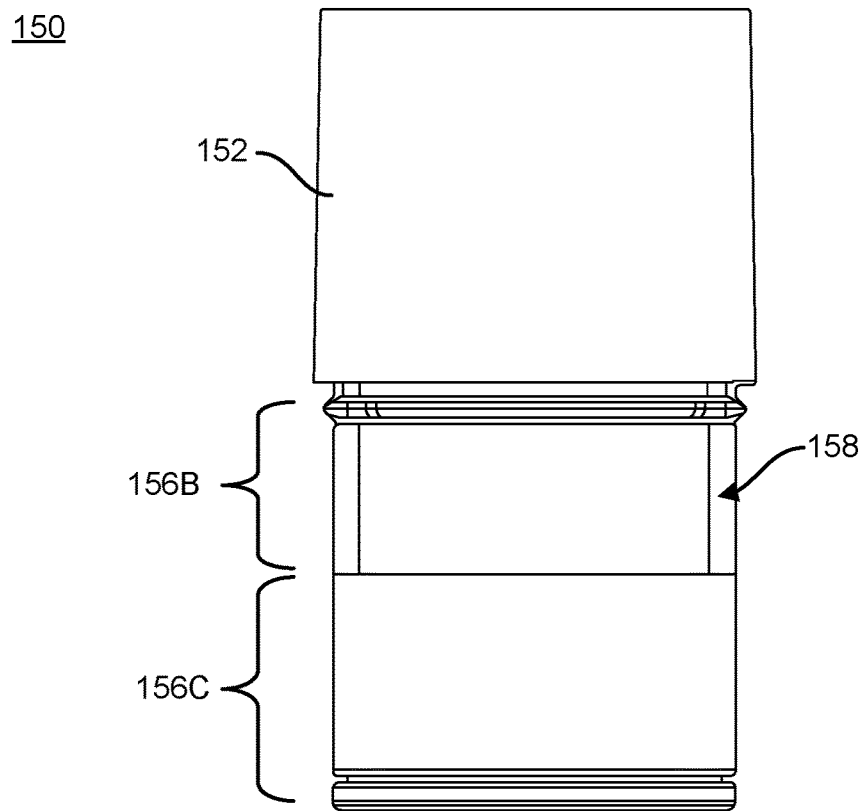
FIG. 16A-FIG. 16B illustrate features relating to volume of a cartridge reservoir consistent with implementations of the current subject matter.
Figure 16B:
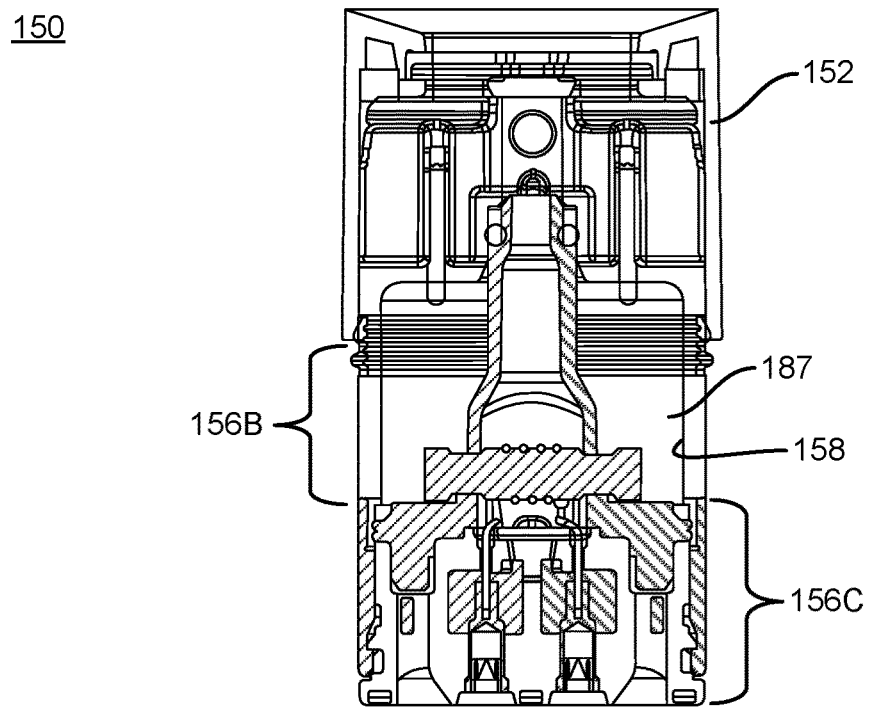

As mentioned above, at least a portion of the cartridge body 156 may be transparent, translucent, opaque, or a combination thereof. The cartridge body 156 may include one or more regions formed of an opaque material such that the contents are not visible from outside the device as well as one or more regions formed of a translucent or transparent material such that the contents are visible from outside the device. For example, the central region 156B of the cartridge body 156 may be translucent to transparent such that the reservoir 158 contained within this portion of the cartridge body 156 may remain visible to a user from outside the cartridge 150. The distal end region 156C of the cartridge body 156 may be opaque such that a majority of the components within this region remain hidden from view. Similarly, the mouthpiece 152 positioned over the proximal end region 156A of the cartridge body 156 may be opaque. FIGS. 16A-16B illustrate a translucent central region 156B of the cartridge body 156. The reservoir 158 and substantially all the vaporizable material 187 contained within the reservoir 158 are visible through this central region 156B of the cartridge body 156. In some implementations, the central region 156B where the oil volume is visible has a width between the opaque mouthpiece 152 and the opaque distal end region 156C that is at least about 4.0 mm up to at least about 8.0 mm. In an implementation, the central region 156B has a visible width between the opaque mouthpiece 152 and the opaque distal end region 156C that is 7.5 mm. Distal end region 156C of the cartridge body 156 and the mouthpiece 152 are both shown as opaque and blocking from view any of the internal components contained within either of those regions. From a usability perspective, a user of the vaporizer device 100 may want to see a remaining amount of vaporizable material 187 within the reservoir 158, but not be distracted with the complexity of the internal components of the cartridge body 156. The translucent to transparent central region 156B may reveal the amount of vaporizable material remaining in the reservoir 158. The central region 156B may avoid blocking a user's view of the distal end (bottom) of the reservoir 158 such that the remaining volume of vaporizable material in the reservoir is visible to a user until the total volume of the vaporizable material is absorbed by the wick.

An opaque plastic may be injection-molded directly over a clear plastic, with the opaque plastic region hiding from view internal components of the cartridge body 156 and the clear plastic region showing a large volume of the reservoir 158 portion of the cartridge body 156 (see also FIGS. 16A-16B). The opaque plastic may be laser-etched to provide a label directly on the cartridge body 156. The cartridge body 156 may include graduations positioned relative to the central region 156B to provide a user with an indication as to the volume of vaporizable material 187 contained within the reservoir 158.

The volume of the reservoir 158 may vary, but is generally sized to hold sufficient vaporizable material for delivering at least one dose of the material. The volume of the reservoir 158 may be between about 0.2 mL to about 2 mL, in other implementations between 0.4 mL to about 1.2 mL, or in still other implementations between about 0.4 mL to about 0.8 mL. The reservoir 158 may be pre-filled or filled prior to, during, and after use as well be described more below.

Again with respect to FIGS. 12-14, the central cannula 172 extending through the reservoir 158 defines the vaporization chamber 1005 that together with the central channel 1015 directs vapor flow towards the mouthpiece 152. The central cannula 172 defining the vaporizing chamber may be a generally cylindrical element extending from a bottom plate 1072 to the proximal tap 1018. The central cannula 172 may extend coaxial with the longitudinal axis A of the cartridge 150 up through the reservoir 158 such that the reservoir 158 surrounds the central cannula 172. The base region of the vaporization chamber 1005 may have an enlarged volume and a greater inner diameter compared to an inner diameter of the proximal tap 1018. As described above, the proximal tap 1018 may insert into and seal (i.e., via the sealing ring 171) with the central channel 1015 of the proximal end region 156A of the cartridge body 156. The proximal tap 1018 may define an opening 1022 near its upper-most end such that the vaporization chamber 1005 of the central cannula 172 may be in fluid communication with the central channel 1015 via the opening 1022. Vapor from the vaporization chamber 1005 may flow through the opening 1022 in the proximal tap 1018 into the central channel 1015 and out the one or more openings 154 of the mouthpiece 152.

Figure 17:
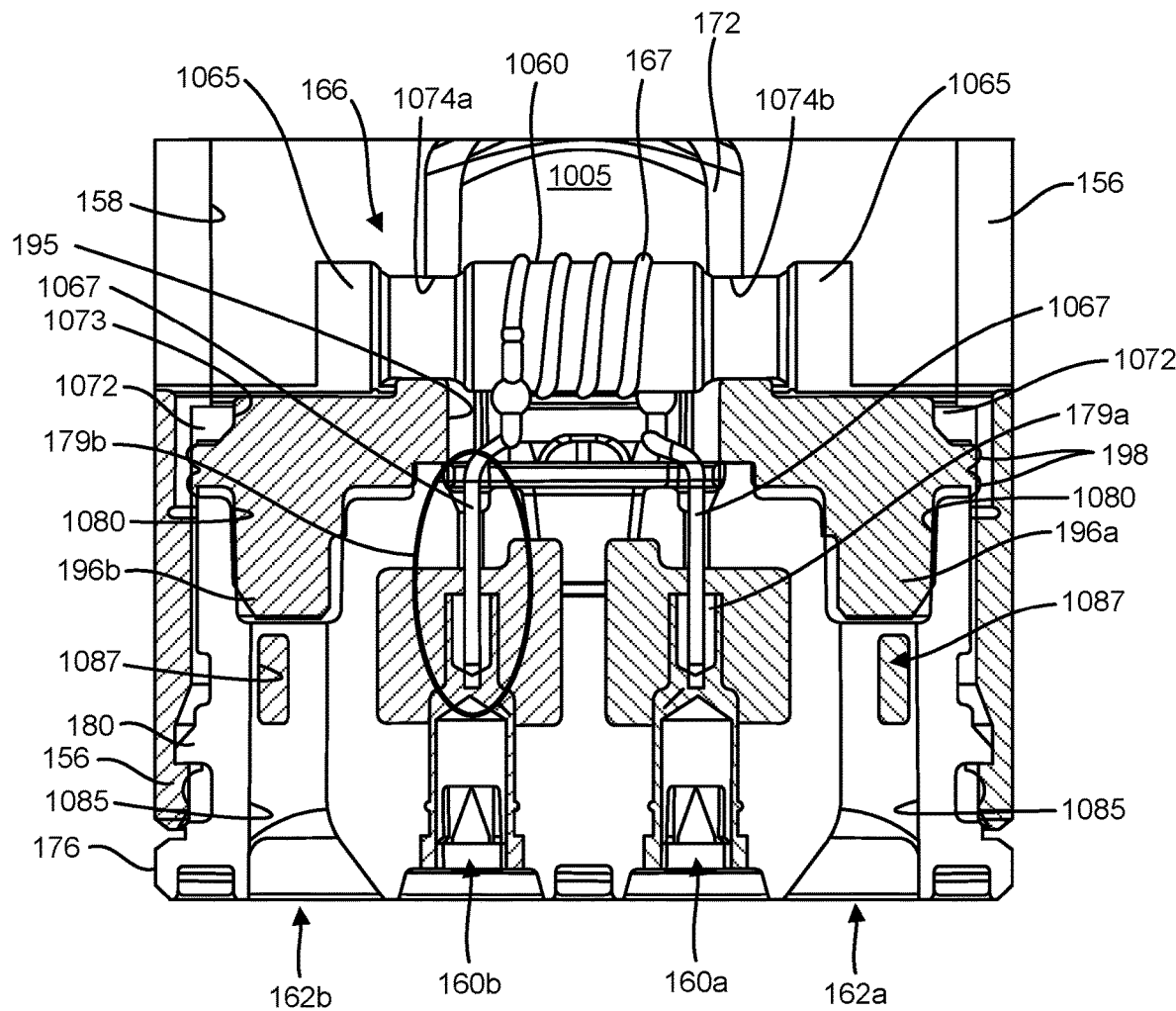
FIG. 17 illustrates features relating to assembly of a heater assembly and internal connections in a cartridge, consistent with implementations of the current subject matter.

The enlarged base of the central cannula 172 may be coupled to the bottom plate 1072. The bottom plate 1072 may be a generally planar feature coupled to the base of the central cannula 172 that forms a rim around the base. The lower surface of the bottom plate 1072 may include distal extensions configured to extend through the internal sealing gasket 173, which will be described in more detail below. The upper surface of the bottom plate 1072 may define, at least in part, a lower surface of the reservoir 158 and the lower surface of the bottom plate 1072 may abut against the internal sealing gasket 173, which will be discussed in more detail below. As best shown in FIGS. 14, 17, and also FIG. 24, the bottom plate 1072 may include a central aperture 1073 such that the vaporization chamber 1005 remains open on a distal end to provide a vapor flow passageway through the cartridge body 156 to the mouthpiece 152. The central aperture 1073 may be elongated such that it forms an oval, elliptical, or other elongate shape having a minor axis and a major axis. A middle portion of the central aperture 1073 may be aligned with the vaporization chamber 1005 and at least partially encircled by the central cannula 172. As such, the middle portion of the central aperture 1073 may be generally rounded or circular in shape similar to a cross-sectional shape of the base of the central cannula 172. Two outer portions of the central aperture 1073 (i.e., along the major axis) may extend beyond the base of the central cannula 172 due to the elongate shape of the central aperture 1073. These outer portions of the central aperture 1073 may be narrower than the middle portion providing the central aperture 1073 with a keyhole shape. The central aperture 1073 may have other shapes and may also be made up of a plurality of openings through the bottom plate 1072.

The cartridge 150 may include a vaporizing assembly of vapor-generating components. The vapor-generating components may include a heater 166 configured to heat the vaporizable material to a sufficient temperature that it may vaporize. The vapor-generating components may be arranged as an atomizer or cartomizer or oven. The vapor may be released to a vaporization chamber where the gas phase vapor may condense, forming an aerosol cloud having typical liquid vapor particles with particles having a diameter of average mass of approximately 1 micron or greater. In some cases, the diameter of average mass may be approximately 0.1-1 micron.

The heater 166 of the vaporizing assembly may cause the vaporizable material to be converted from a condensed form (e.g., a solid, a liquid, a solution, a suspension, a part of an at least partially unprocessed plant material, etc.) to the gas phase. After conversion of the vaporizable material to the gas phase, and depending on the type of vaporizer, the physical and chemical properties of the vaporizable material, and/or other factors, at least some of the gas-phase vaporizable material may condense to form particulate matter in at least a partial local equilibrium with the gas phase as part of an aerosol, which may form some or all of an inhalable dose provided by the vaporizer for a given puff or draw on the vaporizer. It will be understood that the interplay between gas and condensed phases in an aerosol generated by a vaporizer may be complex and dynamic, as factors such as ambient temperature, relative humidity, chemistry, flow conditions in airflow paths (both inside the vaporizer and in the airways of a human or other animal), mixing of the gas-phase or aerosol-phase vaporizable material with other air streams, etc., may affect one or more physical parameters of an aerosol. In some vaporizers, and particularly for vaporizers for delivery of more volatile vaporizable materials, the inhalable dose may exist predominantly in the gas phase (i.e., formation of condensed phase particles may be very limited).

Vaporizers for use with liquid vaporizable materials (e.g., neat liquids, suspensions, solutions, mixtures, etc.) typically include an atomizer in which a wicking element (also referred to herein as a wick 168), which may include any material capable of causing passive fluid motion, for example, by capillary pressure) conveys an amount of a liquid vaporizable material to a part of the atomizer that includes the heating element. The wicking element is generally configured to draw liquid vaporizable material from the reservoir configured to contain (and that may in use contain) the liquid vaporizable material such that the liquid vaporizable material may be vaporized by heat delivered from the heating element.

The heater 166 may be or include one or more of a conductive heater, a radiative heater, and a convective heater. One type of vaporizing heating element is a resistive heating element, which may be constructed of or at least include a material (e.g., a metal or alloy, for example a nickel-chromium alloy, or a non-metallic resistor) configured to dissipate electrical power in the form of heat when electrical current is passed through one or more resistive segments of the heating element. In some implementations of the current subject matter, an atomizer may include a vaporizing heating element that includes resistive coil or other heating element wrapped around, positioned within, integrated into a bulk shape of, pressed into thermal contact with, or otherwise arranged to deliver heat to a wicking element to cause a liquid vaporizable material drawn by the wicking element from a reservoir to be vaporized for subsequent inhalation by a user in a gas and/or a condensed (e.g., aerosol particles or droplets) phase. Other wicking element, heating element, and/or atomizer assembly configurations are also possible, as discussed further below.

Certain vaporizers may also or alternatively be configured to create an inhalable dose of gas-phase and/or aerosol-phase vaporizable material via heating of a non-liquid vaporizable material, such as for example a solid-phase vaporizable material or plant material containing the vaporizable material. In such vaporizers, a resistive heating element may be part of or otherwise incorporated into or in thermal contact with the walls of an oven or other heating chamber into which the non-liquid vaporizable material is placed. Alternatively, a resistive heating element or elements may be used to heat air passing through or past the non-liquid vaporizable material to cause convective heating of the non-liquid vaporizable material. In still other examples, a resistive heating element or elements may be disposed in intimate contact with plant material such that direct conductive heating of the plant material occurs from within a mass of the plant material (e.g., as opposed to only by conduction inward from walls of an oven).

Still with respect to FIGS. 13-14 and also FIG. 17, the heater 166 may be configured to heat and/or vaporize at least a portion of the vaporizable material drawn towards the heater 166 from the reservoir 158. The central cannula 172 defining the vaporization chamber 1005 is configured to couple to the heater 166 configured to generate heat to provide vaporization of the vaporizable material contained in the reservoir 158. In some implementations, the heater 166 of the vaporizing assembly may include a resistive element such as a heating coil 167 in thermal contact with a wick 168 of the vaporizing assembly. The wick 168 may be formed of any of a variety of materials, including metals, polymer, natural fibers, synthetic fibers, or combinations of these. For example, the wick 168 may be formed of silica fibers, cotton, ceramic, hemp, stainless steel mesh, rope cables, and/or any porous medium, such as for example sintered glass beads. The wick 168 is porous and provides a capillary pathway for fluid within the reservoir 158 through and into the wick 168. The capillary pathway is generally large enough to permit wicking of sufficient material to replace vaporized liquid transferred from the reservoir 158 by capillary action (wicking) during vaporization, but may be small enough to prevent leakage of the vaporizable material out of the cartridge during normal operation, including when pressure is applied to outside the cartridge 150. The wick 168 may have a size configured to handle high viscosity liquids. In some implementations, the wick 168 may have a diameter that is at least about 1.5 mm. The wick may be larger than 1.5 mm in diameter (e.g., about 1.9 mm or larger, about 2.0 mm or larger, about 2.1 mm or larger, about 2.2 mm or larger, about 2.3 mm or larger, about 2.4 mm or larger, about 2.5 mm or larger, etc., including between about 1.8 mm and about 5 mm, between about 1.9 mm and about 4 mm, between about 2 mm and about 4 mm, etc.). The material of the wick 168 is configured to draw the liquid vaporizable material from the reservoir 158 into the vaporization chamber 1005 without the need for a pump or other mechanical moving part. In some implementations, the tension of the heating coil 167 wound around the wick 168 may vary. Winding the heating coil 167 tighter and/or with additional windings may create a larger heating surface area to create more intense or concentrated heating of the vaporizable material. Likewise, reducing the diameter of the wick may also create more intense or concentrated heating of the vaporizable material.

Alternative configurations may include gravity-fed, capillary-fed, micro-pump, or collapsible bladders which operate under pressure differentials. Although the heater 166 is described herein as incorporating a heating coil, it should be appreciated that other configurations may be used and that the resistive element need not be shaped as a coil. The heater 166 also need not be a coil/wick configuration. In some implementations, the heater 166 incorporates a piezo aerosolizer to generate droplets of the vaporizable material.

The heating coil 167 may be a resistance wire wrapped around the wick 168 and connected to a positive and negative pole of a current source. The coil 167 may increase in temperature as a result of the current flowing through the wire to generate heat. The heat may be transferred to at least a portion of the vaporizable material through conductive, convective, and/or radiative heat transfer such that at least a portion of the vaporizable material vaporizes. Air drawn into the vaporization chamber 1005 may carry the vapor away from the heater 166.

The heater 166 may extend across the air path within the vaporization chamber 1005, such as in a transverse direction. Still with respect to FIGS. 13-14 and also FIG. 17, the central cannula 172 may be arranged coaxial with the longitudinal axis A of the device and the wick 168 may extend orthogonal to the longitudinal axis A through the central cannula 172. The wick 168 is preferably positioned near a distal-most end region of the reservoir 158 such that the vaporizable material in the reservoir 158 may be fully used. A pair of lateral openings 1074a,b may extend through the walls of the central cannula 172 near its base where the central cannula 172 couples to the bottom plate 1072. The pair of lateral openings 1074a,b may be aligned across from one another on opposing sides of the central cannula 172. The openings 1074a,b are provided and sized for coupling to the heater 166. As described above, the bottom plate 1072 and the central aperture 1073 extending through the bottom plate 1072 may have a major axis and a minor axis. The elongate shape of the central aperture 1073 provides for two outer portions along the major axis of the bottom plate 1072 to extend beyond the base of the central cannula 172. The two outer portions of the central aperture 1073 may be aligned with the lateral openings 1074a,b of the central cannula 172 thereby forming an enlarged slot near the base of the central cannula 172 where it couples with the bottom plate 1072. The wick 168 may extend through these lateral openings 1074a,b and within this slot.

In some implementations, the wick 168 of the heater 166 may include a central portion 1060 and opposing ends 1065a,b. The heating coil 167 may be wrapped around the central portion 1060 of the wick 168, which in turn may be positioned within the vaporization chamber 1005. The opposing ends 1065a,b of the wick 168 may be positioned outside the vaporization chamber 1005 by extending laterally outward through the lateral openings 1074a,b of the central cannula 172. As such, the opposing ends 1065a,b may be positioned within the internal volume of the reservoir 158 whereas the central portion 1060 of the wick 168 wrapped by the heating coil 167 may be positioned inside the vaporization chamber 1005 of the central cannula 172. The leads 1067 of the heating coil 167 may extend away from the central portion 1060 of the wick 168 and down through the central aperture 1073 of the bottom plate 1072 out of the vaporization chamber 1005. The leads 1067 may extend into the distal end region 156C of the cartridge body 156 where the leads 1067 may electrically couple with the power pin receptacles 160*a,b*, which will be described in more detail below.

As mentioned, the distal end region 156C of the cartridge body 156 may house the internal sealing gasket 173 coupled to a lower support structure 174. The internal sealing gasket 173 may be positioned generally under the bottom plate 1072 of the central cannula 172 and attached to an upper surface of the lower support structure 174. This placement of the internal sealing gasket 173 serves to seal the reservoir 158 on the distal or bottom end and thereby reduce or eliminate leaking of vaporizable material out of the reservoir 158, for example, into the electrical components contained in the distal end region 156C of the cartridge 150 as well as the vaporizer body 110. The internal sealing gasket 173 may be, in some implementations, an oversized elastic or rubberized material that plugs various openings in a distal end region of the device and forms a seal between the reservoir 158 and the lower support structure 174 when under compression. Thus, the internal sealing gasket 173 may be sized and shaped to fit between the reservoir 158 and the lower support structure 174 to seal any openings therebetween.

Now with respect to FIGS. 17-18, 19A-19B, the internal sealing gasket 173 may be defined generally by an upper region and a lower region separated by a midline region. A central opening 195 may extend through the internal sealing gasket 173, thus providing the internal sealing gasket 173 with a generally annular structure. The central opening 195 may align with the middle portion of the central aperture 1073 through the bottom plate 1072 to allow for air flow through the internal sealing gasket 173 into the vaporization chamber 1005. When the upper region of the internal sealing gasket 173 abuts against the bottom plate 1072 of the central cannula 172, the distal extensions of the central cannula 172 projecting from the lower surface of the bottom plate 1072 extend down through the central opening 195 of the internal sealing gasket 173. As discussed above, the leads 1067 of the heating coil 167 may extend away from the central portion 1060 of the wick 168 and down through the central aperture 1073 of the bottom plate 1072 and through the central opening 195 of the internal sealing gasket 173 in order to electrically couple with the power pin receptacles 160*a,b*, within the lower support structure 174 which will be described in more detail below.

The upper region of the internal sealing gasket 173 is configured to seal the distal end region of the reservoir 158, the lower region of the internal sealing gasket 173 is configured to seal with the lower support structure 174, and the midline region of the internal sealing gasket 173 is configured to seal with an inner surface of the distal end region 156C of the cartridge body 156. The upper region of the internal sealing gasket 173 may include a pair of surface features 197*a,b* projecting upward from a generally planar upper surface (see FIG. 19B). The generally planar upper surface is configured to abut against the generally planar lower surface of the bottom plate 1072 of the central cannula 172. When the upper surface of the internal sealing gasket 173 abuts against the lower surface of the bottom plate 1072, the surface features 197*a,b* may project through the outer portions of the central aperture 1073 of the bottom plate 1072. The middle portion of the central aperture 1073 is aligned with the longitudinal axis A of the cartridge and at least partially encircled by the central cannula 172. The central aperture 1073 may additionally include two outer portions on either side of the middle portion that are positioned generally outside the perimeter of the central cannula 172 base (i.e., along the major axis of the plate). The pair of surface features 197*a,b* projecting from the upper surface of the internal sealing gasket 173 extends up through the outer portions of the central aperture 1073 on either side of the central cannula 172 thereby sealing these outer portions of the central aperture 1073. At the same time, the distal extensions of the central cannula 172 on the lower surface of the bottom plate 1072 may extend down through the central opening 195 in the internal sealing gasket 173. This provides a tight fit coupling between the bottom plate 1072 of the central cannula 172 and the internal sealing gasket 173. The pair of surface features 197*a,b* projecting from the upper surface of the internal sealing gasket 173 may include a region configured to interface with and laterally support the heater 166. For example, the opposing ends 1065*a,b* of the wick 168 extending through the lateral openings 1074*a,b* may engage with at least a portion of the pair of surface features 197*a,b*. The pair of surface features 197*a,b* may also seal with the wick 168. As such, the pair of surface features 197*a,b* may generally align with the location of the lateral openings 1074*a,b* of the central cannula 172 through which the opposing ends 1065*a,b* of the wick 168 extend.

As described above, the wick 168 may extend orthogonal to the longitudinal axis A at the base of the reservoir 158. The opposing ends 1065*a,b* of the wick 168 may be positioned within the reservoir 158 and the central portion 1060 of the wick 168 wound by the heating coil 167 may be positioned within the vaporization chamber 1005. The upper half of the wick 168 may be sealed by the walls of the central cannula 172 defining the lateral openings 1074*a,b*. The lower half of the wick 168 may engage and seal with the pair surface features 197*a,b* of the internal sealing gasket 173. The pair of surface features 197*a,b* may be sized and shaped to insert through the central aperture 1073 of the bottom plate 1072 helping to seal the central aperture 1073 (see FIGS. 17, 19A-19B). At least a portion of the pair of surface features 197*a,b* extends a distance toward the opposing ends 1065*a,b* of the wick 168. This portion of the pair of surface features 197*a,b* may include a wick mating surface sized and shape to complement the cylindrical surface of the wick 168. For example, the portion may have a semi-circular wick mating surface configured to seal with the cylindrical outer surface of a region of the wick 168. The portion of the pair of surface features 197*a,b* may also laterally support the opposing ends 1065*a,b* of the wick 168.

As mentioned, the internal sealing gasket 173 also may include a midline region between the upper and lower regions. The midline region of the internal sealing gasket 173 may seal with the internal surface of the cartridge body 156. In an implementation, the midline region of the internal sealing gasket 173 may be encircled by a seal having dual sealing beads 198. The dual sealing beads 198 are configured to provide a circumferential seal with the distal end region 156C of the cartridge body 156 (see FIG. 19B). For example, the dual sealing bands 198 may be provided for redundancy, to prevent vaporizable material from leaking from the reservoir 158.

Figure 19A:
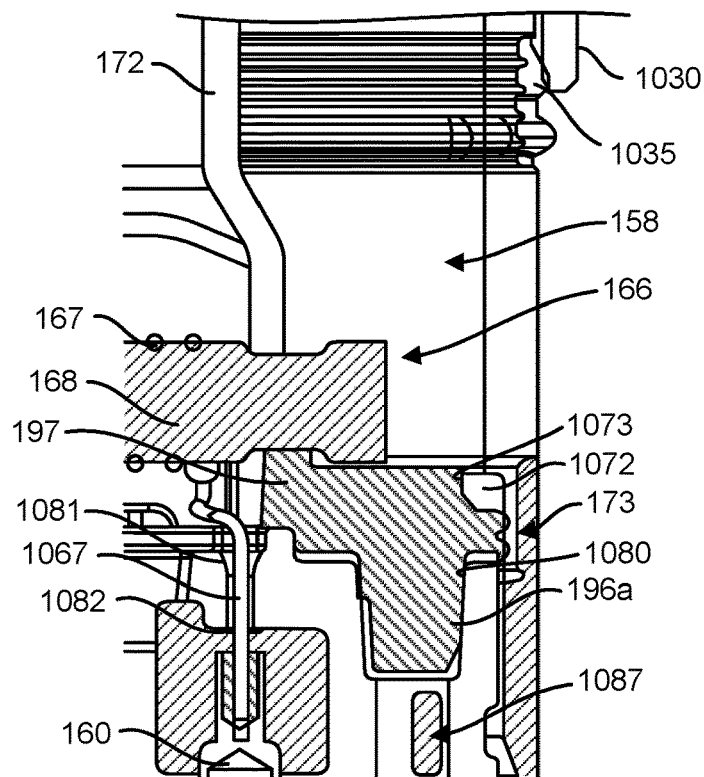
FIG. 19A-FIG. 19C illustrate features of various seals incorporated in cartridge of a vaporizer device consistent with implementations of the current subject matter.
Figure 19B:
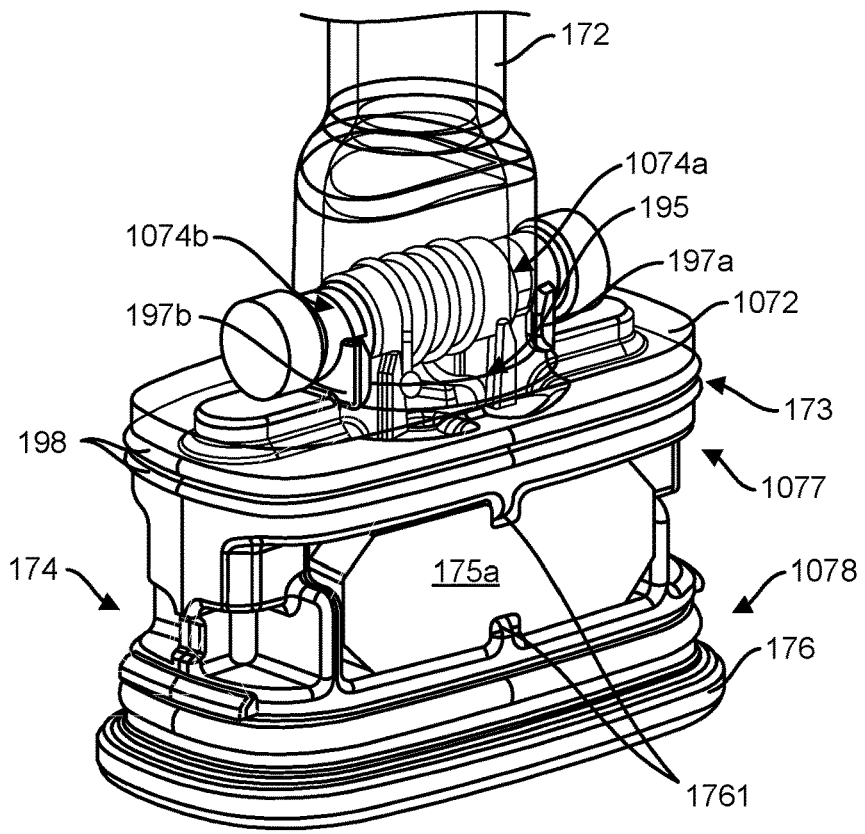

Still with respect to FIGS. 17, and 19A-19B, the lower region of the internal sealing gasket 173 may include a pair of penetrable surface features 196*a,b* projecting downward from the lower surface of the internal sealing gasket 173. When the lower surface of the internal sealing gasket 173 abuts against an upper surface of the lower support structure 174, the pair of penetrable surface features 196*a,b* extend distally and insert within corresponding ones of the pair of openings 1080 in the upper surface of the lower support structure 174, as will be described in more detail below.

The various features of the internal sealing gasket 173 on the upper, lower, and perimeter surfaces form an integrated sealing element that may seal a variety of locations within the cartridge 150 (i.e., the filling ports, the wick, and the distal end of the reservoir 158). The integrated seals provided by the internal sealing gasket 173 may simplify assembly and manufacturing, as will be described in more detail below.

Figure 21A:
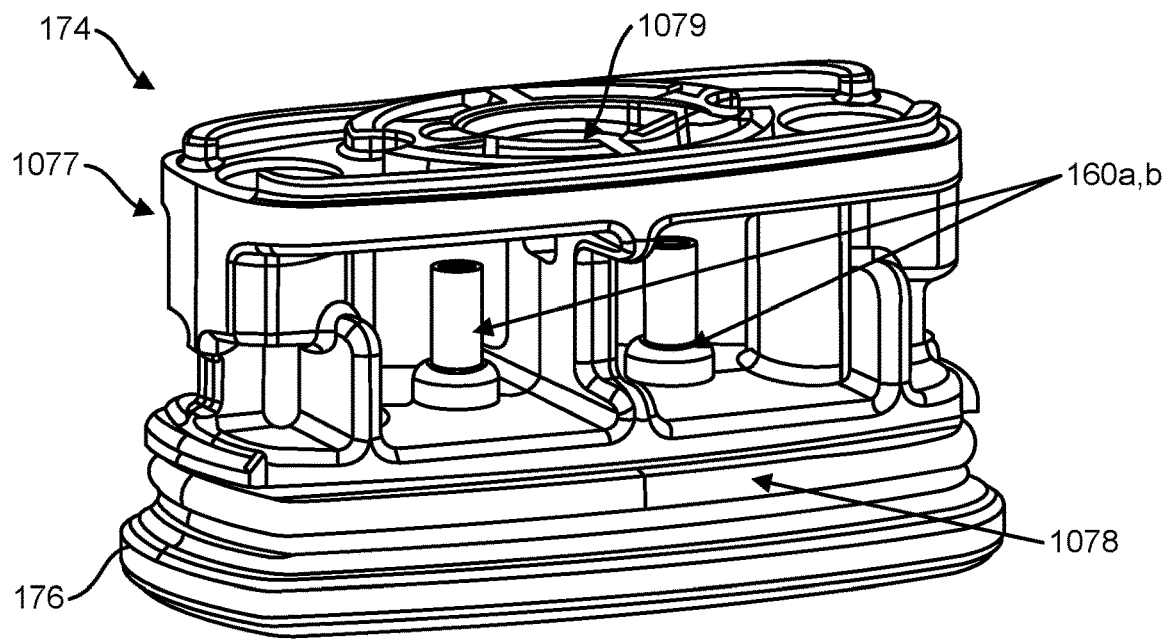
FIG. 21A-FIG. 21B illustrate additional features of a cartridge consistent with implementations of the current subject matter.
Figure 21B:
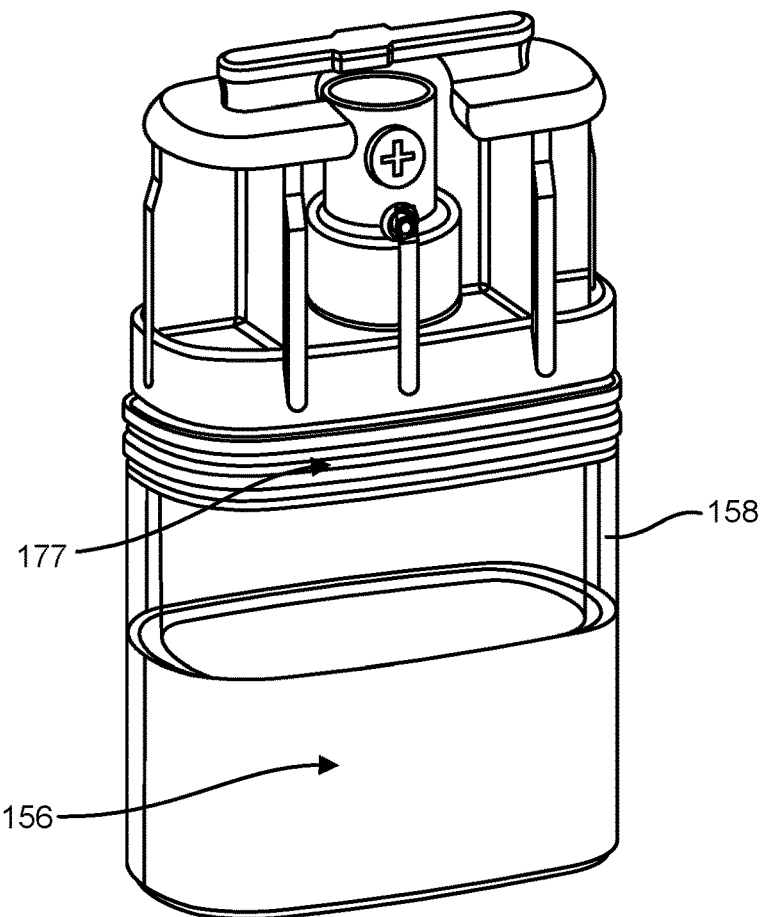

As mentioned, the distal end region 156C of the cartridge body 156 may house the lower support structure 174. The lower support structure 174 may include an upper region 1077 and a lower region 1078 (see FIG. 19B, FIG. 20C, and FIG. 21A). The upper region 1077 is configured to mate with the lower region of the internal sealing gasket 173. For example, the upper region 1077 may include the pair of openings 1080 in the upper surface that are sized and shaped to receive the pair of penetrable surface features 196a,b projecting downward from the lower surface of the internal sealing gasket 173. The upper region 1077 of the lower support structure 174 may also include a central aperture 1079 extending through its thickness that is configured to align with the central opening 195 of the internal sealing gasket 173 that, in turn, aligns with the central aperture 1073 extending through the bottom plate 1072. The central aperture 1073 in the bottom plate 1072, the central opening 195 in the internal sealing gasket 173, and the central aperture 1079 of the lower support structure 174 are configured to receive distal extensions of the central cannula 172 and align with the vaporization chamber 1005 to allow for air flow through the distal end region 156C of the cartridge body 156.

A pair of air flow channels 1085 may extend through the lower support structure 174. The air flow channels 1085 each communicate on a distal end with a respective one of a pair of the air flow inlets 162a,b configured to remain in fluid communication with the atmosphere during use of the device. The distal end of the lower support structure 174 may define the air flow inlets 162a,b into the air flow channels 1085 extending through the lower support structure 174. The air flow channels 1085 extend from the air flow inlets 162a,b through the lower region 1078 of the lower support structure into the upper region 1077 of the lower support structure 174. The air flow channels 1085 extend to the pair of openings 1080 in the upper region 1077 of the lower support structure 174. Thus, the pair of air flow channels 1085 may extend through the entire thickness of the lower support structure 174 between the air flow inlets 162a,b in the lower surface to the pair of openings 1080 in the upper surface. The internal sealing gasket 173 may be positioned in the distal end region 156C of the cartridge body 156 providing sealing between the reservoir 158 and the air flow channels 1085 of the lower support structure 174. The pair of penetrable surface features 196a,b projecting downward from the lower surface of the internal sealing gasket 173 insert through the pair of openings 1080 and seat within an upper portion or proximal end of the air flow channels 1085 thereby sealing the upper end of the air flow channels 1085 preventing leaking of the vaporizable material out of the reservoir 158 through the air flow channels 1085. The pair of air flow inlets 162a,b through the lower surface of the lower support structure 174 into the air flow channels 1085 remain unobstructed. The air flow inlets 162a,b may align with or be positioned in fluid communication with the side air inlets 116a,b, which will be described in more detail below. Each of the air flow channels 1085 extending through the lower support structure 174 from the lower air flow inlets 162a,b to the pair of openings 1080 may additionally include a side channel outlet 1087. The side channel outlet 1087 may be positioned a distance distal to the pair of penetrable surface features 196a,b projecting into the air flow channels 1085 and a distance proximal to the lower air flow inlets 162a,b into the air flow channels 1085. The length of the air flow channels 1085 allows for the positioning of these side channel outlets 1087 away from the lower air flow inlets 162a,b such that, in the event of a leak into the bottom volume of the cartridge body 156, the air flow channels 1085 avoid being significantly filled in a manner that could block the air flow through or cause leaking out of the side channel outlets 1087.

The air flow inlets 162a,b into the air flow channels 1085 form an entry point for air into the cartridge 150 as well as an entry point for a filler to fill the reservoir 158 with vaporizable material, which is described in more detail below.

Figure 18:
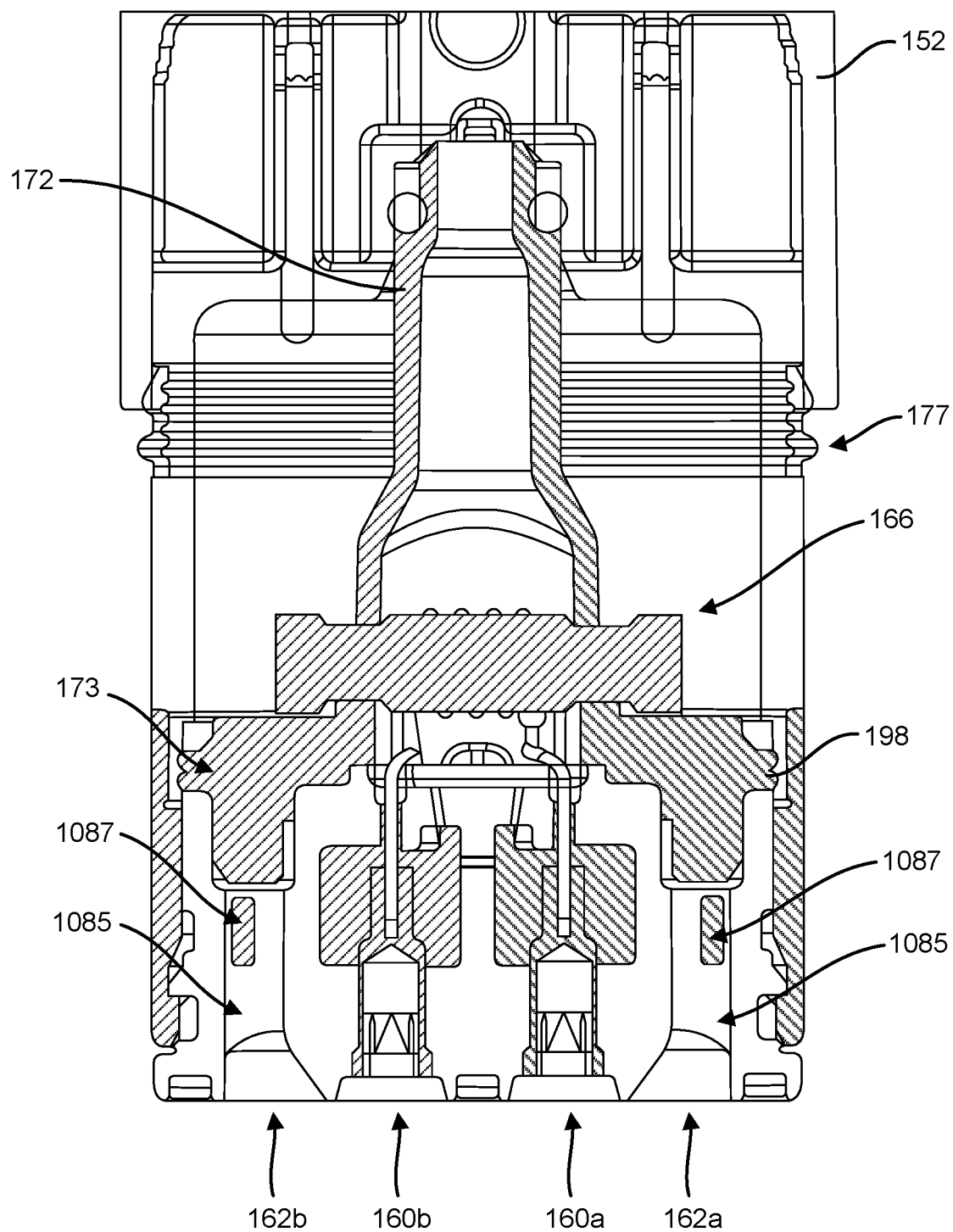
FIG. 18 illustrates additional features relating to filling a cartridge with a vaporizable material consistent with implementations of the current subject matter.

FIGS. 20A-20C illustrate air flow path 181 through the cartridge 150 upon coupling the cartridge 150 to a vaporizer body 110. As described elsewhere herein, the outer shell 112 of the cartridge receptacle 114 of the vaporizer body 110 may include one or more side air inlets 116a,b (see also FIGS. 1C and 1D). As mentioned above, the air inlets 116a,b may be aligned with or positioned in fluid communication with the lower air flow inlets 162a,b leading into the air flow channels 1085 from the lower region 1078 of the lower support structure 174. Air may enter the cartridge 150 through the air inlets 116a,b and continue through the lower air flow inlets 162a,b and into the air flow channels 1085 of the lower region 1078 of the lower support structure 174. FIGS. 20A-20C and also FIGS. 18, 19A-19B show air may pass from the air flow channels 1085 of the lower region 1078 of the lower support structure 174 through the side channel outlets 1087 before passing up through the upper region 1077 into the vaporization chamber 1005. The lower support structure 174 may act as a plenum for the air, which is then directed through the central opening 195 in the internal sealing gasket 173, past the wick 168 and heating coil 167, and through the vaporization chamber 1005 of the central cannula 172. The air flow path 181 may continue through the opening 1022 of the proximal tap 1018, into the central channel 1015 of the proximal end region 156A of the cartridge body 156 and out the opening 154 of the mouthpiece 152. The vapor may then be inhaled by a user. The mouthpiece 152 may incorporate a baffle 1088 near the opening 154 to allow the vapor to cool via a longer, turbulent flow path before entering the mouth of a user (see FIG. 20B).

The lower region 1078 of the lower support structure 174 is configured to mate with the distal end region 156C of the cartridge body 156. As a further leak protection in this region of the cartridge, the lower region 1078 of the lower support structure 174 may include a bottom tank seal 176 extending circumferentially around its perimeter (see FIGS. 15C, 18D, and 22A). The bottom tank seal 176 may further block any material that leaks from the wick 168 into the distal end region 156C of the cartridge body 156 from leaking out of the cartridge body 156. The bottom tank seal 176 may be over-molded around the distal end of the lower region 1078.

Figure 36A:
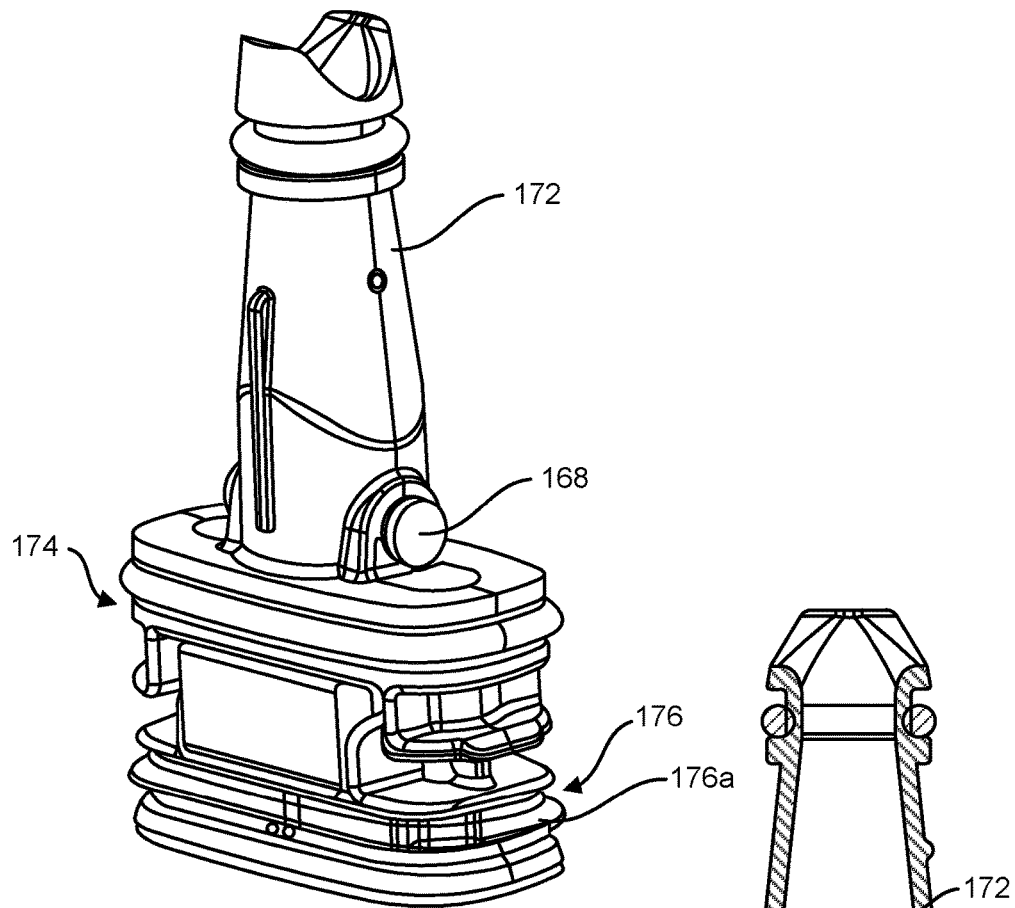
FIG. 36A and FIG. 36B illustrate features of a lower support structure and a cannula of a cartridge of a vaporizer device consistent with implementations of the current subject matter.
Figure 36B:
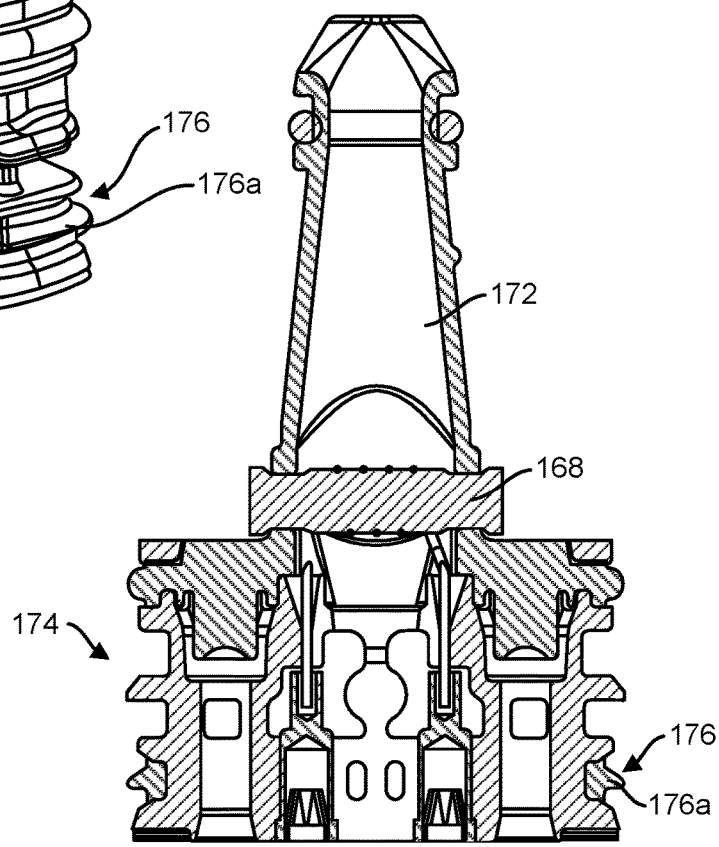

In another implementation, the bottom tank seal 176 may incorporate an outward protruding rib 176a along its circumference, as shown in FIGS. 36A and 36B. FIG. 36A is a front perspective view illustrating details of the central cannula 172 and the lower support structure 174, and FIG. 36B is a front cross-sectional view thereof. The material of the bottom tank seal 176 may be such that it absorbs material that is being blocked and may thus need room to expand to account for this absorption. For example, the bottom tank seal 176 may be a Liquid Silicone Rubber (LSR). The ribbed design shown in FIGS. 36A-36C provides for absorption and expansion of the bottom tank seal 176 through the rib 176a while still blocking leaked material from the distal end region 156C of the cartridge body 156.

The internal sealing gasket 173 and the lower support structure 174 may provide redundant sealing to prevent liquid leaks from the reservoir. As described above, the internal sealing gasket 173 positioned in a distal end region 156C of the cartridge body 156 may include an upper region configured to seal a bottom end of the reservoir 158, a midline region that may include the first circumferential perimeter seal (e.g. 198) that is configured to seal with an inner surface of the cartridge body 156, and a lower region. The lower support structure 174 may also be positioned in the distal end region 156C of the cartridge body 156. The lower support structure 174 may include the upper region 1077 configured to seal with the lower region of the internal sealing gasket 173 and the lower region 1078. The lower region 1078 of the lower support structure 174 may include the second circumferential perimeter seal (e.g., bottom tank seal 176) that is configured to seal with an inner surface of the cartridge body 156. The first circumferential perimeter seal provided by the dual sealing beads 198 and the second circumferential perimeter seal provided by the bottom tank seal 176 provide redundant sealing to prevent liquid leaks from the reservoir 158 and out of the cartridge 150.

One or more absorbent pads 175a,b may be positioned within the distal end region 156C of the cartridge body 156 to prevent leakage of the vaporizable material from the reservoir 158 (see, for example, FIGS. 14 and 19B). The pads 175a,b in addition to the bottom tank seal 176 add a layer of redundancy against vaporizable material leaking from the cartridge 150. The pads 175a,b may be oriented to prevent leakage in this region of the cartridge 150 without disrupting airflow or formation of vapor. For example, the absorbent pads 175a,b may be positioned and fitted within the lower support structure 174 off-axis from the air flow path 181. The configuration of the pads 175a,b may vary. In some implementations, the cartridge 150 may include a pair of absorbent pads 175a,b that are attached to opposing sides of the lower support structure 174, for example, between the upper and lower regions 1077, 1078 to absorb excess vaporizable material. The pads 175a,b may be wedged between the lower support structure 174 and the long, interior walls of the distal end region 156C of the cartridge body 156. The pads 175a,b may align generally parallel to each other and to the flat sides of the device. The pads 175a,b may be spaced away from one another creating a gap between them that prevents the pads from interfering with the air flow path 181 through the distal end region 156C of the cartridge body 156. The pads 175a,b may have any of a variety of shapes configured to fill this region of the cartridge 150 including rectangular, circular, ovoid, triangular, square, rings, or other shape. The size and shape of the pads 175a,b may be selected to minimize interference with the air path through the cartridge 150 while maximizing moisture and particle collection. Also, the size and shape of the pads 175a,b may be configured to fit within open spaces of the lower support structure 174 thereby filling the distal end region 156C of the cartridge body 156. For example, FIG. 19B illustrates the pads 175a,b may incorporate a keyed shape or keying feature 1761. The pads 175a,b having the keyed shape or keying feature 1761 may be configured to wedge within a respective keyed recess 1762 located between the upper region 1077 and the lower region 1078. The keyed recess 1762 may have a shape corresponding to the keyed shape or keying feature 1761 of the respective one of the pads 175a,b. The lower support structure 174 may have a first keyed recess 1762 on a first side configured to receive a first pad 175a and a second keyed recess 1762 on a second side configured to receive a second pad 175b such that each of the first and second keyed recesses may have their own respective pad 175a,b wedged therein. The keying feature 1761 of the pads 175a,b provides a snug, wedged fit with the lower support structure 174 thereby preventing shifting of the pads relative to the device that could impact air flow through the device. As discussed above, air may pass from the air flow channels 1085 of the lower region 1078 of the lower support structure 174 through the side channel outlets 1087 before passing up through the upper region 1077 into the vaporization chamber 1005. The snug, wedged fit of the pads 175a,b prevents the pads from encroaching on this air flow path that could result in blocking the air flow path or reducing the efficiency of the path.

Figure 19C:
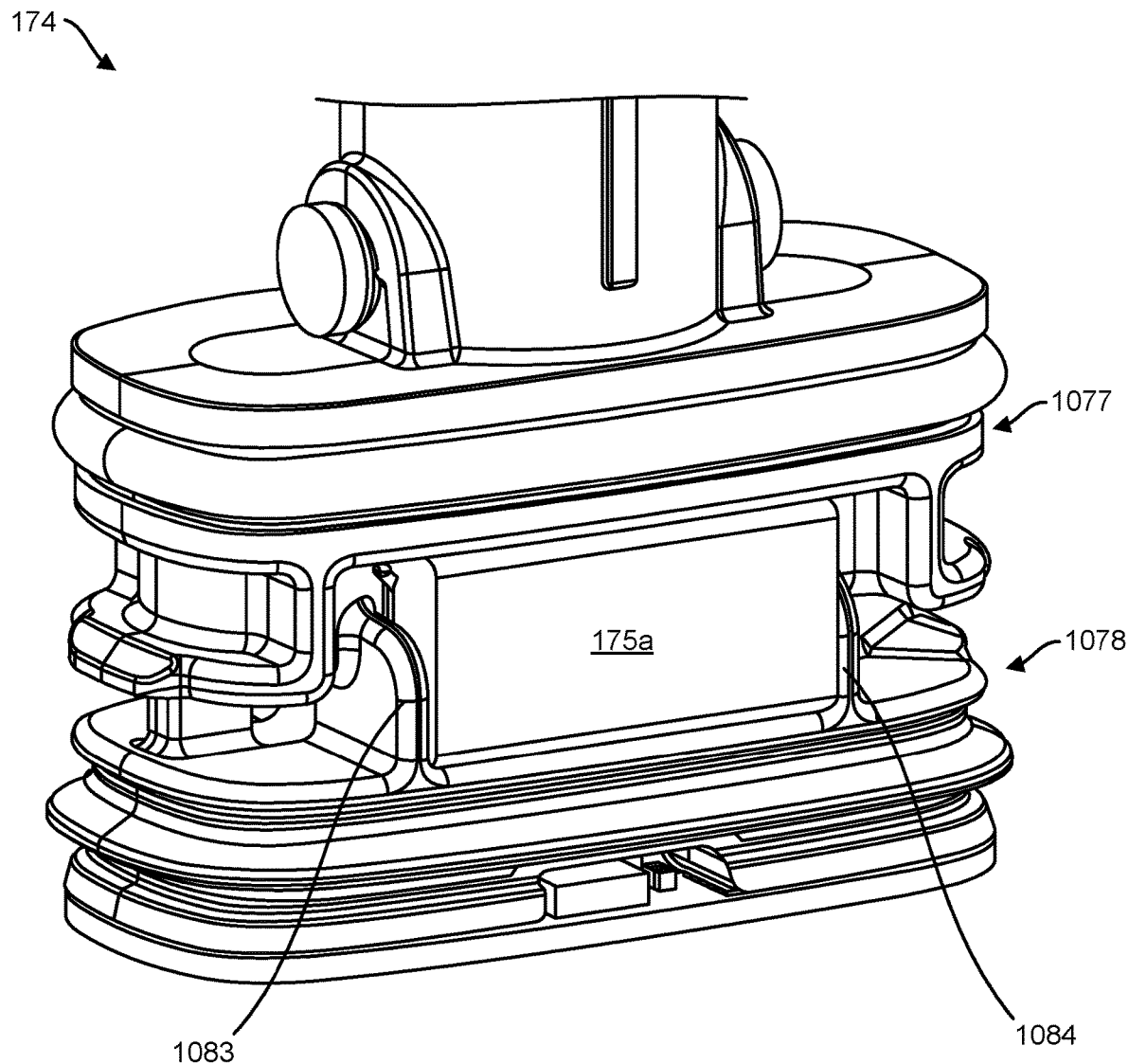

FIG. 19C illustrates an additional implementation consistent with the current subject matter in which the first absorbent pad 175a is positioned and fitted within the lower support structure 174 without the use of the keying feature 1761 shown in FIG. 19B. As shown in FIG. 19C, the first absorbent pad 175a is fitted between the upper and lower regions 1077, 1078 and between side regions 1083, 1084 of the lower support structure 174 to provide a snug, wedged fit with the lower support structure 174. The side regions 1083, 1084 extend upward from the lower region 1078 of the lower support structure 174. The first absorbent pad 175a thus occupies an area into which excess vaporizable material may flow, thereby preventing excess vaporizable material from leaking into the air flow path.

The opposing side of the lower support structure 174 may have a similar configuration and geometry, and may include an absorbent pad and side regions for aiding in holding the absorbent pad to perform the same or similar functions with respect to excess vaporizable material.

Although sets of absorbent pads are shown and described in certain configurations, it should be appreciated that fewer or more pads may be incorporated within the cartridge 150. For example, the absorbent pad 170 in the proximal end region of the cartridge 150 may be formed by more than a single ring-shaped pad (e.g., 2, 3, 4, 5 or more). Similarly, the pair of absorbent pads 175a,b in the distal end region of the cartridge 150 may be a single pad or greater than two pads. Additionally, the absorbent pads may be located in only one region of the cartridge 150.

As mentioned above, the leads 1067 of the heating coil 167 extend through the central aperture 1073 of the bottom plate 1072 as well as through the central opening 195 of the internal sealing gasket 173 into the lower support structure 174. The leads 1067 of the heating coil 167 may electrically couple with the power pin receptacles 160a,b within the lower region 1078 of the lower support structure 174. The power pin receptacles 160a,b may be power pin receptacles configured to mate with the respective power pins (or contacts) 122a,b of the vaporizer body 110, for example, pins projecting upward from a bottom end of the receptacle, as described elsewhere herein. The power pins 122a,b are configured to insert into the respective power pin receptacles 160a,b; the engagement between the power pins 122a,b and the power pin receptacles 160a,b allowing for the transfer of energy from an internal power source of the vaporizer body 110 to the leads 1067 of the heating coil 167. However, the wick 168 and coil 167 assembly performed by hand may pose difficult in ensuring the leads 1067 of the coil 167 are properly inserted into the power pin receptacles 160a,b. Thus, the upper region 1077 of the lower support structure 174 may include a pair of coil guides 179a,b aligned with the central opening 195 and the power pin receptacles 160a,b (see FIGS. 17 and 19A). The coil guides 179a,b are configured to receive and securely hold the leads 1067 of the heating coil 167 as well as reduce the free space between the wick/coil assembly within the vaporization chamber 1005 and the power pin receptacles 160a,b to improve assembly.

The upper surface of the lower support structure 174 may abut against a lower surface of the internal sealing gasket 173 such that the pair of coil guides 179a,b are aligned with and positioned below the central opening 195. The pair of coil guides 179a,b, in turn, may be aligned with and positioned above their respective power pin receptacles 160a,b. The built-in coil guides 179a,b may be provided within an upper region of a respective one or the power pin receptacles 160a,b. The coil guides 179a,b may include a bore extending through a thickness of the upper region 1077 of the lower support structure 174 from a generally circular opening 1081 on the upper surface of the upper region 1077 to another generally circular opening 1082 leading towards the power pin receptacles 160a,b within the lower support structure 174. The bore of the coil guides 179a,b may be cylindrical and have an inner diameter sized to receive and mate with the outer surface of the leads 1067 such that the leads 1067 are securely held within the coil guides 179a,b. The opening 1081 into the bore of the coil guides 179a,b on the upper surface may have an inner diameter that is slightly larger than the inner diameter of the bore. For example, the opening 1081 into the bore of the coil guide 179a,b may be funnel-shaped to ease insertion of each the leads 1067 into their respective coil guides 179a,b. The coil guides 179a,b may advantageously eliminate the cumbersome installation by hand of properly inserting the leads 1067 of the coil 167 into the power pin receptacles 160a,b. The coil guides 179a,b and also the power pin receptacles 160a,b may be insert-molded into the lower support structure 174.

Figure 22A:
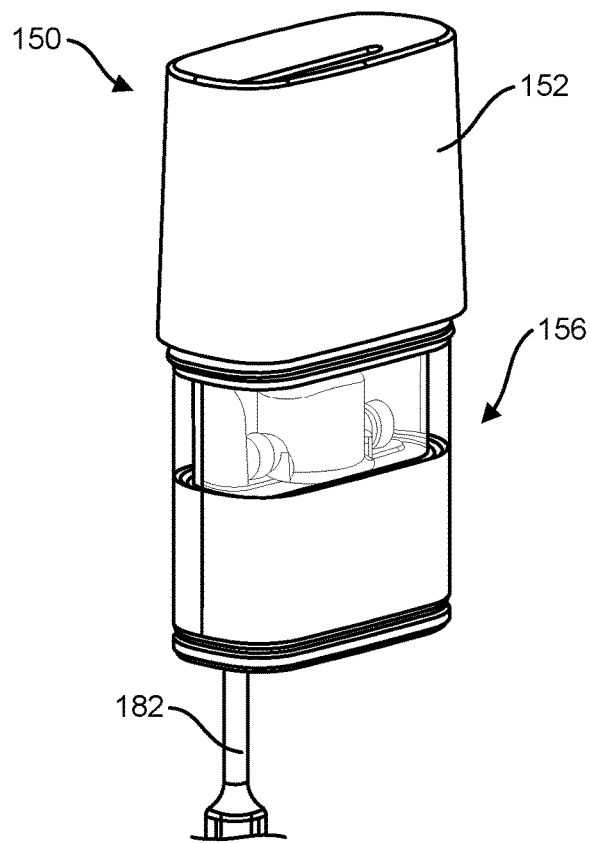
FIGS. 22A-22B illustrate features relating to filling a cartridge with a vaporizable material consistent with implementations of the current subject matter.
Figure 22B:
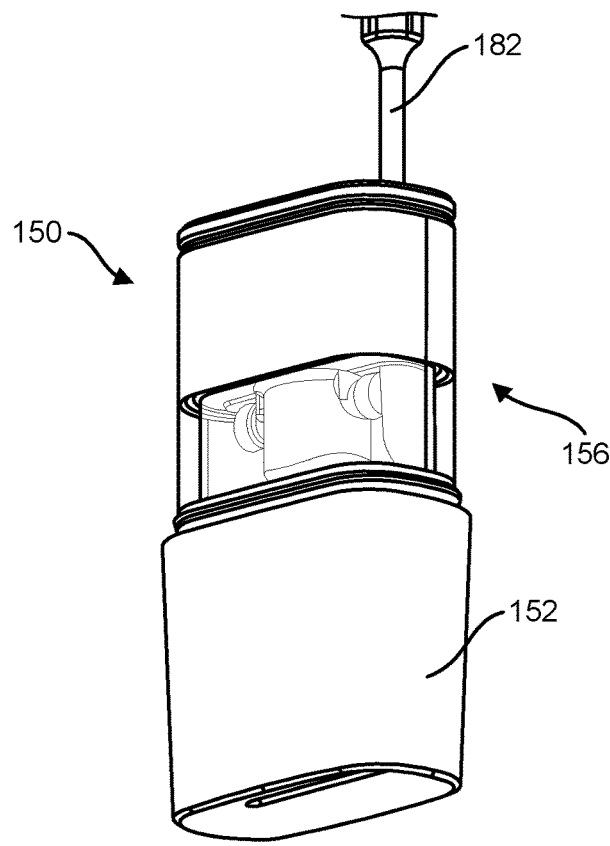

FIGS. 18, 22A-22B illustrate features relating to filling a cartridge 150 with a vaporizable material, in accordance with some implementations of the current subject matter. The cartridge 150 may be filled without the need to disassemble the sealing components of the reservoir 158. As described above, the air flow inlets 162a,b into the air flow channels 1085 form an entry point for air into the cartridge 150 as well as an entry point for a filler to fill the reservoir 158 with vaporizable material. Additionally, the cartridge 150 described herein may be filled through the distal end region 156C of the cartridge 150 where the cartridge 150 is in any orientation relative to gravity. Thus, the cartridge 150 may be filled with a filler 182 in either an upward orientation with the mouthpiece 152 up (FIG. 22A) or a downward orientation with the mouthpiece 152 down (FIG. 22B). In some implementations, the cartridge 150 may be filled in an upward orientation and the fill path for filling the reservoir 158 is the air flow channel 1085. The insertion point for filling the cartridge 150 may be one of the air flow inlets 162a,b (see FIGS. 17-18). The filler 182 may insert through one of the air flow inlets 162a,b from the distal end of the cartridge 150 and into the air flow channel 1085. The filler 182 may be advanced through the air flow channel 1085 until the distal end of the filler 182 makes contact with the penetrable surface feature 196 of the internal sealing gasket 173 positioned within opening 1080 of the lower support structure 174. The filler 182 may penetrate the penetrable surface feature 196 upon further insertion and the distal end of the filler 182 inserted into the lower end of the reservoir 158.

The air flow inlet 162a,b may include an alignment feature for directing the filler 182 towards the penetrable surface feature 196 of the internal sealing gasket 173 in an appropriate orientation. Alternatively or additionally, the arrangement of the air flow channel 1085 and the penetrable surface feature 196 relative to the opposing ends 1065a,b of the wick 168 may be configured to guide the filler 182 into the reservoir 158 such that a distal end of the filler 182 avoids making direct contact with the opposing ends 1065a,b of the wick 168. The distal end of the filler 182 may be inserted a distance beyond the location of the wick 168 towards an upper end region of the reservoir 158. The cartridge 150 may be filled without waiting for the vaporizable material to settle after filling. This upright filling of the cartridge 150 also allows for easier filling using automated filling equipment.

The filler 182 may be any of a variety of tubular structures configured to deliver a fluid through it, including a cannula or a fill needle. The filler 182 may be a needle having a beveled or a sharpened distal tip with at least one opening through which the vaporizable material can exit the bore of the needle. The distal tip of the filler 182 may be configured to pierce the material of the internal sealing gasket 173 and be inserted into a region of the reservoir 158. The material of the internal sealing gasket 173 and the penetrable surface feature 196 may be self-sealing, such that the penetrable surface feature 196 may be pierced by the filler 182 for filling the reservoir 158, and once the filler 182 is removed, the penetrable surface feature of the internal sealing gasket 173 self-seals. The filler 182 may be a non-coring needle such that the integrity of the internal sealing gasket 173 is maintained even after removal of the filler 182 from the penetrable surface feature 196. The filler 182 may also be blunt and the penetrable surface feature 196 of the internal sealing gasket 173 incorporate a mechanical fill port, such as a poppet valve or other type of valve, or a pre-pierced septum feature through which the blunt filler may insert.

Venting the air from the cartridge avoids pressure build-up, which can cause the air to push the vaporizable material out of the cartridge through the wick and create a leak. In some implementations, air within the reservoir 158 prior to filling may be vented during filling of the reservoir 158 with the filler 182. The air inside of the cartridge 150 may be vented through the wick 168. For example, the filler 182 may inject a vaporizable liquid into the reservoir 158. As the vaporizable material fills the reservoir 158 of the cartridge 150, air within the reservoir 158 may be displaced through the porous material of the wick 168. The vented air may pass up through the vaporization chamber 1005 and out the opening 154 in the mouthpiece 152 until the reservoir 158 fills with the vaporizable liquid and no air is entrapped within the reservoir volume.

Air may vent through a dry porous wick 168 easily without much resistance. However, once the wick 168 is wetted, air is substantially prevented from passing through the porous wick 168. As such, controlling when, where, and how the wick 168 is wetted during filling of the reservoir 158 may provide for a more efficient fill of the reservoir 158.

As mentioned above, the reservoir 158 of the cartridge 150 described herein may be filled from the distal end of the cartridge, but in any orientation relative to gravity (i.e., mouthpiece 152 down or up). When the cartridge 150 is positioned relative to gravity with the mouthpiece 152 facing down (see FIG. 22B), the wick 168 is located at an upper end of the reservoir 158. A filler 182 inserted into the reservoir 158 through the penetrable surface feature 196 of the internal sealing gasket 173 may be inserted past the location of the wick 168 to fill the reservoir 158 with vaporizable material without wetting the wick 168 until the reservoir 158 is substantially filled. When the cartridge 150 is positioned relative to gravity with the mouthpiece 152 facing up (see FIG. 22A), the wick 168 is located at a lower end of the reservoir 158. A filler 182 inserted into the reservoir 158 through the penetrable surface feature 196 of the internal sealing gasket 173 may be inserted past the location of the wick 168. However, due to the forces of gravity any vaporizable material injected through the filler 182 may pool near the lower end of the reservoir 158 near the wick 168, thereby wetting it and potentially impacting the ability to vent through the wick 168.

Figure 27:
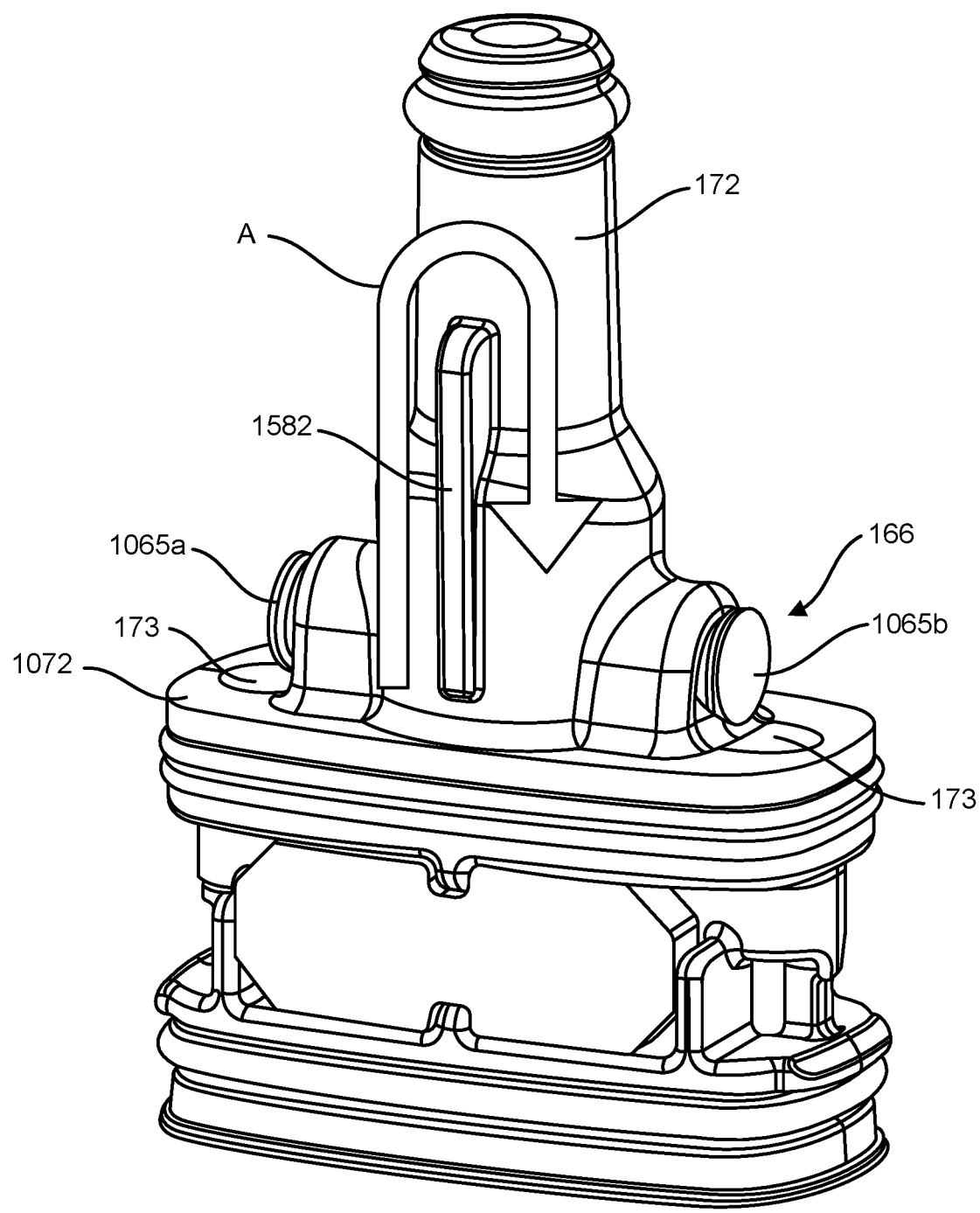
FIG. 27 shows a fill path (arrow A) of vaporizable material entering the reservoir.

The cartridge 150 may incorporate a flow director configured to direct the filling of the reservoir with vaporizable material when the cartridge is filled in the upright orientation. FIG. 27 illustrates an implementation of a flow director 1582. The flow director 1582 may vary in configuration, including but not limited to one or more of a fin, rib or other feature that protects at least one region of the wick 168 from being wetted by the vaporizable material entering the reservoir 158 from the filler 182. As described elsewhere herein, the wick 168 may include the central portion 1060 positioned within the vaporization chamber 1005 of the central cannula 172 and the opposing ends 1065a,b positioned outside the central cannula 172, for example, extending through the lateral openings 1074a,b. The opposing ends 1065a,b may be positioned near the bottom plate 1072 outside the central cannula 172 and the flow director 1582 may be positioned on an outer surface of the central cannula 172 between the opposing ends 1065a,b. The flow director 1582 may be a pair of elongate elements projecting from the outer surface on opposite sides of the central cannula 172. The flow director 1582 may be positioned between the location of the lateral openings 1072a,b such that they project toward the inner wall of the central region 156B of the cartridge body 156. For example, where the opposing ends 1065a,b of the wick 168 project outward from the central cannula 172 towards the minor edges of the cartridge body 156, the pair of flow directors 1582 may project outward from the central cannula 172 towards the major edges of the cartridge body 156. The flow directors 1582 may thereby divide the reservoir 158 into substantially two volumes. The two volumes of the reservoir 158 may be in fluid communication with one another near a proximal end region of the reservoir 158. A first volume of the reservoir 158 may surround a first end 1065a of the wick 168 and a second volume may surround a second end 1065b of the wick 168.

Still with respect to FIG. 27, a fill path of vaporizable material is shown by arrow A. The filler 182 may insert from the distal end region of the cartridge 150 through the internal sealing gasket 173 until the distal end of the filler 182 enters the reservoir (not visible in FIG. 27). The distal end of the filler 182 may insert through the internal sealing gasket 173 and project into the first volume of the reservoir, for example, the region of the reservoir surrounding the first end 1065a of the wick 168. The vaporizable material may be injected into the first volume of the reservoir and wet the first end 1065a of the wick 168. The presence of the flow directors 1582 may initially prevent the vaporizable material from entering the second volume of the reservoir surrounding the second end 1065b of the wick 168 and prevent them from wetting. The second end 1065b of the wick 168 may stay substantially dry as the first volume of the reservoir begins to fill with vaporizable material from the filler. During this initial filling phase, the protected second end 1065b may vent air from the cartridge 150. Once the vaporizable material substantially fills the first volume of the reservoir it may reach an upper end of the flow directors 1582. The vaporizable material may then flow over the upper end of the flow directors 1582 to enter the second volume of the reservoir (see arrow A of FIG. 27). The protected second end 1065b of the wick 168 may become wet and unable to vent air through it, but only after both the first and second volumes of the reservoir become mostly filled with the vaporizable material. The viscosity of the vaporizable material provides fluid dynamics with respect the walls of the cartridge body allow for the vaporizable material flowing over the upper end of the flow directors 1582 from spilling down onto the protected second end 1065b of the wick 168 near the bottom of the reservoir. Instead, the vaporizable material may creep along the walls of the cartridge body 156 towards the bottom of the reservoir allowing the second end 1065b to continue venting air until the second volume of the reservoir substantially fills. As described elsewhere herein, the vaporizable material may include viscous oil-based vaporizable materials, including *cannabis* oils. For example, the vaporizable material may include *cannabis* oil having between 40-100% *cannabis* oil extract. The viscous oil may include a carrier for improving vapor formation, such as propylene glycol, glycerol, etc. The viscosity of the vaporizable materials may be in a range between about 30 cP (centipoise) and 115 KcP (kilocentipoise), or between 40 cP and 113 KcP. These viscosities allow for a controlled flow of the vaporizable material up and over the flow directors 1582 without spilling down onto the second end 1065b of the wick 168 until the second volume of the reservoir is substantially filled with the vaporizable material.

The cartridge 150 may be a single-use cartridge that is not configured to be refilled with vaporizable liquid following use. The cartridge 150 may also be configured for re-filling such that the cartridge 150 may be used more than once. Thus, in some implementations, for example, during refill of the reservoir 158 after the wick 168 is fully wetted, the filler 182 may further incorporate a vent needle to allow for air within the reservoir 158 to exit the cartridge through the vent needle as opposed to through the wick 168. The vent needle may be part of the filler 182. For example, the vent needle may also be arranged coaxially relative to the filler 182, either surrounding a portion of the length of the filler 182 or extending through the bore of the filler 182 such that the filler 182 surrounds the vent. Alternatively, the vent needle may be a separate needle inserted within a region of the reservoir 158, such as through a different portion of the internal sealing gasket 173, to vent air from the reservoir 158 while the fill needle is delivering liquid into the reservoir 158. In either implementation, the vent needle may be positioned or extended to a region of the reservoir 158 that is distant from where the filler 182 is delivering fluid into the reservoir 158 such that as the fluid from the filler 182 fills the reservoir, the air is displaced towards an opening into the vent needle. The filler 182/vent needle arrangement may provide a passive, substantially pressure neutral way to exchange fluids within the reservoir 158 to refill the cartridge.

Any of a variety of materials may be used for the cartridge 150. Portions of the cartridge 150 may be made of harder plastic materials configured to be strong and resist cracking, compression, or other damage when placed under pressure.

For example, one or more regions of the cartridge body 156 such as the region defining the reservoir 158 may be formed of hard plastic materials, such as, for example, Trogamid CX7323 (BPA free). Other plastic materials for the cartridge body 156 and the mouthpiece 152 may include, for example, Veradel A-301 (BPA free). Other regions of the cartridge 150 such as the regions intended to provide for sealing with other harder regions of the cartridge 150 may be made of any of a variety of resilient or elastomeric materials. For example, the bottom tank seal 176 and the internal sealing gasket 173 may be made from a variety of materials including rubber, such as, for example, fluorosilicone rubber (SHIN-ETSU FE-251-U). The mouthpiece seal 177 may also be made from a variety of materials including rubber, such as, for example, clear liquid silicone rubber (LSR). The seals 176 and 177, the sealing ring 171, the internal sealing gasket 173, and the lower support structure 174 may be made from a variety of materials, such as Polypropylene and materials in the Nylon 6/3 or Polyethersulfone-based (PESU) classes, including but not limited to PESU, Nylon, Silicone, Nitrile, ethylene propylene diene monomer (EPDM), PTFE, Fluorocarbons, and Polyethylene Terephthalate (PET). The portions of the cartridge 150 including the reservoir 158, the cartridge body 156, the mouthpiece 152, the sealing ring 171, the internal sealing gasket 173, the bottom tank seal 176, the mouthpiece seal 177, and the lower support structure 174 are formed of durable materials that are suitable for the functions they perform. A variety of materials, including glass, aluminum, stainless steel, titanium, gold, and/or ceramic, may be used for the components of the cartridge 150, including but not limited to the reservoir 158, the cartridge body 156, the mouthpiece 152, the sealing ring 171, the internal sealing gasket 173, the bottom tank seal 176, and the mouthpiece seal 177.

As described above, a data tag 164 may be incorporated within a region of the cartridge 150 to transmit, receive, and/or store relevant information about the cartridge 150 and/or the vaporizable material contained within. The tag 164 may allow for communication between the cartridge 150 and the vaporizer body 110 as well as between the cartridge 150 and an external computing device, such as a user device 305 (e.g., a smartphone, tablet, laptop), or a remote server 307. The communication between the cartridge 150 provided by the tag 164 may be independent of the vaporizer body 110 such that the cartridge 150 may communicate with an external computing device even when the cartridge 150 is not coupled to the vaporizer body 110, as described elsewhere herein.

Figure 23A:
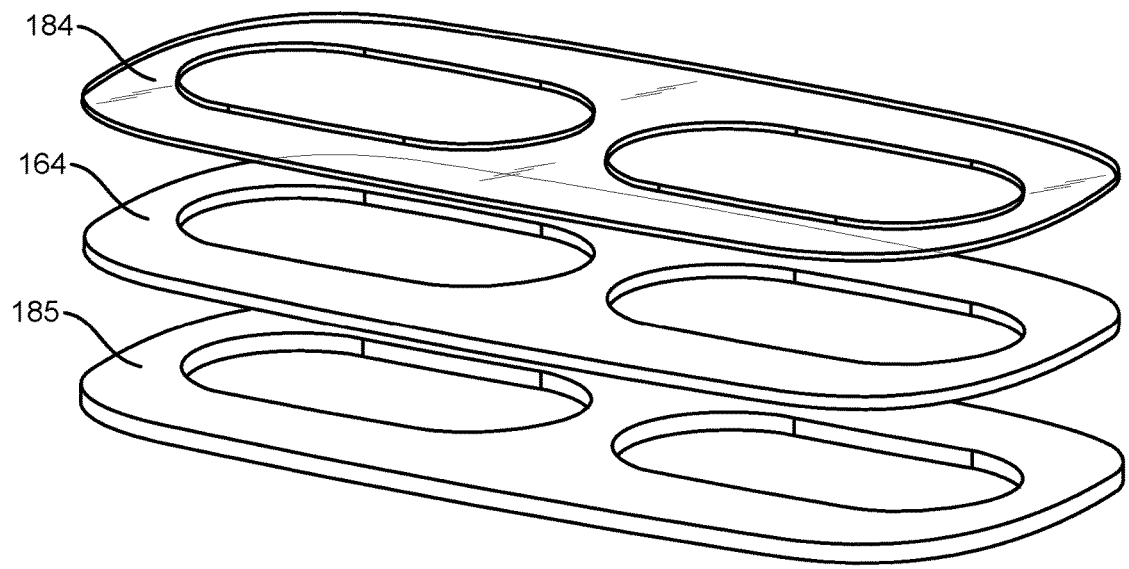
FIG. 23A-FIG. 23B illustrate features of a near-field communication tag incorporated in a cartridge consistent with implementations of the current subject matter.
Figure 23B:
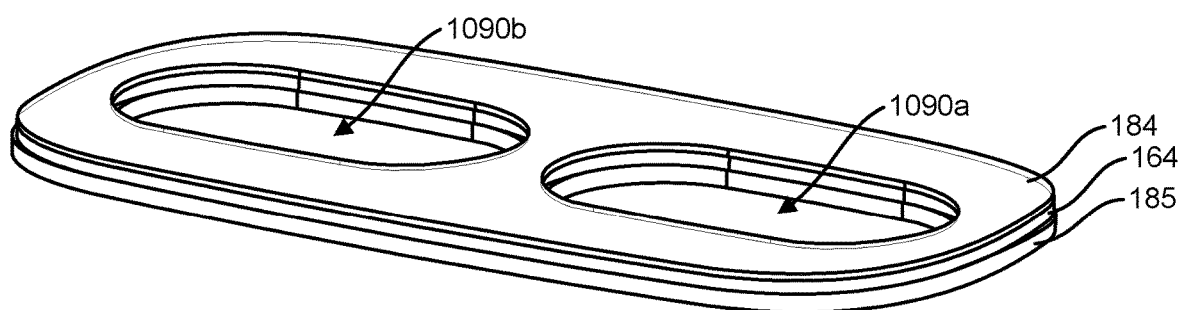

In some implementations, the tag 164 is a near-field communication (NFC) tag positioned near a bottom region of the cartridge 150. The tag 164 may be positioned over a bottom plate of the lower support structure 174. FIGS. 23A and 23B show perspective views of various components in unassembled and assembled configurations respectively. The tag 164 may be adhered to the bottom plate of the lower support structure 174, for example, by using a bottom base plate or base 184 (see FIGS. 23A-23B). The base 184 may be an adhesive, such as a pressure sensitive adhesive (PSA) that is formed from an acrylic material or the like, and may have a thickness of, for example, about 0.06 mm, 0.07 mm, 0.08 mm, 0.09 mm, or 0.10 mm. The tag 164 may be an antenna trace made of copper or a similar material and may have a thickness of, for example, about 0.05 mm, 0.06 mm, 0.07 mm, 0.08 mm, 0.09 mm, or 0.10 mm. The tag 164 may be protected by a protective layer 185, such as, for example, a plastic cover made of polyethylene terephthalate (PET) plastic or other plastics. A variety of non-conductive materials, such as glass or ceramic, may be used for the protective layer 185. The protective layer 185 may have a thickness of, for example, about 0.08 mm, 0.09 mm, 0.10 mm, 0.11 mm, or 0.12 mm. The overall thickness of the tag 164, with or without the base 184 and/or with or without the protective layer 185, may be, for example, about 0.05 mm, 0.06 mm, 0.07 mm, 0.08 mm, 0.10 mm, 0.12 mm, 0.14 mm, 0.16 mm, 0.18 mm, 0.20 mm, 0.22 mm, 0.24 mm, 0.26 mm, 0.28 mm, 0.30 mm, 0.32 mm, 0.34 mm, 0.36 mm, 0.38 mm, 0.40 mm, 0.42 mm, 0.44 mm, 0.46 mm, 0.48 mm, or 0.50 mm.

The tag 164 may be a variety of shapes, including the generally planar element with an upper surface, a lower surface and an outer perimeter such as that shown in the figures. The outer perimeter of the tag 164 may be identical to the outer perimeter of the cartridge 150 at its distal end 1020 such that its shape resembles the cross-sectional shape of the distal end 1020 of the cartridge 150 so as not to interfere with coupling between the cartridge 150 and the vaporizer body 110. The upper surface of the tag 164 is configured to abut flush against the bottom plate of the lower support structure 174. The lower surface is similarly planar. As mentioned above, the tag 164 may be positioned on the cartridge 150 in any of a number of configurations, such as between the power pin receptacle 160a,b or encircling the power pin receptacles 160a,b.

In some implementations, the tag 164 has a circular or partially circular shape. The tag 164 may include at least one aperture extending through its thickness such that the tag 164 surrounds the power pin receptacles 160a,b and air flow inlets 162a,b at the distal end of the cartridge 150. In some implementations, such as those shown in FIGS. 23A and 23B, the tag 164 may include a first aperture 1090a extending through its thickness that is configured to align with a first air flow inlet 162a and a first power pin receptacle 160a of the lower support element 174. The tag 164 may additionally include a second aperture 1090b configured to align with a second air flow inlet 162b and the second power pin receptacle 160b of the lower support structure 174. The apertures 1090a,b allow for the tag 164 to avoid covering the air flow inlets 162a,b and the power pin receptacles 160a,b for proper functioning of the device.

Figure 37A:
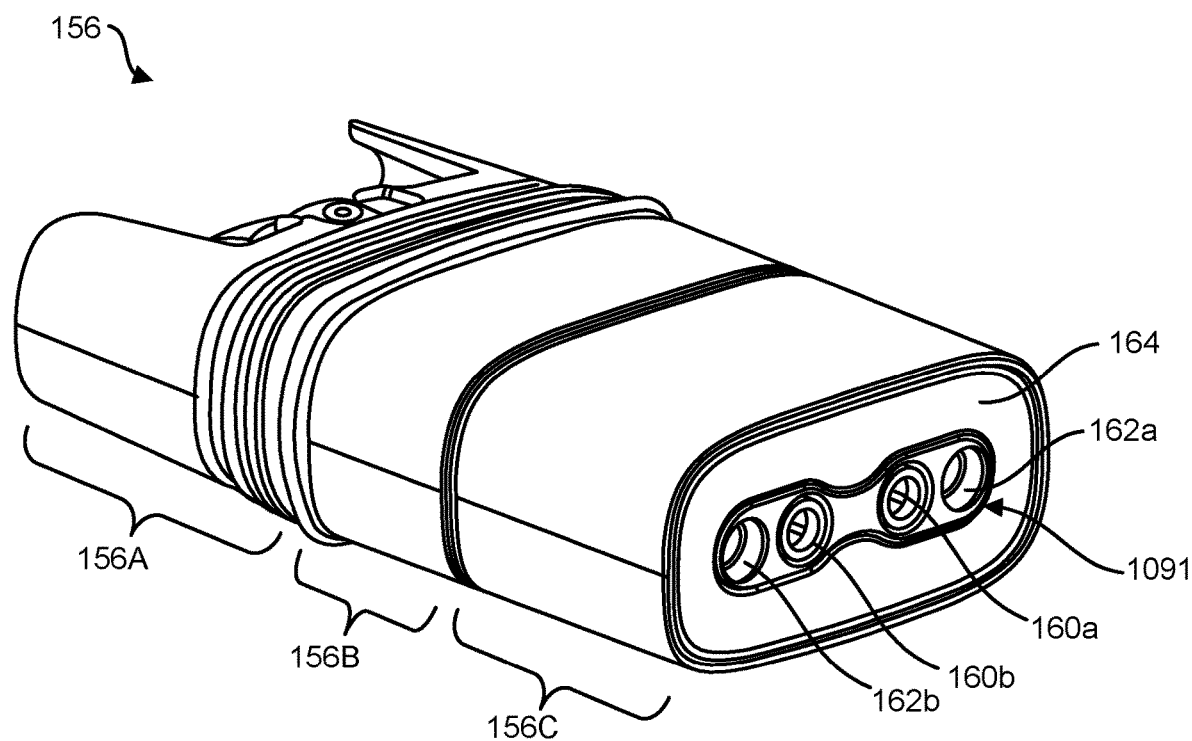
FIG. 37A illustrates features of a cartridge of a vaporizer device consistent with implementations of the current subject matter.

In another implementation, as shown in FIG. 37A which is a bottom perspective view of the cartridge body 156, the tag 164 may include a single aperture 1091 extending through its thickness such that the single aperture 1091 surrounds the power pin receptacles 160a,b and the air flow inlets 162a,b. This configuration eliminates the bridge portion (which may in some cases not adhere sufficiently to the bottom plate of the lower support structure 174 due to its narrow width between the apertures 1090a,b) of the tag 164 between the first and second apertures 1090a,b shown in FIGS. 23A and 23B. The single aperture 1091 may dip or extend slightly between the power pin receptacles 160a,b to provide more usable area of the tag 164 (e.g., providing more room for additional antennae coils). Moreover, the air flow inlets 162a,b may be moved inward to also provide additional usable area of the tag 164.

Figure 37B:
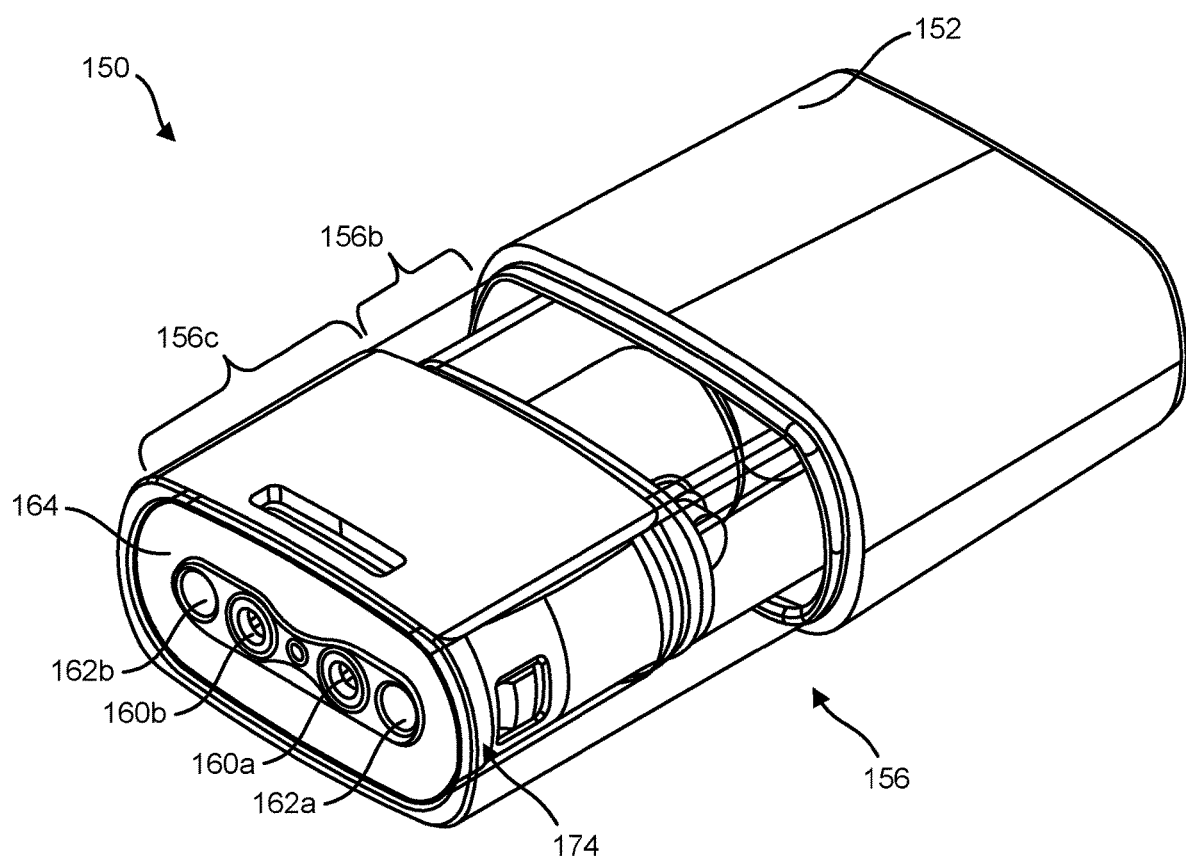
FIG. 37B-FIG. 37D illustrate features of a cartridge of a vaporizer device consistent with additional implementations of the current subject matter.
Figure 37C:
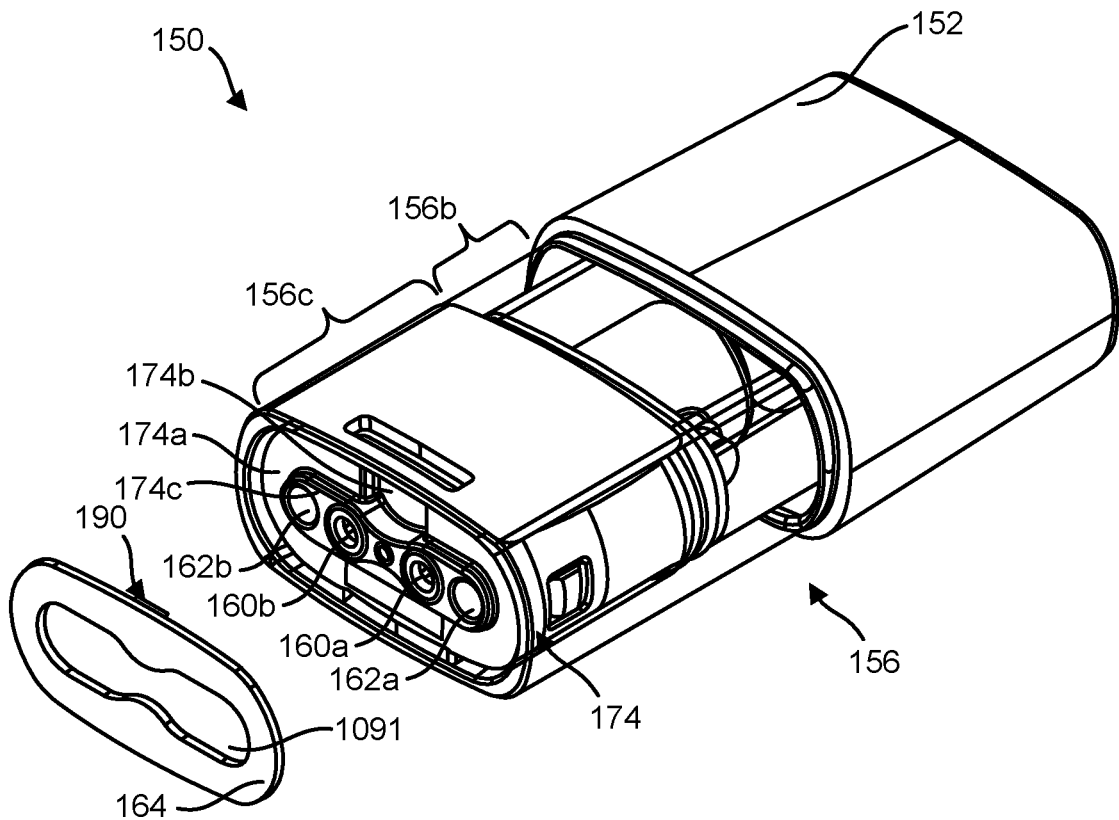
Figure 37D:
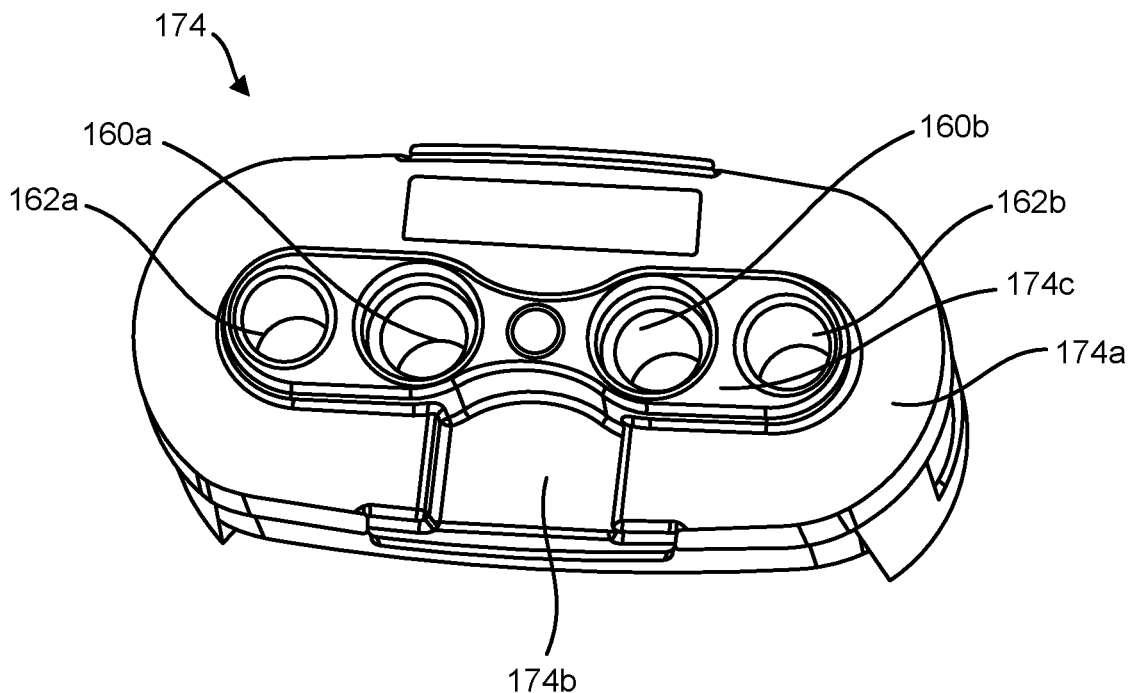

FIGS. 37B-37D illustrate details of an additional implementation of the cartridge 150 with the tag 164 configured to be attached to the bottom plate of the lower support structure 174 of the cartridge 150. FIG. 37B is a bottom perspective view of the cartridge 150 illustrating the central region 156B and the distal end region 156C of the cartridge body 156, with the mouthpiece 152 coupled to the proximal end region 156A of the cartridge body 156 and the tag 164 coupled or otherwise attached to the lower support structure 174 at the distal end region 156C. FIG. 37C is a bottom perspective view of the cartridge 150 and the tag 164, illustrating placement of the tag 164 with respect to the cartridge 150. FIG. 37D is a perspective view of a portion of the lower support structure 174 without the tag 164 adhered thereto. As described elsewhere herein, the placement of the tag 164 on a bottom portion of the cartridge 150 may provide for communication with the vaporizer body 110 via the first antenna 143 at the proximal end of the vaporizer body 110 when the cartridge 150 is engaged with the vaporizer body 110. However, the tag 164 may be positioned at other portions of the cartridge 150.

As shown in the bottom perspective views of the cartridge 150 in FIGS. 37B and 37C, the cartridge body 156 may have a profile or shape that varies from that of the cartridge body 156 shown in, for example, FIG. 37A. For example, the outer and inner perimeters of the cartridge body 156 of the cartridge 150 shown in FIGS. 37B and 37C may include a more rounded shape or cross section at side portions (e.g., the shorter, opposing side portions) of the cartridge body 156 compared to that of the cartridge body 156 shown in FIG. 37A. Some portions of the cartridge body 156 may be opaque while other portions are clear. Moreover, the power pin receptacles 160*a,b* and the air flow inlets 162*a,b* formed through the lower support structure 174 may be spaced apart with respect to one another with distances that vary from that of the cartridge body 156 shown in FIG. 37A.

As shown in FIG. 37C, the tag 164 consistent with implementations of the current subject matter may be sized and shaped to accommodate the shape of the bottom plate of the lower support structure 174, which may be sized and shaped to accommodate the shape of the distal end region 156C of the cartridge body 156. The tag 164 may include the single aperture 1091 extending through its thickness such that the single aperture 1091 surrounds the power pin receptacles 160*a,b* and the air flow inlets 162*a,b* of the lower support structure 174. The single aperture 1091 may dip or extend slightly between the power pin receptacles 160*a,b* to provide more usable area of the tag 164 (e.g., providing more room for additional antennae coils). In some implementations, two apertures (one for each set of receptacle and air flow inlet) may be provided in the tag 164, similar to the configuration shown in FIGS. 23A and 23B.

As shown in FIGS. 37C and 37D, the bottom plate of the lower support structure 174 may include a recessed region 174*a* sized and shaped to accommodate the tag 164. The tag 164 and the recessed region 174*a* may be the same size and shape, or substantially the same size and shape, as one another. In some implementations, the shapes of the tag 164 and the recessed region 174*a* mirror or substantially mirror one another. In some implementations, the size of the tag 164 is slightly smaller than that of the recessed region 174*a* to provide for placement of the tag 164 on the recessed region 174*a*. The recessed region 174*a* may include an indentation or pocket 174*b* to accommodate the microcontroller unit (MCU) 190 and a tuning capacitor 3802 of the tag 164 (see FIGS. 38B and 38C). The bottom plate of the lower support structure 174 may include a raised region 174*c* surrounded by the recessed region 174*a* and through which the power pin receptacles 160*a,b* and the air flow inlets 162*a,b* are formed.

Consistent with implementations of the current subject matter, the size and shape of the tag 164 may vary to accommodate variations of the size and shape of the cartridge body 156. For example, the cartridge body 156 may have a circular, oval, square, rectangular, or other polygonal cross section, and the tag 164 may be sized and shaped to attach to a distal end of the cartridge body 156. The tag 164 may be of various shapes and sizes and is not limited to a shape that mirrors that of the bottom plate fitted within the cartridge body 156. For example, in some implementations, the tag 164 may be of a variety of polygonal shapes to accommodate the antenna 192.

Figure 38A:
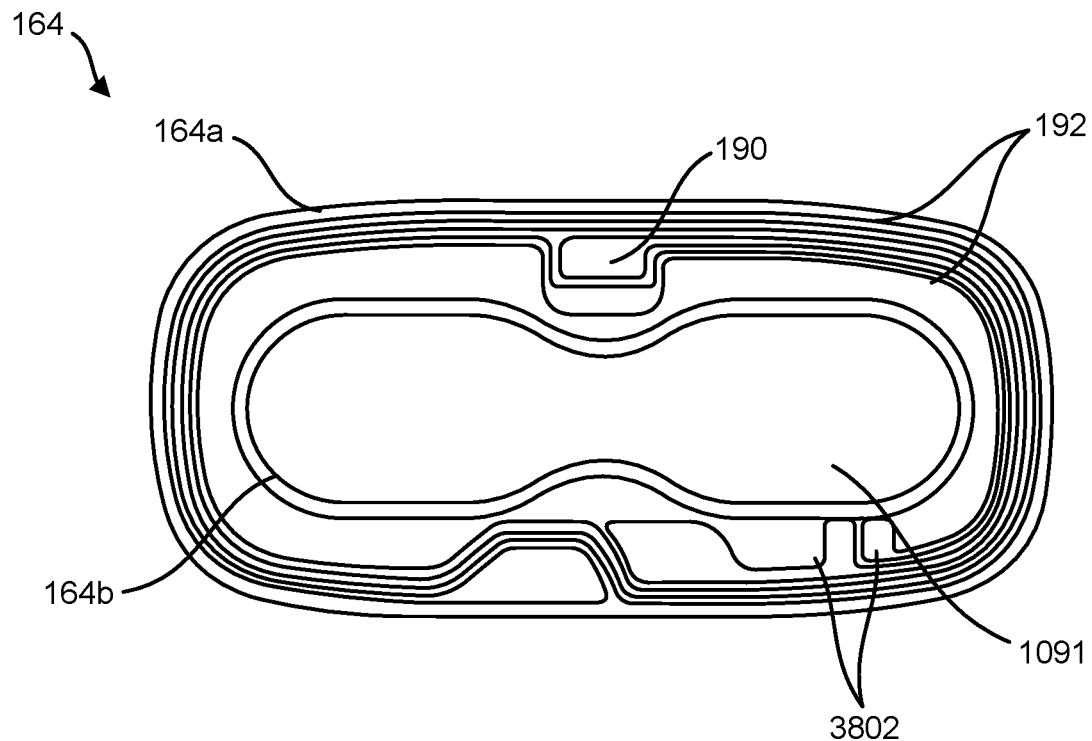
FIG. 38A-FIG. 38C illustrate features of a wireless transceiver of a cartridge body of a cartridge of a vaporizer device consistent with implementations of the current subject matter.

FIG. 38A illustrates features of the tag 164, consistent with some implementations of the current subject matter. As described elsewhere herein and with respect to FIG. 2, the tag 164 may include a microcontroller unit (MCU) 190 and an antenna 192. Shown in FIG. 38A are the MCU 190 and the antenna 192. Also included is the tuning capacitor 3802 that is configured to tune the wireless signal from the antenna 192. Pockets sized and shaped to accommodate the microcontroller unit (MCU) 190 and the tuning capacitor 3802 may be formed on the bottom plate of the lower support structure 174. For example, the pocket 174*b* shown in FIG. 37C may accommodate the microcontroller unit (MCU) 190 and the tuning capacitor 3802 when the microcontroller unit (MCU) 190 and the tuning capacitor 3802 are positioned side-by-side as in FIG. 38B. In implementations in which the microcontroller unit (MCU) 190 and the tuning capacitor 3802 are not side-by-side but are instead spaced apart at different regions of the tag 164, as in FIG. 38A, separate indentations or pockets on the bottom plate of the lower support structure 174 may be provided to accommodate the microcontroller unit (MCU) 190 and the tuning capacitor 3802.

In some implementations, the antenna 192 may be traced or etched onto the tag 164 on the usable area of the tag 164 between an outer perimeter 164*a* and an inner perimeter 164*b* of the tag 164. The outer perimeter 164*a* may be of the same or similar size as that of the bottom plate of the cartridge body 156. The inner perimeter 164*b* may define the single aperture 1091. In one implementation, as shown in FIG. 38A, the antenna 192 may have a racetrack-like configuration in which the antenna 192 is etched on the tag 164 in a plurality of concentric traces. The concentric traces may be shaped to mirror the shape of the outer perimeter of the tag 164 or the inner perimeter of the tag 164. Variations of the concentric traces may be incorporated, such as concentric traces with right angles as opposed to the curved implementation shown in FIG. 38A. The antenna 192 may have a variety of other alternative configurations to enable communication with the vaporizer body 110 or other devices (e.g., the user device 305, the remote server 307, etc.). The other configurations of the antenna 192 may include, for example, helical, parabolic, spiral, zig zag, linear, or circular configurations. As the tag 164 may be of a variety of shapes and sizes, the traces of the antenna 192 may be configured to match, in size or shape, one or more usable areas of the tag 164.

Figure 38B:
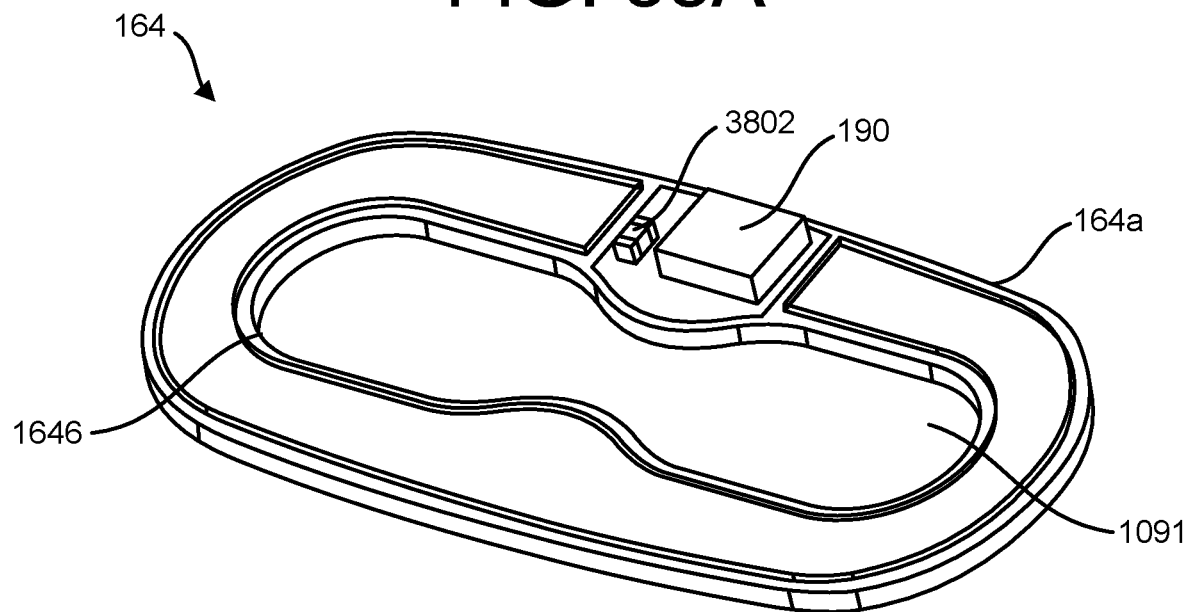
Figure 38C:
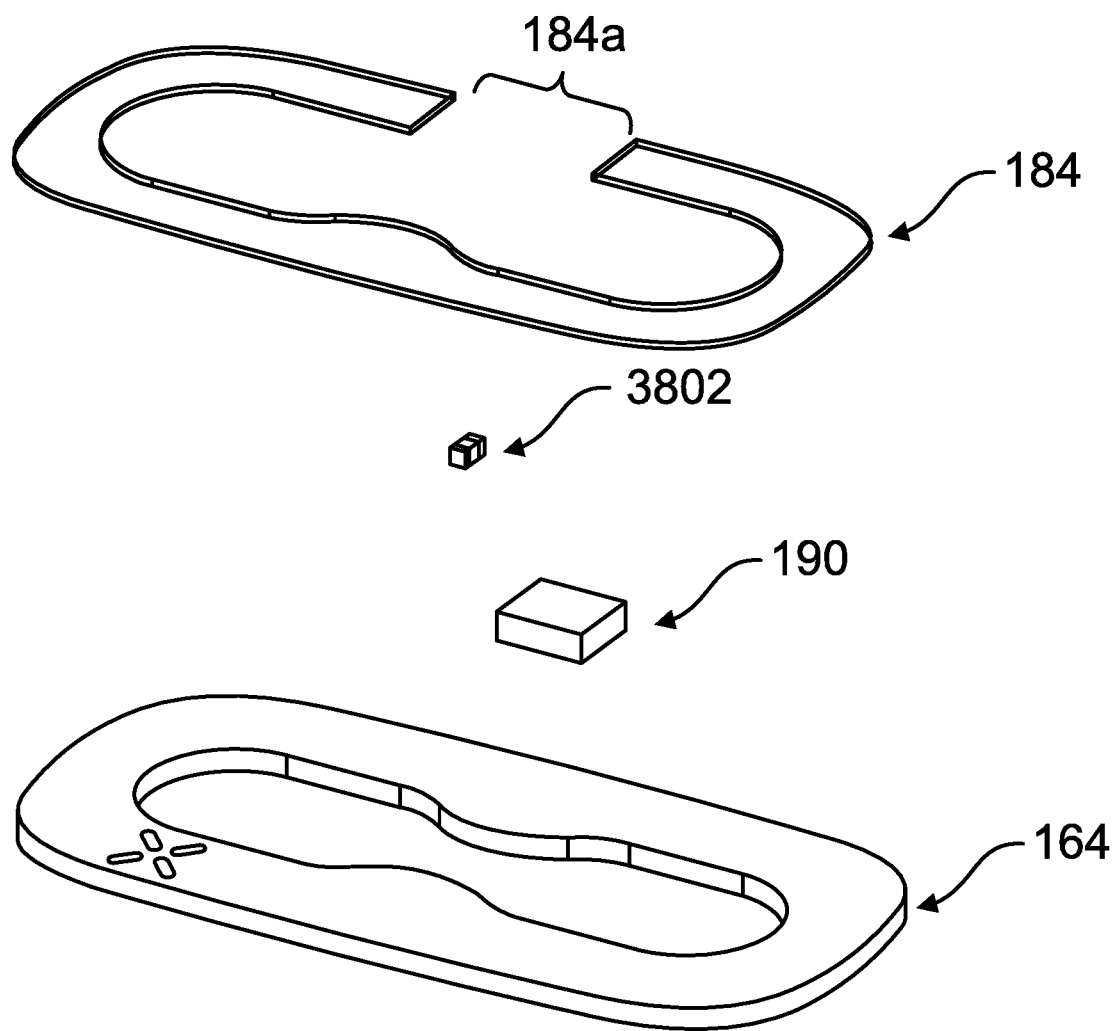

FIGS. 38B and 38C illustrate features of the tag 164 consistent with additional implementations of the current subject matter. FIG. 38B is a bottom perspective view of the tag 164. On a bottom surface of the tag 164, the microcontroller unit (MCU) 190 and the tuning capacitor 3802 are provided on an area of the tag 164 that corresponds to, for example, the pocket 174*b* formed on the bottom plate of the lower support structure 174; although the pocket 174*b* is not required to accommodate such an arrangement of the microcontroller unit (MCU) 190 and the tuning capacitor 3802. The tag 164 may be a printed circuit board with an antenna (i.e., the antenna 192) with the outer perimeter 164*a* and the inner perimeter, where the inner perimeter 164*b* defines the single aperture 1091.

FIG. 38C is an exploded view from a bottom perspective of the tag 164 of FIG. 38B. Shown are the tag 164 (that includes, in some implementations, a printed circuit board with an antenna), the microcontroller unit (MCU) 190, the tuning capacitor 3802, and the base 184 that, as described with respect to FIGS. 23A and 23B, may be an adhesive for adhering the tag 164 to the bottom plate of the lower support structure 174. The base 184 may be sized and shaped to align with at least a portion of the tag 164. In some implementations, the base 184 aligns with at least a portion of the tag 164 and is of the same general shape of the tag 164 but is slightly smaller to allow for proper placement of the tag 164 on the base 184. In some implementations, the base 184 is of the same size and shape of the tag 164. In some implementations, the base 184 includes a gap or a cut-out region 184*a* to accommodate the microcontroller unit (MCU) 190 and the tuning capacitor 3802 on the tag 164. The base 184 may be of various other sizes and shapes and may include multiple pieces, such as two or more strips.

As shown in FIGS. 38B and 38C, the arrangement of the microcontroller unit (MCU) 190 and the tuning capacitor 3802 is such that the microcontroller unit (MCU) 190 and the tuning capacitor 3802 are adjacent or near one another. However, other arrangements, such as that provided in FIG. 38A where the microcontroller unit (MCU) 190 and the tuning capacitor 3802 are spaced apart from one another, are possible consistent with implementations of the current subject matter. The arrangement of the microcontroller unit (MCU) 190 and the tuning capacitor 3802 may be based on various factors, such as tuning, manufacturing considerations, and placement/fitting on the cartridge 150.

The tag 164 may be encased in plastic during injection molding of the mating plastics, or an ultrasonic welding process may be implemented in which the protective layer is welded to mating plastics. The tag 164 may be manufactured like a flexible printed circuit (FPC). In some implementations, the tag 164 may be formed like a rigid printed circuit board. Alternatively, an air coil may be used as a coiled wire for the tag 164, rather than being printed like a FPC. The air coil is conductive with an increased range of performance compared to the FPC method. As another alternative, the tag 164 may be printed or directly etched onto a base, such as for example the PSA base 184, using a laser direct structuring (LDS) method or the like.

In some implementations, the tag 164 may include one or more substrate layers on which the antenna traces, made of copper or a similar material, are etched or formed. In one implementation, the tag 164 includes four traces on one substrate layer. In another implementation, the tag 164 includes two traces on a first substrate layer and 6 traces on a second substrate layer. Various other implementations consistent with the current subject matter are possible. For example, the tag 164 may include any number of traces on any number of layers to achieve desired properties with respect to size, frequency, tuning, range (i.e., range with one or more antennas such as the first antenna 143), and manufacturability.

In one implementation, the antenna traces have a width of about 75 microns and a thickness of 18 microns, and there may be a gap of about 75 microns between each antenna trace. The antenna traces may have a width of, for example, about 20 microns, 25 microns, 30 microns, 35 microns, 40 microns, 45 microns, 50 microns, 55 microns, 60 microns, 65 microns, 70 microns, 75 microns, 80 microns, 85 microns, 90 microns, or 95 microns. The antenna traces may have a thickness of, for example, about 8 microns, 10 microns, 12 microns, 14 microns, 16 microns, 18 microns, 20 microns, 22 microns, 24 microns, 26 microns, 28 microns, or 30 microns. The gap between the antenna traces may be, for example, about 20 microns, 25 microns, 30 microns, 35 microns, 40 microns, 45 microns, 50 microns, 55 microns, 60 microns, 65 microns, 70 microns, 75 microns, 80 microns, 85 microns, 90 microns, or 95 microns. The thickness of the antenna traces on a single substrate may differ from one another or may be the same as one another. The gap between the antenna traces may be the same on a single substrate or may differ such that one gap is larger than another gap.

Figure 24:
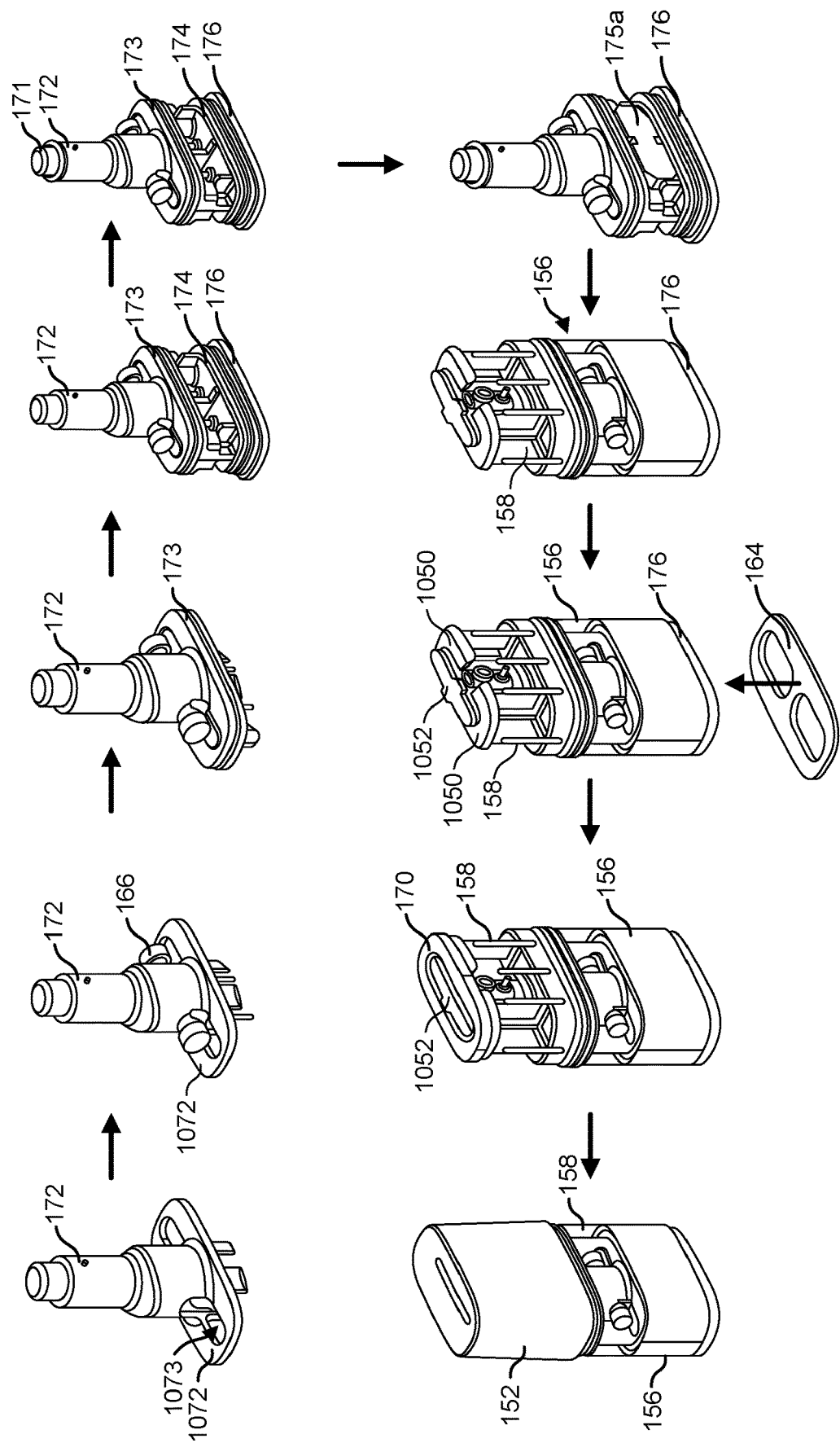
FIG. 24 is a series of diagrams illustrating assembly of a cartridge consistent with implementations of the current subject matter.

FIG. 24 is a series of diagrams illustrating assembly of a cartridge 150 consistent with implementations of the current subject matter. The heater 166 (coil 167/wick 168) may be inserted to the central cannula 172. The internal sealing gasket 173 may be attached to a lower surface of the bottom plate 1072 portion of the central cannula 172. The pair of surface features 197*a,b* on the internal sealing gasket 173 may project through the bottom plate 1072, for example, through slots of the central aperture 1073 of the bottom plate 1072 on either side of the central cannula 172 to engage with opposing ends 1065*a,b* of the wick 168. The lower support structure 174 may be connected to the distal end of the central cannula 172 such that the internal sealing gasket 173 mates with the lower support structure 174. The sealing ring 171 may be added over the proximal tap 1018 at a top end of the central cannula 172. The pair of absorbent pads 175*a,b* may be inserted on opposing open sides of the lower support structure 174 between the upper and lower regions 1077, 1078. The absorbent pads 175*a,b* may be sized and shaped such that they securely fit into and are held within the lower support structure 174. The components of the internal sub-assembly may be snapped together during the aforementioned sub-assembly process. The internal sub-assembly may then be inserted into the cartridge body 156 with the mouthpiece seal 177 positioned over a proximal end region of the body 156. The tag 164 may be adhered to the bottom plate of the lower support structure 174. The absorbent top pad 170 is placed at a proximal end of the cartridge body 156, and the mouthpiece 152 is then secured over the proximal end of the cartridge body 156.

Once assembled, the cartridge 150 may be difficult for a user to take apart. A feature may be incorporated on a region of the cartridge 150 to discourage tampering and disassembly and for internally securing components. The configuration of the feature may vary. In an implementation, the cartridge 150 may include an internal snap feature 180 on one or more outer edges of the lower support structure 174 (at the distal end of the cartridge 150) (see FIG. 17). The feature 180 may be an angled annular projection configured to mate with one or more complementary recesses 183 formed on an internal side of the cartridge body 156 (see FIGS. 14 and 17). The feature 180 may have a proximal-facing ramped surface and a distal-facing flat surface. The lower support structure 174 may be inserted within the distal end region 156C of the cartridge body 156 from the distal end region. The ramped surface slides along the inner surface of the cartridge body 156. Upon proper seating within the distal end region 156C, the ramped surface of the feature 180 inserts within the recess 183 of the internal surface of the cartridge body 156. The distal-facing flat surface of the feature abuts against a corresponding proximal-facing flat surface preventing the lower support structure 174 from sliding in the opposite direction back out from the lower end of the cartridge body 156. Such an internal configuration makes it difficult for a user to take apart the cartridge 150.

Figure 25:
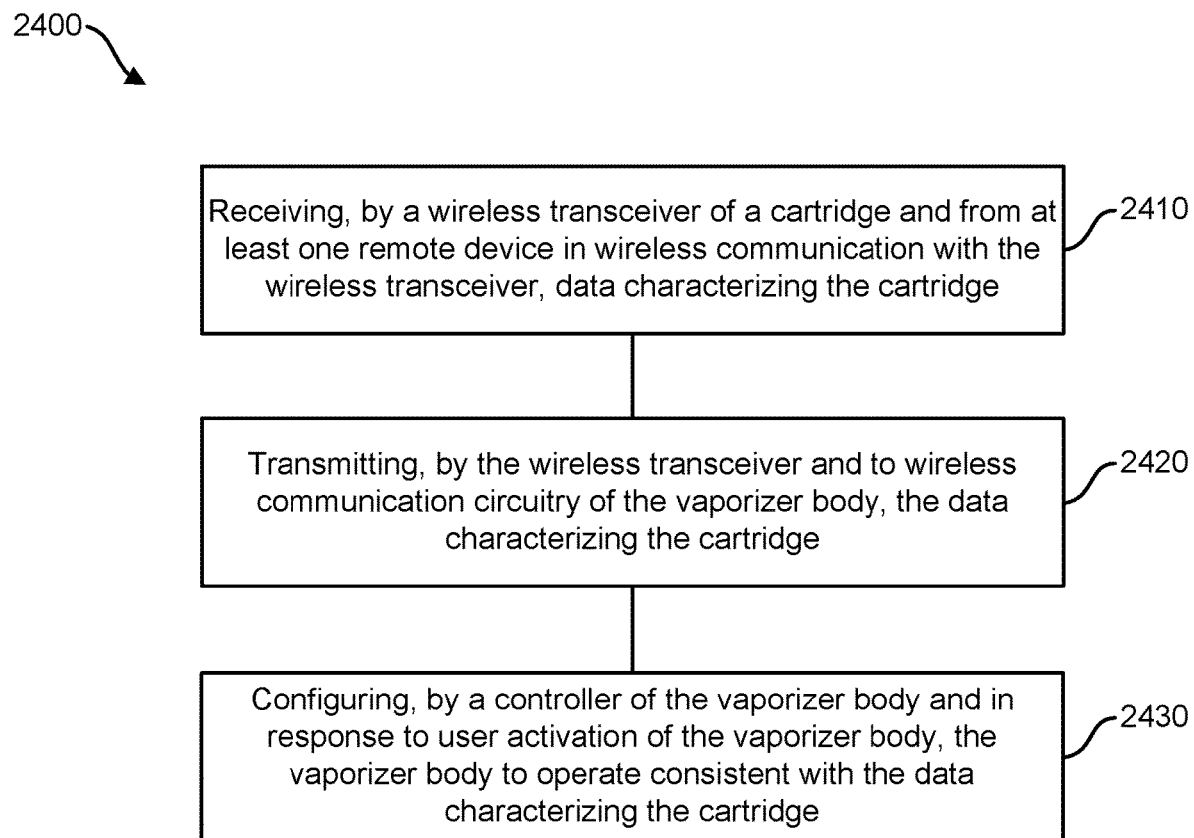
FIG. 25 shows a process flowchart illustrating features of a process consistent with implementations of the current subject matter.

With reference to FIG. 25, a process flow chart 2400 illustrates features of a method, which may optionally include some or all of the following. At 2410, the wireless transceiver (e.g., the tag 164) of the cartridge 150 receives data characterizing the cartridge 150. For example, the tag 164 may be an NFC tag that includes manufacturing data relating to the cartridge 150, filler data relating to the vaporizable material, and/or usage data relating to use of the cartridge 150. At 2420, the wireless transceiver transmits to the vaporizer body 110 the data characterizing the cartridge 150. For example, the tag 164 may transmit to the vaporizer body 110 data relating to the type of vaporizable material contained within the cartridge 150 or configuration parameters related to temperature and/or dose. At 2430, the vaporizer body 110 configures, for example in response to user activation of the vaporizer body 110, the vaporizer body 110 to operate consistent with the data characterizing the cartridge 150. For example, certain operational or configuration parameters may be best suited for a particular vaporizable material, and the vaporizer body 110 may accordingly control, for example, the temperature or dose based on the particular vaporizable material. In some implementations, the operational or configuration parameters include a value for a temperature and/or parameters for controlling a dose, such as time and amount of energy to provide to the heater 166.

In some implementations, an antenna or data tag may also provide power functionality to a cartridge to, for example, heat the vaporizable material contained within a reservoir of the cartridge. Such an implementation provides for wireless heating and communication between a vaporizer body and a cartridge, eliminating the need for power pins and power pin receptacles. By eliminating power pins and power pin receptacles, larger antennae may be incorporated in the vaporizer device and/or cartridge without increasing the overall size of either component.

Figure 28:
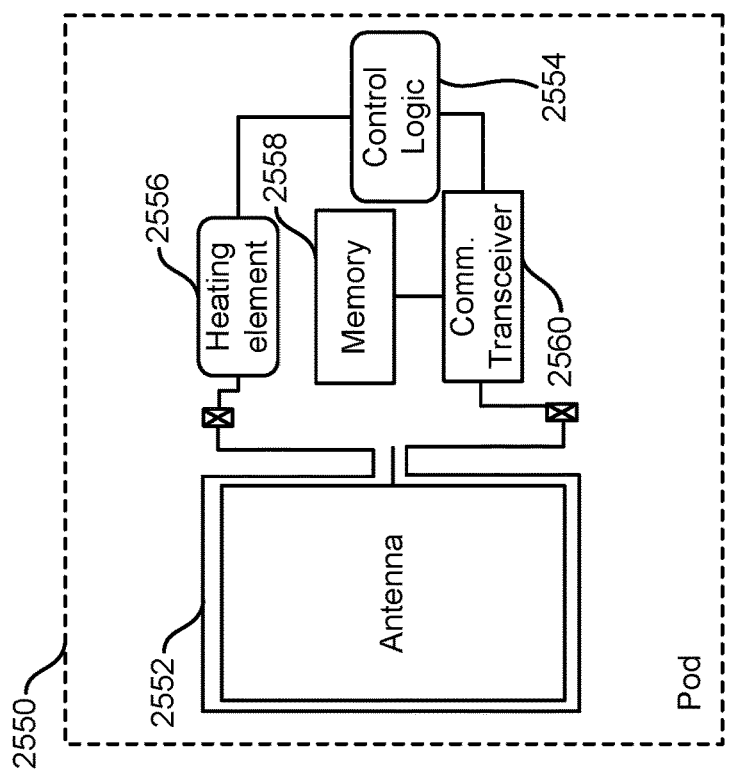
FIG. 28 is a block diagram illustrating aspects related to wireless power transfer and communication consistent with implementations of the current subject matter.
Figure 28:
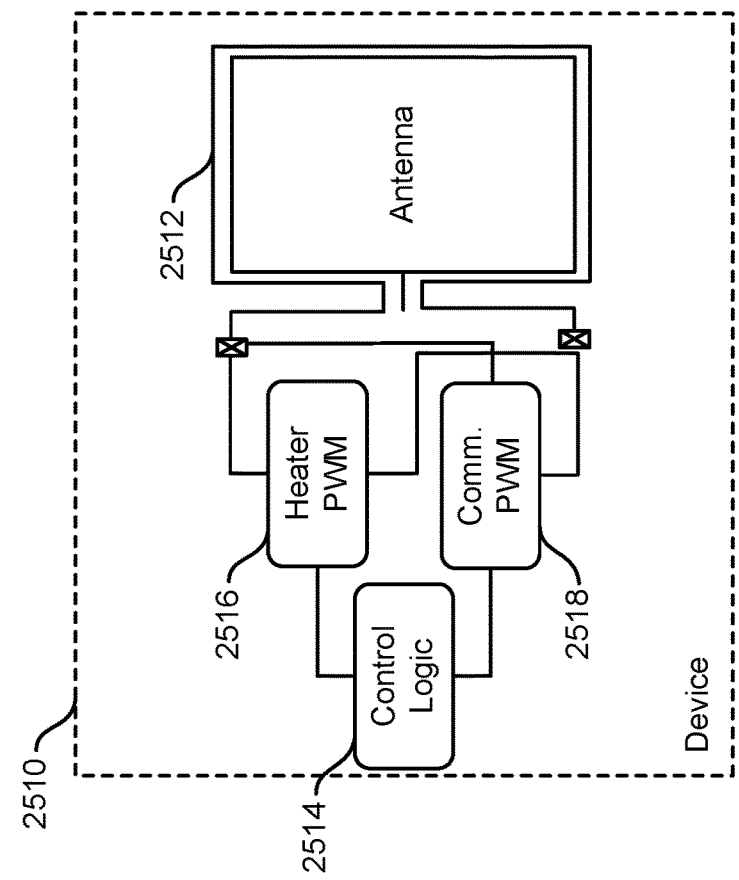

With reference to FIG. 28, a block diagram illustrating aspects related to a dual-purpose antenna for power transfer and communication is provided. A vaporizer body 2510 includes a device antenna 2512 and control logic 2514. A heater pulse width modulation (PWM) module 2516 and a communication PWM module 2518 are coupled to the control logic 2514. The control logic is configured to ensure that signals from the heater PWM module 2516 and the communication PWM module 2518 are not on at the same time.

The cartridge 2550 includes a cartridge antenna 2552 and control logic 2554. A heating element 2556, memory 2558 (e.g., non-volatile memory such as, for example but not limited to, EEPROM), and a communication transceiver 2560 are coupled to the control logic 2554. The communication transceiver 2560 may be an analog front-end (AFE) module but is not limited to this protocol.

When the heater PWM module 2516 is switched at low frequencies, a current on the cartridge antenna 2552 is induced via the device antenna 2512, which serves to heat the heating element 2556. The communication PWM module 2518 operates at higher frequencies to achieve a desired bandwidth. When the higher frequency communication PWM module 2518 is used, a control signal is sent to and read by the control logic 2554 of cartridge 2550. The control signal tells the control logic 2554 to turn on the communication transceiver 2560. The cartridge 2550 then harvests energy produced from the wireless field at the cartridge antenna 2552 to power the memory 2558. This communication transceiver 2560 translates the wireless signal from the vaporizer body 2510 into a protocol with which the memory 2558 may communicate.

Other aspects of the vaporizer body 2510 may be similar or equivalent to those of the vaporizer body 110 described herein, and similarly other aspects of the cartridge 2550 may be similar or equivalent to those of the cartridge 150 described herein.

In operation, after the vaporizer device is fully charged, a user may activate the vaporizer device by drawing (e.g., inhaling) through the mouthpiece. The device may detect a draw (e.g., using a pressure sensor, flow sensors, and/or the like, including a sensor configured to detect a change in temperature or power applied to a heater element) and may increase the power to a predetermined temperature preset. The power may be regulated by the controller by detecting the change in resistance of the heating coil and using the temperature coefficient of resistivity to determine the temperature.

The heater may include a small heating element configured to heat and/or vaporize at least a portion of the vaporizable material and a wicking material that may draw a liquid vaporizable material into the atomizer (e.g., heater). The resistance wire may be a coil. When the resistance wire is activated, the resistance wire (or coil) may have a temperature increase as a result of the current flowing through the resistive wire to generate heat. The heat may be transferred to at least a portion of the vaporizable material through conductive, convective, and/or radiative heat transfer such that at least a portion of the vaporizable material vaporizes.

Air may be drawn into the vaporizer device to carry the vaporized aerosol away from the heating element, where it then cools and condenses to form liquid particles suspended in air, which may then be drawn out of the mouthpiece by the user.

In accordance with some implementations of the current subject matter, a vaporizer device may be controlled so that the temperature used to vaporize the vaporizable material is maintained within a preset range. In general, the controller may control the temperature of the resistive heater (e.g., resistive coil, etc.) based on a change in resistance due to temperature (e.g., TCR). For example, a heater may be any appropriate resistive heater, such as, for example, a resistive coil. The heater is typically coupled to the heater controller via two or more connectors (electrically conductive wires or lines) so that the heater controller applies power (e.g., from the power source) to the heater. The heater controller may include regulatory control logic to regulate the temperature of the heater by adjusting the applied power. The heater controller may include a dedicated or general-purpose processor, circuitry, or the like and is generally connected to the power source and may receive input from the power source to regulate the applied power to the heater.

For example, apparatuses consistent with implementations described herein may include logic for determining the temperature of the heater based on the TCR of the heating element (resistive coil), based on sensed resistance of the coil. The resistance of the heater (e.g., a resistive heater) may be measured (Rheater) and the controller may use the known properties of the heater (e.g., the temperature coefficient of resistance) for the heater to determine the temperature of the heater. For example, the resistance of the heater may be detected by a detection circuit connected at the electrical contacts that connect to the cartridge, and this resistance compared to a target resistance, which is typically the resistance of the resistive heater at the target temperature. In some cases this resistance may be estimated from the resistance of the resistive hearing element at ambient temperature (baseline).

In some example embodiments, the controller 128 may be configured to control a temperature of the heater 166 including, for example, by adjusting and/or maintaining the temperature of the heating coil 167. The temperature of the heating coil 167 may be adjusted and/or maintained by at least controlling a discharge of the battery 124 to the heating coil 167. For instance, the controller 128 may start the discharge of the battery 124 to the heating coil 167 in order to raise the temperature of the heating coil 167. Alternatively or additionally, the controller 128 may stop the discharge of the battery 124 to the heating coil 167 in order maintain and/or decrease the temperature of the heating coil 167.

According to some example embodiments, the controller 128 may apply a proportional-integral-derivative (PID) control technique when adjusting the temperature of the heating coil 167. For example, the controller 128 may adjust the temperature of the heating coil 167, including by starting or stopping the discharge of the battery 124 to the heating coil 167, based on an error in the current temperature of the heating coil 167 relative to a target temperature. It should be appreciated that the temperature of the heating coil 167 may correspond to a resistance through the heating coil 167. That is, the temperature of the heating coil 167 may be correlated to the resistance through the heating coil 167 by a thermal coefficient of resistance associated with the heating coil 167. As such, the current resistance through the heating coil 167 may correspond to the current temperature of the heating coil while the target resistance through the heating coil 167 may correspond to the target temperature of the heating coil 167. Moreover, the controller 128 may start or stop the discharge of the battery 124 to the heating coil 167 based on an error in the current resistance through the heating coil 167 relative to a target resistance.

Figure 30A:
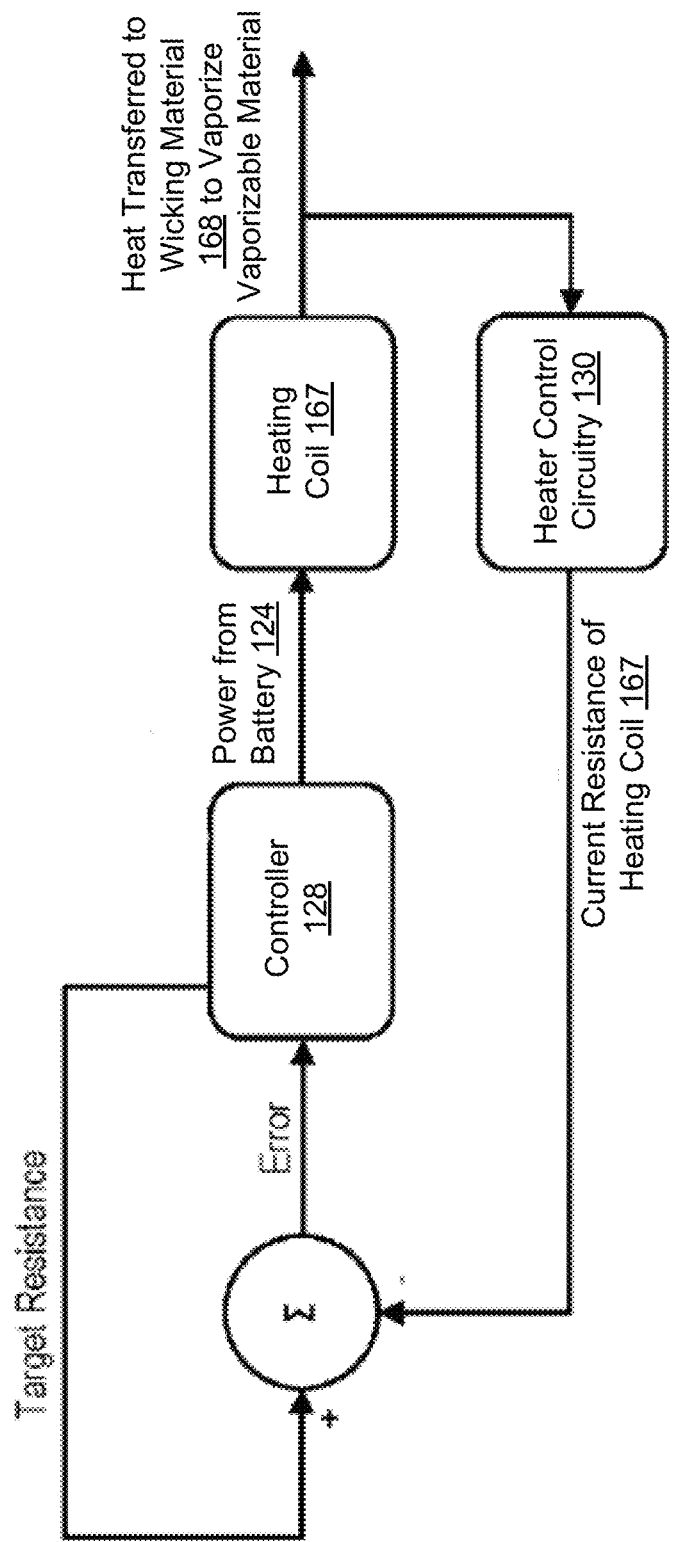
FIG. 30A depicts a block diagram illustrating an example of proportional-integral-derivative (PID) control consistent with implementations of the current subject matter.

To further illustrate, FIG. 30A depicts a block diagram illustrating an example of proportional-integral-derivative (PID) control consistent with implementations of the current subject matter. As shown in FIG. 30A, the controller 128 may control the discharge of the battery 124 to the heating coil 167 in the heater 166 of the cartridge 150. Meanwhile, the flow of current from the battery 124 through the heating coil 167 may generate heat, for example, through resistive heating. The heat generated by the heating coil 167 may be transferred to the wick 168, which may be in thermal contact with the heating coil 167. For instance, the heat that is generated by the heating coil 167 may be transferred to the wick 168 through conductive heat transfer, convective heat transfer, radiative heat transfer, and/or the like. The heat from the heating coil 167 may vaporize at least some of the vaporizable material held by the wick 168.

Referring again to FIG. 30A, the heater control circuitry 130 may be configured to determine a current resistance of the heating coil 167. As noted, the current resistance of the heating coil 167 may correspond to a current temperature of the heating coil 167. Accordingly, the controller 128, when applying a proportional-integral-derivative control technique, may adjust and/or maintain the temperature of the heating coil 167 based at least on an error between the current resistance of the heating coil 167 and a target resistance corresponding to at target temperature for the heating coil 167. As shown in FIG. 30A, the controller 128 may adjust, based at least on the error between the current resistance through the heating coil 167 and the target resistance, the discharge of the battery 124 to the heating coil 167. For example, the controller 128 may start the discharge of the battery 124 to the heating coil 167 if the current resistance of the heating coil 167 is below the target resistance. Alternatively or additionally, the controller 128 may stop the discharge of the battery 124 to the heating coil 167 if the current resistance of the heating coil 167 is equal to and/or above the target resistance.

Figure 30B:
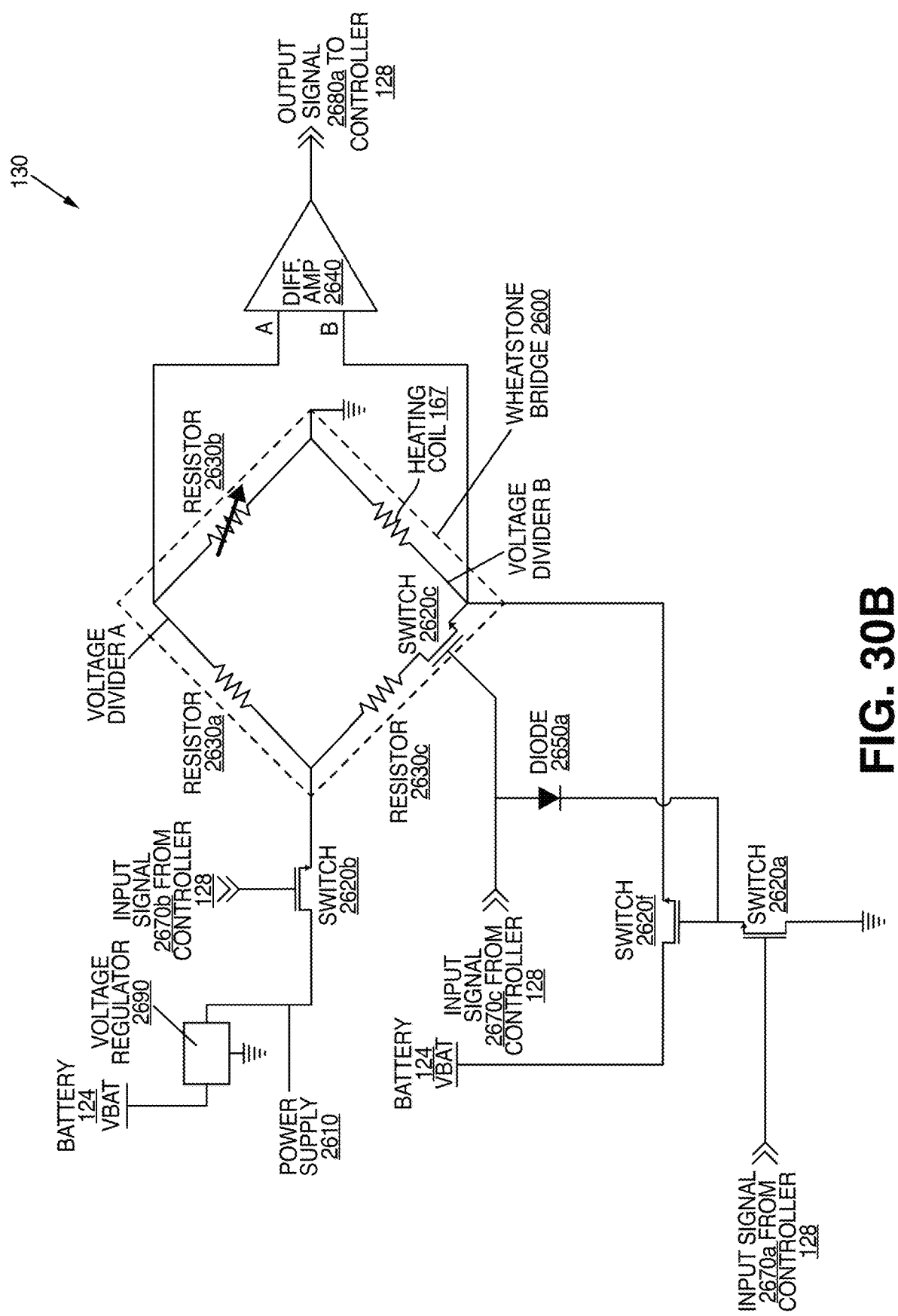
FIG. 30B depicts a schematic diagram illustrating an example of a heater control circuitry consistent with implementations of the current subject matter.

FIG. 30B depicts a schematic diagram illustrating an example of the heater control circuitry 130 consistent with implementations of the current subject matter. As noted, the heater control circuitry 130 may be configured to determine a resistance through the heating coil 167, which may correspond to a temperature of the heating coil 167. In order to determine the resistance through the heating coil 167, the heater control circuitry 130 may include a plurality of resistors having known resistances including, for example, a first resistor 2630a, a second resistor 2630b, and a third resistor 2630c. As shown in FIG. 30B, the heating coil 167, the first resistor 2630a, the second resistor 2630b, and the third resistor 2630c may form a Wheatstone bridge 2600. For instance, the first resistor 2630a may be coupled in series with the second resistor 2630b to form a first voltage divider A in the Wheatstone bridge 2600. Meanwhile, the third resistor 2630c may be coupled in series with the heating coil 167 to form a second voltage divider B in the Wheatstone bridge 2600.

The Wheatstone bridge 2600 may be a scalable Wheatstone bridge having one or more variable resistors. For instance, FIG. 30B shows the second resistor 2630b as a variable resistor having multiple known resistances. The resistance of the second resistor 2630b may be varied by coupling the second resistor 2630b with one or more other resistors having known resistances. In some example embodiments, varying the resistance of the second resistor 2630b may enable the heater control circuitry 130 to operate at different levels of resistances across the heating coil 167 of the cartridge 150. For example, the resistance of the second resistor 2630b may be varied in order to vary the voltage differential that may be measured across the Wheatstone bridge 2600. Varying the value of the voltage differential measured across the Wheatstone bridge 2600 may further vary the range of the temperature increment at the heating coil 167 including, for example, the quantity of steps between a baseline temperature and a target temperature for the heating coil 167.

The Wheatstone bridge 2600 may be coupled to a differential amplifier 2640 configured to determine a voltage differential across the Wheatstone bridge 2600, for example, between the first voltage divider A and the second voltage divider B. As shown in FIG. 30B, one input into the differential amplifier 2640 may be coupled to a node between the first resistor 2630a and the second resistor 2630b while another input into the differential amplifier 2640 may be coupled to a node between the third resistor 2630c and the heating coil 167. Moreover, the differential amplifier 2640 may further provide, to the controller 128, a first output signal 2680a corresponding to the voltage differential across the Wheatstone bridge 2600. For instance, the first output signal 2680a may be an analog signal between ground (e.g., 0 volts) and a positive voltage (e.g., 3 volts) of the power supply 2610. The first output signal 2680a may be output to an analog-to-digital (ADC) at the controller 128 such that the controller 128 may perform an analog to digital conversion to determine the resistance through the heating coil 167.

The resistance of the heating coil 167 may correspond to the voltage differential across the Wheatstone bridge 2600. Accordingly, the controller 128 may determine, based on the first output signal 2680a, the resistance through the heating coil 167. Equations (1)-(6) below illustrate the relationship that may exist between the voltage differential $\Delta V$ across the Wheatstone bridge 2600 and the temperature T of the heating coil 167. It should be appreciated that Equations (1)-(6) assume that the resistance $R_1$ through the first resistor 2630*a* may be equal to the resistance $R_2$ through the second resistor 2630*b*.

$$\Delta V = E\left(\frac{R_3}{R_3 + R_1} - \frac{R_{coil}}{R_2 + R_{coil}}\right) \quad (1)$$

$$\Delta V = E\left(\frac{R_3}{R_2 + R_3} - \frac{R_{coil}}{R_2 + R_{coil}}\right) \quad (2)$$

$$R_{coil} = R_3\left(\frac{ER_3 - \Delta V(R_2 + R_3)}{ER_2 + \Delta V(R_2 + R_3)}\right) \quad (3)$$

$$R_{coil} = R_0 \exp\left(\beta\left[\frac{1}{T} - \frac{1}{T_0}\right]\right) \quad (4)$$

$$\frac{1}{T} = \frac{1}{T_0} + \frac{1}{\beta}\ln\left(\frac{R_{coil}}{R_0}\right) \quad (5)$$

$$\frac{1}{T} = \frac{1}{T_0} + \frac{1}{\beta}\ln\left[\frac{R_2}{R_0}\left(\frac{ER_3 - \Delta V(R_2 + R_3)}{ER_2 + \Delta V(R_2 + R_3)}\right)\right] \quad (6)$$

wherein $T_0$ may denote a reference temperature (e.g., 298° K and/or the like), $R_0$ may denote a resistance at the reference temperature $T_0$, $\beta$ may denote the thermal coefficient of resistance of the heating coil 167 of the heater 166, and $R_3$ may denote the resistance of the third resistor 2630*c*.

The Wheatstone bridge 2600 may be split into two resistor dividers, each of which being configured to scale down an input voltage by a fixed ratio determined based on the resistances $R_1$ and $R_2$ in Equation (7) below.

$$V_{out} = V_{in}\left(\frac{R_2}{R_1 + R_2}\right) \quad (7)$$

The differential amplifier 2640 may amplify the difference between the voltage $V_1$ of the output from the resistor divider coupled with the heating coil 167 and the voltage $V_2$ of the resistor divider serving as a reference. This voltage differential $V_{adc}$ may be sent to the analog-to-digital converter (ADC) at the controller 128, for example, as the first output signal 2680*a*. Because the controller 128 may have an analog-to-digital conversion range (e.g., from 0 to 3 volts), the values $V_{adc}$ at 0 volt and at 3 volts may be used to determine the minimum and maximum resistances each scale is capable of detecting. For instance, as shown in FIG. 30B, the first resistor 2630*a* may have a fixed resistance (e.g., 44.2 Kohms) while the second resistor 2630*b* may be coupled with one or more scaling resistors including, for example, the fourth resistor 2630*d*, the fifth resistor 2630*e*, and/or the sixth resistor 2630*f*. These scaling resistors may be added and/or removed to alter the output of the reference resistor divider. The result is a variety of usable ranges. Since $V_2$ may be fixed for each scale, the minimum and maximum voltage at the analog-to-digital converter may be used to calculate, in accordance with Equation (8) below, the resistance ranges at the heating coil 167 that may be measured for each scale.

$$V_{adc} = \frac{R_2}{R_1}(V_2 - V_1) \quad (8)$$

As noted, each scale of the Wheatstone bridge 2600 may be capable of measuring a range of resistances across the heating coil 167. The scale of the Wheatstone bridge 2600 may be adjusted by at least switching in and/or switching out the one or more scaling resistors coupled with the second resistor 2630*b*. Furthermore, the resistance range associated with each scale may be determined based on the resistances of the one or more scaling resistors including, for example, the fourth resistor 2630*d*, the fifth resistor 2630*e*, and/or the sixth resistor 2630*f*. For instance, the resistances of the one or more scaling resistors may be selected in order to achieve smaller and/or more precise resistance ranges.

For example, a scale of zero may be achieved when none of the scaling resistors coupled with the second resistor 2630*b* are switched in. At scale zero, the resistance across the second resistor 2630*b* may be, for example, 806 ohms while the resistance across the first resistor 2630*a* may remain fixed at 44.2 Kohms. Thus, at scale zero, the voltage $V_2$ of the resistor divider may be constant at 0.0537 volts. The maximum resistance that can be measured at scale zero may be determined based on the required $V_1$ of the output from the resistor divider coupled with the heating coil 167 when $V_{adc}$ is at 3 volts. Based on Equation (8), the required $V_1$ of the output from the resistor divider coupled with the heating coil 167 when $V_{adc}$ is at 3 volts may be determined to be 0.042 volts. Accordingly, the maximum resistance $R_2$ of the heating coil 167 that can be measured at scale zero may be determined to be 1.4199 ohms by at least setting $V_{out}$ in Equation (7) to equal 0.042 volts and $V_{in}$ in Equation (7) to equal 3 volts. Meanwhile, the minimum resistance that can be measured at scale zero may be determined based on the required $V_1$ of the output from the resistor divider coupled with the heating coil 167 when $V_{adc}$ is at 0 volts.

Referring again to FIG. 30B, the heater control circuitry 130 may be coupled with the battery 124 and a power supply 2610. In some example embodiments, the battery 124 may power the heating coil 167. As noted, the controller 128 may control the discharge of the battery 124 to the heating coil 167 in order to adjust and/or maintain the temperature of the heating coil 167. Meanwhile, the heater control circuitry 130 may be powered by the power supply 2610 instead of the battery 124. For example, the power supply 2610 may include a regulated voltage rail that is generated by a voltage regulator 2690, which may be a linear voltage regulator, a switching regulator, and/or the like. The voltage regulator 2690 may regulate the output voltage of the battery 124 in order to provide, to the heater control circuitry 130, the regulated voltage rail having a steady voltage. In the absence of the voltage regulator 2690, the output voltage from the battery 124 may fluctuate. As such, powering the heater control circuitry 130 with directly by the battery 124 may disrupt the measurement of the voltage differential across the Wheatstone bridge 2600. Accordingly, it should be appreciated that instead of being directly powered by the battery 124, the heater control circuitry 130 may be powered by the power supply 2610.

FIG. 30B shows the battery 124 as being coupled to the heater control circuitry 130 at a node between the heating coil 167 and the third resistor 2630*c*. A first switch 2620*a* may be disposed between the battery 124 and the node at which the battery 124 is coupled to the heater control circuitry 130. The first switch 2620*a* may be a transistor including, for example, an n-channel field effect transistor (NFET), a p-channel field effect transistor (PFET), and/or the like. As shown in FIG. 30B, the state of the first switch 2620*a* may be controlled by a first input signal 2670*a* from the controller 128. For example, the controller 128 may change the state of the first switch 2620a in order to start or stop the battery 124 from being discharged to the heating coil 167.

FIG. 30B further shows a sixth switch 2620f as being disposed between the battery 124 and the node at which the battery is coupled to the heater control circuitry 130. The sixth switch 2620f may be a transistor including, for example, an n-channel field effect transistor (NFET), a p-channel field effect transistor (PFET), and/or the like. Moreover, the state of the sixth switch 2620f may also be controlled by the first input signal 2670a from the controller 128. Accordingly, the controller 128 may further start or stop the battery 124 from being discharged to the heating coil 167 by at least changing the state of the sixth switch 2620f.

As noted, the controller 128 may maintain and/or adjust the temperature of the heating coil 167 by at least starting or stopping the discharge of the battery 124 to the heating coil 167. In some example embodiments, the first input signal 2670a may be a pulse width modulation (PWM) signal. Accordingly, the controller 128 may adjust a duty cycle of first input signal 2670a in order to change the state of the first switch 2620a. For instance, while the first switch 2620a is held on by the first input signal 2670a from the controller 128, current may flow from the battery 124 to the heating coil 167 and cause an increase in the temperature of the heating coil 167.

As noted, the heater control circuitry 130 may be powered by the power supply 2610 instead of the battery 124. For example, the power supply 2610 may be coupled to the heater control circuitry 130 at a node between the first resistor 2630a and the third resistor 2630c. In some example embodiments, the heater control circuitry 130 may include one or more switches configured to control the flow of current from the power supply 2610 to the heater control circuitry 130. For instance, the heater control circuitry 130 may include a second switch 2620b and/or a third switch 2620c. The second switch 2620b and/or the third switch 2620c may each be a transistor including, for example, a n-channel field effect transistor (NFET), a p-channel field effect transistors (PFET), and/or the like.

The second switch 2620b may be disposed between the power supply 2610 and the node at which the power supply 2610 is coupled to the heater control circuitry 130. The state of the second switch 2620b, which may be controlled by a second input signal 2670b from the controller 128, may control the flow of current from the power supply 2610 to the heater control circuitry 130. For example, when the second switch 2620b is held on by the second input signal 2670b from the controller 128, current may flow from the power supply 2610 to the heater control circuitry 130, for example, to the first voltage divider A in the Wheatstone bridge 2600.

Alternatively or additionally, the third switch 2620c may be disposed between the third resistor 2630c and the node at which the power supply 2610 is coupled to the heater control circuitry 130. The state of the third switch 2620c may be controlled by a third input signal 2670c from the controller 128. Moreover, the state of the third switch 2620c may further control the flow of current from the power supply 2610 to the heater control circuitry 130. For instance, when the third switch 2620c is held on by the third input signal 2670c from the controller 128, current may flow from the power supply 2610 to the heater control circuitry 130, for example, to the second voltage divider B in the Wheatstone bridge 2600.

In some example embodiments, the controller 128 may control the flow of current from the power supply 2610 to the heater control circuitry 130 based on whether the vaporizer device 100 is use and/or is about to be put in use. For example, the controller 128 may start the flow of current from the power supply 2610 to the heater control circuitry 130 when the controller 128 determines that the vaporizer device 100 is in use and/or is about to be put in use. The controller 128 may determine that the vaporizer device 100 is in use and/or is about to be put in use when the cartridge 150 is inserted into the cartridge receptacle 114 in the vaporizer body 110 of the vaporizer device 100. The controller 128 may also determine that the vaporizer device 100 is in use when a difference between the pressure in the air flow path measured by the pressure sensor 137 and the ambient pressure measured by the ambient pressure sensor 138 indicates that air is being drawn by a user into the vaporizer device 100. Alternatively or additionally, the controller 128 may anticipate the vaporizer device 100 being put in use based on outputs from the accelerometer 139 indicating deliberate movements including, for example, a tapping of the vaporizer device 100, a rolling of the vaporizer device 100, and/or the like. These deliberate movements may indicate a user's intent to put the vaporizer device 100 in use.

Referring again to FIG. 30B, the heater control circuitry 130 may further include a first diode 2650a. The first diode 2650a may be forward biased towards the battery 124 in order to prevent current from the battery 124 from creating an overvoltage across portions of the heater control circuitry 130 including, for example, the first resistor 2630a, the second resistor 2630b, and the third resistor 2630c forming the Wheatstone bridge 2600. For example, as shown in FIG. 30B, a cathode of the first diode 2650a may be coupled to a drain of the first switch 2620a and a gate of the sixth switch 2620f. As noted, the first switch 2620a and the sixth switch 2620f are disposed between the battery 124 and the heater control circuitry 130 to at least enable the controller 128 to control, via the first input signal 2670a, the discharge of the battery 124 to the heating coil 167. Meanwhile, the anode of the first diode 2650a may be coupled to a line carrying the third input signal 2670c controlling the third switch 2620c. While the first switch 2620a is held on by the first input signal 2670a from the controller 128, the first diode 2650a may prevent current from the battery 124 from entering portions of the heater control circuitry 130 including, for example, the first resistor 2630a, the second resistor 2630b, and the third resistor 2630c forming the Wheatstone bridge 2600. Instead, while the first switch 2620a is held on by the first input signal 2670a, current from the battery 124 may be directed to the heating coil 167.

Figure 30C:
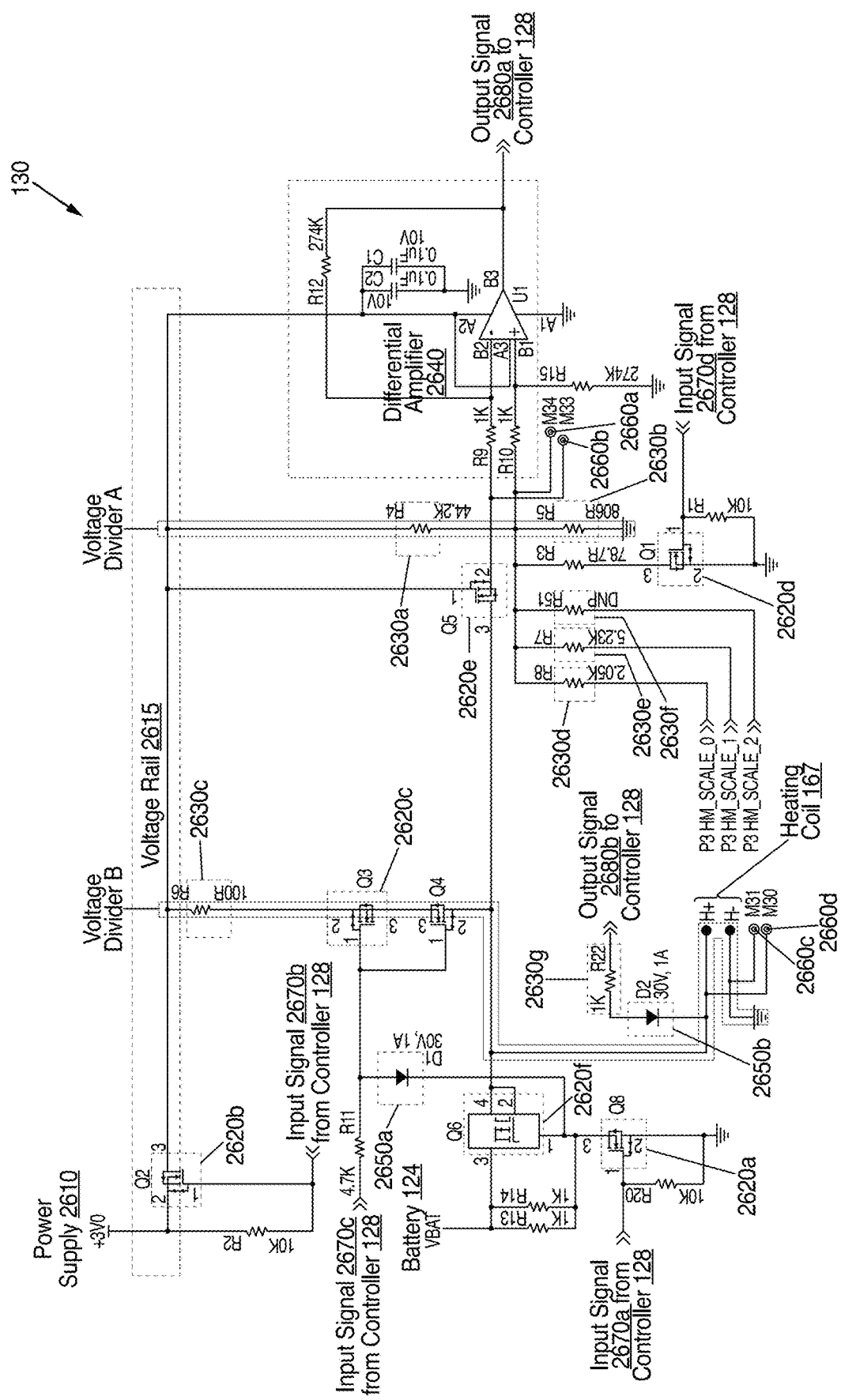
FIG. 30C depicts a schematic diagram illustrating an example of a heater control circuitry consistent with implementations of the current subject matter.

FIG. 30C depicts a schematic diagram illustrating an example of the heater control circuitry 130 consistent with implementations of the current subject matter. The heater control circuitry 130 shown in FIG. 30C may include additional circuit components not shown in FIG. 30B. As noted, in some example embodiments, the heater control circuitry 130 may be configured to determine the resistance through the heating coil 167, which may correspond to the temperature of the heating coil 167. For example, in order to determine the resistance of the heating coil 167, the heater control circuitry 130 may include a plurality of resistors having known resistances including, for example, the first resistor 2630a, the second resistor 2630b, and the third resistor 2630c.

In some example embodiments, the first resistor 2630a, the second resistor 2630b, the third resistor 2630c, and the heating coil 167 may form the Wheatstone bridge 2600 when the heating coil 167 is coupled to the heater control circuitry 130. For example, as shown in FIG. 30C, when the cartridge 150 is inserted into the cartridge receptacle 114 in the vaporizer body 110 of the vaporizer device 100, one end of the heating coil 167 may be coupled to the positive terminal H+ of the heater control circuitry 130 while the other end of the heating coil 167 may be coupled to the negative terminal H− of the heater control circuitry 130. Moreover, the first resistor 2630a and the second resistor 2630b may form the first voltage divider A of the Wheatstone bridge 2600 while the third resistor 2630c and the heating coil 167 may form the second voltage divider B in the Wheatstone bridge 2600.

The Wheatstone bridge 2600 may be coupled to the differential amplifier 2640. As noted, the differential amplifier 2640 may provide, to the controller 128, the first output signal 2680a indicating a voltage differential across the Wheatstone bridge 2600 including, for example, a voltage differential between the first voltage divider A and the second voltage divider B of the Wheatstone bridge 2600. This voltage differential may correspond to the resistance through the heating coil 167. Meanwhile, the resistance through the heating coil 167 may further correspond to the current temperature of the heating coil 167. Accordingly, the controller 128 may adjust and/or maintain, based at least on the first output signal 2680a, the temperature of the heating coil 167. For instance, the controller 128 may apply a proportional-integral-derivative (PID) control technique and adjust the temperature of the heater 166 based on an error in the current temperature of the heating coil 167 relative to a target temperature. The controller 128 may adjust the temperature of the heater 166 by at least adjusting the first input signal 2670a to start or stop the discharge of the battery 124 to the heating coil 167.

In some example embodiments, the heating coil 167 may be formed from two or more different materials (e.g., metals and/or the like). Contact between two different conductive materials may trigger a Seebeck effect and induce an additional voltage across the heating coil 167. This additional voltage may increase as the temperature of the heater 166 increases. As noted, the temperature of the heater 166 may be determined based on the voltage differential across the Wheatstone bridge. Thus, the presence of the additional voltage due to Seebeck effect may introduce an error in the resistance measured for the heating coil 167. Accordingly, in some example embodiments, the controller 128 may perform an open-circuit voltage measurement and use the open-circuit voltage measurement to adjust the voltage differential output by the differential amplifier 2640.

For example, the controller 128 may perform the open-circuit voltage measurement by at least adjusting a fourth input signal 2670d controlling a state of a fourth switch 2620d. The fourth switch 2620d may be a transistor including, for example, an n-channel field effect transistor (NFET), a p-channel field effect transistor (PFET), and/or the like. Moreover, the state of the fourth switch 2620d may control the connection between the first voltage divider A and the second voltage divider B in the Wheatstone bridge 2600. As noted, the first voltage divider A may be formed by the first resistor 2630a and the second resistor 2630b while the second voltage divider B may be formed by the heating coil 167 and the third resistor 2630c. The controller 128 may perform the open-circuit voltage measurement by at least disconnecting the first voltage divider A and the second voltage divider B such that the first output signal 2680a corresponds to the additional voltage that is induced across the heating coil 167 due to Seekbeck effect.

In some example embodiments, the Wheatstone bridge 2600 may be a scalable Wheatstone bridge. As such, the Wheatstone bridge 2600 may include at least one variable resistor having multiple known resistances. For instance, the second resistor 2630b may be a variable resistor whose resistance may be varied by being coupled with one or more other resistors of known resistances including, for example, a fourth resistor 2630d, a fifth resistor 2630e, a sixth resistor 2630f, and/or the like. The range of the voltage differential measured across the Wheatstone bridge 2600 may be adjusted by at least coupling the fourth resistor 2630d, the fifth resistor 2630e, and/or the sixth resistor 2630f to the first voltage divider A of the Wheatstone bridge 2600. As used herein, the range of the voltage differential may refer to a quantity of steps between a maximum voltage differential and a minimum voltage differential indicated by first output signal 2680a. The range of the voltage differential may correspond to the range of the temperature increment at the heating coil 167 including, for example, the quantity of steps between a baseline temperature and a target temperature for the heating coil 167. For instance, the three additional resistors shown in FIG. 30C may allow the heater control circuitry 130 to determine the resistance of the heating coil 167 at eight different levels. It should be appreciated that the heater control circuitry 130 may support resistance measurements at different ranges in order to accommodate the various types of vaporizable material that vaporize at different temperature ranges.

As noted, the heater control circuitry 130 may be coupled with the battery 124 as well as the power supply 2610. However, instead of being powered directly by the battery 124, the heater control circuitry 130 may be powered by the power supply 2610. The power supply 2610 may include a voltage rail 2615 generated by the voltage regulator 2690. For example, as shown in FIG. 26C, the voltage rail 2615 may be a regulated voltage rail having a steady voltage of 3 volts and/or the like. In some example embodiments, the power supply 2610 may power the heater control circuitry 130 instead of the battery 124. To prevent the battery 124 from discharging to the voltage rail 2615 and causing an overvoltage across the first resistor 2630a, the second resistor 2630b, and the third resistor 2630c in the Wheatstone bridge 2600, the heater control circuitry 130 may include the first diode 2650a. While the first switch 2620a is held on by the first input signal 2670a from the controller 128, the first diode 2650a may prevent current from the battery 124 from entering the first resistor 2630a, the second resistor 2630b, and the third resistor 2630c in the Wheatstone bridge 2600. Instead, while the first switch 2620a is held on by the first input signal 2670a, current from the battery 124 may be directed to the heating coil 167.

Alternatively or additionally, the heater control circuitry 130 may also include the third switch 2620c. As noted, the third switch 2620c may control the flow of current from the power supply 2610 to the heater control circuitry 130 including, for example, the second voltage divider B in the Wheatstone bridge 2600. Moreover, the third switch 2620c may also prevent the battery 124 from discharging to the voltage rail 2615 an over voltage on the voltage rail 2615 by at least preventing the battery 124 from discharging to the voltage rail 2615 and causing an over voltage across portions of the Wheatstone bridge 2600 including, for example, the first resistor 2630a, the second resistor 2630b, and the third resistor 2630c in the Wheatstone bridge 2600.

In some example embodiments, the heater control circuitry 130 may further include a fifth switch 2620e. The fifth switch 2620e may be a transistor including, for example, an n-channel field effect transistor (NFET), a p-channel field effect transistor (PFET), and/or the like. As shown in FIG. 30C, the fifth switch 2620e may be disposed at a junction between the voltage rail 2615, the first voltage divider A of the Wheatstone bridge 2600, and the differential amplifier 2640. The fifth switch 2620e may be configured to prevent back powering, which may occur, for example, when current back fed from other components of the heater control circuitry 130 (e.g., the first diode 2650a and/or the like) continues to power the heater control circuitry 130 even when the heater control circuitry 130 is not being powered by the power supply 2610.

For example, FIG. 30C shows the fifth switch 2620e as being coupled to a node on the voltage rail 2615. Furthermore, the fifth switch 2620e may be coupled to the second voltage divider B of the Wheatstone bridge 2600, for example, at a node between the third resistor 2630c and the heating coil 167. As shown in FIG. 30C, the fifth switch 2620e may be further coupled to a line coupling the second voltage divider B to an input into the differential amplifier 2640. As such, the state of the fifth switch 2620e may determine whether current flow from the second voltage divider B into the differential amplifier 2640. For example, the fifth switch 2620e may be held on when the second switch 2620b is held on and current is flowing from the power supply 2610 into the heater control circuitry 130. However, the fifth switch 2620e may be held off when the second switch 2620b is held off and current is not flowing from the power supply 2610 into the heater control circuitry 130. Holding off the fifth switch 2620e may prevent current back fed from other components of the heater control circuitry 130 (e.g., the first diode 2650a and/or the like) from entering portions of the heater control circuitry 130 including, for example, the differential amplifier 2640.

Referring again to FIG. 30C, the controller 128 may be further configured to detect the presence or the absence of the cartridge 150, for example, in the cartridge receptacle 114 in the vaporizer body 110 of the vaporizer device 100. In some example embodiments, the discharge of the battery 124 to the heating coil 167 may depend on whether the cartridge 150 is present or absent from the cartridge receptacle 114. As such, the state of the first switch 2620a, which may control the discharge of the battery 124 to the heating coil 167, may be further determined based on the whether the cartridge 150 is present or absent from the cartridge receptacle 114. For example, the absence of the cartridge 150 may prevent the first switch 2620a from being held off by the first input signal 2670a, thereby preventing the battery 124 from discharging to the heating coil 167.

In some example embodiments, the heater control circuitry 130 may include an interrupt request (IRQ) line configured to detect the presence or an absence of the cartridge 150. The presence or the absence of the cartridge 150 may correspond to a presence or an absence of the heating coil 167 across the positive terminal H+ and the negative terminal H− of the heater control circuitry 130. As shown in FIG. 30C, the interrupt request (IRQ) line may be implemented using a second diode 2650b that is coupled in series with a seventh resistor 2630g. When the cartridge 150 is inserted into the cartridge receptacle 114, the heating coil 167 may be disposed across the positive terminal H+ and the negative terminal H− of the heater control circuitry 130. Accordingly, a second output signal 2680b to the controller 128 may enable the controller 128 to determine whether the cartridge 150 is present or absent from the cartridge receptacle 114 in the vaporizer body 110 of the vaporizer device 100.

For example, when the cartridge 150 is inserted in the cartridge receptacle 114, the presence of the heating coil 167 across the positive terminal H+ and the negative terminal H− of the heater control circuitry 130 forms a low resistance path to the ground that pulls the second output signal 2680b to the controller 128 to ground. By contrast, when the cartridge 150 is absent from the cartridge receptacle 114, the heating coil 167 may also be absent, thereby removing the low resistance path to the ground. Instead, the second output signal 2680b may be pulled high, for example, to the positive voltage (e.g., 3 volts) of the power supply 2610. Accordingly, the controller 128 may determine, based at least on the second output signal 2680b, whether the cartridge 150 is present in the cartridge receptacle 114 in the vaporizer body 110 of the vaporizer device 100.

Referring again to FIG. 30C, the heater control circuitry 130 may include one or more test points. As shown in FIG. 30C, the heater control circuitry 130 may include a first test point 2660a coupled to the first voltage divider A in the Wheatstone bridge 2600 and a second test point 2660b coupled to the second voltage divider B in the Wheatstone bridge 2600. The first test point 2660a may be used to measure the voltage across the first voltage divider A while the second test point 2660b may be used to measure the voltage across the second voltage divider B. In some example embodiments, the first test point 2660a and the second test point 2660b may be used to calibrate the Wheatstone bridge 2600, for example, including by determining correction factors for the known resistances of the first resistor 2630a, the second resistor 2630b, and/or the third resistor 2630c.

Alternatively or additionally, the heater control circuitry 130 may also include a third test point 2660c and a fourth test point 2660d. The fourth test point 2660d may be coupled to a cathode of the second diode 2650d while the third test point 2660c may be coupled to ground. In some example embodiments, the third test point 2660c and the fourth test point 2660d may be used to calibrate the interrupt request (IRQ) line formed by the second diode 2650b and the seventh resistor 2630g. For example, readings from the third test point 2660c and the fourth test point 2660d may be used to determine correction factors for the second output signal 2680b to the controller 128.

Figure 30D:
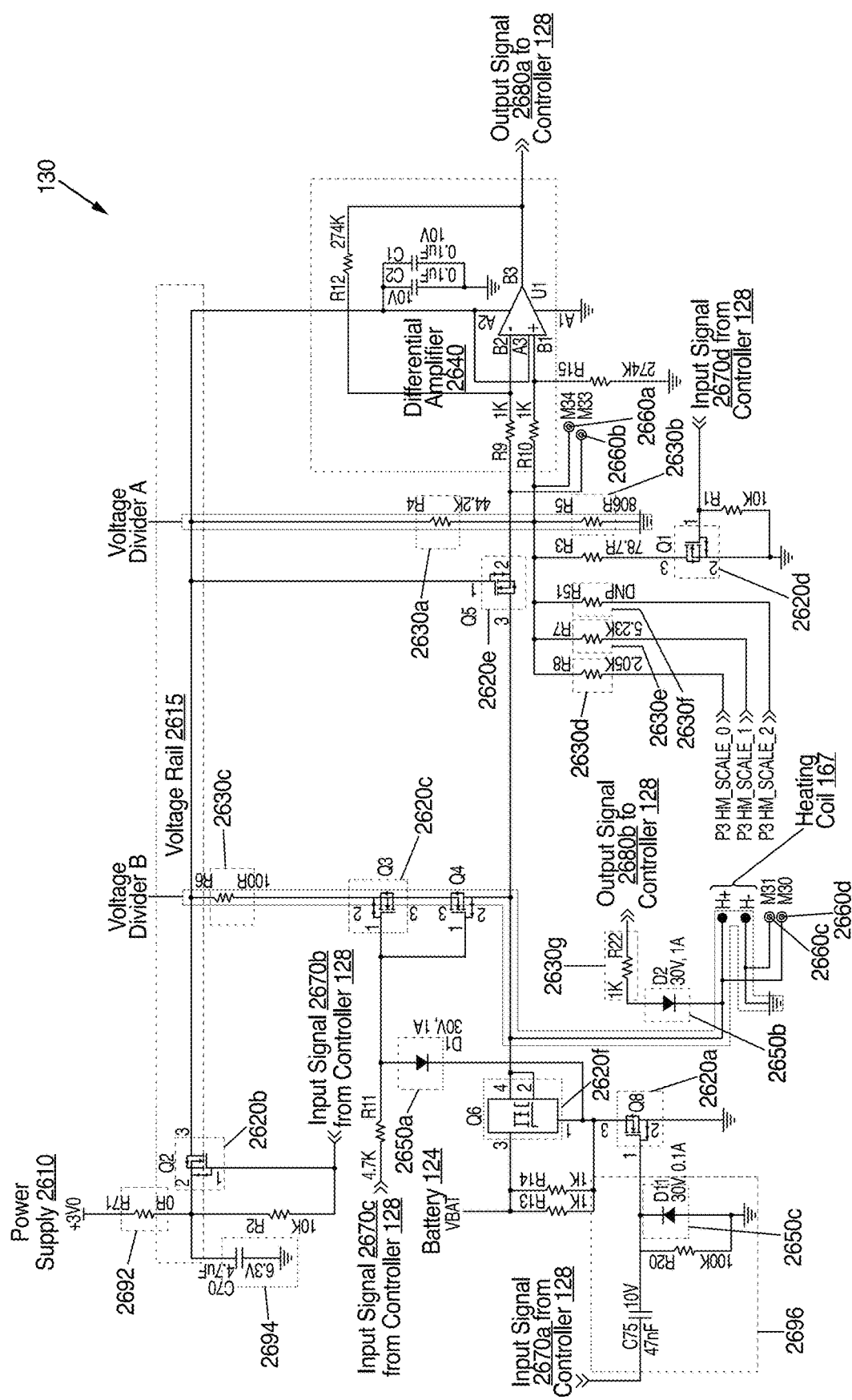
FIG. 30D depicts a schematic diagram illustrating another example of a heater control circuitry consistent with implementations of the current subject matter.

FIG. 30D depicts a schematic diagram illustrating another example of the heater control circuitry 130 consistent with implementations of the current subject matter. The heater control circuitry 130 shown in FIG. 30D may include additional circuit components not shown in FIG. 30B and/or FIG. 30C.

Referring to FIG. 30D, the heater control circuitry 130 may include a suppressor 2692 disposed between the power supply 2610 and the second switch 2620b. The heater control circuitry 130 may further include a reservoir capacitor 2694, which connects between the power supply 2610 and ground. In some example embodiments, the suppressor 2692 may be configured to suppress high frequency noise present in the electrical signal from the power supply 2610. For example, the suppressor 2692 may exhibit a low resistance when subject to a low frequency electrical signal from the power supply 2610 and/or a high resistance when subject to a high frequency electrical signal from the power supply 2610. Moreover, the suppressor 2692 be coupled with the reservoir capacitor 2694 to act as a low-pass filter that rejects any high frequency noise present in the electrical signal from the power supply 2610. The suppressor 2692 may be implemented using a resistor, a zero ohm-resistor, a ferrite bead, and/or the like. Nevertheless, it should be appreciated that implementing the suppressor 2692 using a conventional resistor may consume more power (e.g., quiescent current) when no noise is present, for example, during normal operation.

In some example embodiments, the reservoir capacitor 2694 may be configured to accommodate in-rush current and the concomitant voltage drop on the voltage rail 2615. The reservoir capacitor 2694 may remain charged while the heater control circuitry 130 is powered off, for example, via the second switch 2620b disposed between the power supply 2610 and the node at which the power supply 2610 is coupled to the heater control circuitry 130. Alternatively, when the heater control circuitry 130 is powered on via the second switch 2620b, the reservoir capacitor 2694 may prevent a voltage drop on the voltage rail 2615 and minimize the time-delay associated with stabilizing the supply voltage by at least supplying the in-rush current to the heater control circuitry 130. Furthermore, as noted, the reservoir capacitor 2694 may couple with the suppressor 2692 to serve as a low-pass filter.

Referring again to FIG. 30D, in some example embodiments, the heater control circuitry 130 may further include a high-pass filter 2696 coupled with the first input signal 2670a from the controller 128. In the event of a glitch, for example, at the controller 128, the first input signal 2670a may be driven high permanently and cause the battery 124 to constantly discharge to the heating coil 167 of the heater 166. This constant discharge of the battery 124 to the heating coil 167 may potentially damage and/or destroy the heating coil 167. Accordingly, the heater control circuitry 130 may include the high-pass filter 2696 in order to prevent the battery 124 from constantly discharging to the heating coil 167. For instance, the high-pass filter 2696 may include a third diode 2650c configured to provide a fast-discharge path for the negative voltage on the high-pass filter 2696 when the input to the high-pass filter 2696 switches from a high voltage to a low voltage (e.g., 0 volt) at high duty cycles.

Figure 31:
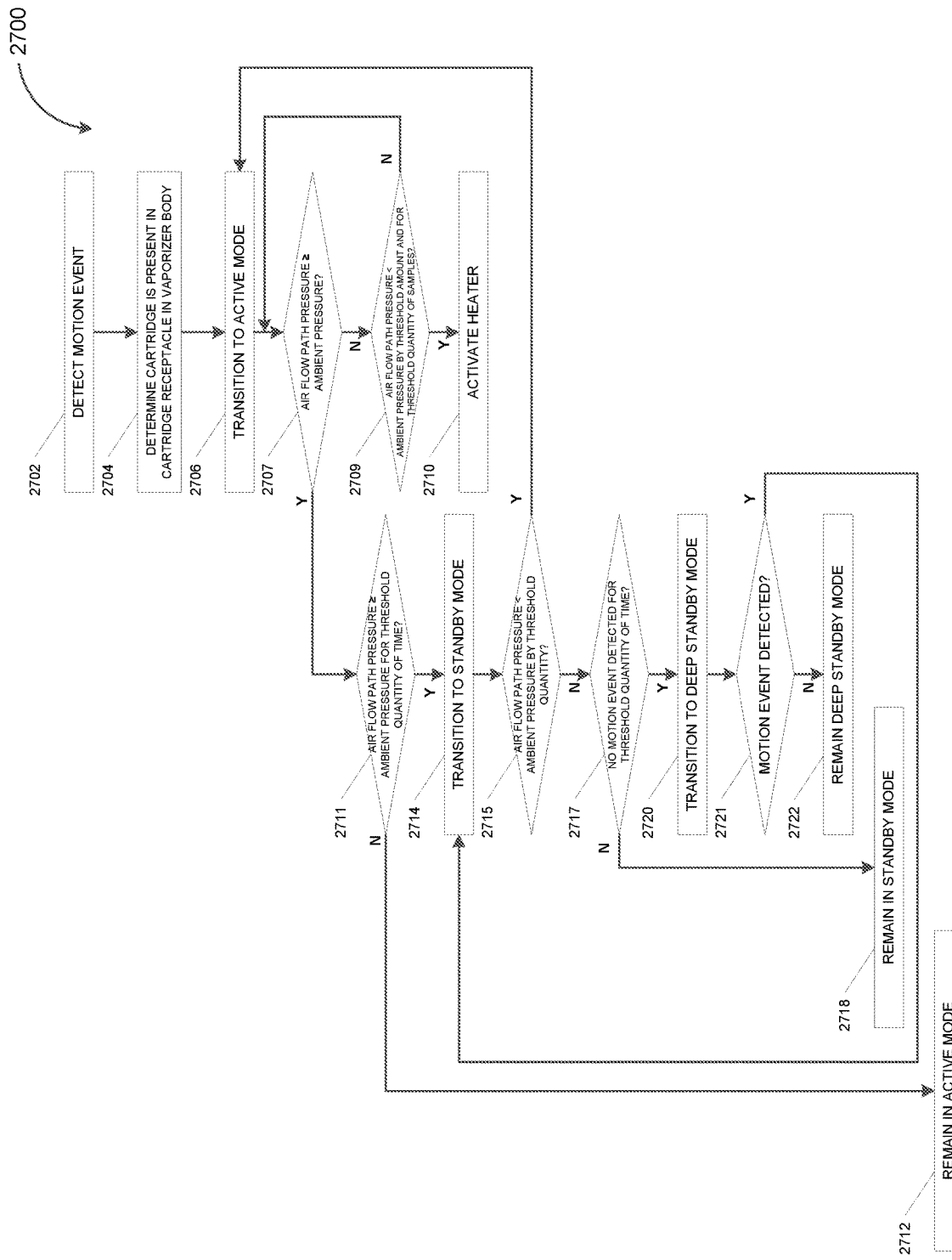
FIG. 31 depicts a flowchart illustrating a process for transitioning the operation mode of a vaporizer device with implementations of the current subject matter.

FIG. 31 depicts a flowchart illustrating a process 2700 for operating the vaporizer device 100 consistent with implementations of the current subject matter. In some example embodiments, the vaporizer device 100, for example, the controller 128, may perform the process 2700 in order to transition between different modes of operation including, for example, an active mode, a standby mode, and/or a deep standby mode. The transition between different modes of operation may change the sampling frequency and/or resolution of the pressure sensor 137 and/or the ambient pressure sensor 138. For example, the pressure sensor 137 and/or the ambient pressure sensor 138 may sample at a higher frequency and/or resolution when the vaporizer device 100 is in an active mode than when the vaporizer device 100 is in a standby mode and/or a deep standby mode.

At 2702, the vaporizer device 100 may detect a motion event. As noted, the vaporizer device 100 may include the accelerometer 139 (and/or other motion sensors, capacitive sensors, flow sensors, strain gauge(s), or the like) capable of detecting movement of the vaporizer body 110 including, for example, tapping, rolling, and/or any other deliberate movements. Such movements may be indicative of user interaction with the vaporizer device 100 and may therefore be interpreted, for example, by the controller 128, as one or more predefined user commands including, for example, a user command to gradually increase the temperature of the heater 166 before the user begin using the vaporizer device 100 and/or while the user is using the vaporizer device 100.

At 2704, the vaporizer device 100 may detect that the cartridge 150 is present in the cartridge receptacle 114 on the vaporizer body 110 of the vaporizer device 100. As noted, in some example embodiments, the heater control circuitry 130 of the vaporizer device 100 may include the second diode 2650b, which may be coupled in series with the seventh resistor 2630g to implement an interrupt request (IRQ) line. The second output signal 2680b from the heater control circuitry 130 to the controller 128 may indicate whether the cartridge 150 is or absent from the cartridge receptacle 114 in the vaporizer body 110 of the vaporizer device 100.

At 2706, the vaporizer device 100 may respond to the presence of the cartridge 150 in the cartridge receptacle 114 of the vaporizer body 110 by at least transitioning to an active mode in which the pressure sensor 137 and/or the ambient pressure sensor 138 operate at a first sampling frequency. In some example embodiments, the vaporizer device 100 may transition to an active mode if the cartridge 150 is present in the cartridge receptacle 114 of the vaporizer body 110. As noted, when the vaporizer device 100 is in the active mode, the pressure sensor 137 and/or the ambient pressure sensor 138 may operate at a higher sampling frequency than when the vaporizer device 100 is in the standby mode and/or the deep standby mode. For example, when the vaporizer device 100 transitions to the active mode, the pressure sensor 137 and/or the ambient pressure sensor 138 may operate at a sampling frequency of 50 hertz.

At 2707, the vaporizer device 100 may determine whether a pressure in the air flow path 181 measured by the pressure sensor 137 is greater than or equal to an ambient pressure measured by the ambient pressure sensor 138. In some example embodiments, the difference between the pressure in the air flow path 181 measured by the pressure sensor 137 and the ambient pressure measured by the ambient pressure sensor 138 may indicate whether air is being drawn into the vaporizer device 100 through the air flow path 181, for example, by the user drawing on the mouthpiece 152. The presence and/or absence of the user's draw may determine whether power is delivered from the battery 124 to the heater 166 in order to maintain and/or adjust the temperature of the heater 166.

At 2707-N, the vaporizer device 100 may determine that the pressure in the air flow path 181 measured by the pressure sensor 137 is not equal to or greater than the ambient pressure measured by the ambient pressure sensor 138. For example, a less than ambient pressure within the air flow path 181 may indicate air being drawn, for example, by the user, into the vaporizer device 100 through the air flow path 181. As such, at 2709, the vaporizer device 100 may determine whether the pressure in the air flow path 181 measured by the pressure sensor 137 is less than the ambient pressure measured by the ambient pressure sensor 138 by a threshold amount and for a threshold quantity of samples. For instance, the vaporizer device 100 may determine whether the pressure in the air flow path 181 measured by the pressure sensor 137 is less than the ambient pressure measured by the ambient pressure sensor 138 by 1.5 hectopascals (hPa) for at least 30 samples at a sampling frequency of 50 hertz.

At 2709-Y, the vaporizer device 100 may determine that the pressure in the air flow path 181 measured by the pressure sensor 137 is less than the ambient pressure measured by the ambient pressure sensor 138 by the threshold amount and for the threshold quantity of samples. For example, the vaporizer device 100 may determine that the pressure in the air flow path 181 measured by the pressure sensor 137 is less than the ambient pressure measured by the ambient pressure sensor 138 by 1.5 hectopascals (hPa) for at least 30 samples at a sampling frequency of 50 hertz. Accordingly, at 2710, the vaporizer device 100 may activate the heater 166. For instance, to activate the heater 166, the controller 128 may adjust the first input signal 2670*a* from the controller 128 to the heater control circuitry 130 to change the state of the first switch 2620*a* to enable the battery 124 to discharge to the heating coil 167 of the heater 166. As noted, the first input signal 2670*a* may be a pulse width modulation (PWM) signal. As such, the controller 128 may adjust the first input signal 2670*a* by at least changing a duty cycle of the pulse width modulation signal.

At 2709-N, the vaporizer device 100 may determine that the pressure in the air flow path 181 measured by the pressure sensor 137 is not less than the ambient pressure measured by the ambient pressure sensor 138 by the threshold amount or for the threshold quantity of samples. For example, the vaporizer device 100 may determine that the pressure in the air flow path 181 measured by the pressure sensor 137 is not less than the ambient pressure measured by the ambient pressure sensor 138 by 1.5 hectopascals (hPa) and/or for at least 30 samples at a sampling frequency of 50 hertz. As such, the process 2700 may resume at operation 2707 where the vaporizer device 100 again determines whether the pressure in the air flow path 181 measured by the pressure sensor 137 is greater than or equal to the ambient pressure measured by the ambient pressure sensor 138. As noted, the difference between the pressure in the air flow path 181 measured by the pressure sensor 137 and the ambient pressure measured by the ambient pressure sensor 138 may indicate whether air is being drawn into the vaporizer device 100 through the air flow path 181, for example, by the user drawing on the mouthpiece 152

At 2707-Y, the vaporizer device 100 may determine that the pressure in the air flow path 181 measured by the pressure sensor 137 is equal to or greater than the ambient pressure measured by the ambient pressure sensor 138. For example, a greater than ambient pressure within the air flow path 181 may indicate that no air being drawn, for example, by the user, into the vaporizer device 100 through the air flow path 181. As such, at 2711, the vaporizer device 100 may determine whether the pressure in the air flow path 181 measured by the pressure sensor 137 is equal to or greater than the ambient pressure measured by the ambient pressure sensor 138 for a threshold quantity of time. For instance, the vaporizer device 100 may determine whether no air is being drawn by the user into the vaporizer device 100 through the air flow path 181 for at least 10 seconds.

At 2711-Y, the vaporizer device 100 may determine that the pressure in the air flow path 181 measured by the pressure sensor 137 is equal to or greater than the ambient pressure measured by the ambient pressure sensor 138 for the threshold quantity of time. For instance, the vaporizer device 100 may determine that the user has not drawn air into the vaporizer device 100 through the air flow path 181 for at least 10 seconds. As such, at 2714, the vaporizer device 100 may transition to a standby mode in which the pressure sensor 137 and/or the ambient pressure sensor 138 operate at a second sampling frequency. In some example embodiments, when the vaporizer device 100 is in the standby mode, the pressure sensor 137 and/or the ambient pressure sensor 138 may operate at an intermediate sampling frequency that is lower than the sampling frequency in the active mode but higher than the sampling frequency in the deep standby mode. For example, when the vaporizer device 100 transitions to the standby mode, the pressure sensor 137 and/or the ambient pressure sensor 138 may operate at a sampling frequency of 10 hertz.

At 2711-N, the vaporizer device 100 may determine that the pressure in the air flow path 181 measured by the pressure sensor 137 is not equal to or greater than the ambient pressure measured by the ambient pressure sensor 138 for the threshold quantity of time. Accordingly, at 2712, the vaporizer device 100 may remain in the active mode while the pressure sensor 137 and/or the ambient pressure sensor 138 continues to operate at the first sampling frequency. For example, if the vaporizer device 100 determines that the lack of air being drawn into the vaporizer device 100 through the air flow path 181 has not lasted for at least 10 seconds, the vaporizer device 100 may remain in the active mode. As noted, while the vaporizer device 100 is in the active mode, the pressure sensor 137 and/or the ambient pressure sensor 138 may operate at a higher sampling frequency (e.g., 50 hertz) than when the vaporizer device 100 is in the standby mode and/or the deep standby mode.

Once the vaporizer device 100 transitions to the standby mode at operation 2714, the process 2700 may continue at operation 2715 at which the vaporizer device 100 may determine whether the pressure in the air flow path 181 measured by the pressure sensor 137 is less than the ambient pressure measured by the ambient pressure sensor 138 by a threshold quantity. For example, the vaporizer device 100 may determine whether the pressure in the air flow path 181 measured by the pressure sensor 137 is less than the ambient pressure measured by the ambient pressure sensor 138 by at least 1.5 hectopascals (hPa).

At 2715-Y, the vaporizer device 100 may determine that the pressure in the air flow path 181 measured by the pressure sensor 137 is a threshold quantity less than the ambient pressure measured by the ambient pressure sensor 138. For instance, the vaporizer device 100 may determine whether the pressure in the air flow path 181 measured by the pressure sensor 137 is at least 1.5 hectopascals less than the ambient pressure measured by the ambient pressure sensor 138. As such, the process 2700 may resume at operation 2706 at which the vaporizer device 100 returns to an active mode such that the pressure sensor 137 and/or the ambient pressure sensor 138 resumes operating at the first sampling frequency. For example, when the vaporizer device 100 returns to the active mode, the pressure sensor 137 and/or the ambient pressure sensor 138 may again operate at a sampling rate of 50 hertz, which may be a higher sampling rate than when the vaporizer device 100 is in the standby mode and/or the deep standby mode.

At 2715-N, the vaporizer device 100 may determine that the pressure in the air flow path 181 measured by the pressure sensor 137 is not less than the ambient pressure measured by the ambient pressure sensor 138 by the threshold quantity. For example, the vaporizer device 100 may determine that the pressure in the air flow path 181 measured by the pressure sensor 137 is not at least 1.5 hectopascals less than the ambient pressure measured by the ambient pressure sensor 138. As such, at 2717, the vaporizer device 100 may determine whether no motion event has been detected for a threshold quantity of time. For instance, the vaporizer device 100 may determine whether no motion has been detected for at least 5 seconds. As noted, the vaporizer device 100 may include the accelerometer 139 (and/or other motion sensors, capacitive sensors, flow sensors, strain gauge(s), or the like) capable of detecting movement of the vaporizer body 110 including, for example, tapping, rolling, and/or any other deliberate movements. Such movements may be indicative of user interaction with the vaporizer device 100 and may therefore be interpreted, for example, by the controller 128, as an intention to begin using the vaporizer device 100.

At 2717-N, the vaporizer device 100 may determine that a motion event has been detected within the threshold quantity of time. For example, the vaporizer device 100 may detect a movement of the vaporizer body 110 including, for example, a tapping, a rolling, and/or any other deliberate movements. Accordingly, the vaporizer device 100 may, at 2718, remain in a standby mode in which the pressure sensor 137 and/or the ambient pressure sensor 138 operates at the first sampling frequency. For instance, while the vaporizer device 100 is in the standby mode, the pressure sensor 137 and/or the ambient pressure sensor 138 may operate at a sampling frequency of 10 hertz, which may be an intermediate sampling frequency that is lower than the sampling frequency in the active mode but higher than the sampling frequency in the deep standby mode.

At 2717-Y, the vaporizer device 100 may determine that no motion event has been detected for the threshold quantity of time. As such, at 2720, the vaporizer device 100 may transition to a deep standby mode in which the pressure sensor 137 and/or the ambient pressure sensor 138 operate at a third sampling frequency. For example, if the vaporizer device 100 detects no motion for at least 5 seconds, the vaporizer device 100 may transition to the deep standby mode. While the vaporizer device 100 is in the deep standby mode, the pressure sensor 137 and/or the ambient pressure sensor 138 may operate at a lower sampling frequency than when the vaporizer device 100 is in the active mode and/or the standby mode. For instance, while the vaporizer device 100 is in the deep standby mode, the pressure sensor 137 may operate at a sampling frequency of 1 hertz while the ambient pressure sensor 138 may operate at a sampling frequency of 2 hertz.

While the vaporizer device 100 is in the deep standby mode, the vaporizer device 100 may determine, at 2721, whether a motion event is detected. At 2721-Y, the vaporizer device 100 may determine that a motion event has been detected. In response to the motion event, the process 2700 may resume at operation 2714 such that the vaporizer device 100 returns to a standby mode and the pressure sensor 137 and/or the ambient pressure sensor 138 resumes operating at the second sampling frequency. For example, if the vaporizer device 100 detects a motion event while the vaporizer device 100 is in the deep standby mode, the vaporizer device 100 may return to the standby mode in which the pressure sensor 137 and/or the ambient pressure sensor 138 operates at a higher sampling frequency (e.g., 10 hertz) than when the vaporizer device 100 is in the deep standby mode.

At 2721-N, the vaporizer device 100 may determine that no motion event has been detected. In the absence of a motion event, the vaporizer device 100 may, at 2722, remain in the deep standby mode in which the pressure sensor 137 and/or the ambient pressure sensor 138 operates at the third sampling frequency. For instance, if the vaporizer device 100 detects no motion while the vaporizer device 100 is in the deep standby mode, the vaporizer device 100 may remain in the deep standby mode. While the vaporizer device 100 remains in the deep standby mode, the pressure sensor 137 and/or the ambient pressure sensor 138 may continue to operate at a lower sampling frequency than when the vaporizer device 100 is in the active mode and/or the standby mode. For example, the pressure sensor 137 may operate at a sampling frequency of 1 hertz and the ambient pressure sensor 138 may operate at a sampling frequency of 2 hertz while the vaporizer device 100 is in the deep standby mode.

It should be appreciated that the process 2700 may be an example of a process for transitioning the operation mode of the vaporizer device 100. Different processes may be implemented for transitioning the operation mode of the vaporizer device 100.

According to an additional aspect of the current subject matter, a vaporizer device may include a vaporizer body including an outer shell defining an interior region of the vaporizer body. The vaporizer body may further include a cartridge receptacle at a proximal end of the outer shell, and wireless communication circuitry positioned within the outer shell and configured to enable communication between the vaporizer body and a first subset of one or more remote devices. The vaporizer device may further include a cartridge configured to connect within the cartridge receptacle. The cartridge may include a reservoir configured to contain a vaporizable material, a mouthpiece configured to deliver an aerosol comprising the vaporizable material to a user, a heating element configured to heat and cause vaporization of the vaporizable material into air drawn into the vaporizer device along an air flow path, and a wireless transceiver configured to store data and to communicate with a second subset of one or more remote devices.

In some variations, one or more of the features disclosed herein including the following features can optionally be included in any feasible combination. The wireless communication circuitry may include a near-field communication antenna and a Bluetooth antenna. The vaporizer body may further include an assembly that includes the wireless communication circuitry and a controller, and a support structure configured to support the assembly within the outer shell. The vaporizer body may further include an antenna window connected to at least a portion of the outer shell and at least partially aligned with the Bluetooth antenna. The wireless communication circuitry may receive operational instructions from an application running on at least a first device of the first subset, and the controller may be configured to implement the operational instructions. The wireless transceiver may communicate with the second subset prior to the cartridge connecting to the vaporizer body. The second subset may include at least the vaporizer body. The data stored on the wireless transceiver may include manufacturing data relating to the cartridge, filler data relating to the vaporizable material, and/or usage data relating to use of the cartridge. The usage data may be provided by the vaporizer body. The cartridge may further include a support structure at a distal end opposite the mouthpiece, and an internal sealing gasket configured to mate with the support structure and isolate the reservoir from the support structure. One or more air flow openings may be formed through a bottom plate of the support structure, the one or more air flow openings aligned with one or more respective air inlets formed in the outer shell of the vaporizer body. One or more power pin receptacles may extend from a bottom plate of the support structure for mating with one or more respective power pins extending from the cartridge receptacle of the vaporizer body. The one or more power pin receptacles may include built-in coil guides for connecting to the heating element. The vaporizer device may further include one or more absorbent pads configured to fit within the support structure off-axis from the air flow path. The wireless transceiver may include near-field communication circuitry.

According to an additional, inter-related aspect of the current subject matter, a vaporizer body may include an outer shell defining an interior region of the vaporizer body, a cartridge receptacle at a proximal end of the outer shell, the cartridge receptacle configured to mate and electrically connect with a cartridge, and a printed circuit board assembly positioned within the outer shell. The printed circuit board assembly may include wireless communication circuitry configured to enable communication between the vaporizer body and a subset of one or more remote devices, the subset including at least the cartridge, and a controller coupled to the wireless communication circuitry and configured to at least identify the cartridge and implement operational instructions, the operational instructions received by the wireless communication circuitry from an application running on at least a first device of the subset and/or based on preset configuration parameters associated with the cartridge.

In some variations, one or more of the features disclosed herein including the following features can optionally be included in any feasible combination. The wireless communication circuitry may include at least a first antenna configured to communicate signals between the vaporizer body and the cartridge, and a second antenna configured to communicate signals between the vaporizer device and at least another device of the subset. The vaporizer body may further include an antenna window connected to at least a portion of the outer shell and at least partially aligned with the second antenna. The printed circuit board assembly may further include a haptics system configured to generate haptic feedback in response to at least one control signal received by the wireless communication circuitry from the application. The printed circuit board assembly may further include a reset circuit coupled to a battery, the reset circuit configured to shut down the vaporizer body in response to a shutdown command received by the wireless communication circuitry from the application. The vaporizer body may further include a light pipe including at least one of a plurality of discrete light pipe components configured to fit within a portion of the outer shell and to correspond to a respective light emitting diode of the printed circuit board assembly.

According to an additional, inter-related aspect of the current subject matter, a cartridge may include a cartridge body including a reservoir configured to contain a vaporizable material, a heating element configured to heat and cause vaporization of the vaporizable material into air drawn into the cartridge along an air flow path, a support structure at a distal end of the cartridge body, and an internal sealing gasket configured to mate with the support structure and isolate the reservoir from the support structure. A mouthpiece may be coupled to a proximal end of the cartridge body opposite the support structure and configured to deliver an aerosol including the vaporizable material to a user, where the air flow path extends through the mouthpiece. A mouthpiece seal may be formed around an outer region of the reservoir, the mouthpiece seal providing a barrier between the reservoir and the mouthpiece. A wireless transceiver may be coupled to the cartridge body and configured to store data and to communicate with one or more remote devices including at least a vaporizer body to which the cartridge connects.

In some variations, one or more of the features disclosed herein including the following features can optionally be included in any feasible combination. The cartridge may further include one or more air flow openings formed through a bottom plate of the support structure, the one or more air flow openings aligned with one or more respective air inlets formed in an outer shell of the vaporizer body. The internal sealing gasket may mate with upper ends of the air flow openings. The air flow openings may include filler openings for filling the reservoir with the vaporizable material. The internal sealing gasket may be configured to self-seal after filling. The cartridge may further include one or more power pin receptacles extending from a bottom plate of the support structure, the one or more power pin receptacles configured to mate with one or more respective power pins extending from the vaporizer body. The one or more power pin receptacles may include coil guides for connecting to the heating element. The cartridge may further include one or more absorbent pads configured to fit within the support structure off-axis from the air flow path. The data stored on the wireless transceiver may include manufacturing data relating to the cartridge, filler data relating to the vaporizable material, and/or usage data relating to use of the cartridge. The filler data may be provided by filling equipment. The usage data may be provided by the vaporizer body. The cartridge may further include a bottom tank seal formed around a bottom region of the support structure.

According to an additional, inter-related aspect of the current subject matter, a method may include receiving, by a wireless transceiver of a cartridge configured to be coupled to a vaporizer body and from at least one remote device in wireless communication with the wireless transceiver, data characterizing the cartridge; transmitting, by the wireless transceiver and to wireless communication circuitry of the vaporizer body, the data characterizing the cartridge; and configuring, by a controller of the vaporizer body and in response to user activation of the vaporizer body, the vaporizer body to operate consistent with the data characterizing the cartridge.

In some variations, one or more of the features disclosed herein including the following features can optionally be included in any feasible combination. The at least one remote device may include assembly equipment, and the data may include manufacturing data relating to the cartridge. The at least one remote device may include filling equipment configured to fill a reservoir of the cartridge with a vaporizable material, and the data may include filler data relating to the vaporizable material. The configuring may include heating the vaporizable material to a predetermined temperature. The configuring may include delivering a predetermined dose of the vaporizable material. The at least one remote device may include the vaporizer body, and the data may include usage data relating to use of the cartridge. The method may further include transmitting the usage data to a user device for display on the user device. The method may further include receiving, by the wireless communication circuitry of the vaporizer body, operational instructions from an application running on a user device.

In some examples, the vaporizable material may include a viscous liquid such as, for example a *cannabis* oil. In some variations, the *cannabis* oil comprises between 0.3% and 100% *cannabis* oil extract. The viscous oil may include a carrier for improving vapor formation, such as, for example, propylene glycol, glycerol, medium chain triglycerides (MCT) including lauric acid, capric acid, caprylic acid, caproic acid, etc., at between 0.01% and 25% (e.g., between 0.1% and 22%, between 1% and 20%, between 1% and 15%, and/or the like). In some variations the vapor-forming carrier is 1,3-Propanediol. A *cannabis* oil may include a cannabinoid or cannabinoids (natural and/or synthetic), and/or a terpene or terpenes derived from organic materials such as for example fruits and flowers. For example, any of the vaporizable materials described herein may include one or more (e.g., a mixture of) cannabinoid including one or more of: CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), CBGM (Cannabigerol Monomethyl Ether), Tetrahydrocannabinol, Cannabidiol (CBD), Cannabinol (CBN), Tetrahydrocannabinolic Acid (THCA), Cannabidioloc Acid (CBDA), Tetrahydrocannabivarinic Acid (THCVA), one or more Endocannabinoids (e.g., anandamide, 2-Arachidonoylglycerol, 2-Arachidonyl glyceryl ether, N-Arachidonoyl dopamine, Virodhamine, Lysophosphatidylinositol), and/or a synthetic cannabinoids such as, for example, one or more of: JWH-018, JWH-073, CP-55940, Dimethylheptylpyran, HU-210, HU-331, SR144528, WIN 55,212-2, JWH-133, Levonantradol (Nantrodolum), and AM-2201. The oil vaporization material may include one or more terpene, such as, for example, Hemiterpenes, Monoterpenes (e.g., geraniol, terpineol, limonene, myrcene, linalool, pinene, Iridoids), Sesquiterpenes (e.g., humulene, farnesenes, farnesol), Diterpenes (e.g., cafestol, kahweol, cembrene and taxadiene), Sesterterpenes, (e.g., geranylfarnesol), Triterpenes (e.g., squalene), Sesquarterpenes (e.g, ferrugicadiol and tetraprenylcurcumene), Tetraterpenes (lycopene, gamma-carotene, alpha- and beta-carotenes), Polyterpenes, and Norisoprenoids. For example, an oil vaporization material as described herein may include between 0.3-100% cannabinoids (e.g., 0.5-98%, 10-95%, 20-92%, 30-90%, 40-80%, 50-75%, 60-80%, etc.), 0-40% terpenes (e.g., 1-30%, 10-30%, 10-20%, etc.), and 0-25% carrier (e.g., medium chain triglycerides (MCT)).

In any of the oil vaporizable materials described herein (including in particular, the cannabinoid-based vaporizable materials), the viscosity may be within a predetermined range. The range may be between, at room temperature (23° C.) about 30 cP (centipoise) and 115 kcP (kilocentipoise), between 30 cP and 200 kcP, although higher viscosities and/or lower viscosities may be implemented as well. For example, the viscosity may be between 40 cP and 113 kcP at room temperature. Outside of this range, the vaporizable material may fail in some instances to wick appropriately to form a vapor as described herein. In particular, it is typically desired that the oil may be made sufficiently thin to both permit wicking at a rate that is useful with the apparatuses described herein, while also limiting leaking (e.g., viscosities below that of ~40 cP at room temperature might result in problems with leaking).

Although the disclosure, including the figures, described herein may described and/or exemplify these different variations separately, it should be understood that all or some, or components of them, may be combined.

Although various illustrative embodiments are described above, any of a number of changes may be made to various embodiments. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. References to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as, for example, "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" "or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, are possible.

In the descriptions above and in the claims, phrases such as, for example, "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. A vaporizer device, comprising:
   a pressure sensor configured to measure a first pressure in an air flow path in the vaporizer device;
   an ambient pressure sensor configured to measure a second pressure corresponding to an atmospheric pressure; and
   a controller configured to at least:
   transition the vaporizer device to a first standby mode when the first pressure is equal to or greater than the second pressure for a first threshold quantity of time; and
   while the vaporizer device is in the first standby mode, transition the vaporizer device to a second standby mode when the first pressure is equal to or greater than the second pressure and no motion event is detected for a second threshold quantity of time.

2. The vaporizer device of claim 1, wherein the pressure sensor and/or the ambient pressure sensor operate at a first sampling frequency while the vaporizer device is in the first standby mode, and wherein the pressure sensor and/or the ambient pressure sensor operate at a second sampling frequency while the vaporizer device is in the second standby mode.

3. The vaporizer device of claim 2, wherein the second sampling frequency is less than the first sampling frequency.

4. The vaporizer device of claim 2, wherein the controller is further configured to at least:
   transition the vaporizer device to an active mode when a cartridge is coupled with the vaporizer device, wherein the pressure sensor and/or the ambient pressure sensor operate at a third sampling frequency when the vaporizer device is in the active mode, and wherein the third sampling frequency is higher than each of the first sampling frequency and the second sampling frequency.

5. The vaporizer device of claim 4, wherein the controller transitions the vaporizer device from the active mode to the first standby mode when the first pressure remains equal to or greater than the second pressure for the first threshold quantity of time.

6. The vaporizer device of claim 4, wherein the vaporizer device remains in the active mode based at least on the first pressure being less than the second pressure within the first threshold quantity of time.

7. The vaporizer device of claim 4, further comprising:
   an interrupt request (IRQ) line, a presence or an absence of a signal on the interrupt request line indicative of whether the cartridge is coupled with the vaporizer device.

8. The vaporizer device of claim 4, further comprising:
   a cartridge receptacle configured to couple the cartridge with the vaporizer device, the cartridge receptacle being a part of a vaporizer body of the vaporizer device.

9. The vaporizer device of claim 4, wherein the controller is further configured to at least:
   determine that the first pressure is the threshold quantity less than the second pressure for a threshold quantity of samples taken by the pressure sensor and/or the ambient pressure sensor while the vaporizer device is in the active mode; and
   in response to determining that the first pressure is the threshold quantity less than the second pressure for the threshold quantity of samples, activate a heater in the cartridge to cause a vaporization of a vaporizable material contained in the cartridge.

10. The vaporizer device of claim 9, wherein the controller activates the heater by at least triggering a discharge of a battery to a heating coil in the heater.

11. The vaporizer device of claim 9, wherein the first pressure being the threshold quantity less than the second pressure for the threshold quantity of samples indicates air being drawn into the vaporizer device along the air flow path.

12. The vaporizer device of claim 1, wherein the vaporizer device remains in the first standby mode in response to a detection of the motion event within the second threshold quantity of time.

13. The vaporizer device of claim 1, wherein the controller transitions the vaporizer device from the second standby mode to the first standby mode in response to the motion event while the vaporizer device is in the second standby mode.

14. The vaporizer device of claim 1, further comprising: a motion sensor configured to detect the motion event.

15. The vaporizer device of claim 14, wherein the motion sensor comprises an accelerometer.

16. The vaporizer device of claim 14, wherein the motion event comprises a tapping and/or a rolling of the vaporizer device.

17. A method, comprising:
measuring, by a pressure sensor, a first pressure in an air flow path of a vaporizer device;
measuring, by an ambient pressure sensor, a second pressure corresponding to an atmospheric pressure;
transitioning the vaporizer device to a first standby mode when the first pressure is equal to or greater than the second pressure for a first threshold quantity of time; and
while the vaporizer device is in the first standby mode, transitioning the vaporizer device to a second standby mode when the first pressure is equal to or greater than the second pressure and no motion event is detected for a second threshold quantity of time.

18. The method of claim 17, wherein the pressure sensor and/or the ambient pressure sensor operate at a first sampling frequency while the vaporizer device is in the first standby mode, and wherein the pressure sensor and/or the ambient pressure sensor operate at a second sampling frequency while the vaporizer device is in the second standby mode.

19. The method of claim 18, wherein the second sampling frequency is less than the first sampling frequency.

20. The method of claim 18, wherein the vaporizer device remains in the first standby mode in response to a detection of the motion event within the second threshold quantity of time.

21. The method of claim 18, further comprising:
transitioning the vaporizer device from the second standby mode to the first standby mode in response to the motion event while the vaporizer device is in the second standby mode.

22. The method of claim 18, further comprising:
detecting, by a motion sensor, the motion event.

23. The method of claim 22, wherein the motion sensor comprises an accelerometer.

24. The method of claim 22, wherein the motion event comprises a tapping and/or a rolling of the vaporizer device.

25. The method of claim 18, further comprising:
transitioning the vaporizer device to an active mode when a cartridge is coupled with the vaporizer device, wherein the pressure sensor and/or the ambient pressure sensor operate at a third sampling frequency when the vaporizer device is in the active mode, and wherein the third sampling frequency is higher than each of the first sampling frequency and the second sampling frequency.

26. The method of claim 25, further comprising:
transitioning the vaporizer device from the active mode to the first standby mode when the first pressure remains equal to or greater than the second pressure for the first threshold quantity of time.

27. The method of claim 25, wherein the vaporizer device remains in the active mode based at least on the first pressure being less than the second pressure within the first threshold quantity of time.

28. The method of claim 25, further comprising:
detecting, based at least on a presence or an absence of a signal on an interrupt request (IRQ) line, whether the cartridge coupled with the vaporizer device.

29. The method of claim 25, further comprising:
determining that the first pressure is the threshold quantity less than the second pressure for a threshold quantity of samples taken by the pressure sensor and/or the ambient pressure sensor while the vaporizer device is in the active mode; and
in response to determining that the first pressure is the threshold quantity less than the second pressure for the threshold quantity of samples, activating a heater in the cartridge to cause a vaporization of a vaporizable material contained in the cartridge.

30. The method of claim 29, wherein the heater is activated by at least triggering a discharge of a battery to a heating coil in the heater.

31. The method of claim 29, wherein the first pressure being the threshold quantity less than the second pressure for the threshold quantity of samples indicates air being drawn into the vaporizer device along the air flow path.

32. A non-transitory computer readable medium storing instructions, which when executed by at least one data processor, result in operations comprising:
transitioning a vaporizer device to a first standby mode when a first pressure is equal to or greater than a second pressure for a first threshold quantity of time, the first pressure comprising a pressure in an air flow path of the vaporizer device, and the second pressure comprising an atmospheric pressure; and
while the vaporizer device is in the first standby mode, transitioning the vaporizer device to a second standby mode when the first pressure is equal to or greater than the second pressure and no motion event is detected for a second threshold quantity of time.

* * * * *